US007985435B2

(12) United States Patent
Arntzen et al.

(10) Patent No.: US 7,985,435 B2
(45) Date of Patent: Jul. 26, 2011

(54) TRITERPENE COMPOSITIONS AND METHODS FOR USE THEREOF

(75) Inventors: Charles J. Arntzen, Ithaca, NY (US);
Mary E. Blake, Tucson, AZ (US);
Jordan U. Gutterman, Houston, TX (US); Joseph J. Hoffmann, Tucson, AZ (US); Gamini S. Jayatilake, Broomfield, CO (US); David T. Bailey, Boulder, CO (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 12/688,651

(22) Filed: Jan. 15, 2010

(65) Prior Publication Data

US 2010/0189824 A1    Jul. 29, 2010

Related U.S. Application Data

(62) Division of application No. 11/295,189, filed on Dec. 6, 2005, now Pat. No. 7,670,632, which is a division of application No. 10/238,647, filed on Sep. 9, 2002, now Pat. No. 7,105,186, which is a division of application No. 10/000,720, filed on Nov. 30, 2001, now Pat. No. 6,962,720, which is a division of application No. 09/314,691, filed on May 19, 1999, now Pat. No. 6,444,233.

(60) Provisional application No. 60/099,066, filed on Sep. 3, 1998, provisional application No. 60/085,997, filed on May 19, 1998.

(51) Int. Cl.
  *A61K 31/704*   (2006.01)
  *A61K 31/7034*  (2006.01)
  *A61K 36/38*    (2006.01)
  *C07H 15/256*   (2006.01)
  *A61P 35/00*    (2006.01)

(52) U.S. Cl. ............. 424/757; 536/18.1; 514/25; 514/33

(58) Field of Classification Search .................. None
See application file for complete search history.

(56) References Cited

U.S. PATENT DOCUMENTS

| | | | |
|---|---|---|---|
| 3,070,623 A | 12/1962 | Gottfried et al. | 560/194 |
| 3,070,624 A | 12/1962 | Baxendale et al. | 560/6 |
| 4,196,265 A | 4/1980 | Koprowski et al. | 435/70.21 |
| 4,376,110 A | 3/1983 | David et al. | 435/5 |
| 4,452,901 A | 6/1984 | Gordon et al. | 435/7.92 |
| 4,526,714 A | 7/1985 | Feijen et al. | 530/363 |
| 4,975,369 A | 12/1990 | Beavers et al. | 435/69.1 |
| 5,049,388 A | 9/1991 | Knight et al. | 424/450 |
| 5,183,756 A | 2/1993 | Schlom | 435/332 |
| 5,221,605 A | 6/1993 | Bard et al. | 435/4 |
| 5,238,808 A | 8/1993 | Bard et al. | 435/4 |
| 5,242,813 A | 9/1993 | Pastan et al. | 435/70.21 |
| 5,310,687 A | 5/1994 | Bard et al. | 436/518 |
| 5,607,915 A | 3/1997 | Patton | 514/12 |
| 5,919,770 A | 7/1999 | Hideo et al. | 514/26 |
| 6,444,233 B1 | 9/2002 | Arntzen et al. | 424/195.1 |
| 6,689,398 B2 | 2/2004 | Haridas et al. | 424/757 |
| 6,746,696 B2 | 6/2004 | Arntzen et al. | 424/757 |
| 6,962,720 B2 | 11/2005 | Haridas et al. | 514/886 |
| 7,105,186 B2 | 9/2006 | Arntzen et al. | 424/757 |
| 2006/0073222 A1 | 4/2006 | Arntzen et al. | 424/757 |

FOREIGN PATENT DOCUMENTS

| | | |
|---|---|---|
| BE | 753773 | 12/1970 |
| GB | 1346871 | 2/1974 |
| JP | 06073084 | 3/1994 |
| JP | HEI 07-165598 | 6/1995 |
| WO | WO 91/01750 | 2/1991 |
| WO | WO 96/02555 | 2/1996 |
| WO | WO 98/18810 | 5/1998 |
| WO | WO 98/37919 | 9/1998 |
| WO | WO 98/40100 | 9/1998 |
| WO | WO 98/52581 | 11/1998 |

OTHER PUBLICATIONS

Agrawal, "NMR spectroscopy in the structural elucidation of oligosaccharides and glycosides," Phytochemistry, 31:3307-3330, 1992.
Akiyama et al., "Genistein, a Specific Inhibitor of Tyrosine-specific Protein Kinases," *J. Biol. Chem.*, 262:5592-5595, 1987.
Alessi and Cohen, "Mechanism of activation and function of protein kinase B," *Curr. Opin. Gene. Dev.*, 8:55-62, 1998.
Anisimov et al., "Comparative study of cytotoxic activity of triterpene glycosides from marine organisms," *Toxicon.*, 18:221-223, 1980.
Anisimov et al., "Mechanism of cytotoxic action of some triterpene glycosides," *Toxicon.*, 16:207-218, 1978.
Arnon et al., "Antiviral response elicited by a completely synthetic antigen with built-in adjuvanticity," *Proc. Natl. Acad. Sci.* 77(11):6769-6772 1980.
Baxter et al., "Sapogenin structure: analysis of the $^{13}$C- and $^{1}$H-NMR spectra of soyasapogenol b," *J. Nat. Prod.*, 53:298-302, 1990.
Bellacosa et al., "Molecular alterations of the *AKT2* oncogene in ovarian and breast carcinomas," *Int. J. Cancer*, 64:280-285, 1995.
Beraud et al., "Involvement of regulatory and catalytic subunits of phosphoinositide 3-kinase in NF-κB activation," *Proc. Natl. Acad. Sci. USA*, 96:429-434, 1999.
Berton et al., "Epidermal proliferation but not the quantity of DNA photodamage is correlated with UV-induced mouse skin carcinogenesis," *Invest. Dermatol.*, 109:340-347, 1997.
Beutler et al., "Isolation and characterization of novel cytotoxic saponins form Archidendron ellipticum," *Bioorg. Med. Chem.*, 5(8):1509-1517, 1997.
Beutler, "Separation of high molecular weight saponins of archidendron ellipticum by hydrophilic interaction chromatography," *J. Liq. Chrom. & Rel. Technol.*, 20:2415-2426, 1997.
Bhandari et al., "A triterpene glycoside from Scrophularia koelzii," *Phytochemistry*, 45:1717-1719, 1997.
Brinkmann et al., "B3(Fv)-PE38KDEL, a single-chain immunotoxin that causes complete regression of a human carcinoma in mice," *Proc. Natl. Acad. Sci. USA*, 88(19):8616-8620, 1991.

(Continued)

*Primary Examiner* — Michele Flood
(74) *Attorney, Agent, or Firm* — Fulbright & Jaworski LLP

(57) ABSTRACT

The invention provides saponin mixtures and compounds which are isolated from the species *Acacia victoriae* and methods for their use. These compounds may contain a triterpene moiety, such as acacic or oleanolic acid, to which oligosaccharides and monoterpenoid moieties are attached. The mixtures and compounds have properties related to the regulation of apoptosis and cytotoxicity of cells and exhibit potent anti-tumor effects against a variety of tumor cells.

12 Claims, 43 Drawing Sheets

OTHER PUBLICATIONS

Cantley and Neel, "New insights into tumor suppression: PTEN suppresses tumor formation by restraining the phosphoinositide 3-kinase/AKT pathway," *Proc. Natl. Acad. Sci. USA*, 96:4240-4245, 1999.

Cha et al., "Ursolic acid-induced down-regulation of MMP-9 gene is mediated through the nuclear translocation of glucocorticoid receptor in HT1080 human fibrosarcoma cells," *Oncogene*, 16:771-778, 1998.

Chatterjee et al., "Ultraviolet B radiation-induced DNA lesions in mouse epidermis," *Biochem. Biophys. Res. Commun.*, 229:590-595, 1996.

Cheatham et al., "Structural and functional analysis of pp70$^{S6k}$," *Proc. Natl. Acad. Sci.*, 92:11696-11700, 1995.

Chen and Snyder, "Diosgenin-bearing, molluscicidal saponins from *Allium vineale*: an NMR approach for the structural assignment of oligosaccharide units," *J. Org. Chem.*, 54:3679-3689, 1989.

Chen et al., "Structure determination of three saponins from the stem bark of Albizzia julibrissin Durazz," *Yaoxue Xuebao*, 32(2):110-115, 1997.

Chen et al., "Studies on the triterpene sapogenins form Albizziae cortex," *Yaoxue Xuebao*, 32(2):144-147, 1997.

Cho et al., "*Agrobacterium rhizogenes*-mediated transformation and regeneration of the legume *Astragalus sinicus* (Chinese milk vetch)," *Plant Science*, 138:53-65, 1998.

Chou and Blenis, "The 70kDa S6 kinase complexes with and is activated by the Rho Family G proteins Cdc42 and Rac1," *Cell*, 85:573-583, 1996.

Christey, "Transgenic crop plants using *Agrobacterium rhizogenes*-mediated transformation," Doran, P.M., (ed.) *Hairy roots: Culture and applications*, Harwood, Amsterdam, 99-111, 1997.

Davis et al., "Regulation of cholesterol synthesis and the potential for its pharmacologic manipulation," *Pharmac. Ther.*, 43:221-236, 1989.

DeNinno et al., "Steroidal glycoside cholesterol absorption inhibitors," *J. Med. Chem.*, 40:2547-2554, 1997.

Doll et al., "Clinical Trial of Triterpenoid Liquorice Compound in Gastric and Duodenal Ulcer," *Lancet*, 1:793-796, 1962.

Downward, "Lipid-regulated kinases: some common themes at last," *Science*, 279:673-674, 1998.

Enari et al., "Involvement of an ICE-like protease in Fas-mediated apoptosis," *Nature*, 375:78-81, 1995.

Felley-Bosco, "Role of nitric oxide in genotoxicity: implication for carcinogenesis," *Cancer and Metastasis*, 17:25-37, 1998.

Frank and Pahl, "Nutraceuticals-Food, dietary supplement or drug?" *Biotech. Law Report*, 18(2):131-143, 1999.

Frechet et al., "Four triterpenoid saponins from dried roots of *Gypsophila* species," *Phytochemistry*, 30:927-931, 1991.

Fujioka et al., "Antitumor Agents. 168$^{1)}$ *Dysoxylum cumingianum*., IV. $^{2)}$ The structures of Cumingianosides G-O, new triterpene glucosides with a 14,18-cycloapotirucallane-type skeleton from *Dysoxylum cumingianum*, and their ctytotoxicity against human cancer cell lines," *Chem. Pharm. Bull*, 45(1):68-74, 1997.

Fulda, et al., "Betulinic Acid Triggers CD95 (APO-1/Fas)- and p53-independent Apoptosis via Activation of Caspases in Neuroectodermal Tumors," *Cancer Research*, 57: 4946-4964, 1997.

Gariboldi et al., "Saponins from *Crossopteryx febrifuga*," *Phytochemistry*, 29(8):2629-2635, 1990.

Gorman, "How to tell the hype from the hope: a special report," *Cancer*, 37-46, 1998.

Green and Reed, "Mitochondria and Apoptosis," *Science*, 281:1309-1312.

Gura, "Cancer models: systems for identifying new drugs are often faulty," *Science*, 278: 1041-1042, 1997.

Hamburger et al., "Acetylated saponins with molluscicidal activity from *Sapindus rarak*: unambiguous structure determination by proton nuclear magnetic resonance and quantitative analysis," *Phytochem. Anal.*, 3:231-237, 1992.

Haridas et al., "Avicins activate innate stress response by redux regulation of gene battery," manuscript by Haridas et al., pp. 1-44, 2003.

Haridas et al., "Avicins, a family of triterpenoid saponins from Acacia victoriae (Bentham), inhibit activation of nuclear factor-kappaB by inhibiting both its nuclear localization and ability to bind DNA," *Proc. Natl. Acad. Sci. USA.*, 98:11557-11562, 2001.

Harmon et al., "Activation of mammalian retinoid X receptors by the insect growth regulator methoprene," *Proc. Natl. Acad. Sci. USA*, 92:6157-6160, 1995.

Harris et al., "Inhibiting cholesterol absorption with CP-88,818 (β-Tigogenin cellobioside; tiqueside): studies in normal and hyperlipidemic subjects," *J. Cardiovascular Pharmacology*, 30:55-60, 1997.

Harwood et al., "Pharmacologic consequences of cholesterol absorption inhibition: alteration in cholesterol metabolism and reduction in plasma cholesterol concentration induced by the synthetic saponin β-tigogenin cellobioside (CP-88,818; tiqueside)," *J. Lipid. Res.* 34:377-395, 1993.

Hassanain et al., "Enhanced gel mobility shift assay for DNA-binding factors," *Anal. Biochem.*, 213:162-167, 1993.

Honda et al., "New enone derivatives of oleanolic acid and ursolic acid as inhibitors of nitric oxide production in mouse macrophages," *Bioorganic Med. Chem. Ltrs*, 7(13):1623-1628, 1997.

Hu and Alfermann, "Diterpenoid production in hairy root cultures of *Salvia miltiorrhiza*," *Phytochemistry*, 32(3):699-703; 1993.

Huang et al., "Inhibition of skin tumorigenesis by rosemary and its constituents carnosol and ursolic acid," *Cancer Research*, 54:701-708, 1994.

Ikeda et al., "Cytotoxic glycosides form Albizzia julibrissin," *J. Nat. Prod.*, 60(2):102-107, 1997.

Inoue et al., "Inhibitory Effect of Glycyrrhetinic Acid Derivatives on Lipoxygenase and Prostaglandin Synthetase," *Chem. Pharm. Bull.*, 6:897-901, 1986.

Jain, "Delivery of molecular medicine to solid tumors," *Science*, 271: 1079-1080, 1996.

Jayatilake et al., "Isolation and structures of avicins D and G: in vitro tumor-inhibitory saponins derived from Acacia victoriae," *J. Nat. Prod.*, 66:779-783, 2003.

Jiang et al., "Triterpenoid glycosides from the bark of *Mimosa tenuiflora*," *Phytochemistry*, 30(7):2357-2360, 1991.

Joshi et al., "Metabolomics of plant saponins: Bioprospecting triperpene glycoside diversity with respect to mammalian cell targets," *OMICS, Jour. Intgrtv. Bio.*, 6(3):235-246, 2002.

Jung et al., "Improvement of the catharanthine productivity in hairy root cultures of *Catharanthus roseus* by using monosaccharides as a carbon source," *Biotech. Lett.*, 14(8):695-700; 1992.

Kamel et al., "Studies on *Balanites aegyptiaca* fruits, an antidiabetic Egyptian folk medicine," *Chem. Pharm. Bull.*, 39(5):1229-1233, 1991.

Kashiwada et al., "Anti-Tumor Agents. 136. Cumingianosides A-F, Potent Antileukemic New Triterpene Glucosides, and Cumindysosides A and B, Trisnor- and Tetranortriterpene Glucosides with a 14,18-Cycloapoeuphane-Type Skeleton from Dysoxylum cumingianum," *J. Org. Chemistry*, 57:6946-6953, 1992.

Kaur et al., "Plants obtained from the Khair tree (Acacia catechu Wild.) using mature nodal segments," *Plant Cell Reports*, 17:427-429, 1998.

Kennedy et al., "The PI 3-kinase/Akt signaling pathway delivers an anti-apoptotic signal," *Genes and Dev.*, 11:701-713, 1997.

Kojima and Ogura, "Configurational studies on hydroxy groups at C-2, 3 and 23 or 24 of oleanene and ursene-type triterpenes by NMR spectroscopy," *Phytochemistry*, 28:1703-1710, 1989.

Kong et al., "Triterpenoid Glycosides from Decaisnea Fargesii," *Phytochemistry*, 33:427-430, 1993.

Lister et al., "Acacia in Australia: Ethnobotany and potential food crop," p. 228-236. In: J. Janick (ed.), *Progress in new crops*. ASHS Press, Alexandria, VA, 1996.

Lyss et al., "The anti-inflammatory sesquiterpene lactone helenalin inhibits the transcription factor NF-κB by directly targeting p65," *J. Biol. Chem.*, 273(50):33508-33516, 1998.

Ma et al., "NMR determination of the structure of Juliboside J1," *Carbohydr. Res.*, 281(1):35-46, 1996.

Mahato et al., "Structure elucidation of two acylated triterpenoid bisglycosides from acacia auriculiformis cunn," *Tetrahedron*, 48:6717-6728, 1992.

Mahato et al., "Structure of acaciaside, a triterpenoid trisaccharide from acaia auriculiformis," *Phytochemistry*, 28:207-210, 1989.

Mangelsdorf et al., "The nuclear receptor superfamily: The second decade," *Cell*, 83:835-839, 1995.
Mannick et al., "Fas-induced caspase denitrosylation," *Science*, 284:651-654, 1999.
Martin et al., "Early redistribution of plasma membrane phosphatidylserine is a general feature of apoptosis regardless of the initiating stimulus: inhibition by overexpression of Bcl-2 and Abl," *J. Exp. Med.*, 182:1545-1556, 1995.
Massiot et al., "Saponins from aerial parts of alfalfa (*Medicago sativa*)," *J. Agric. Food Chem.*, 39:78-82, 1991b.
Massiot et al., "Saponins from *Tridesmostemon claessenssi*," *Phytochemistry*, 29:3291-3298, 1990.
Massiot et al., "Structural elucidation of alfalfa root saponins by mass spectrometry and nuclear magnetic resonance analysis," *J. Chem. Soc., Perkin Trans.*, 1:3071-3079, 1988.
McManus et al., "An activator of calcium-dependant potassium channels isolated from a medicinal herb," *Biochem.*, 32:6128-6133, 1993.
Miller and Marx, "Apoptosis," *Science*, 281:1301-1302, 1998.
Moore, "Diversity and unity in the nuclear hormone receptors: a terpenoid receptor superfamily," *The New Biologist*, 2(1):100-105, 1990.
Mujoo et al., "Adenoviral-mediated p53 tumor supressor gene therapy of human ovarian carcinoma," *Oncogene*, 12:1617-1623, 1996.
Nagamoto et al., "Antitumor Constituents from Bulbs of Crocosmia crocosmiiflora," *Planta Medica.*, 54:305-307, 1988.
Nagao et al., "Studies on the constituents of *Aster tataricus* L. f. II. Structures of aster saponins isolated from the root," *Chem. Pharm. Bull.*, 37(8):1977-1983, 1989.
Nelson et al., "Detection of mutant Ha-*ras* genes in chemically initiated mouse skin epidermis before the development of benign tumors," *Proc. Natl. Acad. Sci. USA*, 89(14):6398-6402, 1992.
Nishino et al., "The structure of the tetrasaccharide unit of camellidins, saponins, possessing antifungal activity," *J. Chem. Soc., Chem. Commun.*, 720-723, 1986.
Norman, "Studies on the mechanism of phosphatidylinositol 3-kinase inhibition by wortmannin and related analogs," *J. Med. Chem.*, 39:1106-1111, 1996.
Oakenfull et al., "Saponins and Plasma Cholesterol," *Atherosclerosis*, 48:301, 1983.
Office Action, in U.S. Appl. No. 09/314,691, mailed Jan. 30, 2001.
Office Action, in U.S. Appl. No. 09/314,691, mailed Sep. 12, 2000.
Office Action, in U.S. Appl. No. 09/992,837, mailed Feb. 25, 2003.
Office Action, in U.S. Appl. No. 09/999,495, mailed Feb. 21, 2003.
Office Action, in U.S. Appl. No. 10/000,720, mailed Apr. 1, 2003.
Office Action, in U.S. Appl. No. 10/000,720, mailed May 29, 2003.
Office Action, in U.S. Appl. No. 10/238,647, mailed Mar. 28, 2005.
Office Action, in U.S. Appl. No. 11/295,189, mailed Feb. 14, 2008.
Office Action, in U.S. Appl. No. 11/295,189, mailed May 27, 2009.
Office Action, in U.S. Appl. No. 11/295,189, mailed Nov. 12, 2008.
Ohkawa et al., "Effects of gibberellic acid on hairy root growth in *Datura innoxia*," *J. Plant Physiol.*, 134:633-636; 1989.
Okabe et al., "Studies on the constituents of *Luffa operculata* COGN. II. Isolation and structure elucidation of saponins in the herb," *Chem. Pharm. Bull.*, 37(4):895-900, 1989.
Okada et al., "Blockage of chemotactic peptide-induced stimulation of neutrophils by wortmannin as a result of selective inhibition of phosphatidylinositol 3-kinase," *J. Bio. Chem.*, 269:3563-3567, 1994.
Partial European Search Report, issued in EP 99924348, dated Oct. 8, 2007.
Pisha et al., "Discovery of betulinic acid as a selective inhibitor of human melanoma that functions by induction of apoptosis," *Nat. Med.*, 1:1046-1051, 1995.
Potterat et al., Saponins with an unusual secoursene skeleton from *Sesamum alatum* THONN[1]., *Helv. Chim. Acta*, 75:833-841, 1992.
Prehn, "Regeneration versus neoplastic growth," *Carcinogenesis*, 18(8):1439-1444, 1997.
Puri et al., "Solasodine and diosgenin: $^1$H and $^{13}$C assignments by two-dimensional NMR spectroscopy," *Mag. Res. Chem.*, 31:278-282, 1993.
Purohit and Tak, "In vitro propagation of an adult tree foreonia limonia 1. through axillary branching," *Ind. J. Exp. Biol.*, 30:377-379, 1992.

Rhodes, et al., "Influence of exogenous hormones on the growth and secondary metabolite formation in transformed root cultures," *Plant Cell Tissue Organ Culture*, 38:143-151; 1994.
Rodriguez et al., "Holothurinosides: new anti-tumour non sulphated triterpenoid glycosides from the sea cucumber *Holothruia forskalii*," *Tetrahedron*, 47:4753-4762, 1991.
Royal and Park, "Hepatocyte growth factor-induced scatter of Madin-Darby canine kidney cells requires phosphatidylinositol 3-kinase," *J. Biol. Chem.* 270(46):27780-27787, 1995.
Schöpke et al., "Bellissaponins $BA_1$ and $BA_2$, acylated saponins from *Bellis perennis*," *Phytochemistry*, 30:627-631, 1991.
Schreiber et al., "Rapid detection of octamer binding proteins with 'mini-extracts', prepared from a smaller number of cells," *Nucleic Acids Res.*, 17(15):6419, 1989.
Schuh et al., "Obligatory wounding requirement for tumorigenesis in v-*jun* transgenic mice," *Nature*, 346:756-760, 1990.
Shao et al., "Saponins from roots of *Kalopanax septemlobus*. (THUNB.) KOIDZ., Ciqiu: structures of kalopanaxsaponins C, D, E and F," *Chem. Pharm. Bull.*, 37(2):311-314, 1989.
Shirazi et al., "Exposure to ultraviolet B radiation increases the tolerance of mouse skin to daily X-radiation," *Rad. Res.*, 145:768-775, 1996.
Sieweke et al., "Mediation of wound-related rous sarcoma virus tumorigenesis by TGF-β," *Science*, 248:1656-1660, 1990.
Smith et al., "Effects of gibberellic acid on hairy root cultures of *Artemisia annua*: growth and artemisinin production," *In Vitro Cell Dev. Biol.*, 33:75-79, 1997.
Spady et al, "Regulation of plasma LDL-cholesterol levels by dietary cholesterol and fatty acids" *Annu. Rev. Nutr.*, 13:355-381, 1993.
Tabas et al., "Rabbit and human liver contain a novel pentacyclic triterpene ester with acyl-CoA: cholesterol acyltransferase inhibitory activity," *J. Biological Chem.*, 265(14):8042-8051, 1990.
Takema et al., "Unusual wrinkle formation after temporary skin fixation followed by UVB irradiation in hairless mouse skin," *Exp. Dermatol.*, 5:145-149, 1996.
Tewari et al., "Yama/CPP32β, a mammalian homolog of CED-3, is a CrmA-inhibitable protease that cleaves the death substrate poly (ADP-ribose) polymerase," *Cell*, 81:801, 1995.
Tezkua et al., "Kinmoonosides A-C, three new cytotoxic saponins from the fruits of Acacia concinna, a medicinal plant collected in myanmar," *J. Nat. Prod.*, 63:1658-1664, 2000.
Thornberry and Lazebnik, "Capases: Enemies Within," *Science*, 281:1312-1316, 1998.
Tomas-Barbaren et al., "A Cytotoxic Triterpenoid and Flavonoids from Crossopteryx febrifuga," *Planta Medica.*, 54:266-267, 1988.
Vitamin USA, www.vitaminusa.com/00-3384-04111.html. Print-out of web page only.
Vlahos et al., "A specific inhibitor of phosphatidylinositol 3-kinase, 2-(4-morpholinyl)-8-phenyl-4H-1-benzopyran-4-one (LY294002)," *J. Bio. Chem.*, 269(7):5241-5248,1994.
Weng et al., "Phosphatidylinositol 3-kinase signals activation of p70 S6 kinase in situ through site-specific p70 phosphorylation," *Proc. Natl. Acad. Sci.*, 92:5744-5748, 1995.
Willy and Mangelsdorf, "Nuclear orphan receptors: The search for novel ligands and signaling pathways," *Hormones and Signaling*, 1:307-358, 1998.
Wink et al., "The multifaceted roles of nitric oxide in cancer," *Carcinogenesis*, 19(5):711-721, 1998.
www.enrich.com/us/library_pub/technicalinfoseries/ nutrientprofil.../black_chohosh.html. Print out of web page only.
Wysokinska and Chmiel, "Transformed root cultures for biotechnology," *Acta Biotechnol.*, 17(2):131-159; 1997.
Xie et al., "Role of transcription factor NF-κB/Rel in induction of nitric oxide synthase," *J. Biol. Chem.*, 269(7):4705-4708, 1994.
Yang and Shamsuddin, "IP6-Induced Growth Inhibiton and Differentiation of HT-29 Human Colon Cancer Cells: Involvement of Intracellular Inositol Phosphates," *Anticancer Res.*, 15:2479-2488, 1995.
Youn et al., "Photoprotective effect of calcipotriol upon skin photoreaction to UVA and UVB," *Photodermatol Photoimmunol. Photomed.*, 13:109-114, 1997.

Zobel et al., "Steady-State Control and Investigation of Root System Morphology," in: Torrey and Winship, (eds.) Applications of Continuous and Steady-State Methods to Root Biology, Kluwer, Amsterdam, 165-182, 1989.

Zou et al., "A new isomer of Julibroside J2 from Albizia julibrissin," *J. Asian Nat. Prod. Res.*, 1(1):59-66, 1998.

Anderson, "The chemical characterization of the gum exudates from eight Australian *Acacia* species of the series *Phyllodineae*," *Food Hydrocolloids*, 2(4):329-336, 1988.

Office Communication, issued in Japanese Patent Application No. 2000-549243, dated Jan. 19, 2010. (English Translation).

Dose: 0.2 ml  ACETONE  Mouse # 133
4 Weeks

Dose: 0.2 ml  ACETONE  Mouse # 150
8 Weeks

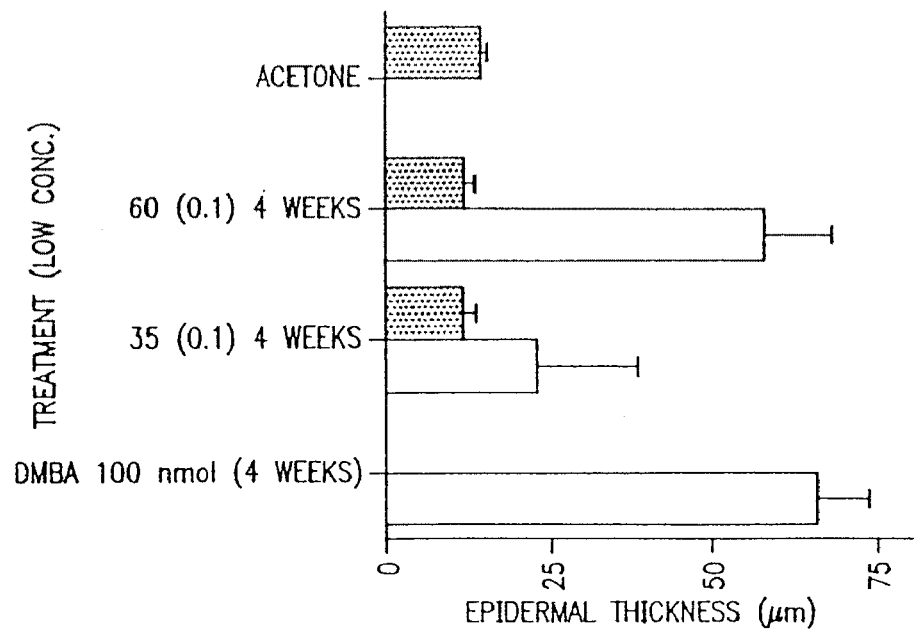
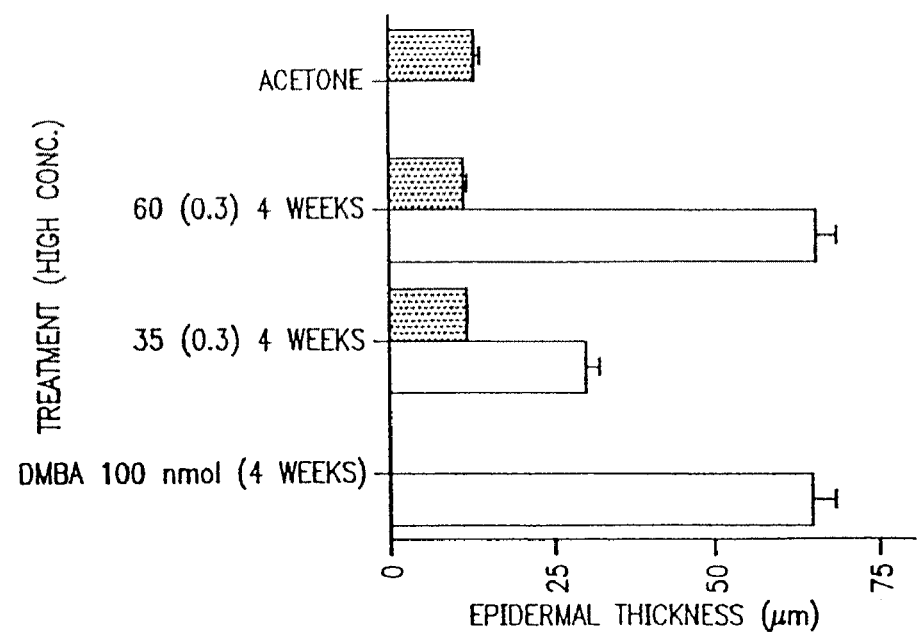

1: Untreated
2: TNF (100pM)
3: F035 (1μg/ml)
4: TNF + F035 (1μg/ml)
5: F035 (2μg/ml)
6: TNF + F035 (2μg/ml)
7: F094 (1μg/ml)
8: TNF + F094 (1μg/ml)
9: F094 (2μg/ml)
10: TNF + F094 (2μg/ml)

STRUCTURE OF ELLIPTOSIDES:

ELLIPTOSIDE E IF R=OH

ELLIPTOSIDE A IF R=H

Fraction 35 treatment

SEQUENCE LISTING

<160> NUMBER OF SEQ ID NOS: 9

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence: SYNTHETIC PRIMER -continued

```
<400> SEQUENCE: 1
agttgagggg actttcccag gctcaactcc cctgaaaggg tccg                      44

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      PRIMER

<400> SEQUENCE: 2
ctaagcctgt tgttttgcag gac                                             23

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: SYNTHETIC
      PRIMER

<400> SEQUENCE: 3
catggcacta tactcttcta                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: SYNTHETIC
      PRIMER

<400> SEQUENCE: 4
catggcacta tactcttctt                                                 20

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: SYNTHETIC
      PRIMER

<400> SEQUENCE: 5
ccttggctaa gtgtgcttct cattgg                                          26

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      PRIMER

<400> SEQUENCE: 6
acagcccacc tctggcaggt agg                                             23

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: SYNTHETIC
      PRIMER

<400> SEQUENCE: 7
```

```
gaggggatcc gatttgcttt tg                                              22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:  SYNTHETIC
      PRIMER

<400> SEQUENCE: 8
ctgatcaggc cccgagagtc                                                 20

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 9
ttgttacaag ggactttccg ctggggactt tccagggagg ctgg                      44
```

TRITERPENE COMPOSITIONS AND METHODS FOR USE THEREOF

The present application is a division of U.S. patent application Ser. No. 11/295,189, filed Dec. 6, 2005, now U.S. Pat. No. 7,670,632 which is a division of U.S. patent application Ser. No. 10/238,647, filed Sep. 9, 2002 now U.S. Pat. No. 7,105,186 which is a division of U.S. patent application Ser. No. 10/000,720, filed Nov. 30, 2001, now issued as U.S. Pat. No. 6,962,720, which is a divisional of U.S. patent application Ser. No. 09/314,691, filed May 19, 1999, now issued as U.S. Pat. No. 6,444,233, which claims the priority of U.S. Patent Applications Ser. Nos. 60/099,066 and 60/085,997, filed Sep. 3, 1998 and May 19, 1998 respectively. The entire text of each of the above-referenced disclosures is specifically incorporated by reference herein without disclaimer.

BACKGROUND OF THE INVENTION

1. Field of the Invention

The present invention relates generally to the field of medicine. More specifically, the invention relates to methods of obtaining novel plant compounds having therapeutic uses in mammals.

2. Description of Related Art

Plants are valuable sources for the identification of novel biologically active molecules. One diverse class of molecules which has been identified in plants is the class of saponins. Saponins are high molecular weight compounds comprising glycosides with a sugar moiety linked to a triterpene or steroid aglycone. Triterpene saponins particularly have been the subject of much interest because of their biological properties.

Pharmacological and biological properties of triterpene saponins from different plant species have been studied, including fungicidal, anti-viral, anti-mutagenic, spermicidal or contraceptive, cardiovascular, and anti-inflammatory activities (Hostettmann et al., 1995). Saponins are known to form complexes with cholesterol by binding plasma lipids, thereby altering cholesterol metabolism (Oakenfull et al., 1983). Triterpene glycosides given in feed also have been shown to decrease the amount of cholesterol in the blood and tissues of experimental animals (Cheeke, 1971). Saponins have been found to be constituents of many folk medicine remedies and some of the more recently developed plant drugs.

The triterpene glycyrrhetinic acid, and certain derivatives thereof, are known to have anti-ulcer, anti-inflammatory, anti-allergic, anti-hepatitis and antiviral actions. For instance, certain glycyrrhetinic acid derivatives can prevent or heal gastric ulcers (Doll et al., 1962). Among such compounds known in the art are carbenoxolone (U.S. Pat. No. 3,070,623), glycyrrhetinic acid ester derivatives having substituents at the 3' position (U.S. Pat. No. 3,070,624), amino acid salts of glycyrrhetinic acid (Japanese Patent Publication JP-A-44-32798), amide derivatives of glycyrrhetinic acid (Belgian Patent No. 753773), and amide derivatives of 11-deoxyglycyrrhetinic acid (British Patent No. 1346871). Glycyrrhetinic acid has been shown to inhibit enzymes involved in leukotriene biosynthesis, including 5-lipoxygenase activity, and this is thought to be responsible for the reported anti-inflammatory activity (Inoue et al., 1986).

Betulinic acid, a pentacyclic triterpene, is reported to be a selective inhibitor of human melanoma tumor growth in nude mouse xenograft models and was shown to cause cytotoxicity by inducing apoptosis (Pisha et al., 1995). A triterpene saponin from a Chinese medicinal plant in the Cucurbitaceae family has demonstrated anti-tumor activity (Kong et al., 1993). Monoglycosides of triterpenes have been shown to exhibit potent and selective cytotoxicity against MOLT-4 human leukemia cells (Kasiwada et al., 1992) and certain triterpene glycosides of the Iridaceae family inhibited the growth of tumors and increased the life span of mice implanted with Ehrlich ascites carcinoma (Nagamoto et al., 1988). A saponin preparation from the plant *Dolichos falcatus*, which belongs to the Leguminosae family, has been reported to be effective against sarcoma-37 cells in vitro and in vivo (Huang et al., 1982). Soya saponin, also from the Leguminosae family, has been shown to be effective against a number of tumors (Tomas-Barbaren et al., 1988). Oleanolic acid and gypsogenin glycosides exhibiting haemolytic and molluscicidal activity have been isolated from the ground fruit pods of *Swartzia madagascariensis* (Leguminosae) (Borel and Hostettmann, 1987).

Genistein, a naturally occurring isoflavonoid isolated from soy products, is a tyrosine kinase inhibitor that has been shown to inhibit the proliferation of estrogen-positive and estrogen-negative breast cancer cell lines (Akiyama et al., 1987). Inositol hexaphosphate (phytic acid), which is abundant in the plant kingdom and is a natural dietary ingredient of cereals and legumes, has been shown to cause terminal differentiation of a colon carcinoma cell line. Phytic acid also exhibits anti-tumor activity against experimental colon and mammary carcinogenesis in vivo (Yang et al., 1995). Some triterpene aglycones also have been demonstrated to have cytotoxic or cytostatic properties, i.e., stem bark from the plant *Crossopteryx febrifuga* (Rubiaceae) was shown to be cytostatic against Co-115 human colon carcinoma cell line in the ng/ml range (Tomas-Barbaren et al., 1988).

While the previous reports have identified triterpene compounds which have any of a number of uses, there still is a great need in the art for the identification of novel biologically active triterpene compounds. Many of these compounds are toxic to normal mammalian cells. Still further, the biological activities of previously identified triterpenes vary widely and many posses limited or varying degrees of efficacy in the treatment of any given human or mammalian condition. The great diversity of different triterpenes which have been identified and the great range of differences and unpredictability in the biological activities observed among even closely related triterpene compounds, underscores the difficulties which have been encountered in obtaining triterpenes which are potential therapeutic agents. Achieving the difficult goal of identifying novel triterpenes with beneficial biological activities could provide entirely new avenues of treatment for a diverse set of human ailments in which therapeutic options currently are limited.

SUMMARY OF THE INVENTION

The present invention relates to the novel use of *Acacia victoriae* (Benth.) (Leguminosae) pods and roots for the isolation of novel biologically useful compounds. *Acacia victoriae* seeds have been used as a source of food material by the indigenous people of Australia for generations (Lister et al., 1996). However, the pods and roots were discarded as waste material. Therefore, the inventors of the present invention have demonstrated the presence of novel anti-cancer and other biologically useful compounds from the parts of the plant that were not used before. For example, the novel biologically active saponin compounds disclosed herein are often specifically cytotoxic to malignant cells.

In one embodiment the present invention provides novel saponin compounds and mixtures thereof which may be isolated from the species *Acacia victoriae* and methods for their use. In this respect, one embodiment of the invention provides a saponin composition comprising a triterpene or other aromatic terpenoid composition. The saponins disclosed herein may also contain a glycosidic group.

For preferred embodiments where the saponin contains a triterpene moiety, this triterpene moiety is typically an acacic or oleanolic acid or other structurally similar triterpenoid moiety. The triterpene or triterpene glycoside compositions may also typically comprise a monoterpene moiety or moieties and one of skill in the art will appreciate that the saponin compositions described herein may be further substituted with other chemical functionalities. Thus, the saponin compounds disclosed herein may comprise a triterpene moiety attached to at least one, and preferably two, three, or more, monoterpene moieties. When more than one monoterpene moiety is present, these moieties may each be attached (i) directly to the triterpene moiety, (ii) to a sugar, or other linking group, which is attached to the triterpene moiety, or (iii) to a monoterpene moiety which is attached to the triterpene moiety directly or through a sugar or other linking groups. Linking groups include sugars, acyl, amide, alkoxy, ketyl, alkyl, alkylene and other similar chemical moieties which would be apparent to one of skill in the art. The triterpene glycosides disclosed herein typically have a molecular weight in the range of 1800 to 2600 amu, or from at least 1800, 1900, 2000, 2100 amu to about 2200, 2300, 2400 or 2600 amu.

An important aspect of the invention provides the isolation of a mixture comprising one or more isolated saponins or triterpene glycosides that may be characterized by the following properties: a) isolatable from the tissues of *Acacia victoriae*; b) containing at least one triterpene glycoside having a molecular weight of from about 1800 to about 2600 amu; c) the ability to induce cytotoxicity in a Jurkat cell; and d) the ability to induce apoptosis in a Jurkat cell.

In particular embodiments of the invention, the triterpene composition may be characterized by the following properties: ability to induce cytotoxicity in a Jurkat cell with an $IC_{50}$ of from about 0.12 to about 0.40 µg/ml. In other embodiments of the invention, the apoptosis is induced when administered to a Jurkat cell at a concentration of from about 100 to about 400 ng/ml. In further embodiments of the invention, the apoptosis is induced when administered to a Jurkat cell at a concentration of from about 200 to about 250, 300, 350 or 400 ng/ml or from about 300 to about 350 or 400 ng/ml.

In still other embodiments of the invention, the apoptosis is measured by the reorganization of plasma membrane of a Jurkat cell by annexin binding. This may be measured by flow cytometry and the apotosis induced may be from 16-18%.

Another embodiments of the invention encompasses a mixture comprising one or more isolated triterpene glycosides characterized by the following properties: a) isolatable from the tissues of *Acacia victoriae*, b) containing at least one triterpene glycoside having a molecular weight of from about 1800 to about 2600; and c) the ability to induce the release of cytochrome c from mitochondria in a Jurkat cell.

Still other embodiments of the invention encompasses a mixture comprising one or more isolated triterpene glycosides characterized by the following properties: a) isolatable from the tissues of *Acacia victoriae*; b) containing at least one triterpene glycoside having a molecular weight of from about 1800 to about 2600; and c) the ability to activate caspase-3 in a Jurkat cell. wherein the Caspase activity is in the range of from about 0.3 to about 1.6 fluorescence units/minutes/mg.

In still other embodiments of the invention, the mixture comprising one or more isolated triterpene glycosides may be characterized by the following properties: a) isolatable from the tissues of *Acacia victoriae*; b) containing at least one triterpene glycoside having a molecular weight of from about 1800 to about 2600; and c) the ability to cause the cleavage of PARP in a Jurkat cell.

In further embodiments of the invention, the mixture comprising one or more isolated triterpene glycosides may be characterized by the following properties: a) isolatable from the tissues of *Acacia victoriae*; b) containing at least one triterpene glycoside having a molecular weight of from about 1800 to about 2600 amu; and c) the ability to inhibit the activity of PI-3-kinase in a Jurkat cell.

In yet other embodiments of the invention, the mixture comprising one or more isolated triterpene glycosides may be characterized by the following properties: a) isolatable from the tissues of *Acacia victoriae*; and b) the ability to inhibit the initiation and promotion of mammalian epithelial cells to a premalignant or malignant state.

In still other embodiments of the invention, the mixture comprising one or more isolated triterpene glycosides may be characterized by the following properties: a) isolatable from the tissues of *Acacia victoriae*; and b) the ability to induce apoptosis in malignant mammalian cells.

An important aspect of the invention provides a nutraceutical composition comprising a triterpene glycoside composition in a pharmacologically acceptable medium such as a buffer, a solvent, a diluent, an inert carrier, an oil, a creme, or an edible material. In one embodiment of the invention, the nutraceutical composition may comprise dried and ground *Acacia victoriae* root, pod or combination thereof in a pharmacologically acceptable medium. The nutraceutical compositions disclosed herein may typically be in the form of a tablet, a capsule, or an ointment.

In another aspect, the invention provides a process for preparing a composition comprising a mixture of one or more isolated triterpene glycosides, comprising: a) obtaining tissue from an *Acacia victoriae* plant; b) extracting the tissue with a solvent to provide an extract; and c) obtaining one or more triterpene glycosides from the extract. The tissues used in this process typically comprises pods, roots, seedlings, or mixtures thereof The solvent used for the extraction may be any organic solvent which is capable of extracting, often by dissolving, the saponin compound of interest. Useful extraction solvents are methanol, ethanol, isopropyl alcohol, dichloromethane, chloroform, ethyl acetate, water, glycerol and mixtures thereof.

This process may include additional steps. For example, the process may further comprise isolating the composition from plant bagasse by filtration after the extracting. In a further embodiment, the process further includes the step of defatting the plant tissue with an organic solvent prior to extracting. The organic solvent may be any solvent suitable for defatting, such as hexane, dichloromethane, chloroform, ethyl acetate or mixtures thereof. In another embodiment, the process of isolation further comprises evaporating the solvent after the extracting.

This process may also comprise obtaining the mixture of the triterpene compositions by chromatographically isolating at least triterpene glycoside composition. Exemplary chromatographic techniques include liquid chromatography, MPLC, or HPLC. Although solvents which may be employed for the chromatographic isolation would be apparent to one of skill in the art, exemplary solvents include methanol, acetonitrile, water, and mixture.

In yet another aspect, the invention provides a process for preparing a composition comprising a mixture of one or more isolated triterpene glycosides, comprising: a) preparing a tissue culture comprising cells of an *Acacia victoriae* plant; and b) extracting the triterpene composition from the cells with a solvent thereby extracting at least a first triterpene compound from the tissue. In one aspect, the tissue culture comprises a hairy root culture. In another aspect of the invention, the tissue culture is prepared by infecting the cells of *Acacia victoriae* with *Agrobacterium rhizogenes* R-1000. In a related aspect of the invention, the tissue culture comprises medium containing sucrose from about 3% to about 4% by weight. In another aspect of the invention, the solvent used to extract the composition is methanol, ethanol, isopropyl alcohol, dichloromethane, chloroform, ethyl acetate, water or a mixture thereof.

In another aspect of the invention, the method further comprises additional steps, such as filtering plant bagasse from the triterpene mixture composition, isolating the triterpene mixture composition by liquid chromatography, and/or evaporating the solvent after the extracting step.

One aspect describes a method of continually propagating the tissues of an *Acacia victoriae* plant from which one may extract the active compounds of the invention. In one embodiment of the invention, a hairy root tissue culture comprising cells of an *Acacia victoriae* plant which have been infected *Agrobacterium rhizogenes* R-1000 in a cell culture medium is described. In a related embodiment, the tissue culture medium comprises sucrose from about 3% to about 4%.

Another aspect of the invention describes a method of continually harvesting an *Acacia victoriae* plant tissue comprising: a) cultivating an *Acacia victoriae* plant in a hydroponic growth system; and b) harvesting tissue from the plant about 1 to about 4 times per year, wherein the harvesting does not kill the plant. In a related embodiment of the invention, the growth system is an aeroponic system. In another related embodiment of the invention, the tissue used for culture is *Acacia victoriae* root tissue.

An important aspect of this invention is a method of inhibiting the initiation and promotion of mammalian epithelial cells to a premalignant or malignant state comprising administering to a the mammalian cell a therapeutically effective amount of the nutraceutical compositions described above. In one embodiment, the epithelial cell is a skin cell, a colon cell, a uterine cell, an ovarian cell, a pancreatic cell, a prostate cell, a renal cell, a lung cell, a bladder cell or a breast cell. In a related embodiment, the mammal is a human. In yet another related embodiment, the mode of administering the nutraceutical is oral. In yet another related embodiment of the invention, the mode of administering the nutraceutical is topical.

The invention also encompasses a method of inducing apoptosis in a malignant mammalian cell, comprising administering to the cell a therapeutically effective amount of a nutraceutical composition described above. In one embodiment, the cell is a skin cell, a colon cell, a uterine cell, an ovarian cell, a pancreatic cell, a prostate cell, a renal cell, a lung cell, a bladder cell or a breast cell. In a related embodiment, the mammal is a human. In yet another related embodiment, the mode of administering the nutraceutical is oral. In an alternative embodiment, the mode of administering the nutraceutical is topical.

The invention also encompasses a method of preventing the abnormal proliferation of mammalian epithelial cells in vitro or in a mammal comprising administering to the mammalian cell or mammal a therapeutically effective amount of the nutraceutical compositions described above. In one aspect of the invention, the epithelial cells are crypt cells. In another aspect of the invention the epithelial cells are colon cells. In a related embodiment of the invention, the mammal is a human. In yet another related embodiment of the invention, the mode of administering the nutraceutical for in vivo application is oral.

The invention also contemplates a method of treating a mammal for inflammation, comprising administering to the mammal a therapeutically effective amount of the nutraceutical compositions described above. In a related embodiment of the invention, the mammal is a human.

The invention also comprises a purified triterpene compound comprising a triterpene moiety attached to a monoterpene moiety having the molecular formula:

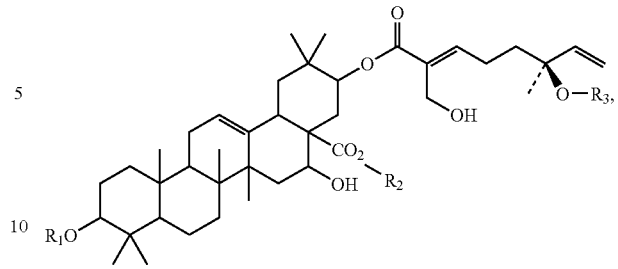

or a pharmaceutical formulation thereof, wherein a) $R_1$ and $R_2$ are selected from the group consisting of hydrogen, C1-C5 alkyl, and an oligosaccharide; b) $R_3$ is selected from the group consisting of hydrogen, hydroxyl, C1-C5 alkyl, C1-C5 alkylene, C1-C5 alkyl carbonyl, a sugar, and a monoterpene group; and c) the formula further comprises $R_4$, wherein $R_4$ is selected from the group consisting of hydrogen, hydroxyl, C1-C5 alkyl, C1-C5 alkylene, C1-C5 alkyl carbonyl, a sugar, C1-C5 alkyl ester, and a monoterpene group, and wherein $R_4$ may be attached to the triterpene moiety or the monoterpene moiety. The invention also contemplates the compound wherein $R_3$ is a sugar. In related embodiments of the invention, the sugar is selected from the group consisting of glucose, fucose, rhamnose, arabinose, xylose, quinovose, maltose, glucuronic acid, ribose, N-acetyl glucosamine, and galactose. In other related embodiments of the invention, the compound further comprises a monoterpene moiety attached to the sugar. The invention also comprises a composition wherein $R_3$ has the following formula

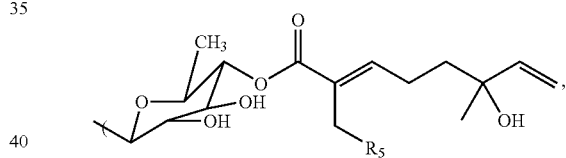

wherein R5 is selected from the group consisting of hydrogen, hydroxyl, C1-C5 alkyl, C1-C5 alkylene, C1-C5 alkyl carbonyl, a sugar, C1-C5 alkyl ester, and a monoterpene group.

In one embodiment of the invention, $R_5$ is a hydrogen or a hydroxyl. In another embodiment of the invention, $R_1$ and $R_2$ each comprise an oligosaccharide. In still other embodiments of the invention $R_1$ and $R_2$ each comprise a monosaccharide, a disaccharide, a trisaccharide or a tetrasaccharide. In related embodiments of the invention $R_1$ and $R_2$ each comprise an oligosaccharide comprising sugars which are separately and independently selected from the group consisting of glucose, fucose, rhamnose, arabinose, xylose, quinovose, maltose, glucuronic acid, ribose, N-acetyl glucosamine, and galactose. In further aspects of the invention, at least one sugar is methylated.

In one embodiment of the invention, $R_4$ is attached to the triterpene moiety through one of the methylene carbons attached to the triterpene moiety. In another embodiment of the invention, the triterpene moiety is oleanolic acid instead of acacic acid.

Another embodiment of the invention describes a composition comprising a triterpene glycoside having the molecular formula:

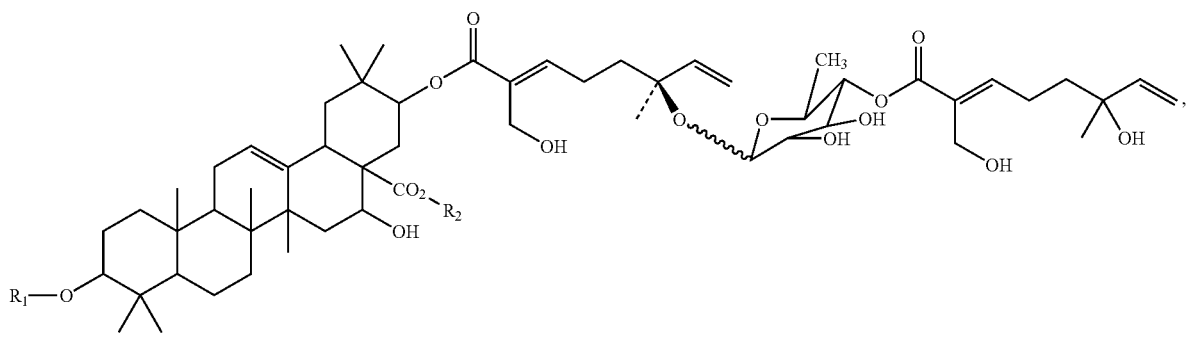

or a pharmaceutical formulation thereof, wherein a) $R_1$ is an oligosaccharide comprising N-acetyl glucosamine, fucose and xylose; and b) $R_2$ is an oligosaccharide comprising glucose, arabinose and rhamnose. In a related embodiment the compound having the molecular formula:

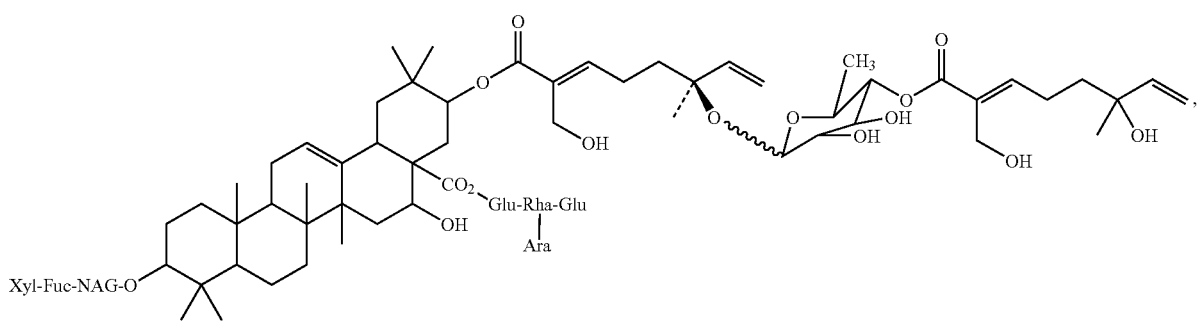

or a pharmaceutical formulation thereof is described.

Another aspect of the invention describes the purification of a composition comprising a triterpene glycoside having the molecular formula:

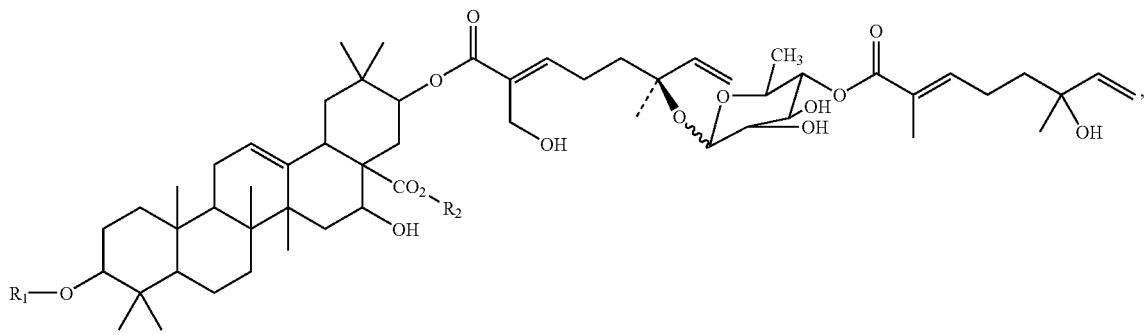

or a pharmaceutical formulation thereof wherein, a) $R_1$ is an oligosaccharide comprising N-acetyl glucosamine, fucose and xylose; and b) $R_2$ is an oligosaccharide comprising glucose, arabinose and rhamnose. A related aspect of the invention describes the purification and characterization of a composition having the molecular formula:

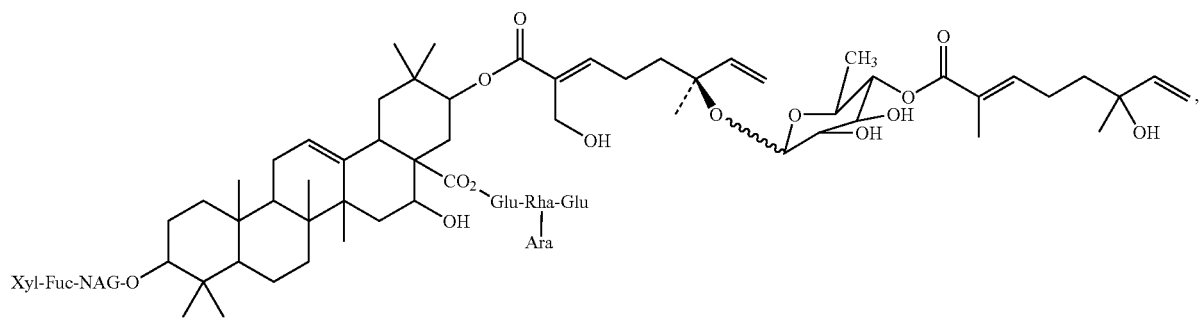

or a pharmaceutical formulation thereof.

Yet another aspect of the invention describes the purification of a composition comprising a triterpene glycoside having the molecular formula:

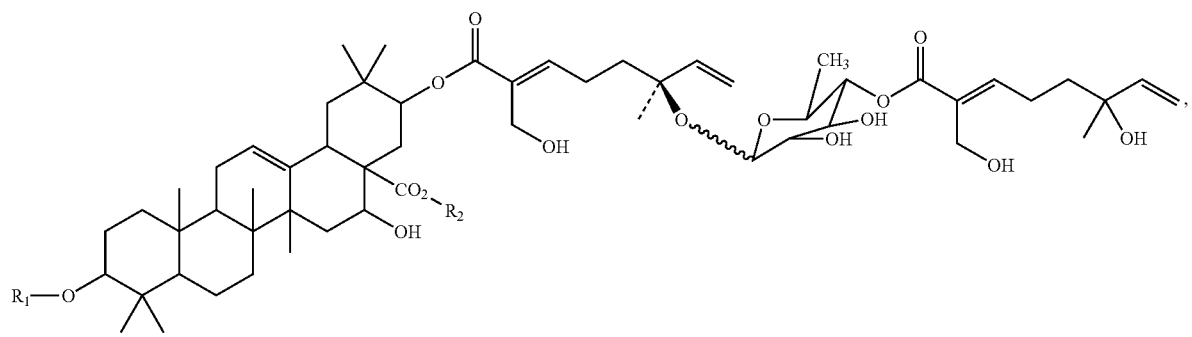

or a pharmaceutical formulation thereof, wherein, a) $R_1$ is an oligosaccharide comprising N-acetyl glucosamine, glucose, fucose and xylose; and b) $R_2$ is an oligosaccharide comprising glucose, arabinose and rhamnose. A related aspect of the invention, describes the purification and characterization of a composition comprising having the molecular formula:

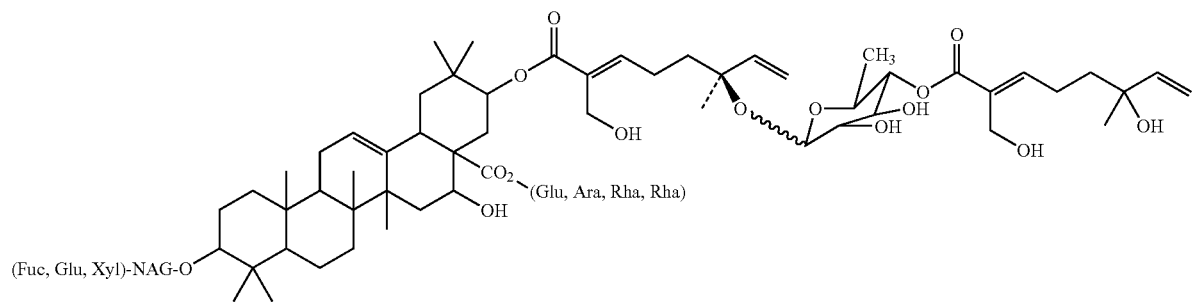

Another aspect of the invention relates to a composition comprising a triterpene moiety, an oligosaccharide and three monoterpene units. In one embodiment the triterpene moiety is acacic acid or oleanolic acid.

An important aspect of the invention contemplates pharmaceutical preparations of the compounds purified and characterized. In one embodiment the pharmaceutical preparation is in a pharmacologically acceptable medium comprising a buffer, a solvent, a diluent, an inert carrier, an oil, a creme, or an edible material. In some aspects of the invention, the pharmaceutical composition is contemplated to further comprises a targeting agent. In related aspects of the invention, the targeting agent can direct the delivery of the pharmaceutical composition to an epithelial cell. In a related embodiment of the invention, the targeting agent comprises an antibody which binds to the epithelial cell.

In certain embodiments of the invention, the pharmaceutical composition comprises at least a second composition that can kill an epithelial cell.

The compounds of this invention have shown chemoprotective effects in mice exposed to the carcinogen DMBA. The invention therefore provides a method of inhibiting the initiation and promotion of a mammalian epithelial cell to a premalignant or malignant state in a mammal comprising administering to the mammal a therapeutically effective amount of the pharmaceutical compositions described above. In one embodiment of the invention, the epithelial cell is a skin cell, a colon cell, a uterine cell, an ovarian cell, a pancreatic cell, a lung cell, a bladder cell, a prostate cell, a renal cell, or a breast cell. In a related embodiment of the invention, the mammal is a human. In yet another related embodiment of the invention, the mode of administering the pharmaceutical is oral. In still another alternative embodiment of the invention, the mode of administering the pharmaceutical is topical. In still other alternative embodiment of the invention, the mode of administering the pharmaceutical is by intratumoral injection. In still another alternative embodiment of the invention, the mode of administering the pharmaceutical is intravenous. In still further alternative embodiments of the invention, the mode of administering the pharmaceutical comprises inhaling an aerosol.

The invention also contemplates the use of the pharmaceutical preparations of the invention in combination with other therapies. In one embodiment the other therapy comprises irradiating the epithelial cell with X-ray radiation, UV-radiation, γ-radiation, or microwave radiation.

The invention also envisions a method of inducing apoptosis in a malignant mammalian cell in a mammal comprising administering to the mammal a therapeutically effective amount of the pharmaceutical compositions described herein. In one embodiment of the invention, the cell is a skin cell, a colon cell, a uterine cell, an ovarian cell, a pancreatic cell, a lung cell, a bladder cell, a prostate cell, a renal cell, or a breast cell.

In one important aspect the invention provides a method of preventing the abnormal proliferation of a mammalian epithelial cell in a mammal comprising administering to the mammal a therapeutically effective amount of the pharmaceutical compositions described above. In one embodiment the epithelial cell is a crypt cell. In another embodiment of the invention, the epithelial cell is a colon cell. In a related embodiment of the invention, the mammal is a human. In yet another related embodiment of the invention, the mode of administering the pharmaceutical is oral. In still another alternative embodiment of the invention, the mode of administering the pharmaceutical is topical. In still other alternative embodiment of the invention, the mode of administering the pharmaceutical is by intratumoral injection. In still another alternative embodiment of the invention, the mode of administering the pharmaceutical is intravenous. In still further alternative embodiments of the invention, the mode of administering the pharmaceutical comprises inhaling an aerosol. The invention also contemplates the use of the pharmaceutical preparations of the invention in combination with other therapies. In one embodiment the other therapy comprises irradiating the epithelial cell with X-ray radiation, UV-radiation, γ-radiation, or microwave radiation.

The invention also contemplates a method of treating a mammal for inflammation comprising administering to the mammal a therapeutically effective amount of the pharmaceutical compositions of the triterpene compounds described herein. In a related embodiment of the invention, the mammal is a human. In yet another related embodiment of the invention, the mode of administering the pharmaceutical is oral. In still another alternative embodiment of the invention, the mode of administering the pharmaceutical is topical. In still further alternative embodiments of the invention, the mode of administering the pharmaceutical comprises inhaling an aerosol.

Another important aspect of this invention is a method of regulating angiogenesis in a mammal comprising administering to the mammal a therapeutically effective amount of the pharmaceutical compositions described. The method may be when the mammal is a human.

Although several of the methods describe herein are in vivo methods it is contemplated that in vivo the triterpene glycoside compounds will exhibit similar effects.

In addition to providing methods of preventing or treating cancer with the compounds of the invention, the inventors have provided a number of other uses for the compounds of the invention. In particular, the compounds of the invention may be used as solvents, antioxidants, anti-fungal and anti-viral agents, piscicides or molluscicides, contraceptives, anti-helmintics, angiogenesis regulators, UV-protectants, expectorants, diuretics, anti-inflammatory agents, regulators of cholesterol metabolism, cardiovascular effectors, anti-ulcer agents, analgesics, sedatives, immunomodulators, antipyretics, as agents for decreasing capillary fragility, as agents to combat the effects of aging, as agents for increasing skin collagen, as agents for enhancing penile function and as agents for improving cognition and memory.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 1 demonstrates the growth inhibition exhibited by ovarian (SK-OV-3, HEY, OVCAR-3), breast (MDA-468), melanoma (A375-M, Hs294t) and human epidermoid (A431) cell lines treated with a crude legume plant extract.

FIG. 2 demonstrates the cytotoxicity exhibited by fraction 23 on ovarian (SK-OV-3, OCC1, HEY, OVCAR-3), T-cell leukemia (Jurkat), prostate (LNCaP), fresh human ovarian tumor cells (FTC), human fibroblast (FS) and endothelial (HUVEC) cells. Only 15-17% cytotoxicity was observed on nontransformed cells compared to the 50-95% cytotoxicity shown by tumor cells.

FIG. 3 demonstrates the cytotoxicity exhibited by Fraction 35 treated human ovarian (HEY, OVCAR-3,C-1, SK-OV-3), pancreatic (PANC-1) and renal (769-P,786-O,A498) cell lines. The $IC_{50}$ for the cell lines ranged from 1-6 µg/ml.

FIG. 4 shows that Fraction 35 exhibited potent cytotoxicity against Jurkat (T-cell leukemia) cells with an $IC_{50}$ of 130 ng/ml and $IC_{50}$ for REH, KG-1 and NALM-6 (B-cell leukemia) cells in the range of 1-3 µg/ml.

FIG. 5 shows that Fraction 35 is a potent inhibitor of endothelial cell proliferation with or without stimulation with bFGF.

FIG. 6 shows no effect on the migration of capillary endothelial cells suggesting lack of toxicity.

FIG. 9A: acetone treatment at 4 weeks. FIG. 9B: acetone treatment at 8 weeks. FIG. 9C: DMBA treatment at 4 weeks. FIG. 9D: DMBA treatment at 8 weeks. FIG. 9E: DMBA+UA-BRF-004-DELEP-F035 treatment at 4 weeks. FIG. 9F: DMBA+UA-BRF-004-DELEP-F035 treatment at 8 weeks.

FIG. 10A: shows the antioxidant effects following treatment with a low concentration of UA-BRF-004-DELEP-F035 (0.1 mg/0.2 ml).

FIGS. 11A,B: Show the epidermal thickness after 4 weeks of treatment with DMBA and UA-BRF-004-DELEP-F035. FIG. 11A: shows the effect on epidermal thickness following treatment with a low concentration of UA-BRF-004-DELEP-F035 (0.1 mg/0.2 ml). FIG. 11B: shows the effect on epidermal thickness following treatment with a high concentration of UA-BRF-004-DELEP-F035 (0.3 mg/0.2 ml).

FIG. 17A: shows an HPLC spectrum of acetylated sugars isolated from the hydrolyzed active constituents found in Fraction 94 ("UA-BRF-004Pod-DELEP-F094" or F094).

FIG. 18A: shows an HPLC spectra of UA-BRF-004-DELEP-F035 and F035-B2. FIG. 18B: shows an HPLC spectra of UA-BRF-004Pod-DELEP-F094. FIG. 18C: shows an HPLC spectra of F140. FIG. 18D: shows an HPLC spectra of F142. FIG. 18E: shows an HPLC spectra of F144. FIG. 18F: shows an HPLC spectra of F145.

FIG. 19A: cell cycle analysis of untreated OVCAR-3 tumor cells.

FIG. 46A) and 2 µg/ml of pure extracts (D1 and G1; FIG. 46B) for 16 hours and NF-kB was activated with 100 pM of TNF for 15 mins at 37° C. The DNA-protein complex was separated on 7.5% native polyacrylamide gels and the radioactive bands were visualized and quantitated by PhosphoImager. NOS were induced in U-937 (FIG. 46C) and Jurkat (FIG. 46D) as described in Methods. Cellular protein was resolved on SDS-PAGE and analyzed using western blot-ECL using anti-iNOS antibody.

DETAILED DESCRIPTION OF THE INVENTION

Figure 1:
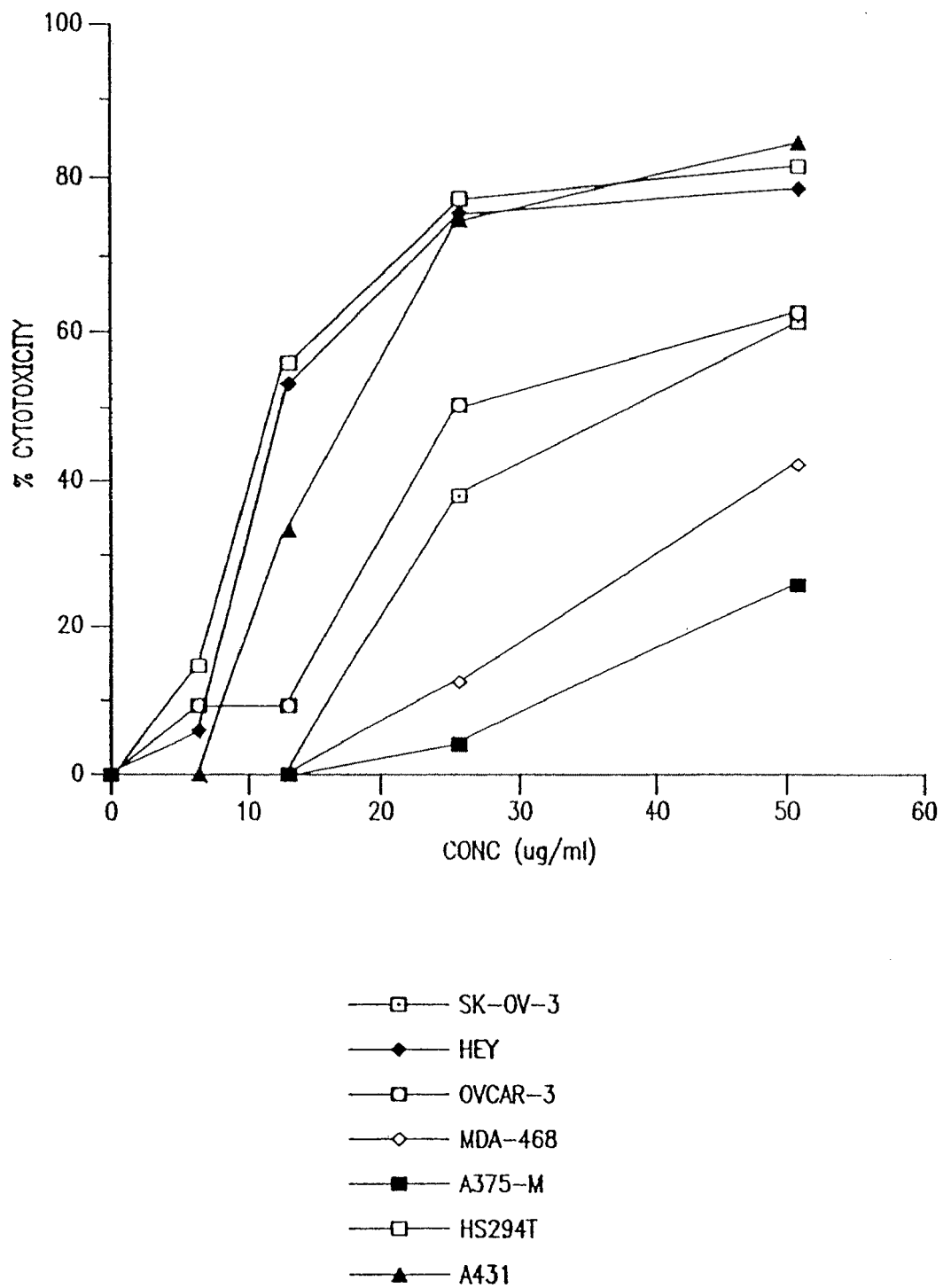
FIG. 1: Effect of UA-BRF-004-DELEP-F001 on human tumor cell lines.

The present invention seeks to overcome limitations in the prior art by providing novel biologically active triterpene glycoside compositions. In particular, the present inventors have identified and purified triterpene compounds from *Acacia victoriae*. The identified compounds exhibit potent anti-tumor activity at concentrations where there is little or no cytotoxicity to normal human cells.

The triterpene compounds of the invention were identified from a targeted screening of 60 plant extracts from selected leguminous species native to arid and semi-arid regions. Of the initial screening, one extract, designated UA-BRF-004-DELEP-F001 and isolated from *Acacia victoriae* (Benth.) (Leguminosae), showed potent anti-tumor activity against a variety of human tumor cell lines. This extract was subsequently further purified into various fractions. In two rounds of purification, an extract was identified which comprised the purified anti-tumor compounds. This extract was identified to contain purified triterpene glycoside saponins. A procedure was subsequently developed for the efficient isolation of the active compounds.

Further testing of the more purified extract further elucidated the biological activities of the extract. The purified extract demonstrated enhanced anti-tumor activity relative to the crude extract, in concentrations that exhibited little or no toxicity to normal human cells. The extract was still further shown to have a chemoprotective effect in mice exposed to carcinogens.

The plant from which the extract was isolated, *Acacia victoriae*, was selected based on factors including native environment and limited prior study of the species. *Acacia victoriae* originates from Australia, but has been introduced as a horticultural variety throughout the world and is commonly known as prickly wattle or elegant wattle. The tree grows at a rate of 60 to 120 cm per year, is tardily drought deciduous and is hardy to at least −15° C. Mature plants grow to 10-15 feet and have bluish-green bipinnate leaves. In the southwest United States, the plant typically flowers from April to May, with pods ripening in June. *Acacia victoriae* has a number of agricultural uses, including wind breaks, shelter belts, food, critical area stabilization, and as a low water-use ornamental. Different *Acacia* species seeds have been used as a source of food material by the indigenous people of Australia for generations (Lister et al., 1996). Among the *Acacia's*, *Acacia victoriae* is the most common and widespread species, present all over Australia, are therefore, the most widely consumed species. *Acacia* seeds, commonly called wattle-seed, are in high demand for use as a ground product in pastries and breads and also as a flavoring in desserts, especially ice-cream. They are also used to produce a high quality coffee-like beverage and among the *Acacia* species, *Acacia victoriae* (Benth.) is generally regarded as having a superior flavor (Lister et al., 1996). However, there is no record of the use of pods and roots of this plant.

The present invention relates to the novel use of *Acacia victoriae* pods and roots for the isolation of biologically useful compounds. The inventors of the present invention have demonstrated the presence of novel anti-cancer and other biologically useful compounds from parts of the plant that were not used before.

II. Purification and Identification of the Triterpenes of the Invention

An important aspect in the use of plant extracts as pharmaceutical preparations is the characterization and determination of the individual active constituents. Such also is the case for triterpene saponin preparations, which often require sophisticated techniques for the isolation, structure elucidation and analysis of their components and glycosides. When biological testing of the pure compounds is to be performed, it is necessary to isolate them in sufficient quantity and purity.

Since triterpenes and other related saponins have relatively large molecular weights and are of high polarity, their isolation can be challenging. A problem involved in the isolation of pure saponins is the presence of complex mixtures of closely related compounds, differing subtly either in the nature of the aglycone or the sugar part (nature, number, positions and chirality of attachment of the monosaccharides). Difficulties also are encountered with labile substituents such as esters. For example, the major genuine soybean saponin, a γ-pyrone derivative (BOA), is only extracted by aqueous ethanol at room temperature. Extraction with heating (80° C.) leads to fission of the ester moiety and formation of soyasaponin I (Bb) (Kudou et al., 1992). In plants, saponins are accompanied by very polar substances, such as saccharides and coloring matter, including phenolic compounds and the like, are not easily crystallized, and can be hygroscopic, making it even more difficult to obtain crystals.

Characterization of pure saponins also is challenging because of the lack of crystalline material. Melting points are imprecise and often occur with decomposition. Therefore, determinations of sample purity will not generally be made only based on the melting point, optical rotation value or another physical constant. A better test of the purity of a saponin can be obtained by TLC or HPLC examination—if possible by co-chromatography with an authentic sample. The coloration of spots on TLC plates after spraying with suitable reagents is an additional indicator of potential individual components. For example, one of the triterpene glycosides of the invention, D1, has a HPLC retention time of 15.2 minutes. This is different from another related compound, elliptoside E, isolated from *Archidendron ellipticum*, by John Beutler et al., 1997, which has a HPLC retention time of 12.5 minutes. Further characterization of the triterpenes of the invention show that this difference in retention time are at least due to differences in chirality and in the double bonds of D1 and the reported features of elliptoside E.

(i) Chemical Purifications

Chemical purification techniques are well known to those of skill in the art. These techniques involve, at one level, the crude fractionation of a plant extract into the triterpene glycoside compounds described herein. Having generally separated the compounds of the invention from plant material, the triterpene glycosides of interest may be further purified using the techniques described herein, for example, chromatographic techniques, to achieve partial or complete purification (or purification to homogeneity). Analytical methods particularly suited to the preparation of a pure triterpene glycoside composition are specifically disclosed herein below.

Certain aspects of the present invention concern the purification, and in particular embodiments, the substantial purification, of triterpene glycosides from plant material. In a preferred embodiment of the invention, the triterpene glycosides are purified from a plant of the family Leguminosae, or more preferably from the genus *Acacia*, and most preferably from the species *Acacia victoriae* and further more preferably from the species *Acacia victoriae* (Bench.). The term "isolated triterpene glycoside" as used herein, is intended to refer to a composition, isolatable from other components, wherein the composition is purified to any degree relative to its naturally-obtainable state.

Generally, "isolated" will refer to an organic molecule or group of similar molecules that have been subjected to fractionation to remove various other components, and which composition substantially retains its expressed biological activity. Where the term "substantially purified" is used, this designation will refer to a composition in which triterpene glycosides form the major component of the composition, such as constituting about 50%, about 60%, about 70%, about 80%, about 90%, about 95% or more of the molecules in the composition.

There is no general requirement that the triterpene compositions of the invention always be isolated and provided in their most purified state. Indeed, it is contemplated that less substantially purified products will have utility in certain embodiments. For example, the inventors envision the use of dried *Acacia victoriae* root and pod and extracts thereof as nutraceuticals. Nutraceuticals by definition contain a mixture of different bioactive compounds that synergistically have beneficial effects on health. The nutraceuticals of the present invention may be in the form of tablets or capsules and can be taken orally or alternately may contain extracts of the plant in an ointment which can be applied topically. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of product, or in maintaining the biological activity of the triterpene compounds.

(ii) Extraction and Preliminary Purification

Extraction procedures should be as mild as possible because certain saponins can undergo transformations including enzymatic hydrolysis during water extraction, esterification of acidic saponins during alcohol treatment, hydrolysis of labile ester groups and transacylation. Therefore, care should be taken to follow the individual steps in an isolation procedure, for example, in thin layer chromatography.

Although numerous variations are possible, current general procedures for obtaining crude saponin mixtures typically include extraction with methanol, ethanol, water or aqueous alcohol; a defatting step, generally with petroleum ether, performed before the extraction step or on the extract itself; dissolution or suspension of the extract in water; shaking or washing the solution or suspension with n-butanol saturated with water; and precipitation (optional) of saponins with diethyl ether or acetone. A dialysis step also can be included in order to remove small water-soluble molecules such as sugars (see, for example, Zhou et al., 1981; Massiot et al., 1988).

The most efficient extraction of dry plant material is achieved with methanol or aqueous methanol. Methanol is also used for fresh plant material. Although water is typically a less efficient extraction solvent for saponins (unless specifically water-soluble glycosides are desired) it has the advantages of being easily lyophilized and giving a cleaner extract. Depending on the proportion of water used for extraction, either monodesmosidic or bidesmosidic saponins may be obtained (Domon and Hostettmann, 1984; Kawamura et al., 1988). Fresh vegetable material contains active enzymes (esterases) which, when homogenized with a solvent, are able to convert bidesmosides into mono-desmosides. Even dry material may contain esterases which are activated in the presence of water. In the case of momordin I (a monodesmosidic oleanolic acid saponin) it was found that conversion to momordin II (the corresponding bidesmoside) takes place in water and in 30% and 60% methanol solutions, but not in 80% and 100% methanol solutions. On the contrary, homogenates of the fresh roots in methanol retained enzyme activity. However, the enzymes could be inactivated by first soaking the fresh roots in 4% hydrochloric acid and the bidesmoside was then shown to be the major component. It is, therefore, clear that the correct choice of extraction procedure is an extremely important first step.

Methods typically used to purify proteins, such as dialysis, ion-exchange chromatography and size-exclusion chromatography, are useful in partially separating saponins in aqueous solution from non-saponin components, but are generally ineffective in separating individual saponins because of the tendency of saponins to form mixed micelles. Hence, effective separation typically requires the use of organic solvents or solvent/water systems that solubilize the amphiphilic saponins as monomers so that the formation of mixed micelles does not interfere with separation.

A common problem observed for furostanol saponins is the formation of 22-$OCH_3$ derivatives during extraction with methanol. However, the genuine 22-hydroxyfurostanols can either be obtained by extraction with another solvent (e.g., pyridine) or by treatment of the methoxylated artifacts with boiling aqueous acetone (Konishi and Shoji, 1979).

(iii) Thin-Layer Chromatography (TLC)

The qualitative analysis of triterpene saponins by TLC is of great importance for all aspects of saponin investigations. TLC plates (usually silica gel) can handle both pure saponins and crude extracts, are inexpensive, rapid to use and require no specialized equipment. A number of visualization reagents are available for spraying onto the plates (Table 2). Methods of preparation of the most common reagents are as follows:

Vanillin-sulfuric acid (Godin reagent). A 1% solution of vanillin in ethanol is mixed in a 1:1 ratio with a 3% solution of perchloric acid in water and sprayed onto the TLC plate. This is followed by a 10% solution of sulfuric acid in ethanol and heating at 110° C.

Liebermann-Burchard reagent. Concentrated sulfuric acid (1 ml) is mixed with acetic anhydride (20 ml) and chloroform (50 ml). Heating at 85-90° C. gives the required coloration on the TLC plate.

Antimony(III) chloride. The TLC plate is sprayed with a 10% solution of antimony chloride in chloroform and heated to 100° C.

Anisaldehyde-sulfuric acid. Anisaldehyde (0.5 ml) is mixed with glacial acetic acid (10 ml), methanol (85 ml) and concentrated sulfuric acid (5 ml). This solution is sprayed onto the TLC plate, which is then heated at 100° C.

Spraying with vanillin-sulfuric acid in the presence of ethanol and perchloric acid, for example, gives a blue or violet coloration with triterpene saponins. With anisaldehyde-sulfuric acid, a blue or violet-blue coloration is produced on heating the TLC plate. Spraying TLC plates with a solution of cerium sulphate in sulfuric acid gives violet-red, blue or green fluorescent zones under 365 nm UV light (Kitagawa et al., 1984b). In some cases, simply spraying the plates with water is sufficient to reveal the saponins present. Additional spray reagents may be found in, for example, Stahl (1969).

The most frequently used solvent for TLC is chloroform-methanol-water (65:35:10), but other solvents are also useful. The solvent n-butanol-ethanol-ammonia (7:2:5) is especially useful for glycosides containing uronic acid residues; i.e., for very polar mixtures. Other widely used solvents include n-butanol-acetic acid-water (4:1:5; upper layer) or chloroform-methanol-acetic acid-water (60:32:12:8).

Systems employed for the TLC of glycoalkaloids typically include ethyl acetate-pyridine-water (30:10:30; upper phase). Visualization is with steroid reagents (anisaldehyde-sulfuric acid) or with alkaloid reagents (Dragendorff reagent, cerium (IV) sulphate). Other TLC solvents and visualization reagents are given by Jadhav et al. (1981) and Baerheim Svendsen and Verpoorte (1983).

Numerous quantitative determinations are possible with TLC. For example, the density of spots obtained with a suitable spray reagent can be measured directly using a densitometer. Alternatively, quantitative determinations are possible by carrying out TLC separations, scraping the relevant band off the plates (located, for example, with iodine vapor), eluting the saponin and measuring the UV absorbance after addition of a suitable reagent (e.g., concentrated sulfuric acid).

Reversed-phase TLC plates are commercially available and provide an excellent analytical method for saponins which is complementary to TLC on silica gel plates. Almost exclusive use of methanol-water and acetonitrile-water mixtures is made for developing reversed-phase plates (for example, Merck RP-8 or RP-18 HPTLC plates). Alternatively, DIOL HPTLC glass-backed plates may be used. These can be used with normal silica gel TLC-type solvents or with methanol-water and acetonitrile-water solvents, as for RP-TLC.

Exemplary reagents for TLC detection and for the spectrophotometric and colorimetric determination of saponins are listed below, in Table 2.

1. Centrifugal Thin-Layer Chromatography (CTLC)

The CTLC technique is a planar method related to preparative thin-layer chromatography (TLC) but without the need to scrape bands off the TLC plate (Hostettmann et al., 1980). CTLC relies on the action of a centrifugal force to accelerate mobile phase flow across a circular TLC plate. The plate, coated with a suitable sorbent (1, 2 or 4 mm thickness), is rotated at approximately 800 r.p.m. by an electric motor, while sample introduction occurs at the center and eluent is pumped across the sorbent. Solvent elution produces concentric bands across the plate. These are spun off at the edges and collected for TLC analysis. Separations of 50-500 mg of a mixture on a 2 mm sorbent layer are possible.

A combination of CTLC with chloroform-methanol-water (100:30:3) and column chromatography has been described for the isolation of ginsenosides (Hostettmann et al., 1980). Saponins also have been obtained with chloroform-methanol-water mixtures on silica gel plates. Two protoprimulagenin A glycosides from *Eleutherococcus senticosus* roots (Araliaceae) were purified by CTLC (chloroform-methanol-water 65:35:7) after column chromatography on silica gel and gel filtration on Sephadex LH-20 (Segiet-Kujawa and Kaloga, 1991). For the isolation of cycloartane glycosides from *Passiflora quadrangularis* (Passifloraceae), the solvent system ethyl acetate-ethanol-water (8:2:1 or 16:3:2) was used at a flow rate of either 1 ml/min (Orsini et al., 1987) or 1.5 ml/min (Orsini and Verotta, 1985).

A Hitachi centrifugal liquid chromatograph, model CLC-5, has been described for use in separation of saponins. Chromatography is carried out with this machine on silica gel plates with the eluent chloroform-methanol-water (7:3:1 (lower phase)→65:35:10 (lower phase)). Using this technique a total of 1 g of semi-purified saponin fraction was chromatographed on the circular plate (Kitagawa et al., 1988; Taniyama et al., 1988).

(iv) Open-Column Chromatography

A number of the classical solvent systems employed for the silica gel column chromatography of saponins have previously been described and may be found in, for example, Woitke et al., 1970 and Adler and Hiller, 1985. Open-column chromatography is often used as a first fractionation step for a crude saponin mixture, but in certain cases may yield pure products. In general, though, the resolution is not high and complex mixtures are only partially separated. Other problems are the loss of material because of irreversible adsorption and the length of time required to perform the separations.

Silica gel chromatography with chloroform-methanol-water eluents is one of the most widely applicable techniques. When a biphasic system is used, the water-saturated chloroform phase is the eluent. Thus, a gradient of chloroform-methanol-water (e.g., 65:35:5→65:40:10) can be employed for the initial separation of a methanol extract of plant tissue on silica gel. Further chromatography on low-pressure columns can be used to yield, for example, a monodesmosidic molluscicidal saponin, while a bidesmosidic saponin can be obtained by silica gel column chromatography with a solvent system such as acetone-n-propanol-water (35:35:5) (Borel et al., 1987).

A complex mixture of triterpene glycosides has been isolated from the corms of *Crocosmia crocosmiiflora* (Iridaceae). Three of these, 2,9,16-trihydroxypalmitic acid glycosides of polygalacic acid, were obtained by a strategy involving open-column chromatography of a crude saponin mixture on silica gel 60 (60-230 μm), employing n-butanol-ethanol-water (5:1:4, upper layer) and chloroform-methanol-water (60:29:6) as eluents. Final purification was by HPLC (Asada et al., 1989).

Extensive use of silica gel chromatography has also enabled the separation of the dammarane glycosides actinostemmosides A-D from *Actinostemma lobatum* (Cucurbitaceae). After an MCI (Mitsubishi Chemical Industries) polystyrene gel column, the relevant fractions were chromatographed with a variety of solvents: chloroform-methanol-water (7:3:0.5, 32:8:1), chloroform-methanol (9:1, 1,1), chloroform-ethanol (17:3), ethyl acetate-methanol (4:1), and chloroform-methanol-ethyl acetate-water (3:3:4:1.5, lower layer). By this means, pure actinostemmoside C was obtained while actinostemmosides A and B required an additional low-pressure LC step and actinostemmoside D required a final separation on a C-18 column eluted with 70% methanol (Iwamoto et al., 1987).

Certain ester saponins have been chromatographed on silica gel impregnated with 2% boric acid (Srivastava and Kulshreshtha, 1986; 1988).

As an addition to normal silica gel, coarse RP sorbents are now employed in the open-column chromatography of saponins. As long as the granulometry is not too fine and the columns not too long, gravity-fed columns are quite suitable. RP chromatography is generally introduced after an initial silica gel separation step and enables a change in selectivity for the substances being separated. Another possibility is to introduce the reversed-phase separation after a DCCC step (Higuchi et al., 1988).

1. Open-Column Chromatography with Polymeric Sorbents

The use of dextran supports, as found in Sephadex column packings, has been current practice for a number of years. Sephadex LH-20 finds the most frequent application but the 'G' series of polymers is not without interest.

In recent work on the isolation of saponins, a new generation of polymers has been exploited, particularly in Japan. Diaion HP-20 (Mitsubishi Chemical Industries, Tokyo), for example, is a highly porous polymer which is widely used for the initial purification steps.

Typically, the polymeric supports are washed with water after loading the sample in order to elute monosaccharides, small charged molecules such as amino acids, and other highly water-soluble substances. Elution with a methanol-water gradient (or with methanol alone) is then commenced to obtain the saponin fractions. Other chromatographic techniques are employed for the isolation of pure saponins.

Elution of HP-20 gels with acetone-water mixtures has also been reported. For example, in the isolation of bidesmosidic glycosides of quillaic acid from the tuber of *Thladiantha dubia* (Cucurbitaceae), methanol extracts were passed through a column of Diaion CHP-20P and washed with water. The crude saponins were eluted with 40% acetone. Further separation involved silica gel chromatography (ethyl acetate-methanol-water 6:2:1) and HPLC (Nagao et al., 1990).

For the isolation of fibrinolytic saponins from the seeds of *Luffa cylindrica* (Cucurbitaceae), a water extract was chromatographed on an Amberlite XAD-2 column eluted with methanol, followed by a second XAD-2 column eluted with 40-70% methanol. The active principles were obtained in the pure state after silica gel column chromatography with chloroform-methanol-water (65:35:10, lower layer→65:40:10) (Yoshikawa et al., 1991).

(v) Medium-Pressure Liquid Chromatography (MPLC)

When relatively large amounts of pure saponins are required, MPLC is very useful. Unlike commercially available LPLC equipment, gram quantities of sample can be loaded onto the columns, while separations are run at pressures of up to 40 bar. The granulometry of the support normally lies in the 25-40 μm range and separations are rapid, requiring considerably less time than open-column chromatography. A direct transposition of separation conditions from analytical HPLC to MPLC can be achieved on reversed-phase supports, thus facilitating the choice of solvent (Hostettmann et al., 1986).

As an example, molluscicidal saponins from *Cussonia spicata* (Araliaceae) were obtained in sufficient quantities for biological testing by MPLC on a C-8 sorbent with methanol-water (2:1) (Gunzinger et al., 1986). In fact, this method required just two steps (one on a silica gel support and the second on RP material) for isolation of saponins from a butanol extract of the stem bark.

The isolation of saponins also can be achieved by combination of MPLC, for example using a LiChroprep RP-8 (25-40 μm, 46×2.6 cm) column with methanol-water mixtures in combination with rotation locular countercurrent chromatography (RLCC) (Dorsaz and Hostettmann, 1986). Another MPLC technique uses axially compressed (Jobin-Yvon) columns (Elias et al., 1991).

Examples of support-solvent combinations which are useful in the separation of triterpenes from plant extracts are given in Table 1, below.

TABLE 1

Applications of MPLC in the Separation of Triterpene Saponins

| Plant | Support | Solvent | Reference |
|---|---|---|---|
| *Cussonia spicata* | Silica gel | $CHCl_3$—MeOH—$H_2O$ (6:4:1) | Gunzinger et al., 1986 |
|  | C-8 | MeOH—$H_2O$ (2:1) | Gunzinger et al., 1986 |
| *Calendula arvensis* | C-8 | MeOH—$H_2O$ (65:35, 73:27) | Chemli et al., 1987 |
| *C. officinalis* | Silica gel | $CHCl_3$ MeOH $H_2O$ (61:32:5) | Vidal-Ollivier et al., 1989 |
|  | C-18 | MeOH—$H_2O$ (60:40, 80:20) | Vidal-Ollivier et al., 1989 |
| *Polygala chamaebuxus* | Silica gel | $CH_2Cl_2$—MeOH $H_2O$ (80:20:2) | Hamburger and Hostettmann, 1986 |
|  | C-8 | MeOH—$H_2O$ (55:45) | Hamburger and Hostettmann, 1986 |
| *Swartzia madagascariensis* | C-8 | MeOH $H_2O$ (65:35) | Borel and Hostettmann, 1987 |
| *Talinum tenuissimum* | C-8 | MeOH—$H_2O$ (60:40) | Gafner et al., 1985 |
| *Sesbania sesban* | C-8 | MeOH—$H_2O$ (55:45, 60:40) | Dorsaz et al., 1988 |
| *Tetrapleura tetraptera* | C-8 | MeOH—$H_2O$ (70:30) | Maillard et al., 1989 |
| *Albizzia lucida* | C-8 | MeOH—$H_2O$ (6:4 → 9:1) | Orsini et al., 1991 |
|  | C-18 | MeOH—$H_2O$ (7:3) | Orsini et al., 1991 |
| *Passiflora quadrangularis* | C-18 | MeOH—$H_2O$ (17:3) | Orsini and Verotta, 1985 |
| *Hedera helix* | C-18 | MeOH—$H_2O$ gradient | Elias et al., 1991 |
| *Primula veris* | C-18 | MeOH—$H_2O$ (5:5 → 7:3) | Calis et al., 1992 |

TABLE 1-continued

Applications of MPLC in the Separation of Triterpene Saponins

| Plant | Support | Solvent | Reference |
|---|---|---|---|
|  | Silica gel | CHCl$_3$—MeOH—H$_2$0 (61:32:7) Steroid saponins | Calis et al., 1992 |
| Balanites aegyptiaca | Silica gel | CHCl$_3$—MeOH—H$_2$0 (80:20:1 → 25:25:2 and 70:30:3) | Hosny et al., 1992 |

(vi) High-Performance Liquid Chromatography (HPLC)

Chromatography by HPLC is a powerful technique for obtaining multi-milligram quantities of saponins from mixtures of closely related compounds and, in this respect, is very frequently employed as a final purification step. Whereas MPLC makes use of larger particles (25-100 μm), semi-preparative HPLC sorbents lie in the 5-30 μm granulometry range and consequently permit a higher separation efficiency.

Semi-preparative HPLC was employed to separate oleanolic acid triglycoside from its partial hydrolysis products. This was necessary in order to determine whether the galactose moiety was attached at position C-3 or C-4 of the glucose residue. Isolation of isomeric saponins was performed on a 7 μm LiChrosorb RP-8 column (250×16 min) with acetonitrile-water (38:62) at a flow rate of 10 ml/min. Detection was at 206 nm and from 50 mg of mixture (Décosterd et al., 1987).

A large-scale separation of saikosaponins a, c and d from *Bupleurum falcatum* (Umbelliferae) roots has been achieved on axially compressed columns, dimensions 100×11 cm I.D. Preliminary purification of a methanol extract was carried out by solvent partition and chromatography on HP-20 polymer. The preparative HPLC column was packed with C-18 silica gel (20 μm particle size; 5 kg) and eluted at a flow rate of 210 ml/min with an aqueous acetonitrile step gradient. A charge of 10 g was sufficient to give 400 mg of saikosaponin c, 1200 mg of saikosaponin a and 1600 mg of saikosaponin d (Sakuma and Motomura, 1987).

Ginsenosides have been isolated from *Panax trifolius* (Araliaceae) by a two-step procedure, involving chromatography on a Waters Prep 500 system (radially compressed columns) with three silica gel cartridges (300×57 min) arranged in series. The eluent was the upper phase of n-butanol-ethyl acetate-water (4:1:5) and charges of 4 g were injected. Semi-preparative HPLC on a carbohydrate column (Waters, 300× 7.8 mm) with acetonitrile-water (86:14 or 80:20) at a flow rate of 2 ml/min was employed for final purification (Lee and der Marderosian, 1988).

The single largest difficulty in detection of HPLC eluent components is the lack of a suitable chromophore for UV detection in most saponins, although this can typically be overcome by employing techniques including refractive index detection, mass detection and derivatization.

However, assuming gradient changes are small, UV detection at around 203-210 nm with suitably pure solvents can generally be used. Successful separations also have been carried out using acetonitrile-water gradients with UV detection. Acetonitrile is preferred to methanol at low wavelengths because of its smaller UV absorption. If the polarity difference is not too great within a series of saponins under test (only small changes in the sugar chain, for example), isocratic elution is possible.

A useful method for separating mixtures of saponins comprises separating on an octyl-bonded column using gradient elution with aqueous acetonitrile. The quantity of acetonitrile is increased from 30% to 40% over 20 min, yielding relatively little baseline drift under UV absorption. More polar bidesmosidic saponins typically elute much quicker than monodesmosidic saponins and glucuronides are less retained than other glycosides. An apolar octylsilyl support may be used for selection of the lipophilic part of the saponins. Using this technique, glycosides of hederagenin were eluted before the same glycosides of the less polar oleanolic acid (Domon et al., 1984).

1. Use of Derivatized Triterpenes

Detection at low wavelengths, which leads to problems of unstable baselines caused by interference from traces of highly UV-active material, can be improved by HPLC analyses with derivatized triterpenes. One possibility is to functionalize free carboxyl groups found in the saponin, as has been reported for the quantitative determination of monodesmosidic saponins. Treatment of oleanolic acid glycosides with 4-bromophenacyl bromide in the presence of potassium bicarbonate and a crown ether results in the formation of bromophenacyl derivatives. The 4-bromophenacyl derivatives strongly absorb at 254 nm and detection can be performed at this wavelength without interference from solvent (Slacanin et al., 1988). The derivatization is as shown below.

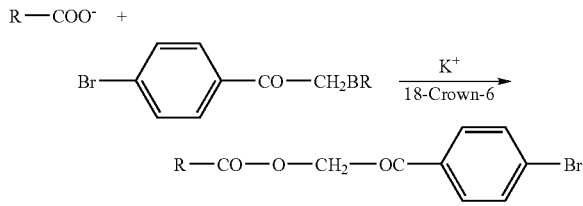

An alternative determination method is to prepare fluorescent coumarin derivatives by esterification of the carboxylic acid moiety. By this means, soyasaponins were analyzed and determined quantitatively in different varieties and different organs of soybeans, with anthracene as internal standard (Kitagawa et al., 1984a; Tani et al., 1985).

2. Sample Purification

In order to remove interfering material, which is often highly UV-absorbing, a pre-purification step may be necessary. This can be achieved, for example. by use of Sep-Pak$^R$ C$_{18}$ (Guédon et al., 1989) or Extrelut$^R$ (Sollorz, 1985) cartridges.

In the case of ionic compounds, such as those containing a free carboxyl group on the aglycone or glucuronic acid moieties, some method of suppressing ion formation is required if peak broadening is to be avoided. This can be achieved by addition of a low UV-absorbing acid to the fluent, such as phosphoric acid or trifluoroacetic acid. Another possibility is to use ion-pair HPLC, with a counter-ion added to the mobile phase. The capacity factor of the ionic compounds is increased by forming ion complexes with the pairing reagent. Derivatization of carboxyl groups (as mentioned above) is an alternative to additives in the mobile phase, resulting in considerable enhancement of peak resolution.

An advantage of quantitative HPLC over photometric methods is that the amounts of the individual saponins in a mixture or extract can be determined. In many instances, HPLC gives better results than those obtained by colorimetric, gas chromatographic and TLC-fluorimetric techniques.

In cases where the peak resolution of saponin mixtures on reversed-phase HPLC columns is insufficient, a number of other methods may be employed including utilization of hydroxyapatite columns, chemically modified porous glass columns, silica gel columns, and HPLC of borate complexes.

3. Hydroxyapatite

Hydroxyapatite ($Ca_{10}(PO_4)_6(OH)_2$) is more hydrophilic than silica gel and can be used with simple binary aqueous solvent systems, thus facilitating detection by UV. It is stable in neutral and alkaline media. Recently, hard spherical particles of hydroxyapatite which are resistant to high pressure (up to 150 kg/cm$^2$) have been prepared, broadening the applications of HPLC. Saponins differing only in the terminal pentose unit and which can not be separated by RP-HPLC can be resolved using this technique (Kasai et al., 1987b). The separation of ginsenosides from *Panax ginseng* (Araliaceae) was achieved in the isocratic mode (acetonitrite-water, 80:20) or, better, with a linear gradient (acetonitrile-water 70:30→90:10) (Kasai et al., 1987b). As is observed for silica gel, the glycosides are eluted in order of increasing polarity, i.e., the opposite of RP-HPLC.

4. Borate Ion-Exchange HPLC

This method has found application in the analysis of mono- and oligosaccharides. The best results with this technique are obtained with an anion exchange column, for example, an Asahipak ES-502N™, 100×7.6 min column from Asahi Kasei Kogyo Co. with 0.4 M $H_3BO_3$ in 20% (v/v) acetonitrile (pH 8) at 75° C. The chromatographic characteristics depend on the formation of borate complexes with cis-diols in the saccharide moiety. After separations, borate can be removed as volatile methyl borate by repeated co-distillation of the eluate with methanol.

5. Chemically Modified Porous Glass

Microporous glass (MPG) has a high chemical resistance and is stable between pH 2 and 12. Octadecyl porous glass (MPG-ODS) has been prepared as a packing for reversed-phase HPLC and used for the rapid and efficient separation of saponins. For example, it is possible to separate both ginsenosides and saikosaponins simultaneously from extracts of combination drugs containing ginseng and bupleurum root using an acetonitrile-water (25.5:74.5) mixture for the separation (Kanazawa et al., 1990a). Comparison of MPG-ODS and silica-ODS columns for the HPLC of ginseng extract and for mixtures of ginsenosides has shown that the retention behavior was similar but that capacity factors were smaller on an MPG-ODS column. The resolution of certain pairs of ginsenosides was better on MPG-ODS columns (Kanazawa et al., 1993).

6. Silica Gel

The use of water-containing mobile phases is often unavoidable for the separation of saponins, and silica gel HPLC does not normally lend itself to such eluents. However, a modification of the column packing has made possible the separation of water-soluble glycosides without column deterioration. The procedure involves first washing the column with methanol, then with the mixture chloroform-methanol-ethanol-water (62:16:16:6) and finally the solvent system to be used for the separation (Kaizuka and Takahashi, 1983). Using, for example, a 5 µm silica gel columns with a water-containing eluent: hexane-ethanol-water (8:2:0.5), efficient analyses of ginseng saponins and saikosaponins from *Bupleurum falcatum* could be achieved.

(vii) Other Chromatographic Techniques

The isolation of pure saponins requires one or, more typically, more than one chromatographic separation steps in order to remove other polar constituents of alcoholic or aqueous plant extracts.

A variety of separation techniques have been described and may be used for separating triterpene saponins including flash chromatography, DCCC, low-pressure liquid chromatography (LPLC), medium-pressure liquid chromatography (MPLC), HPLC and conventional open-column chromatography (See, e.g., Hostettmann et al., 1986, 1991; Marston and Hostettmann, 1991 b). An idea of separation conditions, solvent systems, etc. will be known to those of skill in the art in light of the instant disclosure. The best results are usually achieved by strategies which employ a combination of methods, such as those specifically disclosed herein below.

As a number of saponins are acidic, salts can form and on completion of chromatography, treatment with an ion-exchange resin may be necessary to obtain the free saponin. Examples of suitable resin include Dowex 50W×8 (H$^+$ form) (Kitagawa et al., 1988; Yoshikawa et al., 1991), Amberlite IRC 84 (Okabe et al., 1989; Nagao et al., 1990) and Amberlite MB-3 (Mizutani et al., 1984). However, if neutrality or careful control of pH are necessary to prevent decomposition, steps involving filtration on ion-exchange resins should be avoided.

In certain instances, crude saponin fractions have been methylated (assuming that free COOH groups are present) in order to achieve satisfactory separations of closely related products (Okabe et al., 1989; Nagao et al., 1989, 1990).

1. Flash Chromatography

Flash chromatography is a preparative pressure liquid chromatography method which enables a considerable time saving when compared with conventional open-column chromatography. Ordinary glass columns are used but eluent is driven through a sorbent by compressed air or nitrogen, reaching a maximum pressure of about 2 bar at the top of the column. The granulometry of the sorbent is somewhat reduced because solvent is being delivered under pressure; resolution is consequently higher.

Flash chromatography can be employed as a fast alternative to open-column chromatographic methods of preliminary fractionation. Using this method, separations of 10 mg to 10 g of sample can be achieved in as little as 10 min. For example, molluscicidal and fungicidal hederagenin, bayogenin and medicagenin glucosides from the roots of *Dolichos kilimandscharicus* (Leguminosae) were isolated with this technique. A methanol extract (3.3 g) was fractionated on silica gel (63-200 µm granulometry) in a 60×4 cm column with the solvent system chloroform-methanol-water (50:10:1) at a flow rate of 15 ml/min. This was sufficient to remove contaminating material and obtain two saponin-rich fractions. The pure triterpene glycosides were obtained by a combination of DCCC and LPLC on C-8 supports (Marston et al., 1988a).

Although most applications have involved silica gel sorbents, there is an increasing trend towards RP materials. RP flash chromatography enables the separation of saponins from other, more polar, components such as oligosaccharides.

2. Low-Pressure Liquid Chromatography (LPLC)

LPLC is useful for the isolation of pure saponins because of the speed of separation and ease of manipulation. LPLC employs columns containing sorbents with a particle size of 40-60 µm. High flow rates at pressures of up to 10 bar are possible and columns are mostly made of glass. Commercially available pre-packed columns (the 'Lobar' range from Merck, for example) in different sizes are ideal for the preparative chromatography of saponins in the 50-500 mg sample range. A high and uniform packing density guarantees a good separation efficiency. Still further, it is relatively easy to transpose analytical HPLC conditions onto an LPLC separation, given that the chemistry of the sorbents is similar (Marston and Hostettmann, 1991b).

Most applications have been performed on RP sorbents, eluted with methanol-water mixtures. It is generally only pre-purified samples which are injected in this case. A good illustration of LPLC is provided by the separation of molluscicidal and haemolytic oleanolic acid and gypsogenin glycosides from *Swartzia madagascariensis* (Leguminosae). The dried, ground fruit pods were extracted with water and this extract was partitioned between n-butanol and water. After open-column chromatography of the organic phase, saponins were separated on a Lobar LiChroprep C-8 column (40-63 pro; 27×2.5 cm) with methanol-water (75:25) as eluent (Borel and Hostettmann, 1987).

Joining LPLC columns in series permits an increase in loading capacity and/or separating power. This approach was used during the separation of dammarane glycosides from *Actinostemma lobata* (Cucurbitaceae), when three Lobar 27×2.5 cm columns were connected. The eluent also contained a small amount of water (ethyl acetate-n-propanol-water 20:3:0.3) (Iwamoto et al., 1987).

3. Countercurrent Chromatography

Liquid-liquid partition methods have proved ideal for application to the field of saponins. Very polar saponins lend themselves especially well to countercurrent chromatographic separation, especially as there is no loss of material by irreversible adsorption to packing materials. This aspect has been of especial use for the direct fractionation of crude extracts.

4. Droplet Countercurrent Chromatography (DCCC)

DCCC relies on the continuous passage of droplets of a mobile phase through an immiscible liquid stationary phase contained in a large number of vertical glass tubes. The solute undergoes a continuous partition between the two phases. Depending on whether the mobile phase is introduced at the top or at the bottom of these tubes, chromatography is in the 'descending' or 'ascending' mode, respectively. The separation of closely related saponins by DCCC and even the isolation of pure products has been possible (Hostettmann et al., 1984). In fact, certain separations which have not been possible by liquid-solid chromatography have been achieved by this technique. DCCC was capable of separating isomeric saponins differing only in the positions of substitution of acetate groups on the sugar residues (Ishii et al, 1984).

A number of solvent systems have been employed for the DCCC separation of saponins (see, e.g., Hostettmann et al., 1986) and, of these, the system chloroform-methanol-water (7:13:8) has been involved in the greatest number of applications. Chloroform-methanol-water systems can be used either in the ascending mode for very polar saponins or in the descending mode for saponins possessing one or two sugars and few free hydroxyl groups.

A large-scale DCCC procedure for preliminary purification, using 18 columns (30 cm×10 mm ID.) with n-butanol-saturated water as the stationary phase and water-saturated n-butanol as the mobile phase, has been described (Komori et al., 1983). In some cases, two (or more) DCCC separations are run to obtain the pure saponins.

5. Centrifugal Partition Chromatography (CPC)

The recently introduced technique of CPC holds great promise because of its speed and versatility (Marston et al., 1990). CPC relies on a centrifugal field, produced by rotation at 800-2000 r.p.m. or faster, rather than a gravitational field for retention of the stationary phase. The principle of the method involves a continuous process of non-equilibrium partition of solute between two immiscible phases contained in rotating coils or cartridges.

Instruments based on rotating coils can involve either planetary or non-planetary motion about a central axis. One of these, the high speed countercurrent chromatograph (HSCCC) consists of a Teflon tube of 1.6 or 2.6 mm I.D. wrapped as a coil around a spool. One, two or three spools constitute the heart of the instrument. In the case of cartridge instruments, the cartridges are located at the circumference of a centrifuge rotor, with their longitudinal axes parallel to the direction of the centrifugal force. The number and volume of the cartridges can be varied, depending on the application to which the instrument is put. Compared with DCCC and RLCC, in which separations may take 2 days or longer, CPC can produce the same results in a matter of hours. Instruments based on rotating coils or cartridges have capacities up to the gram scale. A multilayer coil planet instrument has been used, for example, for the preliminary purification of cycloartane glycosides from *Abrus fruticulosus* (Leguminosae) (Fullas et al., 1990). Molluscicidal triterpene glycosides from *Hedera helix* (Araliaceae) have been separated on a different instrument, the Sanki LLN chromatograph (six cartridges; total volume 125 ml). A methanol extract of the fruit was partitioned between n-butanol and water. The butanol fraction was injected directly into the instrument in 100 mg amounts, using the lower layer of the solvent system chloroform-methanol-water (7:13:8) as mobile phase.

The two main saponins asiaticoside and madecassoside from *Centella asiatica* (Umbelliferae) have been separated with the aid of an Ito multi-layer coil separator-extractor (P.C. Inc.) equipped with a 66 m×2.6 mm I.D. column (350 ml capacity), turning at 800 r.p.m. A sample of 400 mg could be resolved with the solvent system chloroform-methanol-2-butanol-water (7:6:3:4; mobile phase was lower phase). Detection was by means of on-line TLC (Diallo et al., 1991). The same instrument was employed during the isolation of a triterpene disaccharide from *Sesamum alatum* (Pedaliaceae). The lower phase of the solvent chloroform-methanol-i-propanol-water (5:6:1:4) was chosen as the mobile phase and a charge of 1.25 g was injected (Potterat et al., 1992), 6. Combination of Methods It is rare that a single chromatographic step is sufficient to isolate a pure saponin from an extract. As a general rule, several preparative techniques are required in series to obtain the necessary product. A combination of classical techniques (such as open-column chromatography) and modern high-resolution methods (such as HPLC) has proved suitable for the separation of many saponins.

For example, a combination of MPLC on silica gel and RP material, LPLC and centrifugal TLC for separation of saponins (Hamburger and Hostettmann, 1986). Similarly, the isolation of five triterpene saponins from *Swartzia madagascariensis* (Leguminosae) required open-column chromatography, LPLC and MPLC (Borel and Hostettmann, 1987).

CPC has been used in conjunction with flash chromatography and OPLC for the isolation of triterpene glycosides from *Abrus fruticulosus* (Leguminosae). A multilayer coil instrument (solvent chloroform-methanol-water 7:13:8, lower phase as mobile phase) provided initial purification, while flash chromatography and OPLC were effective for obtaining the pure substances (Fullas et al., 1990).

The straightforward combination of flash chromatography on unmodified silica gel with either flash chromatography or open-column chromatography on RP material can sometimes be sufficient for the purification of saponins (Schöpke et al., 1991).

Another strategy involves passing extracts (after preliminary partition) over highly porous polymers and following this step by further fractionation of the crude saponin mixtures. This approach was used in the isolation of 3β-hydroxy-olean-12-en-28,29-dioic acid glycosides from *Nothopanax delavayi* (Araliaceae). A methanol extract of the leaves and stems was partitioned between hexane and water. The aqueous layer was chromatographed on a Diaion HP-20 column and eluted with water, 10% methanol, 50% methanol, 80% methanol, methanol and chloroform. The glycosides were obtained by subsequent column chromatography of the 80% methanol eluate on silica gel with ethyl acetate-ethanol-water (7:2:1) (Kasai et al., 1987a). For the isolation of triterpene and non-triterpene saponins from *Acanthopanax senticosus* (Araliaceae), the procedure began with a fractionation of the methanol extract of the leaves on Diaion HP-20 polymer. The fraction eluted with methanol was chromatographed on silica gel (chloroform-methanol-water 30:10:1) and all the resulting fractions were subjected to column chromatography on LiChroprep RP-8. Final purification was achieved by HPLC on TSK-GEL ODS-120T (300×21 min; methanol-water 70:30; 6 ml/min; RI detection) or chromatography on a hydroxyapatite column (acetonitrile-water 85:15) (Shao et al., 1988).

A procedure for separation of oleanic acid glycosides comprises employing a combination of Sephadex LH-20 (methanol), DCCC (chloroform-methanol-water 7:13:8) and HPLC (C-18, methanol-water 65:35) (De Tommasi et al., 1991).

(viii) Color Reactions

Reactions of triterpenes with any of a variety of agents may be used to produce colored compounds for the quantitative or qualitative determination of triterpenes. For example, aromatic aldehydes such as aisaldehyde and vanillin in strong mineral acid, for example, sulfuric, phosphoric, and perchloric acids, give colored products with aglycones, having absorption maxima between 510 and 620 nm. In these reactions, a dehydration is believed to occur, forming unsaturated methylene groups which give colored condensation products with the aldehydes. With vanillin-sulfuric acid, triterpene saponins with a C-23 hydroxyl group have a peak located between 460 and 485 nm (Hiai et al., 1976).

Unsaturated and hydroxylated triterpenes and steroids give a red, blue or green coloration with acetic anhydride and sulfuric acid (Abisch and Reichstein, 1960). Since terpenoid saponins tend to produce a pink or purple shade and steroid saponins a blue-green coloration, differentiation of the two classes is possible using this technique.

A large number of other agents may be used for detection of triterpenes including: cerium(IV) sulphate or iron (III) salts and inorganic acids, such as sulfuric acid, which give a violet-red coloration of the solution; a 30% solution of antimony(III) chloride in acetic anhydride-acetic acid reagent, which gives color reactions with hydroxytriterpenes and hydroxysteroids; antimony(III) chloride in nitrobenzene-methanol, which can be used to differentiate the 5,6-dehydro-derivatives of steroid glycosides (diosgenin and solasodine glycosides) and 5α- or 5β-H-derivatives (e.g., tomatine); and carbazole, which in the presence of borate and concentrated sulfuric acid will indicate the presence of uronic acids (Bitter and Muir, 1962).

Exemplary reagents for detection and for the spectrophotometric and colorimetric determination of saponins are listed below, in Table 2.

TABLE 2

Visualization Reagents for Triterpene Saponins

| Reagent | Reference |
|---|---|
| Vanillin-sulfuric acid | Godin, 1954 |
| Vanillin-phosphoric acid | Oakenfull, 1981 |
| Liebermann-Burchard (acetic anhydride-sulfuric acid) | Abisch and Reichstein, 1960 |
| 1% Cerium sulphate in 10% sulfuric acid | Wagner et al., 1984 |

TABLE 2-continued

Visualization Reagents for Triterpene Saponins

| Reagent | Reference |
|---|---|
| 10% Sulfuric acid in ethanol | Kitagawa et al., 1984b |
| 50% Sulfuric acid | Price et al., 1987 |
| p-Anisaldehyde-sulfuric acid | Price et al., 1987 |
| Komarowsky (p-hydroxybenzaldehyde-sulfuric acid) | Wagner et al., 1984 |
| Antimony (III) chloride | Wagner et al., 1985 |
| Blood | Wagner et al., 1984 |
| Water | Wagner et al., 1984 |

(ix) Isolation of Triterpene Glycosides from *Acacia Victoriae*

Legume extracts were prepared by chloroform:methanol or dichloromethane: chloroform extraction at The University of Arizona (Tucson, Ariz.). The inventors isolated mixtures of triterpene glycosides from *Acacia victoriae* (Benth.) (Leguminosae). The first collection of UA-BRF-004-DELEP-F001 was processed as follows: (1) grinding to 3 mm particle size in Wiley mill, (2) packing into two-liter percolation unit, (3) extracting the ground biomass with dichloromethane:methanol (1:1) for 4 hr. followed by overnight and the combined fractions were dried in vacuo to generate UA-BRF-004-DELEP-F001 (52 g). F001 (51.5 g) was extracted with ethyl acetate to yield active insoluble (34.7 g) material designated as F004. Flash chromatography using 1.7 kg of silica gel (Merck, 23-220 micron particle size) was used to fractionate F004 (34.2), 51 670-ml fractions eluted with dichloromethane: methanol (step-gradient-95-0%: methanol 5-100%). the Column was washed with nine-liters of methanol followed by six-liters of methanol:water (80:20) and then six-liters of same eluent with 1% formic acid added. Based on TLC fractions 23-34 and 39-40 were combined to 17.2 g of F023. Medium Pressure Liquid Chromatography (MPLC, Buchi 632 system) was used twice with 8 g of F023 each on a 4.9×46-cm column packed with Lichroprep C18, 15-25 micron particle size using step gradient of acetonitrile: water (0,10,20,30,50% acetonitrile in water) followed by 100% methanol wash. Of the 16 g 0-20% acetonitrile, yield was seven grams of F027, which was inactive. The remaining material was combined and subjected to repetitive MPLC with the same system using 30-40% acetonitrile to minimize overlap and generate fractions F028-F036. Although most of these fractions demonstrated antitumor activity, F035 (Fraction 35) (highest yield of 2.19 g) was selected for further testing and evaluation.

III. Structural Determination of Triterpenes

Various methods may be employed for the qualitative and quantitative determination of triterpenes and their activities including: piscicidal activity, gravimetry, spectrophotometry, TLC, GC, HPLC, HMQC, HMBC, NOESY, COSY, NMR, X-Ray crystallography etc. Determinations based on classical properties of triterpene saponins (surface activity, fish toxicity) have largely been replaced by photometric methods such as densitometry, colorimetry of derivatives and, more recently, by GC, HPLC and particularly, NMR. Spectrophotometric methods are very sensitive but not typically suitable for estimating triterpenes in crude plant extracts since the reactions are not specific and colored products may form with compounds which accompany the triterpenes, such as phytosterols and flavonoids. Another problem, common to much of the analytical work on saponins, is their incomplete extraction from the plant material. However, a number of techniques are widely available which are suitable for quantitating triterpenes.

There are several basic problems to be solved in the structure elucidation of saponins: the structure of the genuine aglycone; the composition and sequence of the component monosaccharides in the carbohydrate moiety; how the monosaccharide units are linked to one another; the anomeric configuration of each glycosidically linked monosaccharide unit; and the location of the carbohydrate moiety on the aglycone.

The necessary approach is to apply a combination of methods in order to arrive at a final conclusion for the structure. Structural studies are usually a stepwise process, in which the saponin is gradually broken down into smaller fragment's which themselves are analyzed spectroscopically. By a judicious handling of the data from the fragments, an idea of the composition of the saponin is derived.

The quantities of pure saponins isolated are often small, thus the use of highly sensitive, high-resolution and, if possible, non-degradative methods is preferable in order to aid the structure determination of a saponin. Innovations in NMR spectroscopy and mass spectrometry (MS) have provided such necessary abilities for the investigations of complex saponins. Through combinations of these and other techniques, structural determinations can be made. For example, FAB-MS gives information about the molecular weight and, in many cases, the sugar sequence, while I-D and 2-D NMR techniques permit the localization of sugar linkages and contribute to the structure elucidation of the aglycone. Such structural determination and chemical studies have been thoroughly discussed in a review by Tanaka and Kasai (1984).

(i) Nuclear Magnetic Resonance (NMR)

Of all the modern methods for the structure elucidation of oligosaccharides and glycosides, NMR spectroscopy provides the most complete information, with or without prior structural knowledge (Agrawal, 1992). It is the only approach which can, in principle, give a complete structure without resort to any other method.

1. $^{13}$C-Nuclear Magnetic Resonance

Carbon-13 NMR spectroscopy, now widely used for the structure determination of saponins, is a fast and non-destructive method but requires quite large quantities of sample (mg amounts). Analysis of the spectra allows conclusions to be drawn about positions of attachment of the glycosidic chains to the aglycone; the sequence, nature and number of monosaccharides; configuration and conformation of the interglycosidic linkages; the presence of acylglycosides in the chains; the nature of the aglycone; and the structures of attached ester acids.

For assigning chemical shifts, it is helpful to compare observed data with data reported for model and related compounds. As a guide to some of the typical chemical shifts in the $^{13}$C-NMR spectrum of a triterpene saponin, one may use the known shifts of the bayogenin glycoside (Domon and Hostettmann, 1984). Additionally, compilations of assignments of $^{13}$C-NMR signals for oleanane (Patra et al., 1981; Agrawal and Jain, 1992), ursane, lupane (Wenkert et al., 1978; Sholichin et al., 1980), hopane (Wenkert et al., 1978; Wilkins et al., 1987) and lanostane (Parrilli et al., 1979) triterpenes have been made (Nakanishi et al., 1983). The relevant data for dammarane glycosides have been summarized in a review (Tanaka and Kasai, 1984), while $^{13}$C-NMR spectroscopy of saikogenins (Tori et al., 1976a) and of saikosaponins (Tori et al., 1976b) has been described. Ginseng sapogenins and related dammarane triterpenes also have been studied (Asakawa et al., 1977). $^{13}$C-NMR spectroscopy of acacic acid has also been described (Kinjo et al., 1992).

In $^{13}$C-NMR, when hydroxyl groups are derivatized, i.e. glycosylated, methylated (or acetylated), the α- and β-carbons of both the sugar and aglycone moieties undergo characteristic shifts. For example, the α-CH signals are shifted downfield, while the β-C signals are shifted upfield, a shift resulting from the general γ-upfield shift). Thus, glycosylation of an aglycone causes a downfield shift of the α-carbon and an upfield shift (glycosidation shifts) of the adjacent carbon atoms (Tori et al., 1976b; Kasai et al., 1977). In oleananes, glycosidation of the 3β-OH group causes C-3 to shift downfield by c. 8.0-11.5 p.p.m., C-2 and C-4 to shift by +0.9 or −0.9 to −1.9 p.p.m., C-23 to shift upfield by 0.5-5.1 p.p.m. and C-24 to shift by −0.2 to 1.6 p.p.m. Glycosidation of the 28-COOH group causes the carboxylic carbon resonance to move upfield (2.5-5.0 p.p.m.) and the C-17 signal to move downfield (1.0-2.5 p.p.m.) (Agrawal and Jain, 1992). A comparison of the $^{13}$C-NMR data of the aglycone and saponin, therefore, gives the site of the sugar linkage (Seo et al., 1978; Tanaka, 1985).

In a similar fashion, $^{13}$C-NMR will give an indication (in simpler saponins) of interglycosidic linkages by considering displacements of chemical shifts when compared with model compounds (Konishi et al., 1978). Carbon-13 NMR data for methyl β-D-fucopyranoside have been tabulated by Seo et al., (1978), while $^{13}$C-NMR signals for the more complex sugars are listed by Gorin and Mazurek (1975) and Dorman and Roberts (1970). Apiose gives characteristic $^{13}$C-NMR signals and these have been documented (Sakuma and Shoji, 1982; Adinolfi et al., 1987; Reznicek et al., 1990).

2. $^{1}$H-Nuclear Magnetic Resonance

Although $^{13}$C-NMR spectral analysis and signal assignment has become a particularly useful procedure in the structure determination of saponins, the complete assignment of their $^{1}$H-NMR spectra has only seldom been reported. The $^{1}$H-NMR spectra have characteristically proved complex and tedious to analyze. The vast majority of proton resonances of the carbohydrate moiety appear in a very small spectral width of 3.0-4.2 p.p.m., with subsequent problems of overlapping. These derive from the bulk of non-anomeric sugar methine and methylene protons which have very similar chemical shifts in different monosaccharide residues.

However, the methyl peaks of triterpenes are readily discernible and most proton resonance positions in oleanene, ursene and related skeletons have been assigned since the 1960s (Kojima and Ogura, 1989) by a variety of techniques. For example, the complete $^{1}$H- and $^{13}$C-NMR spectral assignments of soyasapogenol B (33) and the configuration of the C-4 hydroxymethyl substituent have been established by a combination of $^{13}$C-DEPT, $^{13}$C-APT, 2-D correlation spectroscopy (COSY) ($^{1}$H-$^{13}$C-COSY, $^{1}$H-$^{1}$H COSY) and $^{1}$H-$^{1}$H ROESY (2-D nuclear Overhauser enhancement (NOE) in a rotating frame) techniques (Baxter et al., 1990). The assignments of quaternary carbon resonances in this sapogenin have been confirmed by $^{1}$H-detected heteronuclear multiple-bond (HMBC) and one-bond (HMQC) spectroscopy (Massiot et al., 1991b). A full interpretation of the $^{1}$H-NMR spectra of diosgenin and solasodine has also been achieved (Puri et al., 1993).

Some useful data can be obtained from $^{1}$H-NMR spectra for the anomeric configurations and linkages of the sugar chain. For example, the coupling constant of the C-1 proton of α-linked glucose units is approximately 3 Hz, while β-linked units have a coupling constant of 6-7 Hz. More details on the coupling constants of anomeric sugar protons can be found elsewhere (Lemieux et al., 1958; Capon and Thacker, 1964; Kizu and Tomimori, 1982).

When difficulties arise in determining configurations of hydroxyl groups at C-2, C-3 and C-23, C-24 of oleanene and ursene triterpenes, analysis of the $^{1}$H-NMR signal peaks of the protons on oxygen-bearing carbon atoms gives valuable information (Kojima and Ogura, 1989).

(ii) 1-D and 2-D NMR Techniques

In practice, certain $^1$H and $^{13}$C NMR spectra can be identified and assigned on the basis of shift arguments, but for interpreting the results of NMR studies in a rigorous manner, an NMR spectrum should be assigned unambiguously, which means establishing which peaks are associated with which carbon and/or hydrogen in the structure. This information, in most cases, cannot be obtained from one-dimensional $^1$H and $^{13}$C NMR spectral data, but can better be determined with the aid of two-dimensional studies. These studies simplify spectral analysis by spreading out information into two frequency domains and by revealing interactions between nuclei. Despite the fact that the mechanisms on which the various pulse sequences are established may be intricate, the interpretation of two-dimensional NMR spectra is usually straightforward. A large number of different two-dimensional NMR studies have been devised to solve chemical structures. Examples of such techniques, as well as other NMR techniques specifically contemplated by the inventors for use in the chemical elucidation of the triterpene saponins of the invention, are described below, and in Table 3.

1. HMBC, HMQC

The use of HMQC and HMBC $^{13}$C multiple-quantum coherence spectra is valuable not only for aglycone assignments, but also for sugar sequence details. The use of HMBC and HMQC is analogous to $^{13}$C-$^1$H heteronuclear correlated spectroscopy (HETCOR), but instead of observing $^{13}$C, the more abundant $^1$H is detected. For example, in the case of bellissaponins from *Bellis perennis* (Asteraceae), it was possible to assign all the chemical shifts in the $^1$H-NMR spectrum by considering $^{13}$C-NMR data in conjunction with 2-D $^1$H-detected HMQC and HMBC spectra. Cross peaks corresponding to two and three bond couplings were observed for nearly all possible correlations in the molecule. Similarly, long-range $^1$H-$^{13}$C correlations in HMQC and HMBC spectra may be used for the determination of the sequence and positions of attachment of sugar moieties (Schopke et al., 1991).

2. 2-D-NOESY

This technique has been applied, for example, in the determination of the sugar sequence of cyclamiretin A glycosides (ardisiacrispins A and B) (Jansakul et al., 1987) and the monosaccharide sequence of saxifragifolin A from *Androsace saxifragifolia* (Primulaceae) (Waltho et al., 1986). The location of rhamnosyl and glucosyl linkages on the arabinose moiety of kalopanax saponin C were confirmed by NOESY after sugar sequence analysis of the permethylated saponin. Cross peaks were observed between H-1 of a rhamnosyl moiety and H-2 of an arabinosyl moiety, as well as between H-1 of the glucosyl moiety and H-3 of the arabinosyl moiety (Shao et al., 1989b). The structures of the sugar moieties of furostanol saponins from *Balanites aegyptiaca* (Balanitaceae) have been elucidated by means of 2-D NOESY on a 400 MHz NMR instrument (Kamel et al., 1991).

The concerted use of 2-D NMR techniques led to complete $^{13}$C and $^1$H assignments for the oligosaccharide segment of the sarsasapogenin glycoside 3-O-[{α-L-rhamnopyranosyl (1→4)}{β-D-glucopyranosyl(1→2)}-β-D-glucopyranosyl]-(25S)-5β-spirostan-3β-ol. A combination of DEPT, HETCOR, long-range HETCOR, different homonuclear techniques, NOESY and INEPT were applied to the structure elucidation in order to resolve problems caused by overcrowding of the proton spectrum (Pant et al., 1988d).

The identification and sequencing of sugars in the pentasaccharide saponin 3-O-[β-D-xylopyranosyl(1→3)-α-L-arabinopyranosyl](1→4)-β-D-glucopyranosyl(1→3)-α-L-rhamnopyranosyl(1→2)-α-L-arabinopy-ranosyl]-hederagenin from *Blighia welwitschii* (Sapindaceae) was possible by NMR techniques alone, using a 500 MHz instrument. The saponin was first acetylated, and subsequent analysis of the DQF-COSY, NOESY and ROESY spectra allowed assignment of structure. Information obtained from NOE data was most helpful for establishing the sugar sequence (Penders et al., 1989).

A saponin containing ten sugar residues from *Solidago gigantea* (Asteraceae) was identified by NMR, based on multi-step RCT studies. This involved COSY, heteronuclear COSY, COSY-type H-H-C coherence transfer and 2-D NOESY studies. Extensive degradation studies were thus avoided and structure determination was possible with 30 mg of the product (Reznicek et al., 1989a; 1989b). Similar techniques were employed for the structure determination of another four glycosides, giganteasaponins 1-4 (bidesmosides of bayogenin containing nine or ten sugar units), from the same plant (Reznicek et al., 1990a).

A combination of 2-D COSY, HMBC and ROESY NMR studies was sufficient to give the sequence and linkage positions of the hexasaccharide in mimonoside A, an oleanolic acid saponin from *Mimosa tenuiflora* (Leguminosae) (Jiang et al., 1991).

The 2-D NMR of peracetylated and underivatized chrysantellin A has allowed the assignment of protons and the sequencing of sugars. The esterified xylose moiety was shown to exist in the β-form and have a $^1C_4$ conformation. Among the techniques employed were HMQC, HMBC and ROESY (or, more precisely, CAMELSPIN (cross-relaxation appropriate for minimolecules emulated by locked spins)) on the peracetylated derivative and HOHAHA, TOCSY on the native saponin. The ROSEY study was particularly useful for determining the sugar sequence (Massiot et al., 1991a).

The sequences of sugar and interglycosidic linkages of triterpene glycosides from marine organisms have been established from $NT_1$ data and NOESY studies (Miyamoto et al., 1990) but this methodology is limited by the complexity of the $^1$H-NMR spectra in the 3-5 p.p.m. region, which usually precludes the measurement of NOE for a large number of protons. However, a combination of COSY, NOESY and direct and XHCORR NMR spectroscopy has allowed complete signal assignment and structural analysis of pentasaccharide triterpene saponins from the sea cucumber *Holothuria forskalii* (Rodriguez et al., 1991).

In the structure determination of santiagoside, an asterosaponin from the Antarctic starfish *Neosmilaster georgianus*, the techniques of COSY, TOCSY, HMQC and ROESY NMR spectroscopy were extensively applied, with ROESY studies being used to resolve the exact sequence of sugars, their points of attachment and the stereochemistry (Vazquez et al., 1992).

3. COSY

There are two fundamental types of 2-D NMR spectroscopy: J-resolved spectroscopy in which one frequency axis contains spin coupling (J) and the other chemical shift information, and correlated spectroscopy in which both frequency axes contain chemical shift (δ) information (Agrawal, 1992). One of the major benefits of 2-D analysis is that it provides a method of overcoming the problem of spectral crowding. In high-field $^1$H-COSY this is especially true of the 2.5-4.0 p.p.m. region, thus simplifying the assignment of saccharide protons. Under favorable conditions, all the protons present in a given sugar residue can be identified.

Several general conclusions may be drawn from COSY spectra. For example, substitution positions of monosaccharide units can be determined by the presence or absence of a corresponding hydroxyl proton; ring sizes of the monosaccharides can be determined directly; and the nature of the cross-peaks reveals the multiplicity of overlapping peaks providing an estimate of coupling constants.

In certain cases, structure elucidation of a saponin, together with its sugar sequence, has been achieved by $^1$H-NMR 1-D and 2-D spectroscopy alone (Massiot et al, 1986; 1988b). The saponin is first peracetylated and if the field strength is sufficient (>300 MHz), the sugar proton resonances split into two zones: one between 4.75 and 5.40 p.p.m. assigned to CHOAc and the other between 3.0 and 4.3 p.p.m. assigned to $CH_2OAc$, CHOR and $CH_2OR$. Anomeric protons are located between these two zones in the case of ether linkages or at a higher frequency than 5.5 p.p.m. for ester linkages.

Peracetylation also gives derivatives which are soluble in chloroform, benzene or acetone. In the equivalent perdeuterated solvents, the mobility of the molecules is such that signals are observed more clearly and coupling constants can be measured with high accuracy. For the acetylated alfalfa root saponin, COSY and long-range COSY studies were sufficient to identify the structure as Ara-$^2$Glc-$^2$Ara-$^3$hederagenin$^{28}$-Glc (Massiot et al., 1986).

The structures of further peracetylated saponins from the leaves of alfalfa, *Medicago sativa* (Leguminosae) and from *Tridesmostemon claessenssi* (Sapotaceae) have been elucidated by similar techniques to those outlined above. Confirmation of assignments and sugar sequences was obtained from HMQC (for $^1$J couplings) and HMBC (for $^2$J and $^3$J couplings) and homonuclear Hartmann-Hahn (HOHAHA) triple relayed COSY and ROESY studies (Massiot et al., 1990; 1991b). The ester sugar chains of the saponins from *T. claessenssi* contain a β-D-xylose moiety in the unusual $^1C_4$ configuration (all the substituents are axial). At 600 MHz, the $^1$H-NMR spectrum may be sufficiently well resolved to allow assignment of all $^1$H chemical shifts without peracetylation (Schöpke et al., 1991).

4. Long-Range COSY

This technique has been employed for the assignment of sugar protons in the steroid saponins from *Allium vineale* (Liliaceae) (Chen and Snyder, 1987; 1989). Long-range $^1$H-$^{13}$C COSY has also been used for aglycone structure determination in a cycloastragenol saponin (Wang et al., 1989b) and for the location of a $^4$J inter-sugar coupling between the anomeric proton of the inner glucose and H-2 of the inner arabinose of the *Medicago sativa* saponin described above (Massiot et al., 1986).

5. Double Quantum Filtered, Phase-Sensitive COSY (DQF-COSY, DQ-COSY)

This technique was applied to the assignment of sugar protons in *Allium* steroid saponins (Chen and Snyder, 1987; 1989) and to the assignments of $^1$H chemical shifts in the 16α-hydroxyproto-bassic acid glycosides from *Crossopteryx febrifuga* (Rubiaceae) roots (Gariboldi et al., 1990). The same technique was used to provide a complete assignment of saccharide protons in the acetylated hederagenin derivative from *Sapindus rarak* (Sapindaceae) fruits (Hamburger et al., 1992). Interglycosidic linkages were established by NOE difference spectroscopy (Hamburger et al., 1992).

6. HOHAHA

The proton coupling networks of aglycones of gypsogenin and quillaic acid glycosides have been completely elucidated by HOHAHA studies. These are similar to COSY studies (and related to total correlation spectroscopy—TOCSY) except that the observed correlation cross peaks are in phase, thereby preventing accidental nulling of overlapping peaks. For the elucidation of carbohydrate chains, vicinal coupling constants extracted from HOHAHA studies allows the determination of the relative stereochemistry of each asymmetric center, thus enabling identification of the monosaccharides. Heteronuclear H-C relay studies may be used for assignment of $^{13}$C resonances in the saccharide moieties and the sugar linkages determined from HMBC spectra (Frechet et al., 1991).

7. FLOCK, COLOC and NOE

Long-range heteronuclear correlation spectroscopy incorporating bilinear rotation decoupling pulses (FLOCK) has been used for the observation of $^1$H-$^{13}$C long distance couplings in alatoside A from *Sesamum alatum* (Pedaliaceae). Thus, interactions between the proton at C-18 and the carbon atoms C-13, C-17 and C-28 were observed. In conjunction with long-range hetero-nuclear $^{13}$C-$^1$H correlation (XH-CORR), much information was gathered about the structure of the novel seco-ursene aglycone (Potterat et al., 1992).

An example of $^{13}$C-$^1$H 2-D correlation spectroscopy (COLOC) optimized for long-range couplings ($^2J_{CH}$ and $^3J_{CH}$) is to be found in the structure elucidation of saponins from *Crossopteryx febrifuga* (Rubiaceae) (Gariboldi et al., 1990).

NOE has found extensive use in the structure determination of saponins, for example, in the assignment of saccharide protons and sugar sequence of luperoside I (Okabe et al., 1989) and camellidins I and II (Nishino et al., 1986). A NOE between the H-2 of arabinose and the anomeric proton of rhamnose helped to confirm the Rha-$^2$Ara-disaccharide linkage in ziziphin (Yoshikawa et al., 1991b). The method has wide applications since connectivities are often observed between the anomeric proton and the aglycone proton at the linkage position. Negative NOE have been observed between the proton at the C-3 position and the anomeric proton of the 3-O-glycoside residue in cycloastragenol and other saponins (Wang et al., 1989b).

TABLE 3

Selected NMR Approaches for Use in the Structure Establishment of Triterpene Saponins

| NMR Study (Acronyms) | Comments |
| --- | --- |
| Attached proton test (APT), Distortionless enhancement by polarization transfer (DEPT), Insensitive nuclei enhancement by polarization transfer (INEPT) | Discriminates among carbon types; Spectral editing |
| Incredible natural abundance double-quantum transfer study (INADEQUATE) | $^{13}$C-$^{13}$C connectivity, establishment of molecular skeleton |
| $^1$H, $^1$H-COSY | Homonuclear shift correlation |
| a) normal | Elucidation of direct couplings |
| b) with delays | Detection of small couplings |

TABLE 3-continued

Selected NMR Approaches for Use in the Structure Establishment of Triterpene Saponins

| NMR Study (Acronyms) | Comments |
| --- | --- |
| c) double-quantum filtered-(DQF) - COSY | Determination of vicinal and geminal coupling constants |
| d) Exclusive COSY (E. COSY) | Accurate determination of J |
| e) Geminal COSY (Gem - COSY) | Identification of geminal spin systems |
| f) Triple-quantum filtered (TQF) - COSY | Detection of three or more mutually coupled spin systems |
| Relayed coherence transfer (RCT), Total correlation (TOCSY), and Hartmann-Hahn study (HOHAHA) | Identification of all protons belonging to a single spin system; Coherence transfer across scalar connectivity (particularly useful in identifying monosaccharide residues) |
| Homonuclear nuclear Overhauser and exchange spectroscopy (NOESY and ROESY) | Identification of protons that are within 5A of one another ($^1$H, $^1$H correlation through space); Stereochemical analysis (orientation of substituents); Intra- and inter-residual connectivities (sequence analysis in sugar chain including sugar - aglycone linkage) |
| 1H{$^{13}$C}SBC (HETCOR and HMQC) | Heteronuclear shift correlation; Assignments of directly bonded $^1$H and $^{13}$C shifts |
| HMQC-TOCSY and HMQC-RELAY | Cross assignments of $^1$H and $^{13}$C shifts |
| 1H{$^{13}$C}MBC (Long-range HETCOR and HMBC) | Assignment of quaternary C; Correlation of a proton resonance with a carbon resonance 2-4 bonds distant; Intra- and inter-residual assignments (inter-glycosidic and sugar-aglycone linkage); Confirmation of molecular structure |

(iii) Spectroscopic and Other Techniques for Structure Elucidation

The structure elucidation of saponins and the corresponding aglycones relies not only on chemical methods but also on spectroscopic and related techniques, e.g., IR, UV, NMR, MS, optical rotary dispersion (ORD), circular dichroism (CD), and X-ray analysis. Modern advances in some of these techniques, most notably in NMR spectroscopy and MS, have facilitated the task of analyzing saponins and their corresponding fragments from cleavage reactions, such that the information can be collated and the relevant structures determined. Furthermore, NMR spectroscopy is a non-destructive technique and both NMR and MS allow examination of the intact saponin.

An integrated approach for solving saponin structures is necessary, with the different spectroscopic techniques each providing a certain contribution to the ensemble of data.

1. Mass Spectrometry (MS)

The choice of ionization method in MS depends on the polarity, liability and molecular weight of the compound to be analyzed. It is principally the so-called 'soft' ionization techniques such as FAB and desorption/chemical ionization (D/CI) which are employed to obtain molecular weight and sugar sequence information for naturally occurring glycosides (Wolfender et al., 1992). These permit the analysis of glycosides without derivatization. In certain cases, fragmentations of aglycones are observed, but electron impact mass spectra (EI-MS) are more useful for this purpose.

2. Fast Atom Bombardment MS (FAB-MS)

In FAB studies, an accelerated beam of atoms (or ions) is fired from a gun towards a target which has been preloaded with a viscous liquid (the 'matrix'-usually glycerol or 1-thioglycerol) containing the sample to be analyzed (Barber et al., 1981; 1982). When the atom beam collides with the matrix, kinetic energy is transferred to the surface molecules, a large number of which are sputtered out of the liquid into the high vacuum of the ion source. Ionization of many of these molecules occurs during the sputtering, giving both positive and negative ions. Either can be recorded by an appropriate choice of instrumental parameters but negative ions have proved more useful, on the whole, for saponin work.

3. Secondary Ion Mass Spectrometry (SIMS)

This is another particle-induced desorption technique, in which keV ions impinging on the surface of a thin film of biomolecule induce the same desorption ionization as in PD-MS (Benninghoven and Sichtermann, 1978). The utility of this method in the structural investigation of three new bidesmosides, acetyl-soyasaponins $A_1$, $A_2$ and $A_3$, isolated from American soybean seeds (*Glycine max*, Leguminosae) has been demonstrated. The significant fragment ion peaks provided information regarding the mode of acetylation in the monosaccharide units, as well as the sequence of these units (Kitagawa et al., 1988).

4. Laser Desorption (LD)

In LD it has been demonstrated that excitation by short duration laser pulses (<10 ns) produces patterns of desorbed molecular ions similar to PD and SIMS. Laser desorption/Fourier transform mass spectrometry (LD/FTMS), a technique which also is suitable for the analysis of complex glycosides, produces spectra which are different from and complementary to FAB-MS.

5. Field Desorption MS (FD-MS)

This technique is practical for determining the molecular weights of saponins, together with the number, nature and sequence of sugar residues (Komori et al., 1985). However, the experimental complexity of FD-MS and the fact that FAB-MS produces longer-lasting spectra has meant that the FD-MS approach has decreased in popularity recently. FD mass spectra have the added drawback that they are complicated by the presence of cationized fragments, making interpretations difficult. All the same, FD-MS has been very successfully applied to the structure elucidation of saponins (Hostettmann, 1980).

(iv) Liquid Chromatography-Mass Spectrometry (LC-MS)

Several types of efficient interfaces for direct and indirect introduction of HPLC column effluent for mass spectrometry analysis have now been developed. For example, qualitative analysis of crude saponin fractions has been carried out by combining semi-micro HPLC with a flit-fast atom bombardment (FRIT-FAB) interface (Hattori et al., 1988). For this application, an $NH_2$ column, (e.g., μS-Finepak SIL $NH_2$, Jasco; 25 cm×1.5 mm internal diameter (I.D.)) is used, rather than an octadecyl silica column, with a 1:20 split ratio of effluent (100 μ/min→5 μl/min). Elution with a linear gradient of acetonitrile and water containing 1% glycerol will typically allow a better peak sharpness than that obtained by isocratic elution. Negative FAB mass spectra have been recorded for saponins with a molecular weight of up to 1235. Pseudomolecular [M−1]− ions as well as fragment ions ascribed to the cleavage of sugar moieties were observed with this technique (Hattori et al., 1988).

A FRIT-FAB LC-MS system has also been described for the separation of a mixture of the isomeric saponins rosamultin and arjunetin (both molecular weight 650) from *Rosa rugosa* (Rosaceae). Rosamultin (an ursane glycoside) and arjunetin (an oleanane glycoside) both have a single glucose residue at C-28 and were analyzed in both the negative and positive FAB modes with xenon as neutral gas. HPLC was performed on an octadecylsilica column (250×1.5 mm) with acetonitrile-water (7:3, containing 0.5% glycerol) as solvent at a flow rate of 1 ml/min. Pseudomolecular [M+1]− and [M+1]+ ions were observed, together with strong peaks caused by the parent aglycones in the negative FAB mass spectra (Young et al, 1988).

It also is possible to detect saponins by dynamic secondary ion mass spectroscopy (SIMS), a technique similar to dynamic FAB interfacing in which eluent is passed directly into the source. Thus, HPLC combined with UV (206 nm) and SIMS detection has been employed to analyze a mixture of one mono- and two bidesmosidic triterpene glycosides (Marston et al., 1991).

A disadvantage with interfaces of the FRIT-FAB and CF-FAB type is the low flow rate required (around 1-5 μl/min). After HPLC separation, effluent splitting is necessary. The thermospray (TSP) interface (Blackley and Vestal, 1983), however, is characterized by its simplicity and its ability to handle flow rates of 1-2 ml/min. This makes the technique more attractive for problems involving the analysis of plant constituents. At the heart of the TSP technique is a soft ionization of molecules, similar to chemical ionization MS. This allows analysis of non-volatile and thermally labile mono-, di- and even triglycosides. Information is provided about the molecular weight of the saponin and the nature and sequence of the sugar chains. TSP LC-MS has been used for the analysis of molluscicidal saponins in a methanol extract of *Tetrapleura tetraptera* (Leguminosae) fruits (Maillard and Hostettmann, 1993). With post-column addition of 0.5 M ammonium acetate (0.2 ml/min) to provide the volatile buffer for ion evaporation ionization, the TSP LC-MS total ion current (mass range 450 to 1000 a.m.u) corresponded well with HPLC-UV analysis at 206 nm. Ion traces at m/z 660, 676, 880 and 822 gave signals representing the pseudomolecular [M+H]+ ions of the major saponins. The TSP mass spectrum acquired for each saponin in the extract displayed a major peak for the pseudomolecular [M+H]+ ion. Fragmentations of the sugar moieties were observed for the principal molluscicidal saponin aridanin, where loss of a N-acetylglucosyl moiety gave rise to an [A+H]+ peak for the aglycone (Maillard and Hostettmann, 1993).

LC-MS, as applied to the investigation of saponins, has great potential utility as GC-MS is of minimal practical use and in HPLC alone the identities of peaks can only be confirmed by their retention times. Not only is LC-MS amenable to the analysis of triterpene glycosides in plant extracts but it will also be of value, via MS-MS, for the structure determination of individual saponins in the extracts.

(v) Infrared Spectroscopy (IR)

Apart from the usual applications of IR, there are one or two features which are of particular relevance to the structure elucidation of saponins. IR is useful for the characterization of steroid sapogenins because several strong bands between 1350 and 875 $cm^{-1}$ are diagnostic for the spiroketal side chain (Jones et al., 1953). Four bands, 980 (A band), 920 (B band), 900 (C band) and 860 $cm^{-1}$ (D band) have been assigned as characteristic of the E and F rings. With 25R-sapogenins the B band has a stronger absorbance than the C band, while in the 25R-series this relationship is reversed. In sapogenins having oxygen substituents in the E and F rings or at position 27, the four bands are considerably changed (Takeda, 1972).

The presence of ionized carboxyl groups in saponins can be ascertained by bands in the IR spectrum at 1610 and 1390 $cm^{-1}$ (Numata et al., 1987). This information is useful during the isolation procedure, when it is important to know whether carboxyl groups in the molecule are ionized.

(vi) X-Ray Crystallography

X-ray crystallography has been used to elucidate the molecular geometry of the trisaccharide triterpene asiaticoside from *Centella asiatica* (Umbelliferae). Crystallization was from dioxane (Mahato et al., 1987). X-ray diffraction analysis was also successful for confirmation of the structure of mollic acid 3-β-D-glucoside (Pegel and Rogers, 1985).

X-ray crystallography is especially useful in solving structural problems of aglycones. Useful information for the determination of the structure of the aglycone of alatoside A from *Sesamum alatum* (Pedaliaceae) was obtained by an X-ray diffraction analysis of the crystalline triacetate of the artifact produced after acid hydrolysis (Potterat et al., 1992). An X-ray crystallographic study of medicagenic acid the parent aglycone of medicagenic acid 3-O-glucoside from the tubers of *Dolichos kilimandscharicus* (Leguminosae), showed the molecule to have cis-fused D and E rings. Ring C had a slightly distorted sofa conformation, while rings A, B, D and E had chair conformations (Stoeckti-Evans, 1989).

(vii) Cleavage Reactions

Triterpene saponins are glycosides in which the hemiacetal hydroxyl groups of saccharides in their cyclic pyranose or furanose forms build acetals with a triterpene or steroid residue. The ether linkage between the hemiacetal hydroxyl and the triterpene or steroid is known as a glycosidic linkage. The monosaccharide constituents of the oligosaccharides also are bound by ether linkages (interglycosidic bonds).

On complete hydrolysis of a glycoside, the glycoside linkage is cleaved to liberate the component monosaccharides and the non-carbohydrate moiety (the aglycone or genin).

The non-carbohydrate portion from the hydrolysis of saponins is termed a sapogenol or sapogenin. All known saponins are O-glycosides, with ether or ester linkages.

Numerous chemical reactions and methods have been employed for breaking down saponins into smaller units for more ready analysis (see, for example, Kitagawa, 1981). Such methods will find particular use in structural determinations of triterpene saponins.

1. Acidic Hydrolysis

Acidic hydrolysis maybe carried out by refluxing the saponin in acid for a fixed length of time, for example, 4 h in 2-4 M hydrochloric acid. The aqueous solution remaining after hydrolysis is extracted with diethyl ether, chloroform or ethyl acetate to obtain the aglycone. Extraction of the sugars from the aqueous layer is performed with pyridine, after neutralizing the solution (with alkali or basic ion exchange resin) (Tschesche and Forstmann, 1957; Sandberg and Michel, 1962) and evaporation to dryness. The saponins are completely cleaved into their constituents by this method so information is obtained as to the identity of the aglycone and the number and nature of monosaccharides present. If a prosapogenin (obtained after cleavage of an ester linkage by basic hydrolysis) is acid hydrolyzed, the nature of the sugar chains which are ether-linked to the aglycone can be established. An aqueous reaction medium can be replaced by alcohol or dioxane.

In addition to hydrochloric acid, sulfuric acid also maybe employed for the hydrolysis of saponins. With sulfuric acid there is less chance of degradation or rearrangement of the molecule but cleavage of ether linkages is not as efficient. A convenient method of obtaining gypsogenic acid from *Dianthus* saponins, for example, involved hydrolysis with 1 M sulfuric acid in dioxane (Oshima et al., 1984). A comparative study of hydrolytic conditions with hydrochloric acid and sulfuric acid in water and water-ethanol has shown that the best recoveries of saccharides are achieved by heating the saponin for 2 h with 5% sulfuric acid/water in a sealed vacuum ampoule (Kikuchi et al., 1987). Somewhat milder hydrolyses can be achieved with trifluoroacetic acid, for example, by refluxing for 3 h in 1 M trifluoroacetic acid.

An alternative to the hydrolysis of saponins in solution is to hydrolyze them directly on a TLC plate by treatment with hydrochloric acid vapors. Once the acid has been evaporated, normal elution with the TLC solvent is performed in order to identify the monosaccharides present (Kartnig and Wegschaider, 1971; He, 1987). By this means, the terminal sugars xylose and galactose were identified after partial hydrolysis of agaveside B. The TLC plate was developed with the solvent chloroform-methanol-water (8:5:1) and the detection was by means of aniline-diphenylamine-$H_3PO_4$-methanol (1:1:5:48) (Uniyal et al., 1990).

2. Basic Hydrolysis

Cleavage of O-acylglycosidic sugar chains is achieved under basic hydrolysis conditions, typically by refluxing with 0.5 M potassium hydroxide. Alternatively, 1-20% ethanolic or methanolic solutions of potassium hydroxide may be used but there is a risk of methylation, especially of the carboxyl group of triterpene acids. Ion exchangers such as Dowex 1 provide mildly basic hydrolysis conditions (Bukharov and Karlin, 1970). Another method is to use lithium iodide in collidine (Kochetkov et al., 1964).

By carefully controlling the reaction conditions, it is possible to selectively cleave different ester moieties. For example, hydrolysis of kizuta saponin $K_{11}$ by refluxing in 0.5 M potassium hydroxide for 30 min removed the sugar at C-28 of the bidesmoside. However, stirring the saponin for 20 h in 0.1 M potassium hydroxide at room temperature selectively removed the acetate group on the C-28 ester glycosidic chain (Kizu et al., 1985b).

3. Partial Hydrolysis

In certain instances, when saponins have highly branched or long sugar chains, a procedure involving partial hydrolysis is necessary in order to obtain fragments more accessible to structure elucidation. This can be achieved with acid or, indeed, with enzymes. The oligosaccharide and/or the remaining saponin portions are isolated and then characterized.

For example, saponin from *Phytolacca dodecandra* (Phytolaccaceae) was hydrolyzed by 0.1 M hydrochloric acid for 45 min, to give a mixture of three products. These compounds were separated by RP-LPLC and their sugar sequences determined by MS, $^{13}$C-NMR and GC-MS of alditol acetates. Putting all this information together enabled the assignment of a chemical formula for the compound, an oleanolic acid derivative (Dorsaz and Hostettmann, 1986).

Hydrolysis in dioxane gives milder conditions and partial hydrolysis is possible. In this example, the saponin was refluxed for 6 h in dioxane-0.1 M hydrochloric acid (1:3) (Ikram et al., 1981). Another method for partially hydrolyzing saponins is to treat a solution of the triterpene glycoside in alcohol with an alkali metal (sodium or potassium) and then add a trace of water (Ogihara and Nose, 1986).

4. Hydrothermolysis

Hydrothermolysis of triterpene glycosides leads to the formation of the corresponding aglycones and thus can aid structure determination. The method involves heating the glycoside with water or water-dioxane at 100° C. to 140° C. for a period of 10 to 140 h, depending on the sample. For example, hydrothermolysis of the triterpene 3,28-O-bisglycosides gives the corresponding 3-O-glycosides (Kim et al., 1992).

5. Enzymatic Hydrolysis

A very efficient and mild method for the cleavage of sugar residues from saponins without artifact formation is enzymatic hydrolysis. Although the relevant hydrolases for all the sugars are not commercially available, cleavages of β-glucose residues by β-glucosidase are perfectly straightforward. A supplementary benefit of cleavage by specific enzymes is that the anomeric configuration of the sugar moiety is automatically proved. Certain enzyme preparations which are particularly contemplated for use in hydrolysis of triterpene glycosides are β-galactosidase hydrolyses, cellulase, crude hesperidinase, pectinase, and naringinase.

A systematic study involving crude preparations of hesperidinase, naringinase, pectinase, cellulase, amylase and emulsin has shown that hesperidinase, naringinase and pectinase were the most effective in hydrolyzing ginsenosides (Kohda and Tanaka, 1975).

(viii) Analysis of Aglycones After Hydrolysis

Once hydrolysis is complete, aglycones can be separated from the hydrolysate either by simple filtration or by a water-organic solvent partition and analyzed against known triterpenes. The most common method is by TLC, using a solvent such as diisopropyl ether-acetone (75:30). Spray reagents are frequently those employed for the analysis of saponins (see Table 2).

Gas-liquid chromatography requires derivatization of triterpenes. For example, methyl esters of oleanolic and ursolic acids have been separated by GC on a glass column packed with 30% OV-17 or SE-30 (Fokina, 1979). Triterpenes can be determined by GC after derivatization with N,O-bis(trimethylsilyl)acetamide and chlorotrimethylsilane, as is the case for soyasapogenols A-E and medicagenic acid in alfalfa (Jurzysta and Jurzysta, 1978).

The technique of GC-MS also is valuable for the characterization of sapogenins. The trimethylsilyl derivatives are normally prepared and then analyzed in the spectrometer. An example is the application to the investigation of oleanane- and ursane-type triterpenes. Nine silylated triterpenes were separated by GC on OV-101 packing and their mass spectral patterns were investigated; those containing a 12-en double bond underwent a characteristic retro-Diels-Alder reaction (Burnouf-Radosevich et al., 1985). This technique has also been used for the determination of triterpenes from licorice (Bombardelli et al., 1979).

HPLC analysis does not require derivatization and gives excellent reproducibility and sensitivity for the analysis of triterpenes. Both normal-phase (analysis of quinoa sapogenins; Burnouf-Radosevich and Delfel, 1984) and RP-HPLC (Lin et al., 1981) can be employed, but a disadvantage of RP-HPLC is that the compounds tend to precipitate in the aqueous mobile phases.

(ix) Analysis of Sugars After Hydrolysis

Analysis of the monosaccharides may be carried out by TLC on, for example, silica gel plates with solvents such as ethyl acetate methanol-water acetic acid (65:25:15:20) and n-butanol ethyl acetate i-propanol acetic acid water (35:100: 60:35:30) (Shiraiwa et al., 1991). Detection is typically with p-anisidine phthalate, naphthoresorcin, thymolsulfuric acid (Kartnig and Wegschaider, 1971) or triphenyltetrazolium chloride (Wallenfels, 1950; Kamel et al., 1991). Alternatively, a quantitative analysis of the monosaccharides is possible by GC or HPLC.

A number of HPLC methods have been reported for analysis of sugars including: analysis on $NH_2$-bonded columns with acetonitrile-water (75:25) (Glombitza and Kurth, 1987); analysis on C-18 columns (acetonitrile-water 4:1) with refractive index detection, for quantitative purposes, integration of the HPLC peaks was compared with standards (Adinolfi et al., 1987); analysis on an Aminex ion exclusion HPX-87H column (BioRad) with 0.005 M sulfuric acid as eluent (0.4 ml/min) (Adinolfi et al., 1990); and analysis of sugar p-bromobenzoates (formed by methanolysis of the saponin with 5% hydrochloric acid-methanol and subsequent p-bromobenzoylation of the methyl sugars) by HPLC and identification by comparison with authentic derivatives (Kawai et al., 1988; Sakamoto et al., 1992).

For GC, the persilylated sugars are used (Wulff, 1965) or a GC-MS analysis of alditol acetate derivatives is carried out. GC-Fourier-transformed IR (FTIR) analysis of suitably derivatized monosaccharides is an alternative procedure (Chen and Snyder, 1989).

The most commonly found sugars are D-glucose, D-galactose, L-arabinose, D-xylose, D-fucose, L-rhamnose, D-quinovose, D-glucuronic acid and D-ribose.

IV. Derivatives of the Compounds of the Invention

As described in detail herein, it is contemplated that certain benefits may be achieved from the manipulation of the triterpene glycosides to provide them with novel characteristics, a longer in vivo half-life or other beneficial properties. Such techniques include, but are not limited to, manipulation or modification of the mixtures of triterpene glycosides or an individual triterpene molecule itself, modification or removal of sugars, and conjugation of triterpene compounds to inert carriers, such as various protein or non-protein components, including immunoglobulins and Fc portions. It will be understood that longer half-life is not coextensive with the pharmaceutical compositions for use in "slow release." Slow release formulations are generally designed to give a constant drug level over an extended period. Increasing the half-life of a drug, such as a triterpene glycoside in accordance with the present invention, is intended to result in high plasma levels upon administration, which levels are maintained for a longer time, but which levels generally decay depending on the pharmacokinetics of the compound.

(i) Conjugates of Triterpenes and Linked Molecules

As described above, the triterpene compounds of the invention identified herein may be linked to particular molecules in order to improve the efficacy of the triterpene glycosides in treating patients for any ailment treatable with the compounds of the invention. Illustrative embodiment of such molecules include targeting agents and agents which will increase the in vivo half life of the triterpene compounds. The triterpene compounds may be linked to such secondary molecules in any operative manner that allows each region to perform its intended function without significant impairment of biological activity, for example, the anti-tumor activity of the compounds disclosed herein.

The triterpene compositions of the present invention may be directly linked to a second compound or may be linked via a linking group. By the term "linker group" is intended one or more bifunctional molecules which can be used to covalently couple the triterpene compounds or triterpene mixture to the agent and which do not interfere with the biological activity of the triterpene compounds. The linker group may be attached to any part of the triterpene so long as the point of attachment does not interfere with the biological activity, for example, the anti-tumor activity of the compounds of the invention.

An exemplary embodiment for linking the triterpene compounds of the invention to a second agent is by the preparation of an active ester of the triterpene followed by reaction of the active ester with a nucleophilic functional group on the agent to be linked. The active esters may be prepared, for example, by reaction of a carboxyl group on the triterpene with an alcohol in the presence of a dehydration agent such as dicyclohexylcarbodiimide (DCC), 1-(3-dimethylaminopropyl)-3-ethylcarbodiimide (EDC), and 1-(3-dimethylaminopropyl)-3-ethylcarbodiimide methiodide (EDCI). The use of EDC to form conjugates is disclosed in U.S. Pat. No. 4,526, 714; PCT Appl. Publ. No. WO91/01750, and Arnon et al., 1980, the disclosures of which are specifically incorporated herein by reference in their entirety. The agent to be linked to the triterpene, for example, a tumor-specific antibody, is then mixed with the activated ester in aqueous solution to give the conjugate.

Where a linker group between the triterpene and the agent is desired, the active ester of the triterpene glycoside may be prepared as described above and reacted with a linker group, for example, 2-aminoethanol, an alkylene diamine, an amino acid such as glycine, or a carboxy-protected amino acid such as glycine tert-butyl ester. If the linker contains a protected carboxy group, the protecting group is removed and the active ester of the linker is prepared (as described above). The active ester is then reacted with the second molecule to give the conjugate. Alternatively, the second agent could be derivatized with succinic anhydride to give an agent-succinate conjugate which may be condensed in the presence of EDC or EDCI with a triterpene-linker derivative having a free amino or hydroxyl group on the linker (see, for example, WO91/01750, the disclosure of which is specifically incorporated herein by reference in its entirety).

It also is possible to prepare a triterpene glycoside conjugate comprising a linker with a free amino group and crosslink the free amino group with a heterobifunctional cross linker such as sulfosuccinimidyl 4-(N-maleimidocyclohexane)-1-carboxylate which will react with the free sulfhydryl groups of protein antigens.

The triterpene glycoside also may be coupled to a linker group by reaction of the aldehyde group with an amino linker to form an intermediate imine conjugate, followed by reduction with sodium borohydride or sodium cyanoborohydride. Examples of such linkers include amino alcohols such as 2-aminoethanol and diamino compounds such as ethylenediamine, 1,2-propylenediamine, 1,5-pentanediamine, 1,6-hexanediamine, and the like. The triterpene glycoside may then be coupled to the linker by first forming the succinated derivative with succinic anhydride followed by condensation with the triterpene glycoside-linker conjugate with DCC, EDC or EDCI.

In addition, the triterpene glycoside or aglycone may be oxidized with periodate and the dialdehyde produced therefrom condensed with an amino alcohol or diamino compound listed above. The free hydroxyl or amino group on the linker may then be condensed with the succinate derivative of the antigen in the presence of DCC, EDC or EDCI. Many types of linkers are known in the art and may be used in the creation of triterpene conjugates. A list of exemplary linkers for use with the invention is given below, in Table 4.

TABLE 4

Hetero-Bifunctional Cross-Linkers

| Linker | Reactive Toward | Advantages and Applications | Spacer Arm Length\after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A | the invention or a fragment thereof. This could be accomplished by X-ray crystallography, computer modeling or by a combination of both approaches. An alternative approach, involves the random replacement of functional groups throughout the triterpene molecule, and the resulting affect on function determined.

It also is possible to isolate a triterpene compound specific antibody, selected by a functional assay, and then solve its crystal structure. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have improved biological activity, for example, anti-tumor activity, relative to a starting triterpene compound. By virtue of the chemical isolation procedures and descriptions herein, sufficient amounts of the triterpene compounds of the invention can be produced to perform crystallographic studies. In addition, knowledge of the chemical characteristics of these compounds permits computer employed predictions of structure-function relationships.

(ii) Rational Drug Design

The goal of rational drug design is to produce structural analogs of biologically active compounds. By creating such analogs, it is possible to fashion drugs which are more active or stable than the natural molecules, which have different susceptibility to alteration or which may affect the function of various other molecules. In one approach, one would generate a three-dimensional structure for the triterpene compounds of

V. Treatment of Cancer with the Triterpene Compounds of the Invention

In the development of cancer, mammalian cells go through a series of genetically determined changes that lead to abnormal proliferation. This can occur in steps, generally referred to as (1) initiation: when an external agent or stimulus triggers a genetic change in one or more cells and (2) promotion: involving further genetic and metabolic changes, which can include inflammation. During the "promotion stage," cells begin a metabolic transition to a stage of cellular growth in which apoptosis is blocked.

Cancer cells are characterized by a loss of apoptotic control in addition to a loss of control of the regulatory steps of the cell cycle. Cancer cells (malignant cells) escape normal growth control mechanisms through a series of metabolic changes during the initiation and promotion stages at the onset of malignancy. These changes are a consequence of genetic alterations in the cells. These genetic alterations may include (i) activating mutations and/or increased expression of protooncogenes and/or (ii) inactivating mutations and/or decreased expression of one or more tumor suppressor genes. Most oncogene and tumor suppressor gene products are components of signal transduction pathways that control cell cycle entry or exit, promote differentiation, sense DNA damage and initiate repair mechanisms, and/or regulate cell death programs. Nearly all tumors have mutations in multiple oncogenes and tumor suppressor genes. One can conclude that cells employ multiple parallel mechanisms to regulate cell growth, differentiation, DNA damage control, and apoptosis.

The triterpene compounds of the invention can be administered to a subject in need thereof to treat the subject either prophylactically preventing cancer or therapeutically after the detection of cancer. To inhibit the initiation and promotion of cancer, to kill cancer/malignant cells, to inhibit cell growth, to induce apoptosis, to inhibit metastasis, to decrease tumor size and to otherwise reverse or reduce the malignant phenotype of tumor cells, using the methods and compositions of the present invention, one would generally contact a "target" cell with the triterpene compositions described herein. This may be achieved by contacting a tumor or tumor cell with a single composition or pharmacological formulation that includes the triterpene compounds of the invention, or by contacting a tumor or tumor cell with more than one distinct composition or formulation, at the same time, wherein one composition includes a triterpene of the invention and the other includes a second agent.

Preferred cancer cells for treatment with the instant invention include epithelial cancers such as skin, colon, uterine, ovarian, pancreatic, lung, bladder, breast, renal and prostate tumor cells. Other target cancer cells include cancers of the brain, liver, stomach, esophagus, head and neck, testicles, cervix, lymphatic system, larynx, esophagus, parotid, biliary tract, rectum, uterus, endometrium, kidney, bladder, and thyroid; including squamous cell carcinomas, adenocarcinomas, small cell carcinomas, gliomas, neuroblastomas, and the like. However, this list is for illustrative purposes only, and is not limiting, as potentially any tumor cell could be treated with the triterpene compounds of the instant invention. Assay methods for ascertaining the relative efficacy of the compounds of the invention in treating the above types of tumor cells and other tumor cells are specifically disclosed herein and will be apparent to those of skill in the art in light of the present disclosure.

The compounds of the present invention are preferably administered as a nutraceutical composition or a pharmaceutical composition comprising a pharmaceutically or pharmacologically acceptable diluent or carrier. The nature of the carrier is dependent on the chemical properties of the compound(s) employed, including solubility properties, and/or the mode of administration. For example, if oral administration is desired, a solid carrier may be selected, and for i.v. administration a liquid salt solution carrier may be used.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

a. Nutraceuticals

Nutraceutical compositions are preparations of natural ingredients that are multi-component systems consisting of preferably synergistic natural products and supplements to promote good health. Nutraceutical compounds can be derived from medicinal plants. Information about numerous plants and herbs used to prepare nutraceutical compositions has been compiled and is available in publications including the *German Commission E Monographs, Botanical Safety Handbook*, and *HerbalGram*, a quarterly publication of the American Botanical Council which references numerous clinical trials that have been performed using nutraceuticals.

Information on description and constituents, modern uses, dosage (in a variety of forms), actions, contraindications, side effects, interactions with conventional drugs, mode of administration, duration of application, regulatory status, AHPA botanical safety rating, and comments are available for a number of plants and include among others bilberry, cascara, cat's claw, cayenne, cranberry, devil's claw, dong quai, *echinacea*, evening primrose oil, feverfew, garlic, ginger, *ginkgo*, Asian *ginseng*, Siberian *ginseng*, goldenseal, gotu kola, grape seed, green tea, hawthorn, kava, licorice, milk thistle, saw palmetto, St. John's wort, and valerian.

The actions of these nutraceutical compounds may be fast or/and short-term or may help achieve long-term health objectives. The current invention focuses on phytomedicines derived from *Acacia victoriae*. The invention envisions nutraceutical compositions comprising dried and ground *Acacia victoriae* roots and pods or extracts from these tissues in a pharmacologically acceptable medium as a natural approach for, among other things, the prevention and treatment of cancer. The nutraceutical composition may be used to prevent the initiation and promotion of carcinogenesis and also for the induction of apoptosis in malignant cancer cells. The nutraceutical compositions disclosed herein may also be used as anti-inflammatory, anti-fungicidal, anti-viral, anti-mutagenic, spermicidal or contraceptive, cardiovascular and cholesterol metabolism regulatory agents. The nutraceutical compositions may be contained in a medium such as a buffer, a solvent, a diluent, an inert carrier, an oil, a creme, or an edible material.

The nutraceutical may be orally administered and may be in the form of a tablet or a capsule. Oral intake may be preferred for the treatment of colon cancer and other internal tumors.

Alternatively the nutraceutical may be in the form of an ointment which has extracts of *Acacia victoriae* roots or pods in an oil or cream which can be topically applied to the skin. This form of nutraceutical composition is useful for the preventing the initiation of skin cancers. The use of these nutraceuticals formulations provide a method of inhibiting the initiation and promotion of mammalian epithelial cells to a premalignant or malignant state wherein a therapeutically effective amount of the nutraceutical composition is administered to a given mammalian cell. This is especially useful for epithelial cell cancers such as skin cancer.

b. Pharmaceuticals

Figure 39:
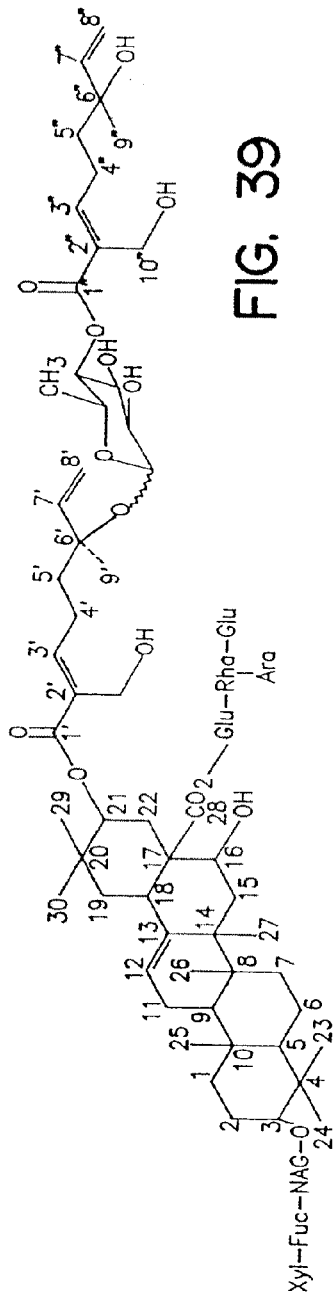
FIG. 39: Structure of triterpene glycoside D1
Figure 40:
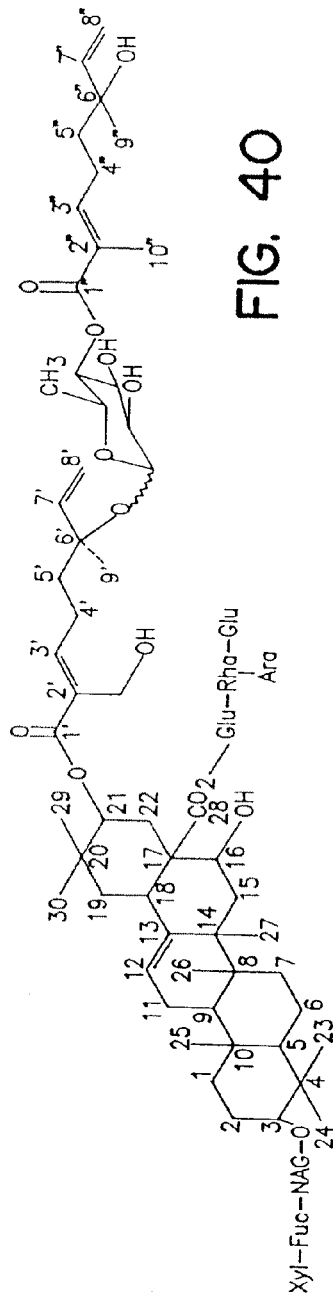
FIG. 40: Structure of triterpene glycoside G1
Figure 41:
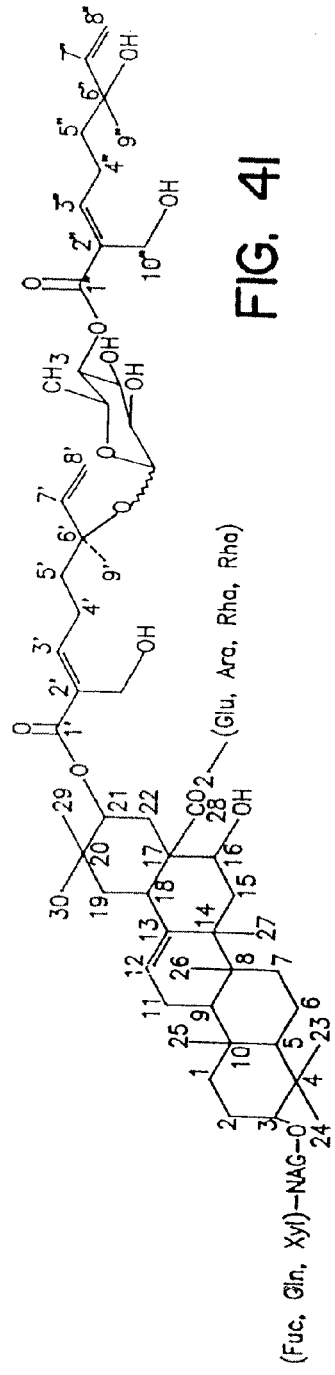
FIG. 41: Structure of triterpene glycoside B1
Figure 43:
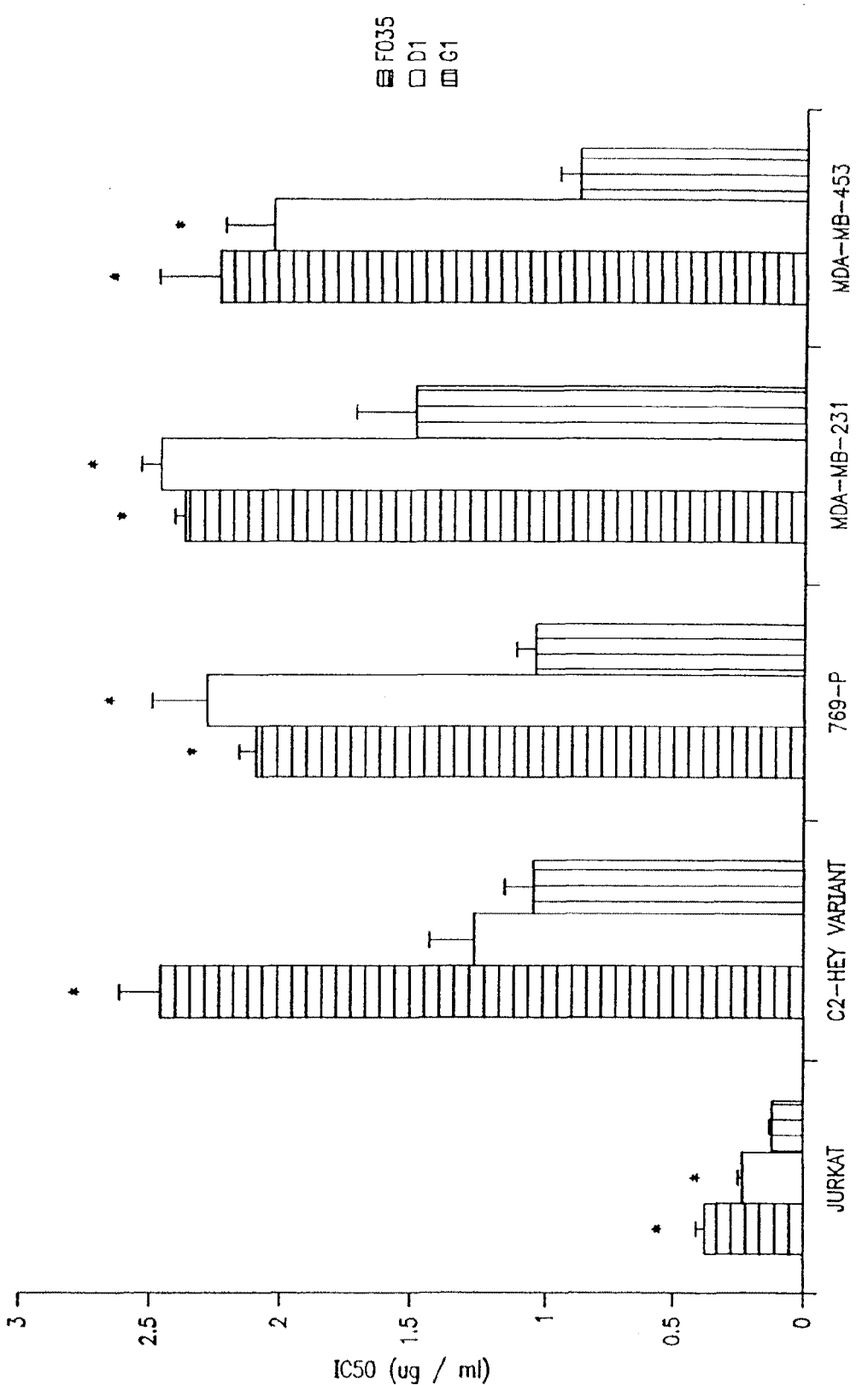
FIG. 43: Cytotoxicity profile of purified triterpene glycosides D1 and G1 on human cancer cell lines: The purified extracts were evaluated for their activity on following human cancer cell lines: Jurkat (T-cell leukemia), C-2 Hey Variant (ovarian), 769-P (renal), MDA-MB-231, MDA-MB-453 (breast). The results are shown as mean+SEM.
Figure 44A:
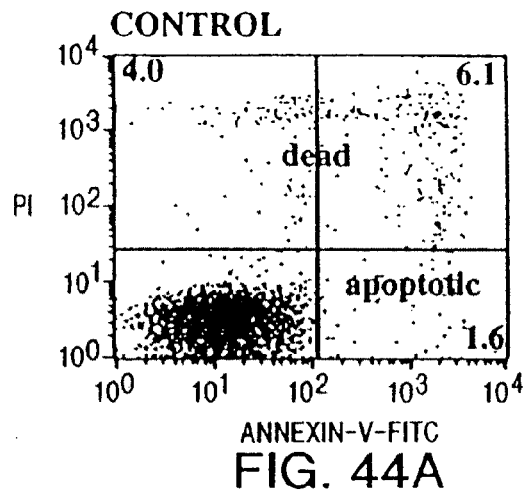
FIG. 44: Effect of purified compounds D1 and G1 and a mixture of triterpene glycosides (F035) on apoptosis: Apoptosis was measured using Annexin V binding assay in which the cells were stained with annexin V-FITC and for DNA content with propidium iodide (PI) and analyzed using flow cytometry. Cells were incubated for 16 hours with 0.5-1.0 µg/ml of extracts. After 16 hours of treatment, three populations of cells were observed. Cells that had died or were in late stage of apoptosis (Annexin V-FITC and PI positive), cell undergoing apoptosis (Annexin V-FITC positive and PI negative), and the cells that were viable and not undergoing apoptosis (Annexin V-FITC and PI negative; lower left quadrant).
Figure 44B:
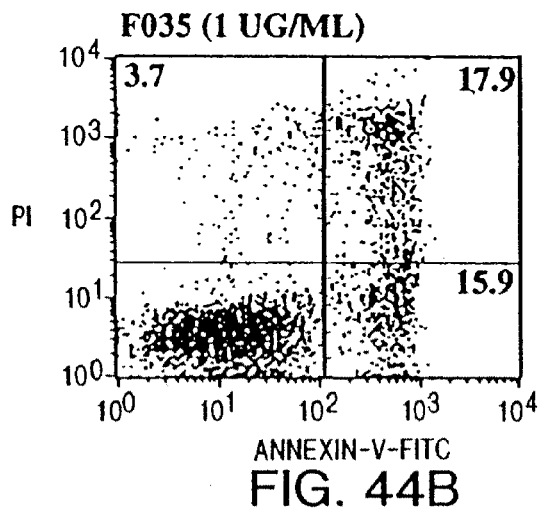
Figure 44C:
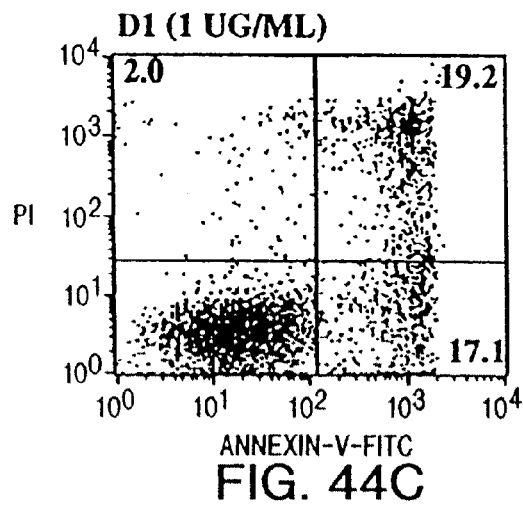
Figure 44D:
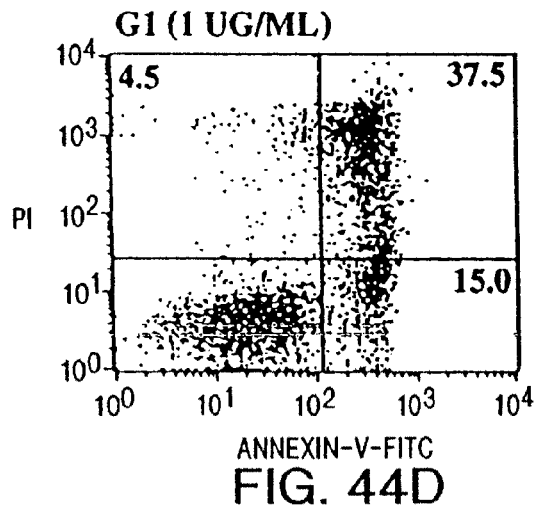
Figure 44E:
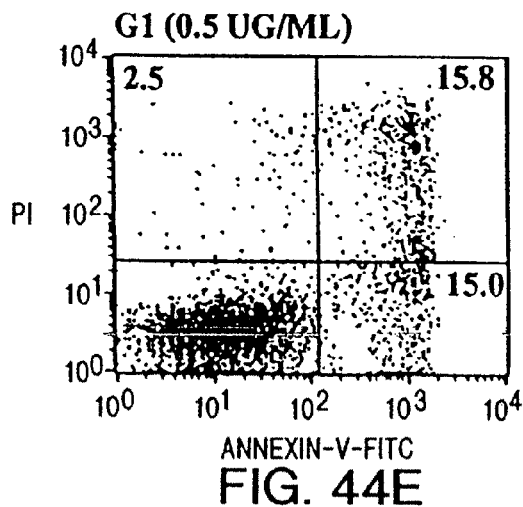

The invention further describes isolated compositions from *Acacia victoriae* which have been partially or wholly purified and structurally characterized. The purification and characterization of these triterpene glycoside compounds is described in detail the Examples. D1, G1 and B1 are three compositions that have been wholly purified and their structural characterization is almost complete (FIG. 39, FIG. 40 and FIG. 41). Bioassays performed with these compounds on cancer cell lines has demonstrated cell growth inhibition and the induction of apoptosis in malignant cells (FIG. 43, FIG. 44). Furthermore, partially purified compositions of these saponins isolated from *Acacia victoriae* also demonstrate chemoprotective effects in mice exposed to the carcinogen DMBA (FIGS. 8, 9, 11, 12 and 13). Thus, these compositions have anti-cancer activities and work by several mechanisms to induce apoptosis in cancer cells. Pharmaceutical compositions of these compounds are envisioned as powerful chemotherapeutic drugs which may be used by themselves or in combination with other forms of cancer therapy such as chemotherapy, radiation therapy, surgery, gene therapy and immunotherapy. The combination therapies are described below in detail. One of skill in the art will determine the effective dosages and the combination therapy regimen.

c. Methods of Administration (i) Parenteral Administration

One embodiment of the invention provides formulations for parenteral administration of triterpene compositions, e.g., formulated for injection via the intravenous, intramuscular, sub-cutaneous or other such routes, including direct instillation into a tumor or disease site. The preparation of an aqueous composition that contains a triterpene composition will be known to those of skill in the art in light of the present disclosure. Typically, such compositions can be prepared as injectables, either as liquid solutions or suspensions; solid forms suitable for using to prepare solutions or suspensions upon the addition of a liquid prior to injection also can be prepared; and the preparations also can be emulsified.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

The triterpene compounds can be formulated into a composition in a neutral or salt form. Pharmaceutically acceptable salts include the acid addition salts (formed with the free amino groups of the protein) which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

(ii) Other Modes of Administration

Other modes of administration will also find use with the subject invention. For instance, the triterpene compounds of the invention may be formulated in suppositories and, in some cases, aerosol and intranasal compositions. For suppositories, the vehicle composition will include traditional binders and carriers such as polyalkylene glycols or triglycerides. Such suppositories may be formed from mixtures containing the active ingredient in the range of about 0.5% to about 10% (w/w), preferably about 1% to about 2%.

Oral compositions may be prepared in the form of solutions, suspensions, tablets, pills, capsules, sustained release formulations, or powders. These compositions can be administered, for example, by swallowing or inhaling. Where a pharmaceutical composition is to be inhaled, the composition will preferably comprise an aerosol. Exemplary procedures for the preparation of aqueous aerosols for use with the current invention may be found in U.S. Pat. No. 5,049,388, the disclosure of which is specifically incorporated herein by reference in its entirety. Preparation of dry aerosol preparations are described in, for example, U.S. Pat. No. 5,607,915, the disclosure of which is specifically incorporated herein by reference in its entirety.

Also useful is the administration of the invention compounds directly in transdermal formulations with permeation enhancers such as DMSO. These compositions can similarly include any other suitable carriers, excipients or deluents. Other topical formulations can be administered to treat certain disease indications. For example, intranasal formulations may be prepared which include vehicles that neither cause irritation to the nasal mucosa nor significantly disturb ciliary function. Diluents such as water, aqueous saline or other known substances can be employed with the subject invention. The nasal formulations also may contain preservatives such as, but not limited to, chlorobutanol and benzalkonium chloride. A surfactant may be present to enhance absorption of the subject compounds by the nasal mucosa.

(iii) Formulations and Treatments

Upon formulation, solutions will be administered in a manner compatible with the dosage formulation and in such amount as is therapeutically effective. The formulation of choice can be accomplished using a variety of excipients including, for example, pharmaceutical grades of mannitol, lactose, starch, magnesium stearate, sodium saccharin cellulose, magnesium carbonate, and the like.

Typically, the compounds of the instant invention will contain from less than 1% to about 95% of the active ingredient, preferably about 10% to about 50%. Preferably, between about 10 mg/kg patient body weight per day and about 25 mg/kg patient body weight per day will be administered to a patient. The frequency of administration will be determined by the care given based on patient responsiveness. Other effective dosages can be readily determined by one of ordinary skill in the art through routine trials establishing dose response curves.

Regardless of the mode of administration, suitable pharmaceutical compositions in accordance with the invention will generally include an amount of the triterpene composition admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, which reference is specifically incorporated herein by reference in its entirety. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

The therapeutically effective doses are readily determinable using an animal model, as shown in the studies detailed herein. For example, experimental animals bearing solid tumors are frequently used to optimize appropriate therapeutic doses prior to translating to a clinical environment. Such models are known to be very reliable in predicting effective anti-cancer strategies.

In certain embodiments, it may be desirable to provide a continuous supply of therapeutic compositions to the patient. For intravenous or intraarterial routes, this is accomplished by drip system. For topical applications, repeated application would be employed. For various approaches, delayed release formulations could be used that provided limited but constant amounts of the therapeutic agent over and extended period of time. For internal application, continuous perfusion of the region of interest may be preferred. This could be accomplished by catheterization, post-operatively in some cases, followed by continuous administration of the therapeutic agent. The time period for perfusion would be selected by the clinician for the particular patient and situation, but times could range from about 1-2 hours, to 2-6 hours, to about 6-10 hours, to about 10-24 hours, to about 1-2 days, to about 1-2 weeks or longer. Generally, the dose of the therapeutic composition via continuous perfusion will be equivalent to that given by single or multiple injections, adjusted for the period of time over which the injections are administered. It is believed that higher doses may be achieved via perfusion, however.

1. Treatment Protocol

Two primary approaches are envisioned by the inventors for the use of the triterpene compounds of the invention either alone or in combination therapy. The first is the use in metastatic cancer either in patients who have not received prior chemo, radio, or biological therapy or in previously untreated patients. Patients would be treated by systemic administration, that is, intravenous, subcutaneous, oral administration or by intratumoral injection. The pharmaceutical dose(s) administered would preferably contain between 10 and 25 mg of the triterpene compositions of the invention per kg of patient body weight per day, including about 13, 16, 19, and 22 mg/kg/day. Alternatively, the patient could be treated with one or more pharmaceutical compositions comprising from about 1 mg/kg/day of the triterpene compositions of the invention to about 100 mg/kg/day, including about 3, 6, 9, 12, 15, 18, 21, 28, 30, 40, 50, 60, 70, 80 and 90 mg/kg/day of the triterpene compositions of the invention.

The treatment course typically consists of daily treatment for a minimum of eight weeks or one injection weekly for a minimum of eight weeks. Upon election by the clinician, the regimen may be continued on the same schedule until the tumor progresses or the lack of response is observed.

Another application of the compounds of the invention is in treating patients who have been rendered free of clinical disease by surgery, chemotherapy, and/or radiotherapy. Adjuvant therapy would be administered in the same regimen as described above for a minimum of one year to prevent recurrent disease.

2. Prevention of Cancer with the Compounds of the Invention

Another application of the compounds and mixtures of the invention is in the prevention of cancer in high risk groups. Such patients (for example, those with genetically defined predisposition to tumors such as breast cancer, colon cancer, skin cancer, and others) would be treated by mouth (gastrointestinal tumors), topically on the skin (cutaneous), or by systemic administration for a minimum period of one year and perhaps longer to determine prevention of cancer. This use would include patients and well defined pre-neoplastic lesions, such as colorectal polyps or other premalignant lesions of the skin, breast, lung, or other organs.

3. Clinical Protocol

A clinical protocol has been designed by the inventors to facilitate the treatment of cancer using the triterpene compounds of the invention. In accordance with this protocol, patients having histologic proof of cancer, for example, ovarian cancer, pancreatic cancer, renal cancer, prostate cancer, lung, or bladder will be selected. Patients may, but need not have received previous chemo-, radio- or gene therapies. Optimally, patients will have adequate bone marrow function (defined as peripheral absolute granulocyte count of >2,000/mm$^3$ and platelet count of 100,000/mm$^3$), adequate liver function (bilirubin$\leq$1.5 mg/dl) and adequate renal function (creatinine<1.5 mg/dl).

The protocol calls for single dose administration, via intratumoral injection, of a pharmaceutical composition containing about 10 to 25 mg of the triterpene compounds of the invention per kg of patient body weight. For tumors of $\geq$4 cm, the volume administered will be 4-10 ml (preferably 10 ml), while for tumors<4 cm, a volume of 1-3 ml will be used (preferably 3 ml). Multiple injections will be delivered for a single dose, in 0.1-0.5 ml volumes, with spacing of approximately 1 cm or more.

The treatment course consists of about six doses, delivered over two weeks. Upon election by the clinician, the regimen may be continued, six doses each two weeks, or on a less frequent (monthly, bimonthly, quarterly, etc.) basis.

Where patients are eligible for surgical resection, the tumor will be treated as described above for at least two consecutive two-week treatment courses. Within one week of completion of the second (or more, e.g., third, fourth, fifth, sixth, seventh, eighth, etc.) course, the patient will receive surgical resection. Prior to close of the incision, 10 ml of a pharmaceutical composition containing the triterpene compounds of the invention will be delivered to the surgical site (operative bed) and allowed to remain in contact for at least 60 minutes. The wound is closed and a drain or catheter placed therein. On the third post-operative day, an additional 10 ml of the pharmaceutical composition is administered via the drain and allowed to remain in contact with the operative bed for at least two hours. Removal by suction is then performed, and the drain removed at a clinically appropriate time.

4. Treatment of Artificial and Natural Body Cavities

One of the prime sources of recurrent cancer is the residual, microscopic disease that remains at the primary tumor site, as well as locally and regionally, following tumor excision. In addition, there are analogous situations where natural body cavities are seeded by microscopic tumor cells. The effective treatment of such microscopic disease would present a significant advance in therapeutic regimens.

Thus, in certain embodiments, a cancer may be removed by surgical excision, creating a "cavity." Both at the time of surgery, and thereafter (periodically or continuously), the therapeutic composition of the present invention is administered to the body cavity. This is, in essence, a "topical" treatment of the surface of the cavity. The volume of the composition should be sufficient to ensure that the entire surface of the cavity is contacted by the expression construct.

In one embodiment, administration simply will entail injection of the therapeutic composition into the cavity formed by the tumor excision. In another embodiment, mechanical application via a sponge, swab or other device may be desired. Either of these approaches can be used subsequent to the tumor removal as well as during the initial surgery. In still another embodiment, a catheter is inserted into the cavity prior to closure of the surgical entry site. The cavity may then be continuously perfused for a desired period of time.

In another form of this treatment, the "topical" application of the therapeutic composition is targeted at a natural body cavity such as the mouth, pharynx, esophagus, larynx, trachea, pleural cavity, peritoneal cavity, or hollow organ cavities including the bladder, colon or other visceral organs. In this situation, there may or may not be a significant, primary tumor in the cavity. The treatment targets microscopic disease in the cavity, but incidentally may also affect a primary tumor mass if it has not been previously removed or a pre-neoplastic lesion which may be present within this cavity. Again, a variety of methods may be employed to affect the "topical" application into these visceral organs or cavity surfaces. For example, the oral cavity in the pharynx may be affected by simply oral swishing and gargling with solutions. However, topical treatment within the larynx and trachea may require endoscopic visualization and topical delivery of the therapeutic composition. Visceral organs such as the bladder or colonic mucosa may require indwelling catheters with infusion or again direct visualization with a cystoscope or other endoscopic instrument. Cavities such as the pleural and peritoneal cavities may be accessed by indwelling catheters or surgical approaches which provide access to those areas.

(iv) Therapeutic Kits

The present invention also provides therapeutic kits comprising the triterpene compositions described herein. Such kits will generally contain, in suitable container means, a pharmaceutically acceptable formulation of at least one triterpene compound in accordance with the invention. The kits also may contain other pharmaceutically acceptable formulations, such as those containing components to target the triterpene compound to distinct regions of a patient where treatment is needed, or any one or more of a range of drugs which may work in concert with the triterpene compounds, for example, chemotherapeutic agents.

The kits may have a single container means that contains the triterpene compounds, with or without any additional components, or they may have distinct container means for each desired agent. When the components of the kit are provided in one or more liquid solutions, the liquid solution is an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent also may be provided in another container means. The container means of the kit will generally include at least one vial, test tube, flask, bottle, syringe or other container means, into which the triterpene glycoside, and any other desired agent, may be placed and, preferably, suitably aliquoted. Where additional components are included, the kit will also generally contain a second vial or other container into which these are placed, enabling the administration of separated designed doses. The kits also may comprise a second/third container means for containing a sterile, pharmaceutically acceptable buffer or other diluent.

The kits also may contain a means by which to administer the triterpene compositions to an animal or patient, e.g., one or more needles or syringes, or even an eye dropper, pipette, or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

VI. Chemotherapeutic Combinations and Treatment

In certain embodiments of the present invention, it may be desirable to administer the triterpene compositions of the invention in combination with one or more other agents having anti-tumor activity including chemotherapeutics, radiation, and therapeutic proteins or genes. This may enhance the overall anti-tumor activity achieved by therapy with the compounds of the invention alone, or may be used to prevent or combat multi-drug tumor resistance.

To use the present invention in combination with the administration of a second chemotherapeutic agent, one would simply administer to an animal a triterpene composition in combination with the second chemotherapeutic agent in a manner effective to result in their combined anti-tumor actions within the animal. These agents would, therefore, be provided in an amount effective and for a period of time effective to result in their combined presence within the tumor vasculature and their combined actions in the tumor environment. To achieve this goal, the triterpene composition and chemotherapeutic agents may be administered to the animal simultaneously, either in a single composition or as two distinct compositions using different administration routes.

Alternatively, the triterpene composition treatment may precede or follow the chemotherapeutic agent, radiation or protein or gene therapy treatment by intervals ranging from minutes to weeks. In embodiments where the second agent and triterpene composition are administered separately to the animal, one would generally ensure that a significant period of time did not expire between the time of each delivery, such that the additional agent and triterpene composition would still be able to exert an advantageously combined effect on the tumor. In such instances, it is contemplated that one would contact the tumor with both agents within about 5 minutes to about one week of each other and, more preferably, within about 12-72 hours of each other, with a delay time of only about 24-48 hours being most preferred. In some situations, it may be desirable to extend the time period for treatment significantly, where several days (2, 3, 4, 5, 6 or 7) or even several weeks (1, 2, 3, 4, 5, 6, 7 or 8) lapse between the respective administrations. It also is conceivable that more than one administration of either the triterpene glycoside or the second agent will be desired. To achieve tumor regression, both agents are delivered in a combined amount effective to inhibit its growth, irrespective of the times for administration.

A variety of agents are suitable for use in the combined treatment methods disclosed herein. Chemotherapeutic agents contemplated as exemplary include, e.g., etoposide (VP-16), adriamycin, 5-fluorouracil (5-FU), camptothecin, actinomycin-D, mitomycin C, and cisplatin (CDDP).

As will be understood by those of ordinary skill in the art, the appropriate doses of chemotherapeutic agents will be generally around those already employed in clinical therapies wherein the chemotherapeutics are administered alone or in combination with other chemotherapeutics. By way of example only, agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Further useful agents include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of polynucleotide precursors also may be used. Particularly useful are agents that have undergone extensive testing and are readily available. As such, agents such as 5-fluorouracil (5-FU) are preferentially used by neoplastic tissue, making this agent particularly useful for targeting to neoplastic cells. Although quite toxic, 5-FU is applicable in a wide range of carriers, including topical, with intravenous administration in doses ranging from 3 to 15 mg/kg/day being commonly used.

Exemplary chemotherapeutic agents that are useful in connection with combined therapy are listed in Table 5. Each of the agents listed therein are exemplary and by no means limiting. In this regard, the skilled artisan is directed to "Remington's Pharmaceutical Sciences" 15th Edition; chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

TABLE 5

Chemotherapeutic Agents Useful In Neoplastic Disease

| CLASS | TYPE OF AGENT | NONPROPRIETARY NAMES (OTHER NAMES) | DISEASE |
|---|---|---|---|
| Alkylating Agents | Nitrogen Mustards | Mechlorethamine (HN$_2$) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Melphalan (L-sarcolysin) | Multiple myeloma, breast, ovary |
| | | Chlorambucil | Chronic lymphocytic leukemia, primary macroglobulinemia, Hodgkin's disease, non-Hodgkin's lymphomas |
| | Ethylenimenes and Methylmelamines | Hexamethylmelamine | Ovary |
| | | Thiotepa | Bladder, breast, ovary |
| | Alkyl Sulfonates | Busulfan | Chronic granulocytic leukemia |
| | Nitrosoureas | Carmustine (BCNU) | Hodgkin's disease, non-Hodgkin's lymphomas, primary brain tumors, multiple myeloma, malignant melanoma |
| | | Lomustine (CCNU) | Hodgkin's disease, non-Hodgkin's lymphomas, primary brain tumors, small-cell lung |
| | | Semustine (methyl-CCNU) | Primary brain tumors, stomach, colon |
| | | Streptozocin (streptozotocin) | Malignant pancreatic insulinoma, malignant carcinoid |
| | Triazines | Dacarbazine (DTIC; dimethyltriazenoimidazolecarboxamide) | Malignant melanoma, Hodgkin's disease, soft-tissue sarcomas |

TABLE 5-continued

Chemotherapeutic Agents Useful In Neoplastic Disease

| CLASS | TYPE OF AGENT | NONPROPRIETARY NAMES (OTHER NAMES) | DISEASE |
|---|---|---|---|
| Antimetabolites | Folic Acid Analogs | Methotrexate (amethopterin) | Acute lymphocytic leukemia, choriocarcinoma, mycosis fungoides, breast, head and neck, lung, osteogenic sarcoma |
| | Pyrimidine Analogs | Fluouracil (5-fluorouracil; 5-FU) Floxuridine (fluorode-oxyuridine; FUdR) | Breast, colon, stomach, pancreas, ovary, head and neck, urinary bladder, premalignant skin lesions (topical) |
| | | Cytarabine (cytosine arabinoside) | Acute granulocytic and acute lymphocytic leukemias |
| | Purine Analogs and Related Inhibitors | Mercaptopurine (6-mercaptopurine; 6-MP) | Acute lymphocytic, acute granulocytic and chronic granulocytic leukemias |
| | | Thioguanine (6-thioguanine; TG) | Acute granulocytic, acute lymphocytic and chronic granulocytic leukemias |
| | | Pentostatin (2-deoxycoformycin) | Hairy cell leukemia, mycosis fungoides, chronic lymphocytic leukemia |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | Epipodophyllotoxins | Etoposide Tertiposide | Testis, small-cell lung and other lung, breast, Hodgkin's disease, non-Hodgkin's lymphomas, acute granulocytic leukemia, Kaposi's sarcoma |
| | Antibiotics | Dactinomycin (actinomycin D) | Choriocarcinoma, Wilms' tumor, rhabdomyosarcoma, testis, Kaposi's sarcoma |
| | | Daunorubicin (daunomycin; rubidomycin) | Acute granulocytic and acute lymphocytic leukemias |
| | | Doxorubicin | Soft-tissue, osteogenic and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung and genitourinary tract; Hodgkin's disease, non-Hodgkin's lymphomas |
| | | Plicamycin (mithramycin) | Testis, malignant hypercalcemia |
| | | Mitomycin (mitomycin C) | Stomach, cervix, colon, breast, pancreas, bladder, head and neck |
| | Enzymes | L-Asparaginase | Acute lymphocytic leukemia |
| | Biological Response Modifiers | Interferon alfa | Hairy cell leukemia., Kaposi's sarcoma, melanoma, carcinoid, renal cell, ovary, bladder, non-Hodgkin's lymphomas, mycosis fungoides, multiple myeloma, chronic granulocytic leukemia |
| Miscellaneous Agents | Platinum Coordination Complexes | Cisplatin (cis-DDP) Carboplatin | Testis, ovary, bladder, head and neck, lung, thyroid, cervix, endometrium, neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essental thrombocytosis, malignant melanoma |
| | Methyl Hydrazine Derivative | Procarbazine (N-methylhydrazine, MIH) | Hodgkin's disease |
| | Adrenocortical Suppressant | Mitotane (o,p'-DDD) Aminoglutethimide | Adrenal cortex Breast |
| Hormones and Antagonists | Adrenocorticosteroids | Prednisone (several other equivalent preparations available) | Acute and chronic lymphocytic leukemias, non-Hodgkin's lymphomas, Hodgkin's disease, breast |

TABLE 5-continued

Chemotherapeutic Agents Useful In Neoplastic Disease

| CLASS | TYPE OF AGENT | NONPROPRIETARY NAMES (OTHER NAMES) | DISEASE |
|---|---|---|---|
| | Progestins | Hydroxyprogesterone caproate Medroxyprogesterone acetate Megestrol acetate | Endometrium, breast |
| | Estrogens | Diethylstilbestrol Ethinyl estradiol (other preparations available) | Breast, prostate |
| | Antiestrogen | Tamoxifen | Breast |
| | Androgens | Testosterone propionate Fluoxymesterone (other preparations available) | Breast |
| | Antiandrogen | Flutamide | Prostate |
| | Gonadotropin-releasing hormone analog | Leuprolide | Prostate |

Other factors that cause DNA damage and have been used extensively include what are commonly known as γ-rays, X-rays, and/or the directed delivery of radioisotopes to tumor cells. Other forms of DNA damaging factors also are contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

VII. Targeted Cancer Therapy

The triterpene compounds described herein may be linked to one or more molecules which target the compounds to tumor cells. Targeting is beneficial in that it can be used to increase the overall levels of a drug at the site of treatment, for example, at tumor sites, while minimizing systemic exposure to the drug. In common with the chemotherapeutic agents discussed above, it is possible that the use of a targeted triterpene compound may be used in combination with a second agent, such as a chemotherapeutic agent. Both the triterpene and the second agent be directed to the same or different targets within the tumor environment. This should result in additive, greater than additive or even markedly synergistic results.

Exemplary targeting agents employed in combination with the triterpene compounds of the present invention will be those targeting agents that are capable of delivering the triterpene molecules to the tumor region, i.e., capable of localizing within a tumor site. Similarly desired will be those agents which target the vasculature of a tumor region. The targeting of the triterpene glycoside compounds is specifically contemplated to allow for greater effective concentrations in tumor regions without or with the minimization of potential side effects which could be observed with a somewhat wider or systemic distribution of the triterpene compounds. Specifically, the targeting agent may be directed to components of tumor cells; components of tumor vasculature; components that bind to, or are generally associated with, tumor cells; components that bind to, or are generally associated with, tumor vasculature; components of the tumor extracellular matrix or stroma or those bound therein; and even cell types found within the tumor vasculature.

(i) Tumor Cell Targets and Antibodies

The malignant cells that make up the tumor may be targeted using a bispecific antibody that has a region capable of binding to a relatively specific marker or antigen of the tumor cell. For example, specific tumor cell inhibition or killing may be achieved by the binding of an antibody-triterpene composition conjugate to a target tumor cell.

Many so-called "tumor antigens" have been described, any one which could be employed as a target in connection with the targeted aspects of the present invention. A large number of exemplary solid tumor-associated antigens are listed herein below. The preparation and use of antibodies against such antigens is well within the skill of the art and specifically disclosed herein. Exemplary antibodies include those from gynecological tumor sites (see, e.g., the ATCC Catalogue): OC 125; OC 133; OMI; Mo v1; Mo v2; 3C2; 4C7; $ID_3$; DU-PAN-2; F 36/22; $4F_7/7A_{10}$; OV-TL3; B72.3; $DF_3$; $2C_8/2F_7$; MF 116; Mov18; CEA 11-H5; CA 19-9 (1116NS 19-9); H17-E2; 791T/36; $NDOG_{2,H}317$; 4D5, 3H4, 7C2, 6E9, 2C4, 7F3, 2H11, 3E8, 5B8, 7D3, SB8; HMFG2; 3.14.A3; from breast tumor sites: DF3; NCRC-11; 3C6F9; MBE6; CLNH5; MAC 40/43; EMA; HMFG1 HFMG2; 3.15.C3; M3, M8, M24; M18; 67-D-11; D547Sp, D75P3, H222; Anti-EGF; LR-3; TA1; H59; 10-3D-2; HmAB1,2; MBR 1,2,3; 24-17-1; 24-17-2 (3E1-2); F36/22.M7/105; C11, G3, H7; B6-2; B1-1; Cam 17-1; SM3; SM4; C-Mul (566); 4D5 3H4, 7C2, 6E9, 2C4, 7F3, 2H11, 3E8, 5B8, 7D3, 5B8; OC 125; MO v2; DU-PAN-2; $4F_7/7A_{10}$; $DF_3$,-B72-3; cccccCEA 11; H17-E2; 3-14-A3; FO23C5; from colorectal tumor sites: B72-3; (17-1A) 1083-17-1A; CO17-1A; ZCE-025; AB2; HT-29-15; 250-30.6; 44X14; A7; GA73-3; 791T/36; 28A32; 28.19.8; X MMCO-791; DU-PAN-2; $ID_3$; CEA 11-H5; $2C_8/2F_7$; CA-19-9 (1116NS 19-9); PR5C5; PR4D2; PR4D1; from melanoma sites 4-1; 8-2 $M_{17}$, 96-5; 118-1, 133-2, (113-2); $L_1$, $L_{10}$, $R_{10}(R_{19})$; $I_{12}$; $K_5$; 6-1; R24; 5-1; 225.28S; 465.12S; 9-2-27; F11; 376.96S; 465.12S; 15-75; 15-95; Mel-14; Mel-12; Me3-TB7; 225.28SD; 763.24TS; 705F6; 436910; M148; from gastrointestinal tumors: ID3; DU-PAN-2; OV-TL3; B72-3; CEA 11-H5; 3-14-A3; C COLI; CA-19-9 (1116NS 19-9) and CA50; OC125; from lung tumors: 4D5 3H4, 7C2, 6E9, 2C4, 7F3, 2H11, 3E8, 5B8, 7D3, SB8; MO v2; B72-3; DU-PAN-2; CEA 11-H5; MUC 8-22; MUC 2-63; MUC 2-39; MUC 7-39; and from miscellaneous tumors: PAb 240; PAb 246; PAb 1801; ERIC-1; M148; FMH25; 6-1; CA1; 3F8; $4F_7/7A_{10}$; $2C_8/2F_7$; CEA 11-H5.

Another means of defining and targeting a tumor is in terms of the characteristics of a tumor cell itself, rather than describing the biochemical properties of an antigen expressed by the cell. A number of exemplary tumor cell lines are known and may be used for the preparation of targeting agents. For example, whole cells or cell homogenates from known tumor lines could be used to prepare anti-tumor antibodies for the targeting of related tumors types. Similarly, such tumor cell lines may find use in the implementation of various in vitro assays. In this regard, the skilled artisan is referred to the ATCC catalogue for the purpose of exemplifying human tumor cell lines that are publicly available (from ATCC Catalogue). Exemplary cell lines include J82; RT4; ScaBER; T24; TCCSUP; 5637; SK-N-MC; SK-N-SH; SW 1088; SW 1783; U-87 MG; U-118 MG; U-138 MG; U-373 MG; Y79; BT-20; BT-474; MCF7; MDA-MB-134-VI; MDA-MD-157; MDA-MB-175-VII; MDA-MB-361; SK-BR-3; C-33 A; HT-3; ME-180; MS751; SiHa; JEG-3; Caco-2; HT-29; SK-CO-1; HuTu 80; A-253; FaDu; A-498; A-704; Caki-1; Caki-2; SK-NEP-1; SW 839; SK-HEP-1; A-427; Calu-1; Calu-3; Calu-6; SK-LU-1; SK-MES-1; SW 900; EB1; EB2; P3HR-1; HT-144; Malme-3M; RPMI-7951; SK-MEL-1; SK-MEL-2; SK-MEL-3; SK-MEL-5; SK-MEL-24; SK-MEL-28; SK-MEL-31; Caov-3; Caov-4; SK-OV-3; SW 626; Capan-1; Capan-2; DU 145; A-204; Saos-2; SK-ES-1; SK-LMS-1; SW 684; SW 872; SW 982; SW 1353; U-2 OS; Malme-3; KATO III; Cate-1B; Tera-1; Tera-2; SW579; AN3 CA; HEC-1-A; HEC-1-B; SK-UT-1; SK-UT-1B; SW 954; SW 962; NCI-H69; NCI-H128; BT-483; BT-549; DU4475; HBL-100; Hs 578Bst; Hs 578T; MDA-MB-330; MDA-MB-415; MDA-MB-435S; MDA-MB-436; MDA-MB-453; MDA-MB-468; T-47D; Hs 766T; Hs 746T; Hs 695T; Hs 683; Hs 294T; Hs 602; JAR; Hs 445; Hs 700T; H4; Hs 696; Hs 913T; Hs 729; FHs 738Lu; FHs 173We; FHs 738B1; NIH:0VCAR-3; Hs 67; RD-ES; ChaGo K-1; WERI-Rb-1; NCI-H446; NCI-H209; NCI-H146; NCI-H441; NCI-H82; H9; NCI-H460; NCI-H596; NCI-H676B; NCI-H345; NCI-H820; NCI-H520; NCI-H661; NCI-H510A; D283 Med; Daoy; D341 Med; AML-193 and MV4-11.

One may consult the ATCC Catalogue of any subsequent year to identify other appropriate cell lines. Also, if a particular cell type is desired, the means for obtaining such cells, and/or their instantly available source, will be known to those of skill in the particular art. An analysis of the scientific literature will thus readily reveal an appropriate choice of cell for any tumor cell type desired to be targeted.

As explained above, antibodies constitute a straightforward means of recognizing a tumor antigen target. An extensive number of antibodies are known that are directed against solid tumor antigens. Certain useful anti-tumor antibodies are listed above. However, as will be known'to those of skill in the art, certain of the antibodies listed will not have the appropriate biochemical properties, or may not be of sufficient tumor specificity, to be of use therapeutically. An example is MUC8-22 that recognizes a cytoplasmic antigen. Antibodies such as these will generally be of use only in investigational embodiments, such as in model systems or screening assays.

Generally speaking, antibodies for use in these aspects of the present invention will preferably recognize antigens that are accessible on the cell-surface and that are preferentially, or specifically, expressed by tumor cells. Such antibodies will also preferably exhibit properties of high affinity, such as exhibiting a $K_d$ of <200 nM, and preferably, of <100 nM, and will not show significant reactivity with life-sustaining normal tissues, such as one or more tissues selected from heart, kidney, brain, liver, bone marrow, colon, breast, prostate, thyroid, gall bladder, lung, adrenals, muscle, nerve fibers, pancreas, skin, or other life-sustaining organ or tissue in the human body. The "life-sustaining" tissues that are the most important for the purposes of the present invention, from the standpoint of low reactivity, include heart, kidney, central and peripheral nervous system tissues and liver. The term "significant reactivity," as used herein, refers to an antibody or antibody fragment that, when applied to the particular tissue under conditions suitable for immunohistochemistry, will elicit either no staining or negligible staining with only a few positive cells scattered among a field of mostly negative cells.

Particularly promising antibodies contemplated for use in the present invention are those having high selectivity for the solid tumor. For example, antibodies binding to TAG 72 and the HER-2 proto-oncogene protein, which are selectively found on the surfaces of many breast, lung and colorectal cancers (Thor et al., 1986; Colcher et al., 1987; Shepard et al., 1991); MOv18 and OV-TL3 and antibodies that bind to the milk mucin core protein and human milk fat globule (Miotti et al., 1985; Burchell et al., 1983); and the antibody 9.2.27 that binds to the high $M_r$ melanoma antigens (Reisfeld et al., 1982). Further useful antibodies are those against the folate-binding protein, which is known to be homogeneously expressed in almost all ovarian carcinomas; those against the erb family of oncogenes that are over-expressed in squamous cell carcinomas and the majority of gliomas; and other antibodies known to be the subject of ongoing pre-clinical and clinical evaluation.

The antibodies B3, KSI/4, CC49, 260F9, XMMCO-791, D612 and SM3 are believed to be particularly suitable for use in clinical embodiments, following the standard pre-clinical testing routinely practiced in the art. B3 (U.S. Pat. No. 5,242,813; Brinkmann et al., 1991) has ATCC Accession No. HB 10573; KS1/4 can be made as described in U.S. Pat. No. 4,975,369; and D612 (U.S. Pat. No. 5,183,756) has ATCC Accession No. HB 9796.

Another means of defining a tumor-associated target is in terms of the characteristics of the tumor cell, rather than describing the biochemical properties of an antigen expressed by the cell. Accordingly, the inventors contemplate that any antibody that preferentially binds to a tumor cell may be used as the targeting component of an triterpene-targeting conjugate. The preferential tumor cell binding is again based upon the antibody exhibiting high affinity for the tumor cell and not having significant reactivity with life-sustaining normal cells or tissues, as defined above.

The invention also provides several means for generating an antibody for use in the targeting of triterpene glycosides to tumor cells as described herein. To generate a tumor cell-specific antibody, one would immunize an animal with a composition comprising a tumor cell antigen and, as described more fully below, select a resultant antibody with appropriate specificity. The immunizing composition may contain a purified, or partially purified, preparation of any of the antigens listed above; a composition, such as a membrane preparation, enriched for any of the antigens in listed above; any of the cells listed above; or a mixture or population of cells that include any of the cell types listed above.

Of course, regardless of the source of the antibody, in the practice of the invention in human treatment, one will prefer to ensure in advance that the clinically-targeted tumor expresses the antigen ultimately selected. This is achieved by means of a fairly straightforward assay involving antigenically testing a tumor tissue sample, for example, a surgical biopsy, or perhaps testing for circulating shed antigen. This can readily be carried out in an immunological screening assay such as an ELISA (enzyme-linked immunosorbent assay), wherein the binding affinity of antibodies from a "bank" of hybridomas are tested for reactivity against the tumor. Antibodies demonstrating appropriate tumor selectivity and affinity are then selected for the preparation of bispecific antibodies of the present invention.

Due to the well-known phenomenon of cross-reactivity, it is contemplated that useful antibodies may result from immunization protocols in which the antigens originally employed were derived from an animal, such as a mouse or a primate, in addition to those in which the original antigens were obtained from a human cell. Where antigens of human origin are used, they may be obtained from a human tumor cell line, or may be prepared by obtaining a biological sample from a particular patient in question. Indeed, methods for the development of antibodies that are "custom-tailored" to the patient's tumor are known (Stevenson et al., 1990) and are contemplated for use in connection with this invention.

1. Methods for Antibody Production

As indicated, antibodies may find use in particular embodiments of the instant invention. For example, antibodies may be produced which are specific for a particular region in a patient or a particular tissue type. These antibodies may then be conjugated to a triterpene compound of the invention, thereby allowing the specific targeting of the triterpene compounds to the tissue for which the antibody is directed to. An exemplary embodiment of such an antibody is one which binds to a tumor cell. In a preferred embodiment of the invention, an antibody is a monoclonal antibody. Means for preparing and characterizing monoclonal and polyclonal antibodies are well known in the art and specifically disclosed herein below (see, e.g., Howell and Lane, 1988).

Briefly, a polyclonal antibody is prepared by immunizing an animal with an immunogen comprising the desired target antigen and collecting antisera from that immunized animal. A wide range of animal species can be used for the production of antisera. Typically an animal used for production of antiantisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of particular cell types or, alternatively, the compounds of the present invention, can be used to immunize one or more experimental animals, such as a rabbit or mouse, which will then proceed to produce specific antibodies against the antigens. Polyclonal antisera may be obtained, after allowing time for antibody generation, simply by bleeding the animal and preparing serum samples from the whole blood.

It is believed that the monoclonal antibodies of the present invention will find useful application in immunochemical procedures which may be applied to screening for the presence of the triterpene compounds of the invention in species other than Acacia victoriae, or in other procedures which may utilize antibodies specific to particular antigens. As discussed, an exemplary embodiment of the use of antibodies with the invention comprises preparing antibodies directed to tumor-specific antigens, linking the antibodies to the triterpene compounds of the invention, and treating human patients with the antigen-triterpene conjugate, whereby the triterpene compounds of the invention are specifically targeted to tumor cells or other cells which are involved in a condition which can be treated with the triterpene compounds of the invention. In general, both polyclonal and monoclonal antibodies against various antigens may be employed in different embodiments of the invention. For example, they may be employed in purifying triterpene compounds in an antibody affinity column. Means for preparing and characterizing such antibodies are well known in the art and are disclosed in, for example, Harlow and Lane, 1988, the disclosure of which is specifically incorporated herein by reference in its entirety.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin also can be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of route's can be used to administer the immunogen (subcutaneous, intramuscular, intradermal, intravenous and intraperitoneal). The production of polyclonal antibodies may be monitored by sampling blood of the immunized animal at various points following immunization. A second, booster, injection also may be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196, 265, the disclosure of which is specifically incorporated herein by reference in its entirety. Typically, this technique involves immunizing a suitable animal with a selected immunogen composition, for example, a purified or partially purified tumor-specific antigen, polypeptide or peptide or tumor cell. The immunizing composition is administered in a manner effective to stimulate antibody producing cells. Rodents such as mice and rats are preferred animals, however, the use of rabbit, sheep or frog cells also is possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency and enzyme deficiencies that render them incapable of growing in certain selective media which support the growth of only the desired fused cells (hybridomas).

Any one of a number of myeloma cells may be used, as are known to those of skill in the art. For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions (see, e.g., Goding, 1986; Campbell, 1984; and the ATCC Catalogue).

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et aL, (1977). The use of electrically induced fusion methods also is appropriate (Goding, 1986).

Fusion procedures usually produce viable hybrids at low frequencies, around $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

(iii) Further Tumor Cell Targets and Binding Ligands

In addition to the use of antibodies, other ligands could be employed to direct a triterpene compounds of the invention to a tumor site by binding to a tumor cell antigen. For tumor antigens that are over-expressed receptors (e.g., an estrogen receptor, EGF receptor), or mutant receptors, the corresponding ligands could be used as targeting agents.

In an analogous manner to endothelial cell receptor ligands, there may be components that are specifically, or preferentially, bound to tumor cells. For example, if a tumor antigen is an over-expressed receptor, the tumor cell may be coated with a specific ligand in vivo. Therefore, the ligand could then be targeted either with an antibody against the ligand, or with a form of the receptor itself. Specific examples of these type of targeting agents are antibodies against TIE-1 or TIE-2 ligands, antibodies against platelet factor 4, and leukocyte adhesion binding protein.

(iv) Toxins

For certain applications, it is envisioned that the second therapeutic agents used in combination with the triterpene compounds described herein will be pharmacologic agents conjugated to antibodies or growth factors, particularly cytotoxic or otherwise anti-cellular agents having the ability to kill or suppress the growth or cell division of endothelial cells. In general, the invention contemplates the use of any pharmacologic agent, including and in supplement to the triterpene compounds described herein, that can be conjugated to a targeting agent, preferably an antibody, and delivered in active form to the targeted, tumor cells. Exemplary anticellular agents include chemotherapeutic agents, radioisotopes as well as cytotoxins. In the case of chemotherapeutic agents, the inventors believe that agents such as a steroid hormone; an anti-metabolite such as cytosine arabinoside, fluorouracil, methotrexate or aminopterin; an anthracycline; mitomycin C; a vinca alkaloid; demecolcine; etoposide; mithramycin; or an anti-tumor alkylating agent such as chlorambucil or melphalan, will be particularly preferred. Other embodiments may include agents such as a cytokine, growth factor, bacterial endotoxin or the lipid A moiety of bacterial endotoxin. In any event, it is believed that agents such as these may, if desired, be successfully linked together with the triterpene compounds of the invention to targeting agents, preferably an antibody, in a manner that will allow their targeting, internalization, release or presentation to blood components at the site of the targeted cells as required using known conjugation technology (see, e.g., Ghose et al., 1983 and Ghose et al., 1987).

A variety of chemotherapeutic and other pharmacologic agents have now been successfully conjugated to antibodies and shown to function pharmacologically (see, e.g., Vaickus et al., 1991). Exemplary antineoplastic agents that have been investigated include doxorubicin, daunomycin, methotrexate, vinblastine, and various others (Dillman et al., 1988; Pietersz et al, 1988). Moreover, the attachment of other agents such as neocarzinostatin (Kimura et al., 1983), macromycin (Manabe et al., 1984), trenimon (Ghose, 1982) and α-amanitin (Davis & Preston, 1981) has been described. Specific means for preparing conjugates between the triterpene compounds of the instant invention and appropriate targeting molecules are specifically disclosed herein above.

VIII. Other Uses of the Compounds of the Invention

The inventors specifically contemplate the use of the compounds of this invention for a range of applications in addition to the treatment or prevention of cancer. In particular, the inventors contemplate the use of the triterpene compounds of the invention as solvents, anti-fungal and anti-viral agents, piscicides or molluscicides, contraceptives, antihelmintics, UV-protectants, expectorants, diuretics, anti-inflammatory agents, regulators of cholesterol metabolism, cardiovascular effectors, anti-ulcer agents, analgesics, sedatives, immunomodulators, antipyretics, angiogenesis regulators, as agents for decreasing capillary fragility, as agents to combat the effects of aging, and as agents for improving cognition and memory.

The compounds of this invention have a role in the regulation of angiogenesis. Angiogenesis or neovascularization is defined as the growth of new blood vessels. Tumors and cancers induce angiogenesis to provide a life-line for oxygen and nutrients for the tumor to thrive. The development of new blood vessels also provide exits for malignant cancer cells to spread to other parts of the body. Angiogenesis inhibition therefore benefits cancer patients. On the other hand, angiogenesis is required at times such as wound healing. These wounds can be external wounds or internal organ wounds that result from accidents, burns, injury and surgery. Thus, agents that promote angiogenesis have a great potential for use in therapy for wound healing.

The application of the compounds of the invention for modulation of cholesterol metabolism is also contemplated. In particular, the compounds and nutraceuticals of the invention are contemplated for use in lowering the serum cholesterol levels of human patients. Therefore, by treating patients with the triterpene compounds of the invention, either orally or intravenously, it is believed the morbidity associated with high cholesterol and related cardiovascular diseases may be decreased.

For the treatment of cardiovascular conditions, it is contemplated that the compounds of the invention may be used for the treatment of arrhythmic action and further may be used as a vascular relaxant, resulting in an antihypertensive activity.

Another particularly significant use contemplated for the compounds of the invention is as an anti-inflammatory agent. The inventors have shown that the active triterpene compounds of the invention are potent inhibitors of transcription factor NF-κB, which plays an important role in the inflammatory response. This finding is particularly significant given the increasing amount of evidence suggesting the central role of inflammatory response in carcinogenesis. Treatment of patients with the triterpene compounds provided herein may, therefore, potentially alleviate a wide degree of ailments associated with inflammation, including tumorigenesis and tissue damage.

The initial stages of an inflammatory response are characterized by increased blood vessel permeability and release (exudation) of histamine, serotonin and basic polypeptides and proteins. This is accompanied by hyperaemia and oedema formation. Subsequently, there is cellular infiltration and formation of new conjunctive tissue. It is believed that treatment with the compounds of the invention can limit these early stages of inflammation and, thereby, decrease the negative effects associated with the inflammatory condition.

The plant species from which the compounds of the invention were identified, *Acacia victoriae*, was selected, in part, because it is native to and regions. An important function of the metabolism of plants from these regions is the production of compounds which protect cells from ultraviolet radiation. The inventors specifically contemplate that the triterpene compounds of the invention are capable of serving as such UV-protectants. It is, therefore, believed that the compounds of the invention will find wide use in applications in which protection from ultraviolet radiation is desired. For example, a suitable application comprises the use of the triterpene compounds of the invention as an ingredient in sunblock, or other similar lotions for application to human skin.

The potential benefit of such a composition is indicated by the chemoprotective effects demonstrated for the compounds of the invention herein. Lotions and sunblocks containing the triterpene compounds of the invention would, therefore, be particularly suited to those with a predisposition to various forms of skin cancer. Examples of such include the fair skinned and, particularly, those with a genetic predisposition to skin cancel. Such predispositions include heritable oncogene mutations or mutations in the cellular mechanisms which mediate DNA repair to UV-induced damage. Particularly significant are mutations in genes controlling genetic repair mechanisms, for example, the excision of UV-induced thymine-thymine dimers. Similarly, the compounds of the invention could be added to any other composition for which increased UV-protection is desired, and these compounds applied to any animate or inanimate object for which UV-protection is sought.

Other possible application of the triterpene compounds include protection in the central nervous system damage, in effect, memory loss or enhanced cognitive function, use as an antioxidant (monitoring blood levels of oxidative molecules), or increase of nitric oxide (NO), for the treatment of hypertension or atherosclerosis. In addition, the inventors specifically envision the topical application of the triterpene compounds of the invention for enhanced penile function. Also contemplated by the inventors is the topical administration of the compounds of the invention for increasing skin collagen, thereby combating the effects of skin aging.

IX. Assays and Methods for Screening Active Compounds

A number of assays are known to those of skill in the art and may be used to further characterize the triterpene compounds of the invention. These include assays of biological activities as well as assays of chemical properties. The results of these assays provide important inferences as to the properties of compounds as well as their potential applications in treating human or other mammalian patients. Assays deemed to be of particular utility in this regard include in vivo and in vitro screens of biological activity and immunoassays.

In Vivo Assays

The present invention encompasses the use of various animal models. Here, the identity seen between human and mouse provides an excellent opportunity to examine the function of a potential therapeutic agent, for example, a triterpene compound of the current invention. One can utilize cancer models in mice that will be highly predictive of cancers in humans and other mammals. These models may employ the orthotopic or systemic administration of tumor cells to mimic primary and/or metastatic cancers. Alternatively, one may induce cancers in animals by providing agents known to be responsible for certain events associated with malignant transformation and/or tumor progression.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intra-tumoral injection.

Determining the effectiveness of a compound in vivo may involve a variety of different criteria. Such criteria include, but are not limited to, survival, reduction of tumor burden or mass, arrest or slowing of tumor progression, elimination of tumors, inhibition or prevention of metastasis, increased activity level, improvement in immune effector function and improved food intake.

One particularly useful type of in vivo assay of anti-tumor activity comprises the use of a mouse skin model. The mouse skin model, which represents one of the best understood experimental models of multistage carcinogenesis, has permitted the resolution of three distinct stages in the development of cancer: initiation, promotion, and progression. It is now apparent that the cellular evolution to malignancy involves the sequential alteration of proto-oncogenes and/or tumor suppressor genes, whose gene products participate in critical pathways for the transduction of signals and/or regulation of gene expression. The skin tumor promotion and progression stages are characterized by selective and sustained hyperplasia, differentiation alterations, and genetic instability leading to specific expansion of the initiated cells into papillomas and carcinomas. It has been indicated that the induction of a sustained hyperplasia correlates well with the skin tumor promoting activity of various agents such as phorbol esters, several peroxides, and chrysarobin. In the mouse skin model all known carcinogens and tumor promoters have been shown to produce a sustained epidermal hyperplasia. In general, this is preceded by an inflammatory response.

Extensive data has revealed a good correlation between carcinogenicity and mutagenicity. Most tumor-initiating agents either generate or are metabolically converted to electrophilic reactants, which bind covalently to cellular DNA. Some free radicals and modified DNA bases are free radicals have been implicated in the tumor initiation and/or tumor promotion stages of carcinogenesis. Strong evidence has indicated that activation of the Ha-ras gene occurs early in the process of mouse skin carcinogenesis and perhaps is equivalent to an initiation event. For example, it has been shown that the presence of an activated c-Ha-ras gene in mouse skin papillomas and carcinomas induced by 7,12-dimethylbenz[a]anthracene was associated with a high frequency of A-T transversions at codon 61. Subsequent studies demonstrated that this type of mutation was dependent upon the chemical initiator and independent of the promoter, suggesting a direct effect of the initiator on c-Ha-ras. Furthermore, infection of mouse skin by a virally activated Ha-ras gene (v-Ha-ras) can serve as the initiating even in two-stage carcinogenesis. It should be emphasized that all skin chemical carcinogens and skin tumor initiators have been shown to produce a mutation in Ha-ras oncogene. However, skin tumor promoters do not cause a mutation in Ha-ras.

(ii) Confirmatory In Vivo and Clinical Studies

It will be understood by those of skill in the art that chemotherapeutic agents, including the triterpene compounds of the invention, or combinations of such with additional agents, should generally be tested in an in vivo setting prior to use in a human subject. Such pre-clinical testing in animals is routine in the art. To conduct such confirmatory tests, all that is required is an art-accepted animal model of the disease in question, such as an animal bearing a solid tumor. Any animal may be used in such a context, such as, e.g., a mouse, rat, guinea pig, hamster, rabbit, dog, chimpanzee, or such like. In the context of cancer treatment, studies using small animals such as mice are widely accepted as being predictive of clinical efficacy in humans, and such animal models are therefore preferred in the context of the present invention as they are readily available and relatively inexpensive, at least in comparison to other experimental animals.

The manner of conducting an experimental animal test will be straightforward to those of ordinary skill in the art. All that is required to conduct such a test is to establish equivalent treatment groups, and to administer the test compounds to one group while various control studies are conducted in parallel on the equivalent animals in the remaining group or groups. One monitors the animals during the course of the study and, ultimately, one sacrifices the animals to analyze the effects of the treatment.

One of the most useful features of the present invention is its application to the treatment of cancer. Accordingly, anti-tumor studies can be conducted to determine the specific effects upon the tumor vasculature and the anti-tumor effects overall. As part of such studies, the specificity of the effects should also be monitored, including the general well being of the animals.

In the context of the treatment of solid tumors, it is contemplated that effective amounts of the triterpene compounds of the invention will be those that generally result in at least about 10% of the cells within a tumor exhibiting cell death or apoptosis. Preferably, at least about 20%, about 30%, about 40%, or about 50%, of the cells at a particular tumor site will be killed. Most preferably, 100% of the cells at a tuinor site will be killed.

The extent of cell death in a tumor is assessed relative to the maintenance of healthy tissues in all of the areas of the body. It will be preferable to use doses of the compounds of the invention capable of inducing at least about 60%, about 70%, about 80%, about 85%, about 90%, about 95% up to and including 100% tumor necrosis, so long as the doses used do not result in significant side effects or other untoward reactions in the animal. All such determinations can be readily made and properly assessed by those of ordinary skill in the art. For example, attendants, scientists and physicians can utilize such data from experimental animals in the optimization of appropriate doses for human treatment. In subjects with advanced disease, a certain degree of side effects can be tolerated. However, patients in the early stages of disease can be treated with more moderate doses in order to obtain a significant therapeutic effect in the absence of side effects. The effects observed in such experimental animal studies should preferably be statistically significant over the control levels and should be reproducible from study to study.

Those of ordinary skill in the art will further understand that combinations and doses of the compounds of the invention that result in tumor-specific necrosis towards the lower end of the effective ranges may nonetheless still be useful in connection with the present invention. For example, in embodiments where a continued application of the active agents is contemplated, an initial dose that results in only about 10% necrosis will nonetheless be useful, particularly as it is often observed that this initial reduction "primes" the tumor to further destructive assault upon subsequent re-application of the therapy. In any event, even if upwards of about 40% or so tumor inhibition is not ultimately achieved, it will be understood that any induction of thrombosis and necrosis is nonetheless useful in that it represents an advance over the state of the patients prior to treatments. Still further, it is contemplated that a dose of the compounds of the invention which prevents or decreases the likelihood of either metastasis or de novo carcinogenesis would also be of therapeutic benefit to a patient receiving the treatment.

As discussed above in connection with the in vitro test system, it will naturally be understood that combinations of agents intended for use together should be tested and optimized together. The compounds of the invention can be straightforwardly analyzed in combination with one or more chemotherapeutic drugs, immunotoxins, coaguligands or such like. Analysis of the combined effects of such agents would be determined and assessed according to the guidelines set forth above.

(iii) In Vitro Assays

In one embodiment of the invention, screening of plant extracts is conducted in vitro to identify those compounds capable of inhibiting the growth of or killing tumor cells. Killing of tumor cells, or cytotoxicity, is generally exhibited by necrosis or apoptosis. Necrosis is a relatively common pathway triggered by external signals. During this process, the integrity of the cellular membrane and cellular compartments is lost. On the other hand, apoptosis, or programmed cell death, is a highly organized process of morphological events that is synchronized by the activation and deactivation of specific genes (Thompson et al., 1992; Wyllie, 1985).

An efficacious means for in vitro assaying of cytotoxicity comprises the systematic exposure of a panel of tumor cells to selected plant extracts. Such assays and tumor cell lines suitable for implementing the assays are well known to those of skill in the art. Particularly beneficial human tumor cell lines for use in in vitro assays of anti-tumor activity include the human ovarian cancer cell lines SKOV-3, HEY, OCC 1, and OVCAR-3; Jurkat T-leukemic cells; the MDA-468 human breast cancer line; LNCaP human prostate cancer cells, human melanoma tumor lines A375-M and Hs294t; and human renal cancer cells 769-P, 786-0, A498. A preferred type of normal cell line for use as a control constitutes human FS or Hs27 foreskin fibroblast cells.

In vitro determinations of the efficacy of a compound in killing tumor cells may be achieved, for example, by assays of the expression and induction of various genes involved in cell-cycle arrest (p21, p27; inhibitors of cyclin dependent kinases) and apoptosis (bcl-2, bcl-$x_L$ and bax). To carry out this assay, cells are treated with the test compound, lysed, the proteins isolated, and then resolved on SDS-PAGE gels and the gel-bound proteins transferred to nitrocellulose membranes. The membranes are first probed with the primary antibodies (e.g., antibodies to p21, p27, bax, bcl-2 and bcl-$x_l$, etc.) and then detected with diluted horseradish peroxidase conjugated secondary antibodies, and the membrane exposed to ECL detection reagent followed by visualization on ECL-photographic film. Through analysis of the relative proportion of the proteins, estimates may be made regarding the percent of cells in a given stage, for example, the G0/G1 phase, S phase or G2/M phase.

Cytotoxicity of a compound to cancer cells also can be efficiently discerned in vitro using MTT or crystal violet staining. In this method, cells are plated, exposed to varying concentrations of the sample compounds, incubated, and stained with either MTT (3-(4,5-dimethylethiazol-2-yl)-2,5-diphenyle tetrazolium bromide; Sigma Chemical Co.) or crystal violet. MTT treated plates receive lysis buffer (20% sodium dodecyl sulfate in 50% DMF) and are subject to an additional incubation before taking an OD reading at 570 nm. Crystal violet plates are washed to extract dye with Sorenson's buffer (0.1 M sodium citrate (pH 4.2), 50% v/v ethanol), and read at 570-600 nm (Mujoo et al., 1996). The relative absorbance provides a measure of the resultant cytotoxicity.

(iv) Immunoassays

Immunoassays may find use with the current invention, for example, in the screening of extracts from plant species other than *Acacia victoriae* for the triterpene compounds of the invention. Immunoassays encompassed by the present invention include, but are not limited to those described in U.S. Pat. No. 4,367,110 (double monoclonal antibody sandwich assay) and U.S. Pat. No. 4,452,901 (Western blot). Other assays include immunoprecipitation of labeled ligands and immunocytochemistry, both in vitro and in vivo.

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections also is particularly useful.

In one exemplary ELISA, anti-triterpene antibodies are immobilized onto a selected surface exhibiting protein affinity, such as a well in a polystyrene microtiter plate. Then, a test composition suspected of containing the triterpene compounds of the instant invention, such as a plant extract from a plant related to *Acacia victoriae*, is added to the wells. After binding and washing to remove non-specifically bound immune complexes, the bound antigen may be detected. Detection is generally achieved by the addition of another antibody specific for the desired antigen and which is linked to a detectable label. This type of ELISA is a simple "sandwich ELISA". Detection also may be achieved by the addition of a second antibody specific for the desired antigen, followed by the addition of a third antibody that has binding affinity for the second antibody, with the third antibody being linked to a detectable label.

Variations of ELISA techniques are know to those of skill in the art. In one such variation, the samples suspected of containing the desired antigen are immobilized onto the well surface and then contacted with the prepared antibodies. After binding and appropriate washing, the bound immune complexes are detected. Where the initial antigen specific antibodies are linked to a detectable label, the immune complexes may be detected directly. Again, the immune complexes may be detected using a second antibody that has binding affinity for the first antigen specific antibody, with the second antibody being linked to a detectable label.

Competition ELISAs also are possible in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal.

Irrespective of the format employed, ELISAs have certain features in common, such as coating, incubating or binding, washing to remove non-specifically bound species, and detecting the bound immune complexes. These are described as below.

Antigen or antibodies also may be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of the antigen or antibody to the well, coating with a non-reactive material to reduce background, and washing to remove unbound material, the immobilizing surface is contacted with the clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The suitable conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. Washing often includes washing with a solution of PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation, e.g., incubation for 2 hours at room temperature in a PBS-containing solution such as PBS-Tween.

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer. Alternatively, the label may be a chemiluminescent one. The use of such labels is described in U.S. Pat. Nos. 5,310,687, 5,238,808 and 5,221,605.

Methods for in vitro and in situ analysis are well known and involve assessing binding of antigen-specific antibodies to tissues, cells or cell extracts. These are conventional techniques well within the grasp of those skilled in the art. For example, the antibodies to tumor cell antigens may be used in conjunction with both fresh-frozen and formalin-fixed, paraffin-embedded tissue blocks prepared for study by immunohistochemistry (IHC). Each tissue block may consist of 50 mg of residual "pulverized" tumor. The method of preparing tissue blocks from these particulate specimens has been successfully used in previous IHC studies of various prognostic factors, e.g., in breast cancer, and is well known to those of skill in the art.

Briefly, frozen-sections may be prepared by rehydrating 50 ng of frozen pulverized tumor at room temperature in PBS in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25-50 serial sections containing an average of about 500 remarkably intact tumor cells.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

In light of the present disclosure, one could utilize screening assays for the identification of compounds having essentially the same chemical characteristics and biological activity as those described herein. In particular, the present disclosure would allow one to employ assays for biologically active triterpene glycosides from those plants closely related to *Acacia victoriae*, for example, members of the genus *Acacia*. These assays may make use of a variety of different formats' and may depend on the kind of "activity" for which the screen is being conducted. Preferred assays comprise those directed to screening for anti-tumor activity, such as described herein for extracts from *Acacia victoriae*. As used herein, "anti-tumor activity" refers to the inhibition in tumor cells of cell-to-cell signaling, growth, metastasis, cell division, cell migration, soft agar colony formation, contact inhibition, invasiveness, angiogenesis, tumor progression or other malignant phenotype or the induction of apoptosis. Particularly contemplated are functional assays which include measures of the use of the compounds of the invention as anti-fungal and anti-viral agents, piscicides or molluscicides, contaceptives, anthelmintics, UV-protectants, expectorants, diuretics, anti-inflammatory agents, regulators of cholesterol metabolism, cardiovascular effectors, anti-ulcer agents, analgesics, sedatives, immunomodulators, antipyretics, regulators of angiogenesis, and as agents for decreasing capillary fragility. Such assays will be well known to those of skill in the art in light of the instant disclosure. As well as in vitro and in vivo direct assays for activity, these assays may include measures of inhibition of binding to a substrate, ligand, receptor or other binding partner by a compound of the invention.

X. Growth and Tissue Cultures of *Acacia victoriae*

An important aspect in the preparation of the compounds of the invention will be the availability of tissue of *Acacia victoriae*. As the inventors have shown that the compounds of the invention are concentrated in roots and pods of *Acacia victoriae*, the availability of these tissues will be particularly important. The inventors have also shown that young seedlings, are another source for isolating the compounds of this invention. *Acacia victoriae* grows in the southwest United States and in Australia, and therefore, plant tissue is available to the public. Additionally, a deposit of 2500 seeds of *Acacia victoriae* has been made by the inventors with the American Type Culture Collection (ATCC), 10801 University Blvd., Manassas, Va. 20110-2209 on (May 7, 1998). Those deposited seeds have been assigned ATCC Accession No. 209835. The deposit was made in accordance with the terms and provisions of the Budapest Treaty relating to deposit of microorganisms and is made for a term of at least thirty (30) years and at least five (05) years after the most recent request for the furnishing of a sample of the deposit was received by the depository, or for the effective term of the patent, whichever is longer, and will be replaced if it becomes non-viable during that period.

Therefore, in light of the instant disclosure, one of skill in the art could plant those deposited seeds, grow plants therefrom, and isolate tissue from the plants for the preparation of the triterpene compounds and nutraceuticals of the invention. Also, one could isolate tissue from naturally occurring *Acacia victoriae* populations. However, the preparation of tissue for isolation of the compounds of the invention would be more readily achieved if a suitable cultivation technique were designed for the propagation of *Acacia victoriae* tissue. One option for the preparation of tissue would be the large-scale cultivation of the species. More preferable options, however, include tissue cultures of *Acacia victoriae* and implementation of an aeroponic growth system.

Aeroponic Growth Techniques

A number of advantages may be realized by utilization of an aeroponic system of cultivation for *Acacia victoriae*. First; the growth rate of the plants is approximately twice that achieved with conventional growing techniques. Second, the roots can be easily harvested as needed without harming the plants. The cutting of roots further leads to extensive lateral growth of fibrous roots. Therefore, the roots could be harvested several time a year. In wild populations of *Acacia victoriae*, collection of pods is limited to several weeks a year, and collection of roots is difficult without harming or killing the plant.

An aeroponic growth system is a closed system in which plant roots are suspended in air and misted with a complete nutrient solution. The roots are enclosed in a watertight box misted at intervals with the nutrient solution. The nutrient solution contains all of the essential elements the plants needs to complete its life cycle. Despite the fact that different plants require different levels and formulations for optimum growth, an over-all, single-balanced solution gives satisfactory results.

(ii) Tissue Cultures of *Acacia victoriae*

Tissue cultures represent another option for cultivation of *Acacia victoriae*. For the development of tissue cultures, *Acacia victoriae* seeds are washed thoroughly in tap water with an anti-microbial soap and treated with a 20% solution of commercial bleach for 15 minutes. After repeated washing in deionized water, the seeds are treated with boiling water to induce germination and incubated overnight. The next morning, seeds are once again disinfected with commercial bleach and rinsed 2-3 times in sterile deionized water. The decontaminated seeds are then cultured on MS medium (Murashige et al., 1962) supplemented with MS vitamins and 2% sucrose (for the explant cultures, 3% sucrose was used) and the medium gelled with either 0.7% agar or 0.2% gelrite.

Explants used for culturing may comprise potentially any tissue type including shoot tips, nodal segments, hypocotyls and root segments. The explants are generally cultured on MS alone or MS supplemented with growth regulators, such as IAA, NAA, IBA, 2,4-D and BAP (either individually or in combination). The cultures are typically maintained at 25±2° C. under a 16 hour light photoperiod at 1000 lux produced by cool white fluorescent tubes. Resulting plantlets are kept under mist in the green house one month for hardening before transferring them to a greenhouse, field or aeroponic growth system.

Hairy root cultures of *Acacia victoriae* have been developed in the present invention. Infection of the plant with *Agrobacterium rhizogenes* strain R-1000, leads to the integration and expression of T-DNA in the plant genome, which causes development of a hairy roots. Hairy root cultures grow rapidly, show plagiotropic root growth and are highly branched on hormone-free medium and also exhibit a high degree of genetic stability (Aird et al., 1988). The genetic transformation and induction of hairy roots in *Acacia victoriae* and the optimum conditions for growth are described in detail in the section on Examples. Hairy root cultures allow the rapid growth of tissue on a large scale which can be used for the isolation of the triterpene compounds of this invention.

An advantage of tissue culturing is that clonal cultures may potentially be prepared which express the compounds of the invention. These cultures could be grown on a large scale and potentially be expanded to an industrial capacity growth system for the preparation of plant tissue for the isolation of triterpene compounds. Additionally, plants regenerated from tissue cultures frequently display significant variation. Therefore, using tissue cultures, clonal cell lines or plants regenerated from such cultures may be produced which are "elite" with regard to their production of the triterpene compounds of the invention. Plants produced could be selfed over generation and selected at each breeding generation to produce true-breeding elite lines.

Elite varieties need not necessarily arise from tissue cultures, however, as significant genetic variation exists within wild populations of *Acacia victoriae*. It is, therefore, contemplated by the inventors that the genetic variation found in wild populations of *Acacia victoriae* includes variations in genes controlling the endogenous levels of triterpene production. As such, it should be possible to identify those members of *Acacia victoriae* populations which produce enhanced levels of triterpenes relative to other members of wild populations, and to select these varieties for use in growth systems directed to producing tissue for the isolation of the triterpene compounds of the invention. The growth system may constitute, for example, convention farming, aeroponic growth techniques, tissue culturing, or any other suitable technique for the propagation of *Acacia victoriae* tissue. Still further, these plants may be selected for use in breeding protocols to produce varieties which are more elite and which are also true-breeding.

XI. Definitions

"A" means "one or more." Thus, a moiety may refer to one, two, three, or more moieties.

Active constituents refers to the most pure extract that retains activity. In the present invention, the "active component" or "active compound" refers to the active triterpene compounds identified by the instant inventors. These compounds have been purified and identified in, for example, fraction UA-BRF-004-DELEP-F094.

Pods are defined as seedpods of *Acacia victoriae*.

Cytotoxic is defined as cell death while the term "cytostatic" is defined as an inhibition of growth and/or proliferation of cells.

Apoptosis is defined as a normal physiologic process of programmed cell death which occurs during embryonic development and during maintenance of tissue homeostasis.

The process of apoptosis can be subdivided into a series of metabolic changes in apoptotic cells. Individual enzymatic steps of several regulatory or signal transduction pathways can be assayed to demonstrate that apoptosis is occurring in a cell or cell population, or that the process of cell death is disrupted in cancer cells. The apoptotic program is also observed by morphological features which include changes in the plasma membrane (such as loss of asymmetry), a condensation of the cytoplasm and nucleus, and internucleosomal cleavage of DNA. This is culminated in cell death as the cell degenerates into "apoptotic bodies".

Techniques to assay several enzymatic and signaling processes involved in apoptosis have been developed as standard protocols for multiparameter apoptosis research. One example of an early step in apoptosis, is the release of cytochrome c from mitochondria followed by the activation of the caspase-3 pathway (PharMingen, San Diego, Calif.). Induction of the caspases (a series of cytosolic proteases) is one of the most consistently observed features of apoptosis. In particular, caspase-3 plays a central role in the process. When caspases are activated, they cleave target proteins; one of the most important of these is PARP (poly-(ADP-ribose) polymerase, which is a protein located in the nucleus). Therefore, assays detecting release of cytochrome c, detecting caspase-3 activity and detecting PARP degradation are effective determinants of apoptosis.

Furthermore, agents that cause the release of cytochrome c from the mitochondria of malignant cells can be concluded to be likely therapies for restoring at least some aspects of cellular control of programmed cell death.

Another apoptotic assay is the Annexin-V detection (Bio-Whitaker, Walkerville, Md.). Normally, phosphotidylserine (PS) is localized on the inner membrane of the plasma membrane. However, during the early stages of apoptosis, externalization of PS takes place. Annexin-V is a calcium binding protein which binds to PS and can be observed with annexin-V-FITC staining by flow cytometry (Martin et al., 1995). The ability of cells treated with the Acacia victoriae compounds described in this invention, to bind annexin-V, is taken as an indication that cells were undergoing apoptosis.

In other examples, the inventors have used PI-3-Kinase assay and to detect the apoptotic activity in cells treated with mixtures of the anti-cancer compounds isolated from Acacia victoriae. Phosphoinositide 3-kinase (PI3K), a cell membrane associated enzyme, is capable of phosphorylating the 3-position of the inositol ring of phosphatidylinositol, thus defining a new lipid signaling pathway in those cells where PI3K is active. When PI3K is active, a kinase called AKT is recruited to the cell membrane. AKT is the product of an oncogene which is catalytically activated after recruitment to the membrane. Fully activated AKT plays a crucial role in cell survival. The PI3K/AKT pathway provides a mechanism by which cells evade apoptosis. Thus, a means to inhibit PI3K in malignant cells, is a likely therapy for restoring at least some aspects of the cellular control of apoptosis.

Abnormal Proliferation is defined as a series of genetically determined changes that occur in mammalian cells in the pathological state known as cancer. This process eventually results in the loss of control of apoptosis in cancer cells. This can occur in steps, generally referred to as 1. initiation, which is defined as the stage when an external agent or stimulus triggers a genetic change in one or more cells, and 2. promotion, which is defined as the stage involving further genetic and metabolic changes, which can include inflamation. During the "promotion stage", cells begin a metabolic transition to a stage of cellular growth in which apoptosis is blocked.

Malignant cells are defined as cancer cells that escape normal growth control mechanisms through a series of metabolic changes during the initiation and promotion stages of the onset of malignancy. These changes are a consequence of genetic alterations in the cells (either activating mutations and/or increased expression of protooncogenes—and/or inactivating mutations and/or decreased expression of one or more tumor suppressor genes). Most oncogene and tumor suppressor gene products are components of signal transduction pathways that control cell cycle entry or exit, promote differentiation, sense DNA damage and initiate repair mechanisms, and/or regulate cell death programs. Cells employ multiple parallel mechanisms to regulate cell growth, differentiation, DNA damage control, and apoptosis. Nearly all tumor and malignant cells have mutations in multiple oncogenes and tumor suppressor genes.

Extract or fraction refers to consecutive samples collected from tissues by various means. These "extracts" or "fractions" may be analyzed for the desired anti-tumor activity, and further "extracted" or "fractionated" to produce successively more pure components corresponding to the, active component.

Triterpene or Triterpene Glycoside refers to the novel and/or biologically active saponin compounds identified herein from Acacia victoriae. The triterpene or triterpene glycosides need not be isolated from Acacia victoriae, as one of skill in the art, in light of the instant disclosure, could isolate the compounds from related species, or chemically synthesize analogs of the triterpenes and triterpene glycosides disclosed herein. "Triterpenes" of this invention include the saponin compounds described herein which have at least a triterpene unit(s) and, in the case of triterpene glycosides, a sugar or saccharide. These terms also refer to compounds containing additional moieties or chemical functionalities including, but not limited to, monoterpene units as will be apparent from the rest of the specification. Thus, triterpenes of this invention also include the aglycones formed by hydrolysis of sugar units and further includes other modification of the triterpenoid compounds, whereby the modifications do not destroy the biological activity of the compounds.

XII. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Preliminary Screening and Purification of Anti-Tumor Active Constituents from *Acacia victoriae*

Sixty plant species were chosen from the Desert Legume Project (DELEP) with the goal of identifying novel compounds having beneficial biological activities. The DELEP (University of Arizona, Tucson) is a collection of desert legume species developed through a collaboration between the University of Arizona and the Boyce Thompson Southwestern Arboretum. Experimental field samples were collected from each of the plant species, air-dried for 3-4 days, ground to three millimeter particle size with a Wiley mill (3 mm screen size) and extracted two or three times by percolation with a 1:1 mixture of dichloromethane (DCM) and methanol (MeOH). Each percolation extraction proceeded for at least 5 hours and often continued overnight. The majority of the extracted biomass was collected from the first two percolations. The biomass was then washed with a volume of methanol equal to half the void volume, and the crude extract contained in the methanol aliquots isolated. The samples were typically isolated and prepared for bioassay by removing the methanol in vacuo, passing the aqueous phase through RP-C 18 particles, recovering the active constituents in MeOH, and then rotovapping the MeOH to collect the extract as a solid. The crude extract was then resuspended in H20, DMSO or mixtures thereof (less polar compounds were resuspended in DMSO, while more polar compounds were resuspended in water or water and DMSO mixtures; aglycones were resuspended in DMSO).

Each of the extracts was then screened against a panel of human tumor and non-tumor cells including human ovarian cancer cell lines, T-leukemic cells, human epidermoid cells, human breast cancer cells, human prostate cancer cells, human foreskin fibroblast cells, human endothelial cells, and human renal cancer cells. The cells were first plated in 96-well plates for 18-24 hours at 37° C. The cells were then exposed to varying concentrations of the plant extracts, and incubated for 72 hours at 37° C., and stained with either MTT (3-(4,5-dimethylethiazol-2-yl)-2,5-diphenyl tetrazolium bromide; Sigma Chemical Co.) for 4 hours or crystal violet (Sigma Chemical Co.) for 20 minutes at room temperature. The MIT plates received lysis buffer (20% sodium dodecyl sulfate in 50% DMF) and were incubated for an additional 6 hours before taking an OD reading at 570 nm. The crystal violet plates were washed, dye was extracted for 3-4 hours with Sorenson's buffer (0.1 M sodium citrate (pH 4.2), 50% v/v ethanol), and the plates were read at 570-600 nm (Mujoo et al., 1996). Cytotoxicity of the screened extracts was indicated by comparing the OD readings between the treated media alone and the cells treated with the plant extract. Percent cytotoxicity was calculated by 100-% of control, where % of control=[((OD of cells treated with plant extract (treated sample))/(OD of cells exposed to media alone (untreated sample)))×100].

Of the initial screening, one plant extract showed potent growth inhibition of cancer cells while demonstrating little toxicity to normal human fibroblast cells. This extract, coded UA-BRF-004-DELEP-F001, was isolated from the leguminous plant *Acacia victoriae*. The extract exhibited an $IC_{50}$ at approximately 12 µg/ml (SKOV-3) 26 µg/ml (OVCAR-3) and 13 µg/ml (HEY) using human ovarian cancer cell lines; at greater than 50 µg/ml (A375-M) and at about 38 µg/ml (HS294T) with human melanoma cells; at about 15 µg/ml for human epidermoid cells (A431); and at greater than 50 µg/ml for the breast cancer cell line MDA-468 (FIG. 1) (see Example 13 for a description of cell lines). Among normal human foreskin fibroblast cells (FS) and mouse fibroblast cells (L929) treated with the same extract, no cytotoxicity was observed.

Figure 15:
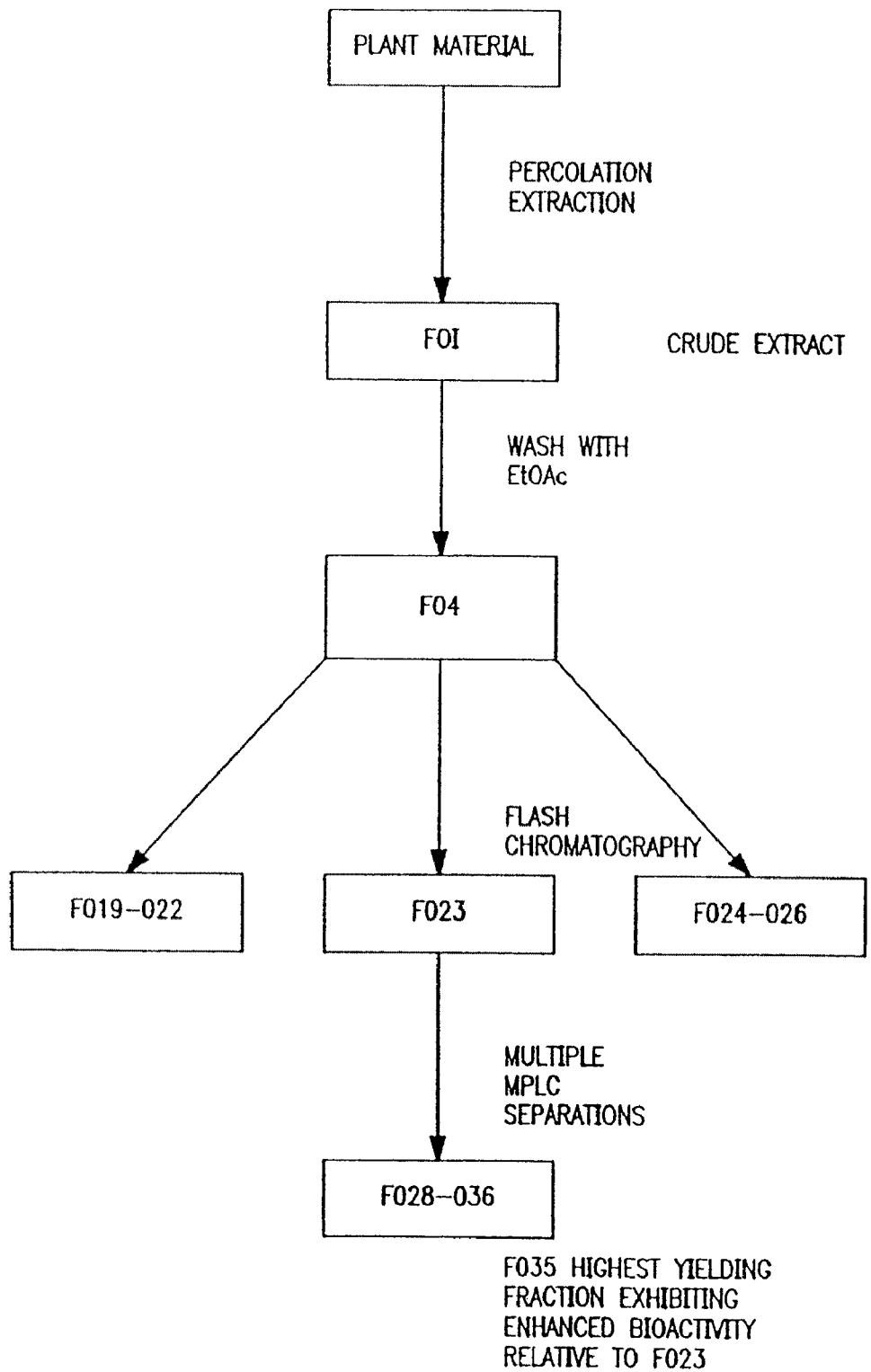
FIG. 15: Shows the initial strategy employed for purifying and isolating the biologically active triterpene compounds from *Acacia victoriae*.
Figure 16:
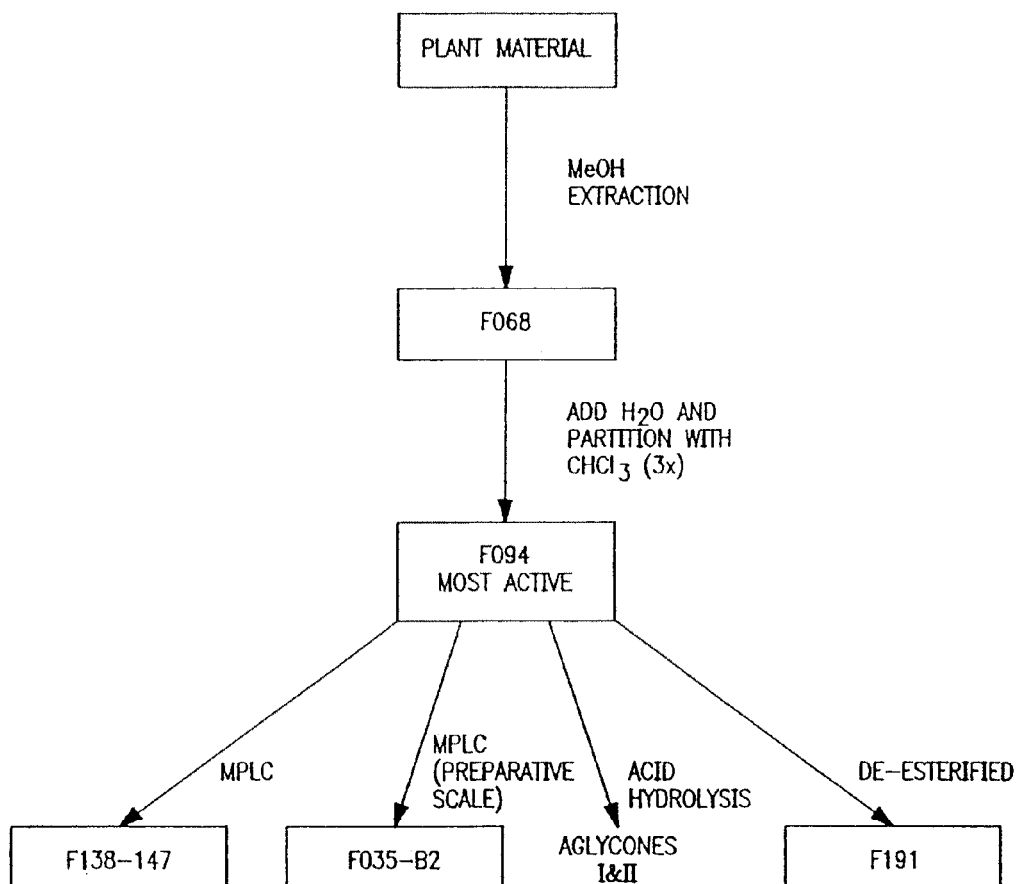
FIG. 16: Shows a general, improved scheme for the purification, isolation, and characterization of the active constituents from *Acacia victoriae*.

This extract appeared to contain a mixture of many constituents by TLC. Therefore, preliminary efforts focused on purifying this extract to isolate the active constituents responsible for the selective cytotoxicity. Chromatographic fractions enriched in the active constituents were isolated from original extract according to the general scheme shown in FIG. 15.

The original extract, UA-BRF-004-DELEP-F001, was prepared from 538 g of plant material from *Acacia victoriae* by percolation (twice) as described above. The extract was then dried in vacuo yielding approximately 52.0 g of powder. Then, 51.5 g of the dried material was treated 3 times with 1 L ethyl acetate ("EtOAc"). Approximately 15.75 g of the EtOAc soluble material was subject to column chromatography on silica gel (1.5 kg). Fifty-four 670 ml subfractions eluted employing increasingly polar mixtures of hexane, EtOAc, and MeOH. The 54 subfractions were collected into thirteen separate fractions, labeled as UA-BRF-004-DELEP-F006 to UA-BRF-004-DELEP-F018. These fractions were then screened for anti-tumor activity using the procedure described above. None of the fractions examined demonstrated the potent anti-tumor activity observed in UA-BRF-004-DELEP-F001.

The EtOAc insoluble material (approximately 34.7 g) was also subject to chromatography on silica gel (1.7 kg). Fifty-one 670 ml subfractions and three additional subfractions totaling 21 L were eluted employing increasingly polar mixtures of DCM, MeOH and water. These subfractions were collected into eight separate fractions labeled UA-BRF-004-DELEP-F019 to UA-BRF-004-DELEP-F026, according to Table 6.

TABLE 6

Elution of fractions UA-BRF-004-DELEP-F019 to UA-BRF-004-DELEP-F026

| Fraction Identifier | Collected From Subfractions[1] | Total Weight (mg) | Eluent |
|---|---|---|---|
| F019 | 1-13 | 1015 | 5% MeOH/DCM (1-6) 10% MeOH/DCM (7-12) 20% MeOH/DCM (13) |
| F020 | 14-16 | 723 | 20% MeOH/DCM |
| F021 | 17-19 | 3080 | 20% MeOH/DCM (17-18) 35% MeOH/DCM (19) |
| F022 | 20-22 | 4618 | 35% MeOH/DCM |
| F023 | 23-34 39-40 | 17216 | 35%-50% MeOH/DCM (23-34) 65% MeOH/DCM (39) 100% MeOH (40) |
| F024 | 35-38 41-51 | 3030 | 65% MeOH/DCM (35-38) 100% MeOH (41-51) |
| F025 | 9 L and 6 L subfractions | 3980 | MeOH (9 L) 20% water/MeOH (6 L) |
| F026 | 6 L subfraction | 4507 | 20% water and 1% HCOOH in MeOH |

[1]Each subfraction consisted of 670 ml unless otherwise indicated.

Figure 2:
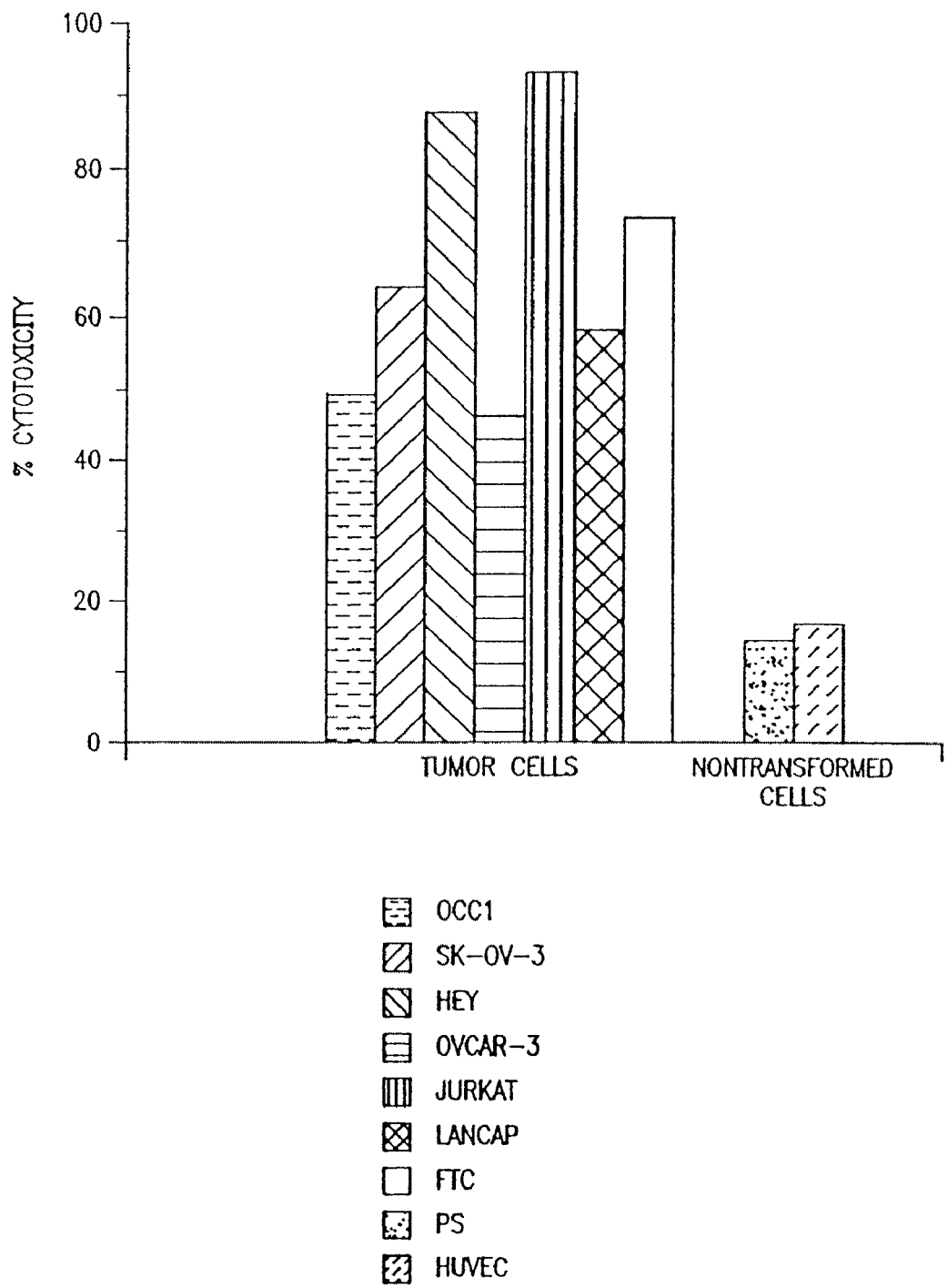
FIG. 2: Effect of UA-BRF-004-DELEP-F023 (Fraction 23) on transformed and nontransformed cell lines.

Each of the fractions were then screened for anti-tumor activity against a panel of human tumor cells as described above for the crude extract. One of the fractions, UA-BRF-004-DELEP-F023, exhibited an anti-tumor activity which was more potent than that of UA-BRF-004-DELEP-F001. These results revealed that 6 µg/ml of fraction UA-BRF-004-DELEP-F023 exhibited 50% (OCCl), 63% (SKOV-3), 85% (HEY), and 48% (OVCAR-3) cytotoxicity on human ovarian cancer cells; approximately 60% cytotoxicity on human prostate cancer cells (LNCaP); about 92% cytotoxicity on leukemic cells (Jurkat) and about 73% cytotoxicity on fresh human ovarian cancer cells from the ascites of patients (FTC). Bioassays of non-transformed cells revealed an $IC_{50}$ of 10.6 µg/ml for FS cells and 23 µg/ml for HUVEC cells (FIG. 2).

The biologically active component(s) in UA-BRF-004-DELEP-F023 were further purified by multiple reversed phase mode (RP) medium pressure liquid chromatographic (MPLC) separations to aid in the isolation and characterization of the active component(s). The samples, were eluted from degassed mixtures of increasing concentrations of acetonitrile (ACN) in water in 4 L increments of 10% according to the following steps: 0, 10%, 20%, 30%, 40% ACN/water. Then a 2-4 L fraction was eluted with MeOH. Ten fractions were collected after repeated runs, labeled UA-BRF-004-DELEP-F027 to UA-BRF-004-DELEP-F036, according to Table 7.

TABLE 7

Elution of Fractions UA-BRF-004-DELEP-F027 to UA-BRF-004-DELEP-F036

| Fraction Identifier | Total Weight (g) | Eluent |
|---|---|---|
| F027 | 6.95 | 0-20% ACN in water |
| F028 | 0.99 | 30-40% ACN in water |
| F029 | 1.46 | 30-40% ACN in water |
| F030 | 0.86 | 30-40% ACN in water |
| F031 | 0.15 | 30-40% ACN in water |
| F032 | 1.01 | 30-40% ACN in water |
| F033 | 0.54 | 30-40% ACN in water |
| F034 | 0.50 | 30-40% ACN in water |
| F035 | 2.19 | 30-40% ACN in water |
| F036 | 1.17 | 30-40% ACN in water |

Several of these fractions appeared similar by TLC. One'of the higher yielding fractions, UA-BRF-004-DELEP-F035 (Fraction 35), was found to exhibit potent anti-tumor activity.

Figure 3:
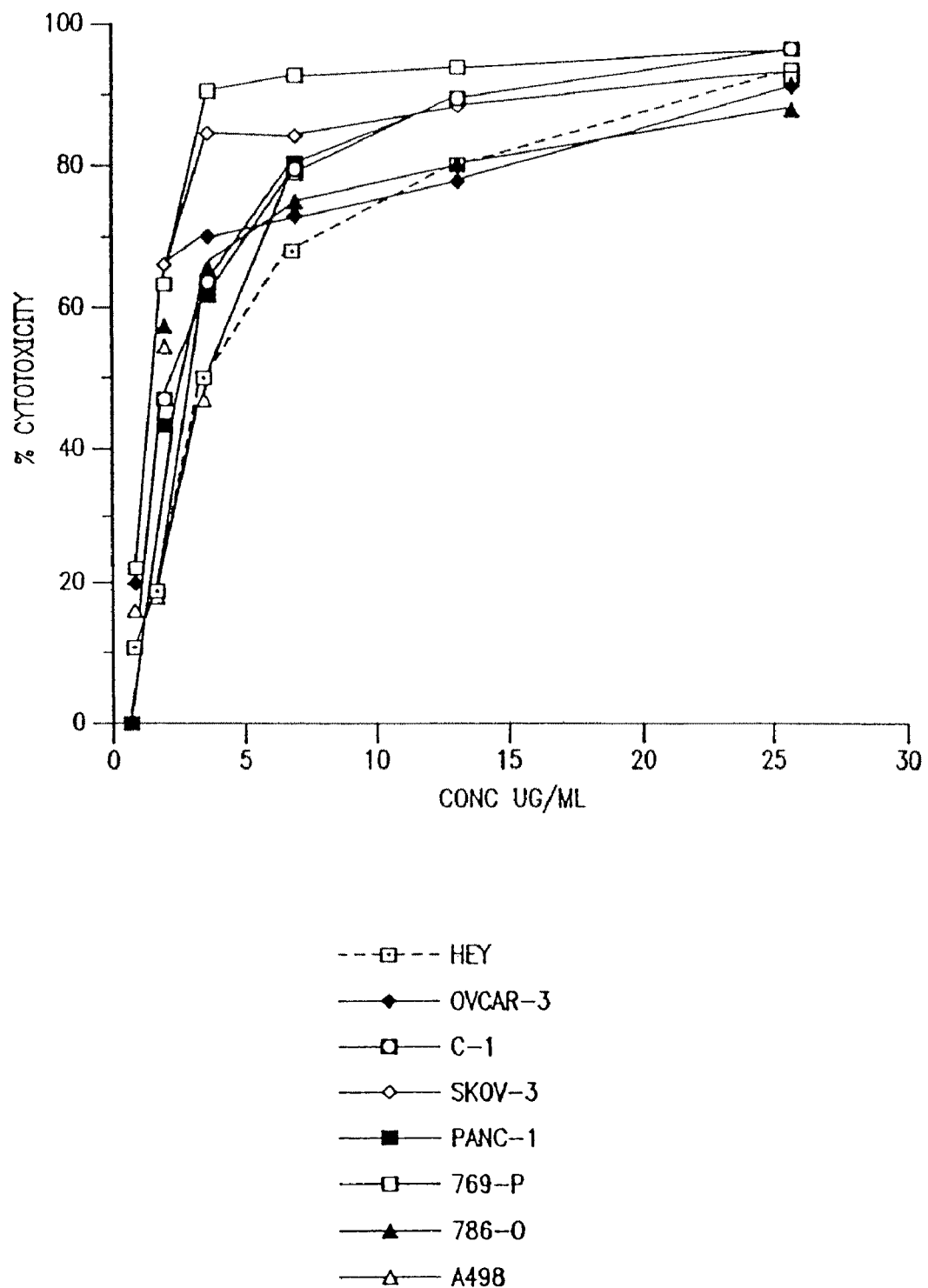
FIG. 3: Effect of Fraction 35 ("UA-BRF-004-DELEP-F035" or "F035") on human tumor cell lines.
Figure 4:
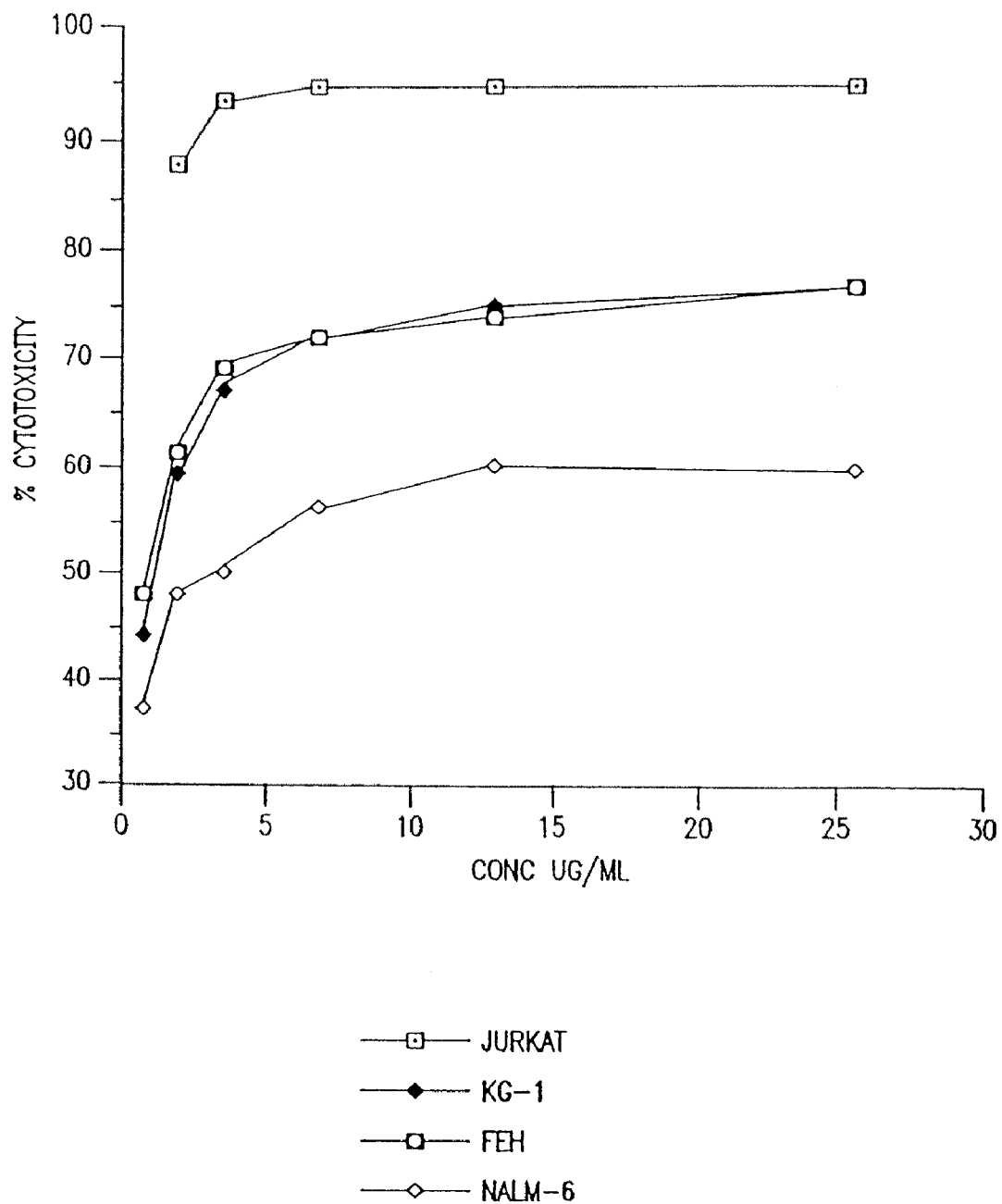
FIG. 4: Effect of Fraction 35 on Leukemia cell lines.

The screening of UA-BRF-004-DELEP-F035 for anti-tumor activity revealed an $IC_{50}$ at 3.0, 1.2, 2.0 and 3.5 μg/ml, respectively, against the ovarian cancer cell lines HEY, SKOV-3, OVCAR-3 and C-1 (cisplatin resistant OVCAR-3); an $IC_{50}$ of 2.4 μg/ml against pancreatic cancer cells (Panc-1); an $IC_{50}$ of 1.2 pg/ml, 3.0 μg/ml, and 3.7 μg/ml, respectively for the renal cancer cell lines 769-P, 786-0, and A498; an $IC_{50}$ of 130 ng/ml for Jurkat T-leukemic cells; and an $IC_{50}$ between 1-3 μg/ml for the B-leukemic cell lines KG1, REH and NALM-6 (FIG. 3, FIG. 4). As shown in Table 8, purification of the crude plant extract increased the bioactivity dramatically.

TABLE 8

Cytotoxicity Of Crude Extract Versus UA-BRF-004-DELEP-F035

| | $IC_{50}$ (μg/ml) | |
|---|---|---|
| Human Cancer Cells | crude extract | UA-BRF-004-DELEP-F035 |
| HEY | 12 | 3.0 |
| SKOV-3 | 25 | 1.2 |
| OVCAR-3 | 25 | 2.0 |
| MDA-468 | 50 | 9.0 |

Fraction 35 exhibited an $IC_{50}$ of approximately 4.7 μg/ml to normal human FS cells and an $IC_{50}$ of approximately 13.3 μg/ml to normal human Hs27 cells. When the effect of Fraction 35 (F035) was evaluated on normal human erythroid and myleoid colonies (cells isolated from bone marrow), 12-18% inhibition was observed at 3.0 μg/ml (Table 9).

TABLE 9

Effect of Fraction 35 on Erythroid and Myeloid Colonies

| | Erythrocyte (# of colonies) | Percent inhibition | Myleoid (# of colonies) | Percent Inhibition |
|---|---|---|---|---|
| untreated | 261 | — | 111 | — |
| F035 (30 μg/ml) | 16 | 94 | 53 | 52 |
| F035 (3 μg/ml) | 212 | 18 | 97 | 12 |
| F035 (0.3 μg/ml) | 248 | 5.0 | 119 | 7 (stimulation) |

In light of the above findings indicating the potent anti-tumor activity of Fraction 35, a bioassay was conducted as described above using concentrations of Fraction 35 as low as 0.095 μg/ml. In this study, varying concentrations of Fraction 35 were used against an expanded panel of tumor lines. The results of the screening indicate that even at concentrations of 1.56 μg/ml Fraction 35 exhibited potent anti-tumor activity against a number of cell lines (Table 10).

TABLE 10

Cytotoxicity of Varying Concentrations of UA-BRF-004-DELEP-9F035 Against Different Tumor Cell Lines.

| UA-BRF-004-DELEP-F035 | 50 μg/ml | 25 μg/ml | 12.5 μg/ml | 6.25 μg/ml | 3.12 μg/ml | 1.56 μg/ml | 0.78 μg/ml | 0.39 μg/ml | 0.195 μg/ml | 0.095 μg/ml |
|---|---|---|---|---|---|---|---|---|---|---|
| SKOV-3 | 94% | 83.40% | 78.50% | 71% | 54% | 27% | 0% | 0% | 0% | |
| OVCAR-3 | 95% | 92.80% | 91% | 87% | 79% | 46% | 9% | 21.40% | 18% | |
| C-1 (OVCAR-3 VARIANT) | 97% | 71% | 87% | 77% | 59% | 29% | 0% | 0% | 0% | |
| HEY | 97% | 79.10% | 53.90% | 43.30% | 19.20% | 0% | 0% | 0% | 0% | |
| C-2(HEY VARIANT) | 96% | 93.20% | 90.50% | 88.90% | 86.80% | 82.50% | 73.40% | 50% | 36.10% | |
| A-8(HEY VARIANT) | 97.20% | 95.70% | 94.80% | 89% | 75.00% | 59.30% | 18% | 0% | 0% | |
| MCF-7 | 79.70% | 23% | 5% | 3.10% | 8.10% | 17.20% | 8.60% | 17.40% | 19.20% | |
| BT-20 | 83% | 90% | 0% | 4% | 12.50% | 15.50% | 21.30% | 24% | 34% | |
| MDA-MB-453 | 98.40% | 97.20% | 94.60% | 89.90% | 85.40% | 81.60% | 65.70% | 54.90% | 38.50% | |
| MDA-468 | 96.50% | 93.80% | 82% | 65% | 39% | 8% | 8% | 8% | 8% | |
| SKBR-3 | 83.90% | 62.70% | 51.70% | 47.80% | 45.20% | 39.60% | 35.90% | 28.60% | 21.90% | |
| PANC-1 | 97.30% | 90.20% | 66.80% | 30.40% | 0% | 0% | 0% | 0% | 0% | |
| 769-P | 96.80% | 97% | 90% | 95% | 94.00% | 91.70% | 63% | 18% | 10% | 17.80% |
| 786-O | 97.90% | 89% | 80.30% | 75% | 66% | 32% | 0% | 0% | 0% | |
| A-498 | 99% | 97% | 95.50% | 80% | 47% | 19% | 16% | 15% | 14% | |
| LLC-1 | 84.70% | 42.70% | 17.80% | 6.60% | 10.70% | 10.90% | 3.80% | 6.80% | 0% | |

TABLE 10-continued

Cytotoxicity of Varying Concentrations of UA-BRF-004-DELEP-9F035 Against Different Tumor Cell Lines.

| UA-BRF-004-DELEP-F035 | 50 µg/ml | 25 µg/ml | 12.5 µg/ml | 6.25 µg/ml | 3.12 µg/ml | 1.56 µg/ml | 0.78 µg/ml | 0.39 µg/ml | 0.195 µg/ml | 0.095 µg/ml |
|---|---|---|---|---|---|---|---|---|---|---|
| A549 | 96.60% | 91.10% | 59.70% | 34.80% | 21.20% | 15.60% | 0% | 0% | 0% | |
| JURKAT | 88.40% | 88.70% | 88.80% | 89.60% | 88.60% | 88.50% | 80% | 69.30% | 46.60% | 0% |
| Hs27 | 88% | 83% | 47% | 0% | 6% | 11% | 11% | 13% | 18% | |
| FS FIBRO | 78.30% | 74.70% | 73.70% | 66.50% | 42.30% | 0% | 0% | 16% | 23.20% | |
| HL-60 | 63.00% | 22.00% | 30.00% | 25.00% | 0.00% | 0.00% | 0.00% | 0.00% | 0% | 0% |
| MDA-MB-435 | 96.50% | 96.40% | 97% | 96% | 94% | 84.70% | 40.60% | 15% | 14.70% | |
| DOV-13 | 95.80% | 92.30% | 86.70% | 77.80% | 57.50% | 14.20% | 17.50% | 11.10% | 12.20% | 17.20% |
| MCF-10A | 97.50% | 11.70% | 0% | 1% | 0% | 0% | 0% | 0% | 0% | |
| MCF-10F | 97.70% | 5.80% | 0% | 0% | 0% | 0% | 0% | 0% | 0% | |
| KG-1 | 77% | 75% | 72% | 67% | 59% | 44% | 35% | 13% | 0% | 0% |
| OCl-2 | 46.40% | 21% | 12% | 12.30% | 9% | 12% | 3% | 0% | 0% | 0% |
| OCl-3 | 71% | 60% | 45% | 41% | 30% | 5.60% | 0% | 0% | 0% | 0% |

Example 2

Procedures for Isolating Active Constituents from *Acacia victoriae*

A procedure was developed for the direct preparation of fractions containing the active constituents contained in UA-BRF-004-DELEP-F035, isolated during the preliminary purification detailed in Example 1. Approximately 9665 g of freshly collected pod tissue from *Acacia victoriae* was ground in a hammer mill with a 3 mm screen and then extracted with 80% MeOH in $H_2O$ (3×) followed by filtration. 8200 g of bagasse was discarded. The three washings were collected separately and assigned fraction identifiers as follows: F068 in 21.5 L (first wash); F069 in 24 L (second wash); and F070 in 34.3 L (third wash). F068 was further purified by partitioning into 1 L aliquots, adding 400 ml $H_2O$ to each aliquot and washing with $CHCl_3$ (2×250 ml). The combined polar phases (28.5 L) were assigned the fraction identifier of F078 and the combined organic phases F079 (yielding 42.g after removal of the organic solvent by rotovap).

The MeOH was removed from F078 in vacuo and F078 was further fractionated by RP MPLC using a 29×460 mm column loaded with 530 g recovered Bakerbond RP-C18, 40 µm particles. 500 ml of aqueous solution was aspirated onto the column and fractions collected according to Table 11.

TABLE 11

Elution of Fractions F091 to F094.

| Fraction Identifier | Volume Collected (L) | Total Weight (g) | Eluent | Comments |
|---|---|---|---|---|
| — | 4 | — | 100% water | Sugars and some strong RBC lysis component |
| F091 | 4 | ~40 | 10% ACN in water | 19.6 g obtained from runs 16-29 |
| F092 | 4 | 89 | 20% ACN in water | Flavonoids |
| F093 | 4 | 351 | 30% ACN in water | Light fluffy solid, slight respiratory irritant |
| F094 | 1.3 | 577 | 100% MeOH | Fine powder, respiratory irritant |

Each fraction was then desiccated by removal of MeOH, passing over C-18 particles, recovering in MeOH, and isolated as a solid in vacuo. The solid was resuspended in water and subject to testing for anti-tumor effects (for some less polar fractions, DMSO was added to the water; aglycones were resuspended in DMSO). The results indicated that the biological activity of the 100% MeOH eluent, designated F094 was essentially equivalent to that of fraction similarity of fractions F094 and F035 was confirmed by TLC and HPLC, although F094 appeared to contain additional components.

TABLE 12

Cytotoxicity of Varying Concentrations of F094 Against Different Tumor Cell Lines.

| UA-BRF-004Pod-DELEP-F094 | 50 µg/ml | 25 µg/ml | 12.5 µg/ml | 6.25 µg/ml | 3.12 µg/ml | 1.56 µg/ml | 0.78 µg/ml |
|---|---|---|---|---|---|---|---|
| 769-P | 96.60% | 93.30% | 92.80% | 92.40% | 88.30% | 63.20% | 21.80% |
| PANC-1 | 97% | 93.50% | 74.60% | 50.60% | 21.90% | 1.10% | 0% |
| HEY | 95% | 66.50% | 50.10% | 17.90% | 0% | 0% | 0% |
| MDA-MB-453 | 94.20% | 92.80% | 87.10% | 85% | 77.30% | 58.50% | 47% |
| JURKAT | 89.60% | 89.80% | 89.40% | 89.30% | 89% | 88% | 73.80% |

F094 was further fractionated according to Table 13 and analyzed by TLC and bioassayed in order to obtain the purified active component(s). The results of the bioassay of varying amounts of the obtained fractions (F138-F147) are given in Table 14.

TABLE 13

Elution of Fractions F138 to F147.

| Fraction Identifier | Subfractions Collected (ml) | Total Weight (g) | Eluent |
|---|---|---|---|
| — | 1-5 (160) | 1 | 60% MeOH in water |
| F138 | 6 (65) | 13 | 60% MeOH in water (6) |
|  | 7-8 (50) |  | 70% MeOH in water (7-8) |
| F139 | 9 (25) | 39 | 70% MeOH in water |
| F140 | 10 (20) | 93 | 70% MeOH in water |
| F141 | 11 (35) | 57 | 70% MeOH in water |
| F142 | 12 (50) | 54 | 70% MeOH in water |
| F143 | 13 (55) | 62 | 70% MeOH in water |
| F144 | 14 (70) | 29 | 70% MeOH in water |
| F145 | 15 (65) | 17 | 70% MeOH in water |
| F146 | 16 (80) | 54 | 80% MeOH in water |
| F147 | 17 (80) | 7 | 80% MeOH in water (17) |
|  | 18 (100) |  | 100% MeOH in water (18) |

TABLE 14

Bioassay of Fractions F137, F140, F142, F144, and F145

|  | 50 μg/ml | 25 μg/ml | 12.5 μg/ml |
|---|---|---|---|
| F137 |  |  |  |
| 769-P | 81.50 | 45.50 | 18.10 |
| Panc-1 | 74 | 11 | 0 |
| HEY | 6.2 | 0 | 0 |
| MDA-MB-453 | 76.70 | 38.80 | 26.80 |
| JURKAT | 67.70 | 67.50 | 67.80 |
| F138 |  |  |  |
| 769-P | 96.50 | 95.60 | 95.30 |
| Panc-1 | 95.50 | 93.45 | 73.50 |
| HEY | 65.30 | 58.30 | 21.50 |
| MDA-MB-453 | 96.10 | 94.20 | 92.5 |
| JURKAT | 87.50 | 88 | 87.50 |
| F139 |  |  |  |
| 769-P | 97.30 | 94.20 | 94.20 |
| Panc-1 | 96.60 | 94.10 | 86 |
| HEY | 89.70 | 65.80 | 60.50 |
| MDA-MB-453 | 95 | 95 | 91.90 |
| JURKAT | 88.50 | 88.50 | 88.50 |
| F140 |  |  |  |
| 769-P | 91.70 | 88.90 | 87.50 |
| Panc-1 | 95 | 94.60 | 92.50 |
| HEY | 95.40 | 72.10 | 62.80 |
| MDA-MB-453 | 86.20 | 80.20 | 75.20 |
| JURKAT | 68.40 | 67.80 | 68.10 |
| F141 |  |  |  |
| 769-P | 97.80 | 95.10 | 95 |
| Panc-1 | 96.80 | 95 | 85.60 |
| HEY | 96 | 68.80 | 60.6 |
| MDA-MB-453 | 95 | 94.50 | 94 |
| JURKAT | 88.50 | 88.40 | 88 |
| F142 |  |  |  |
| 769-P | 92.50 | 90.20 | 88.20 |
| Panc-1 | 96 | 93.60 | 88.60 |
| HEY | 98 | 74.80 | 66 |
| MDA-MB-453 | 86.10 | 75.40 | 72.90 |
| JURKAT | 67.90 | 67.10 | 66.30 |
| F143 |  |  |  |
| 769-P | 98.30 | 96.80 | 98.30 |
| Panc-1 | 96.70 | 94.70 | 85.60 |
| HEY | 98.50 | 73 | 64 |
| MDA-MB-453 | 96.70 | 95 | 94.10 |
| JURKAT | 88.00 | 88 | 88 |
| F144 |  |  |  |
| 769-P | 89.80 | 88.60 | 89.50 |
| Panc-1 | 96.60 | 93.80 | 90.90 |
| HEY | 98.50 | 75.30 | 62.20 |
| MDA-MB-453 | 86.70 | 78.50 | 75.80 |
| JURKAT | 65.70 | 65.70 | 65 |
| F145 |  |  |  |
| 769-P | 92 | 90.20 | 86.30 |
| Panc-1 | 96.70 | 91.40 | 84.80 |
| HEY | 97.50 | 82.30 | 58.60 |
| MDA-MB-453 | 85.40 | 74.40 | 48.90 |
| JURKAT | 67.90 | 68.40 | 68.60 |
| F146 |  |  |  |
| 769-P | 97.30 | 97.30 | 63.30 |
| Panc-1 | 97 | 88.90 | 43.40 |
| HEY | 97.60 | 70.50 | 22 |
| MDA-MB-453 | 95 | 94.80 | 78 |
| JURKAT | 88.60 | 88.20 | 88.10 |
| F147 |  |  |  |
| 769-P | 44.30 | 23.40 | 5 |
| Panc-1 | 40 | 11 | 0 |
| HEY | 0 | 0 | 0 |
| MDA-MB-453 | 70 | 50 | 57 |
| JURKAT | 86.30 | 84 | 78.70 |

Percent Growth Inhibition.

Although the above procedures focused on the isolation of active constituents from pods of *Acacia victoriae*, the active constituents may also be extracted from roots. In this case, the roots are ground for ½ hour and covered with 100% MeOH. The mixture is then filtered and diluted to 80% MeOH in water. If large amounts of roots are to be extracted, then it may be preferable to extract via percolation as described above. The reason for the differences in these extraction procedures is that roots are typically extracted fresh while the pods are often dried prior to extraction.

Example 3

Preparative Scale Procedure for Preparing Active Constituents from Fraction UA-BRF-004-DELEP-F094

A modified extraction/separation procedure was used for the scaled-up preparation of mixtures of active constituents from fraction UA-BRF-004Pod-DELEP-F094 (F094). This procedure was repeated multiple times, consistently yielding highly active fractions. Typically, 20-25 g of F094 or its equivalent was dissolved in 150-175 ml of 50% MeOH in $H_2O$ which was then aspirated onto a column ((26 mm×460 nun) +(70 mm×460 mm), RP-C18, 40 μm, 1200 g, equilibrated with 60% MeOH/$H_2O$). The fractions were eluted in steps of 8 L in 60% MeOH/$H_2O$; 7.5 L 70% MeOH/$H_2O$; and 2 L MeOH and assigned fraction identifiers as shown in Table 15. Fraction F035-B2 contains a mixture of the active components contained in F094, F133-136 (isolated from F093) and F138-147 (isolated from F094) as shown in FIGS. 18A-18F. F094 is an acceptable substitute for F035 with a one- to two-fold decrease in potency and F035-B2 has less potency than F094.

TABLE 15

Isolation of F035-B2.

| Fraction Identifier | Volume Collected (L) | Total Weight (g) | Eluent |
|---|---|---|---|
| F237 | 8 | 1.8 | 60% MeOH in water |
| F238 | 1 | 8 | 70% MeOH in water |
| F035-B2 | 3.5 | 80 | 70% MeOH in water |
| F239 | 3 | 19 | 70% MeOH in water |
| F240 | 2 | 20 | 100% MeOH in water |

Figure 18A:
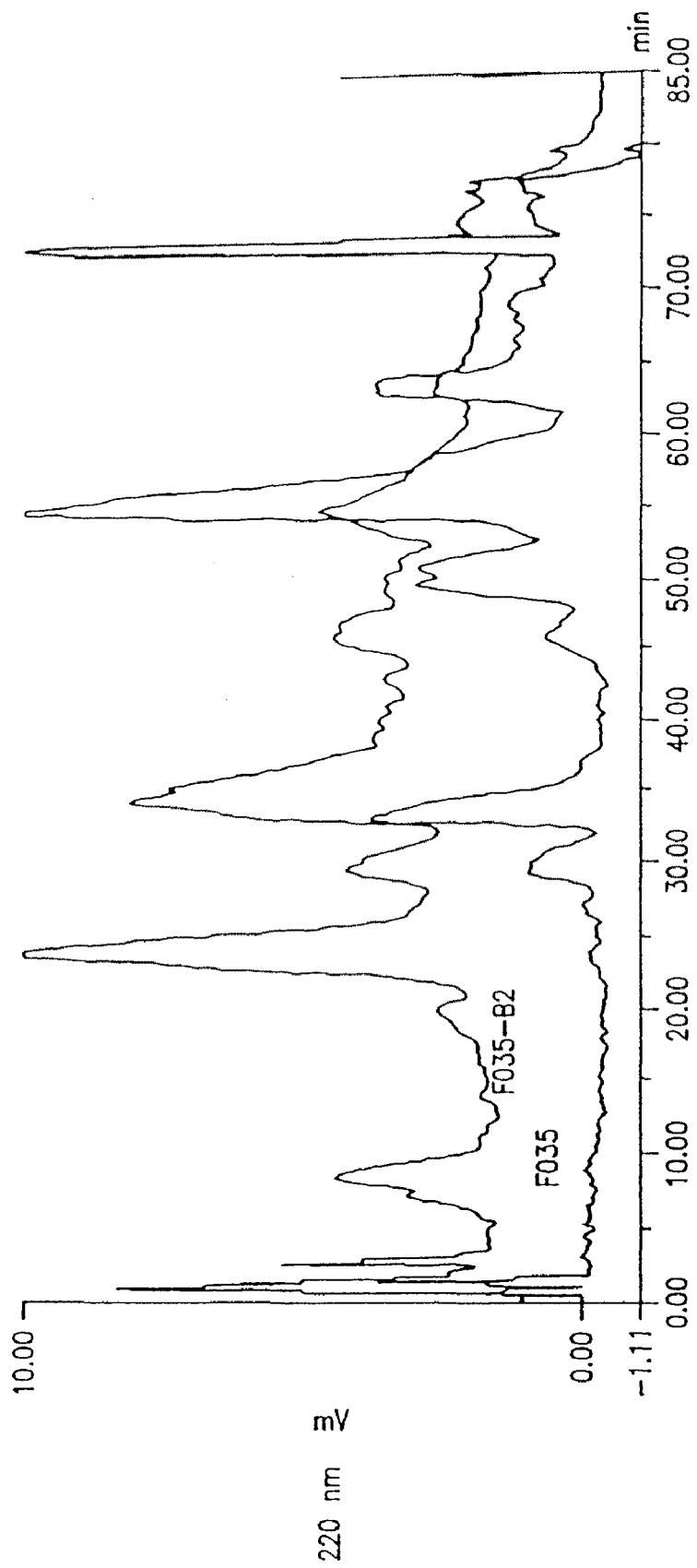
FIGS. 18A-F.
Figure 18B:
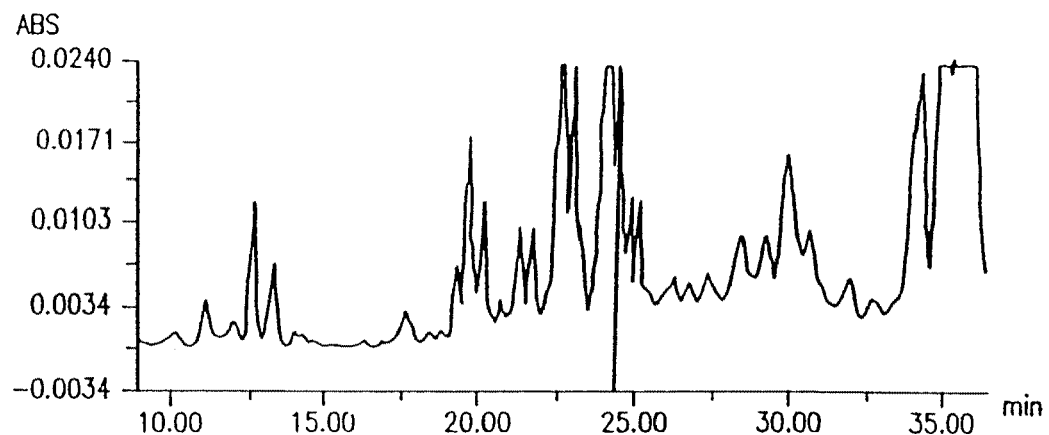
Figure 18C:
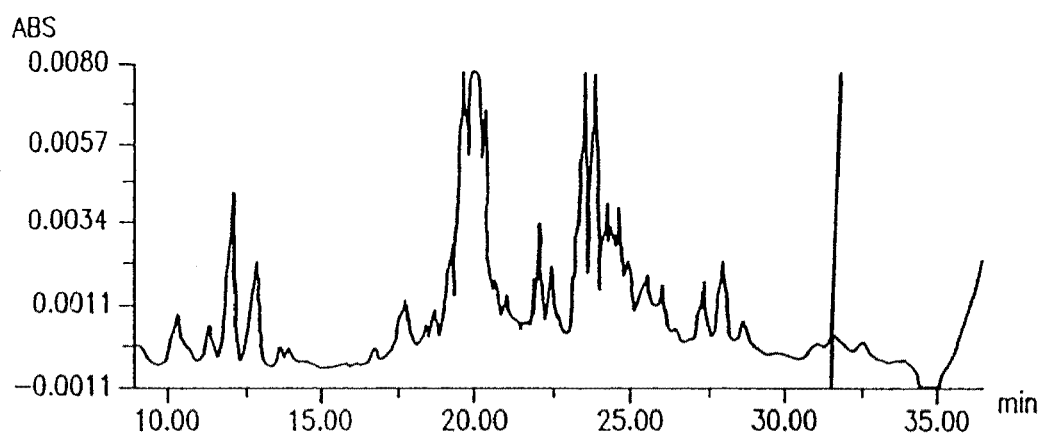
Figure 18D:
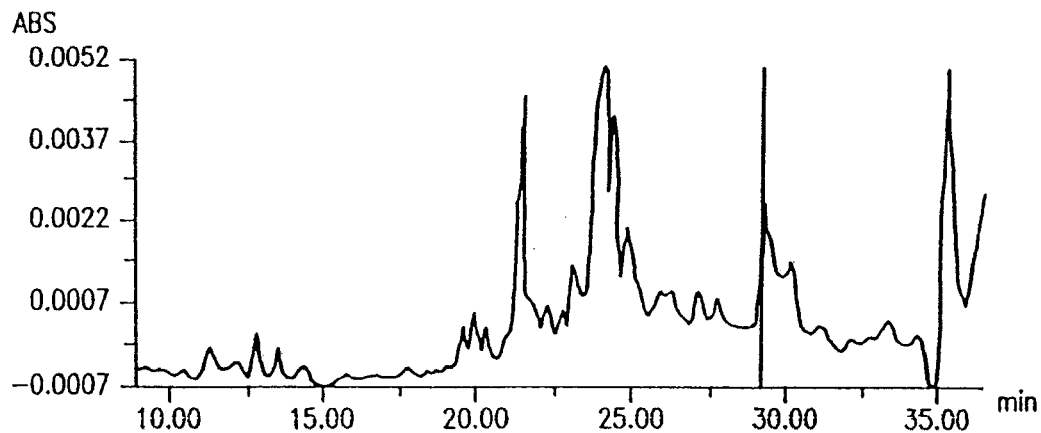
Figure 18E:
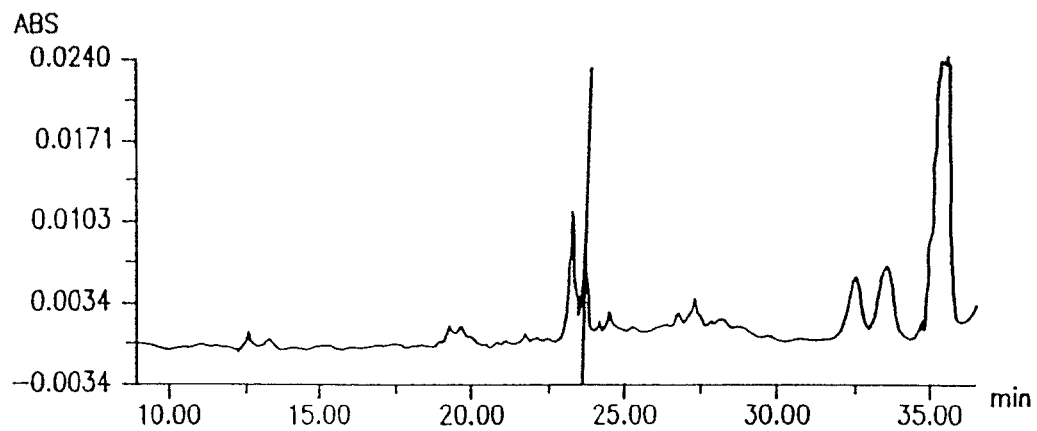
Figure 18F:
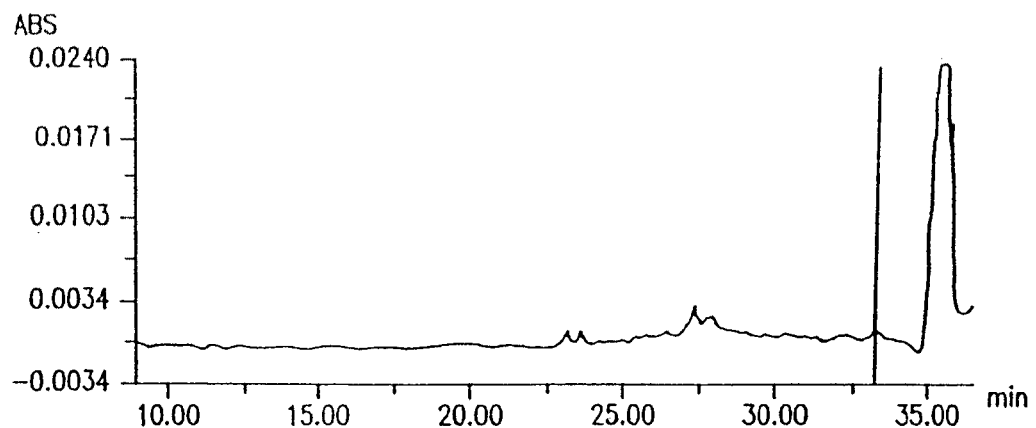

A procedure was designed by the inventors for the further purification of the active components in Fraction F035-B2 to give fractions having the analytical HPLC characteristics of UA-BRF-004-DELEP-F035. The procedure is as follows: Additional preparative HPLC is carried out on Fraction F035-B2 using 10 micron reversed phase chromatography columns to elute with step gradient mixtures of acetonitrile and water ranging from 26% acetonitrile in water up to 40% acetonitrile in water in 1-2% step gradient fashion, followed by a 100% acetonitrile wash and 100% methanol wash, which will produce a unique breakdown of F035-B2 into several fractions containing the 0 to 20 minute peaks (per standard six micron HPLC RP-18 analytical method), which are not contained in the original F035 fraction (FIG. 18A). The remaining fractions obtained provide one to three component fractionation of F035. As indicated by the testing above, fractions F139-F147 are similar to these fractions, with some degree of enhanced anti-tumor in certain cancer cell lines relative to others. The unique mixture of active components present in fraction F035 can be produced in bulk by modifying the original composition of the front end solvents between 16% and 26% acetonitrile in water followed by MPLC purification to produce multi-gram quantities of the equivalent of UA-BRF-004-DELEP-F035.

Further improvements to the above extraction procedure, as well as the other extraction procedures disclosed herein, may be realized by using tri-solvent mixtures of acetonitrile, methanol and water. The percentage ranges can be dynamically produced and optimized by anyone familiar with standard chromatographic techniques. Likewise, bonded phase silicas can be varied by using a combination of RP systems, including, but not limited to C-8, CN, dimethyl diol and C-18. In the final steps, even normal phase silica can be utilized for final purification procedures.

Example 4

Alternative Procedures for Isolating Active Constituents from *Acacia victoriae*

Fractions F094 (250 g), F035 (50 mg), and *Acacia victoriae* ground pods (1 Kg) (i.e. seedpod powder) were obtained as described above. The analytical methodology used to analyze fraction F094 and the subsequent fractionation of the F094 are described in this example.

4.1 Analytical Methodology

Several methods involving various C8 and C18 columns under gradient and isocratic conditions were tried to resolve fraction F094. The monitoring included both UV at 220 nm and evaporative light scattering detection (ELSD). Better peak resolution was seen with mobile phases containing trifluoroacetic acid (TFA). The method, called herein as *Acacia* 257, is described below. This method provides good resolution along with a short run time.

The HPLC was equipped with a diode array detector (DAD) or variable wavelength detector and a 4.6×150 mm Inertsil C18 3μ, column (MetaChem). The detector was set at 220 nm.

The following gradient was run.

| Time (min) | % Acetonitrile | % H$_2$O with 0.1% TFA |
|---|---|---|
| 0 | 30 | 70 |
| 36 | 36 | 64 |
| 42 | 42 | 58 |
| 42.1 | 30 | 70 |
| 47 | 30 | 70 |

Figure 25:
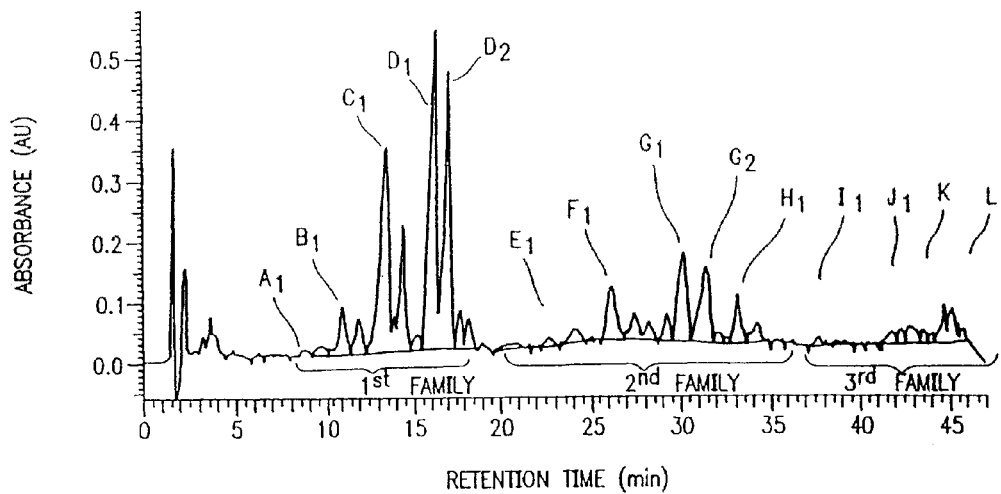
FIG. 25: HPLC separation of the constituents in F094.
Figure 26:
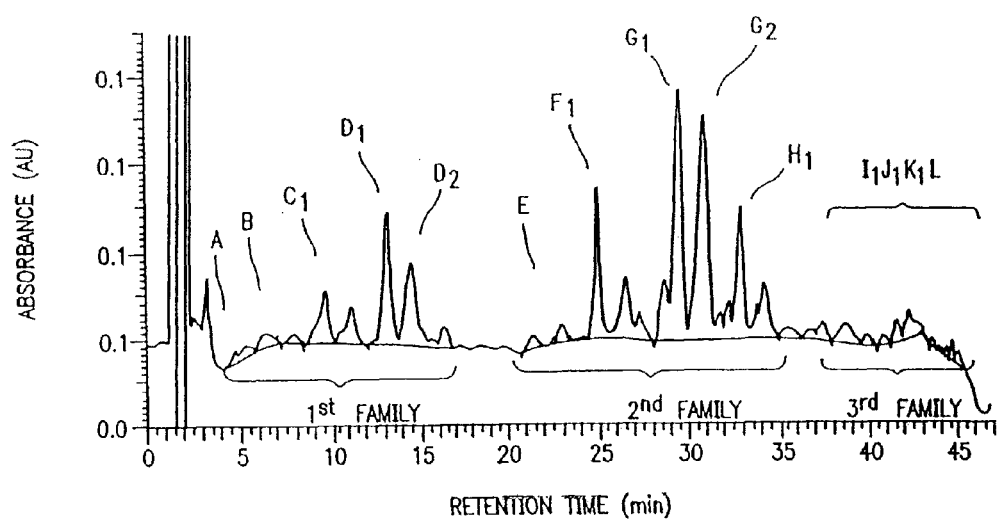
FIG. 26: HPLC separation of the constituents in F035.

FIG. 25 shows the chromatogram of F094 obtained by this method. F094 consists of three groups or families with a number of peaks in each family. Family-1 (8 to 20 min; peaks A-D), Family-2 (22 to 35 min; peaks E-H) and Family-3 (36 to 47 min; peaks I-L). Fraction F035 was also analyzed by this method, and the chromatogram is shown in FIG. 26. The peaks of the second family are more abundant in F035 compared to F094 where first family peaks are more abundant.

4.2 Fractionations 4.2.1 First Fractionation

Figure 27:
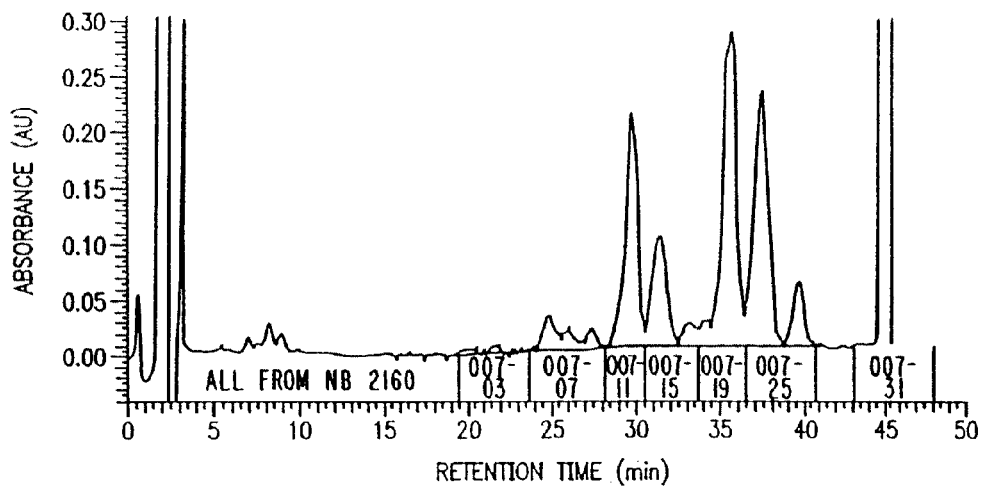
FIG. 27: First-fractionation by semi-prep HPLC of F094.

The first fractionation focused on the peaks in Family-1. A Symmetry C8 semi-prep column (7.8×300 mm, 7μ) (Waters) was employed for this purpose with a gradient elution program as shown below. Seven sub-fraction cuts were made as shown in FIG. 27. The last fraction cut (#2160-007-31) includes all peaks in both Family-2 and Family-3. These fractions as well as the starting material (F094) were sent for bioassay.

| Time (min) | % Acetonitrile | % H$_2$O with 0.1% TFA |
|---|---|---|
| 0.0 | 27 | 73 |
| 38.0 | 30 | 70 |
| 42.1 | 90 | 10 |
| 48.0 | 90 | 10 |
| 49.0 | 27 | 73 |
| 65.0 | 27 | 73 |

4.2.2 Second Fractionation

Figure 28:
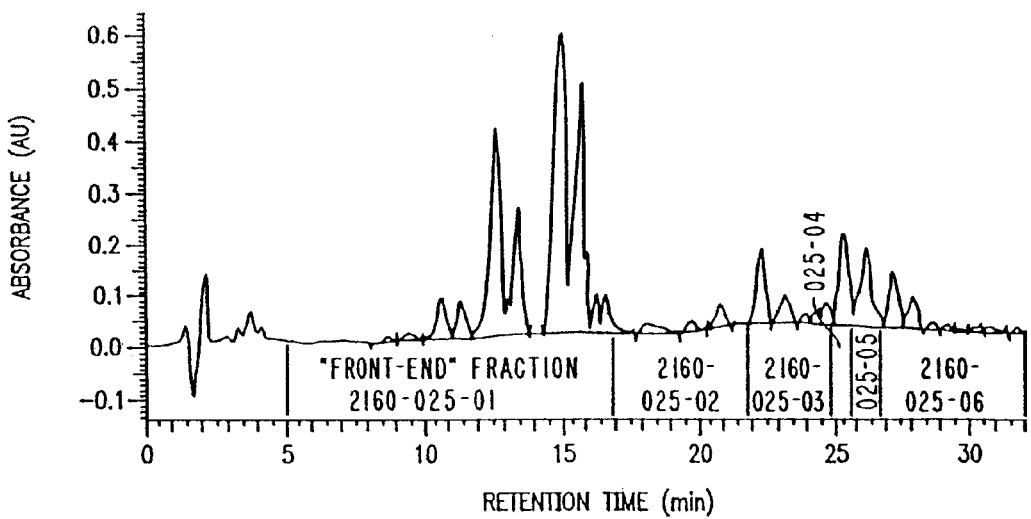
FIG. 28: Second-fractionation by semi-prep HPLC of F094.

The separation of the peaks in second family of compounds was the target of this fractionation. This was achieved with the usage of the same C8 semi-prep column. The mobile phase was isocratic 32% acetonitrile in water containing 0.1% TFA. The chromatographic trace indicating where seven fraction cuts were made is shown in FIG. 28. The first fraction cut here includes all the peaks in family-1.

4.2.3 Bioassays

The bioassay results of the sub-fractions from the first and second fractionations are shown Tables 16 and 17 respectively.

TABLE 16

Cytotoxicity in Jurkat cells of sub-fractions from First fractionation

| Fraction No. | Weight (mg)* | Cytotoxicity IC$_{50}$ (μg/ml) |
|---|---|---|
| 2160-007-03 | 2.7 | Not active |
| 2160-007-07 | 1.9 | Not active |
| 2160-007-11 | 1.3 | Not active |
| 2160-007-15 | 1.6 | Not active |
| 2160-007-19 (Peak D1) | 1.7 | 1.2 |
| 2160-007-25 (Peak D2) | 2.9 | 5.7 |
| 2160-007-31 | 3.2 | 1.3 |
| 2160-007-34 (FO94) | 9.3 | 0.17 |

*These weights are approximate ±20%

TABLE 17

Cytotoxicity in Jurkat cells of sub-fractions from Second fractionation

| Fraction No. | Weight (mg)* | Cytotoxicity IC$_{50}$ (µg/ml) |
|---|---|---|
| 2160-025-01 | 7.24 | 1.2 |
| 2160-025-02 | 4.74 | 2.8 |
| 2160-025-03 | 3.63 | 1.0 |
| 2160-025-04 (Peak G1) | 1.37 | 0.64 |
| 2160-025-05 (Peak G2) | 2.07 | 1.56 |
| 2160-025-06 | 3.64 | 0.33 |
| 2160-007-34 (F094) | 12.09 | 0.17 |

*These weights are approximate ±20%

Two purified triterpenoid glycosides, namely D1 and G1, were obtained from the *Acacia* fraction F094. Acid hydrolysis of D1 produces an aglycone.

4.4 Prep Scale Fractionation to Obtain D and G/H Region Peaks

Figure 29:
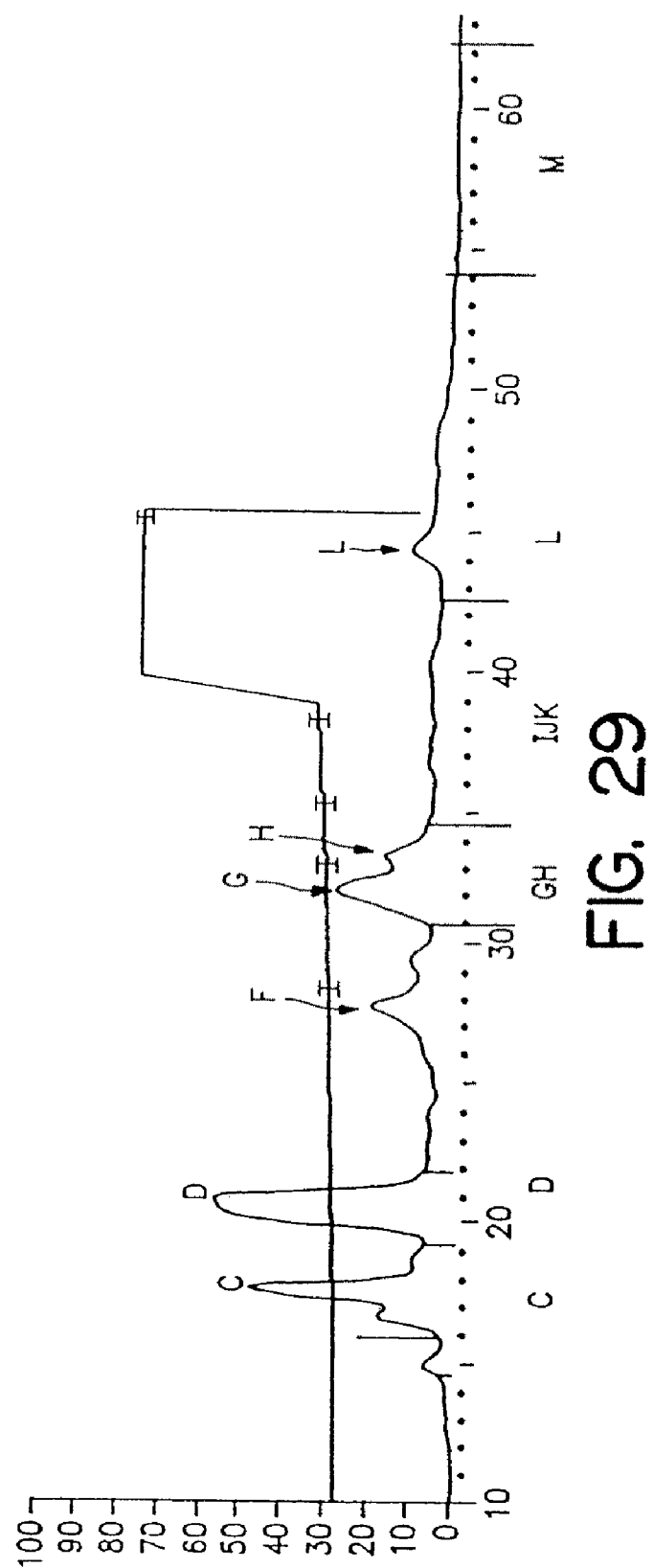
FIG. 29: Preparative -fractionation of F094.
Figure 30:
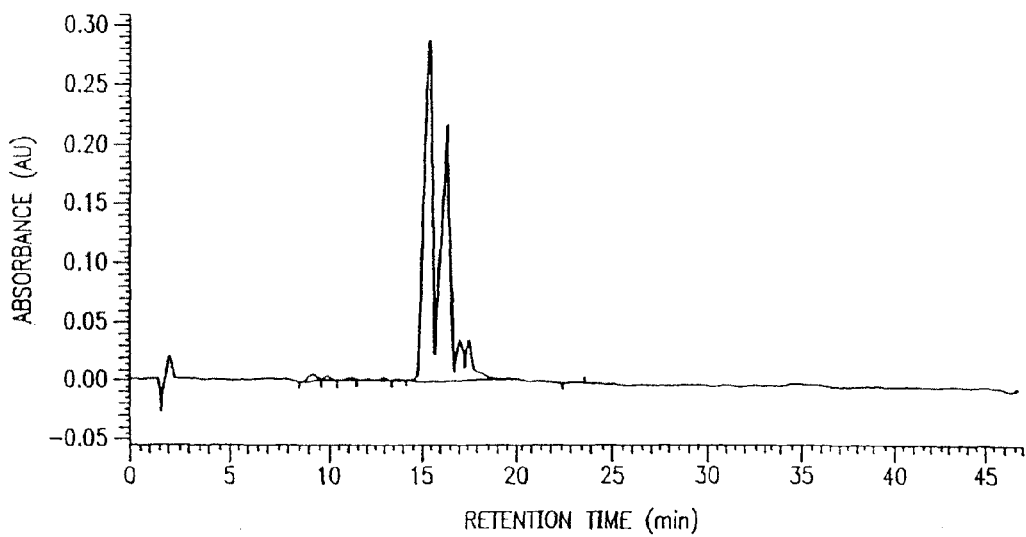
FIG. 30: Analysis of preparative-fraction D.
Figure 31:
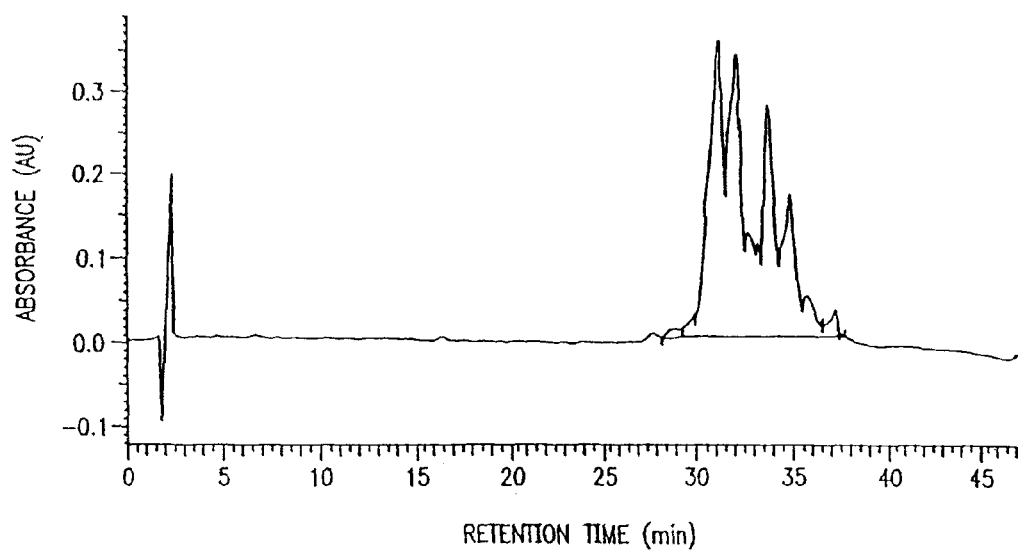
FIG. 31: Analysis of preparative-fraction G/H.

F094 (2.3 g) was fractionated on a HPLC Prep PFP (pentafluorophenyl) column (50×250 mm, 10 µm). The mobile phase was acetonitrile/water containing 0.1% trifluoroacetic acid (TFA) run in gradient mode from 27% to 32% acetonitrile over 38 min. As shown in FIG. 29 this method separated fractions containing D and G/H peaks. The fraction cuts from this prep run were sent for bioassays. The analytical assays of D and G/H are shown in FIGS. 30 and 31. The method used here is *Acacia* 257 and which was described earlier in the same section.

The fraction GM was further purified first on the PFP Prep column to obtain G1 with 68% chromatographic purity, and this material was further purified on a C-18 semi-Prep column to obtain pure G1.

About 100 mg of G/H mixture was loaded on to the same PFP column described before. The following gradient was run.

| Time (min) | % Acetonitrile | % H$_2$O with 0.1% TFA |
|---|---|---|
| 0 | 27 | 73 |
| 1 | 29 | 71 |
| 40 | 34 | 66 |

Figure 32:
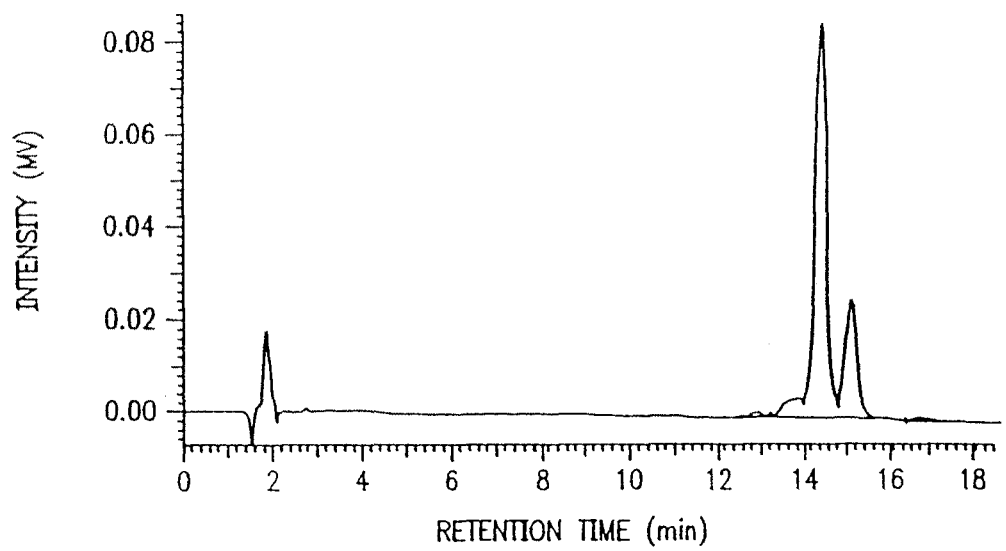
FIG. 32: Compound G1 after second PFP column purification.

Five fractions were collected (G1, G2, G3, H1 and H2). Analytical on G1 (FIG. 32) indicated a chromatographic purity of 68%. This fraction was further purified on a semi-prep column.

Figure 33:
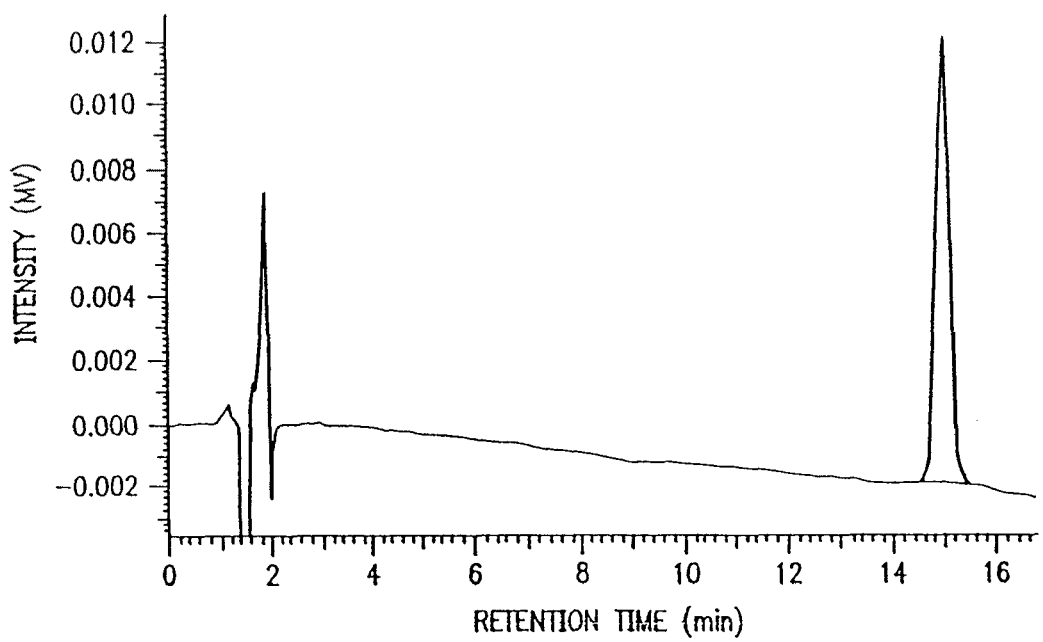
FIG. 33: Compound G1 after final C-18 purification.

A YMC C18-Aq column (10×250 mm, 5 µm) was employed. The mobile phase was 31% acetonitrile in water with 0.1% TFA. The final G1 product had a chromatographic purity of 100%. (FIG. 33).

Figure 34:
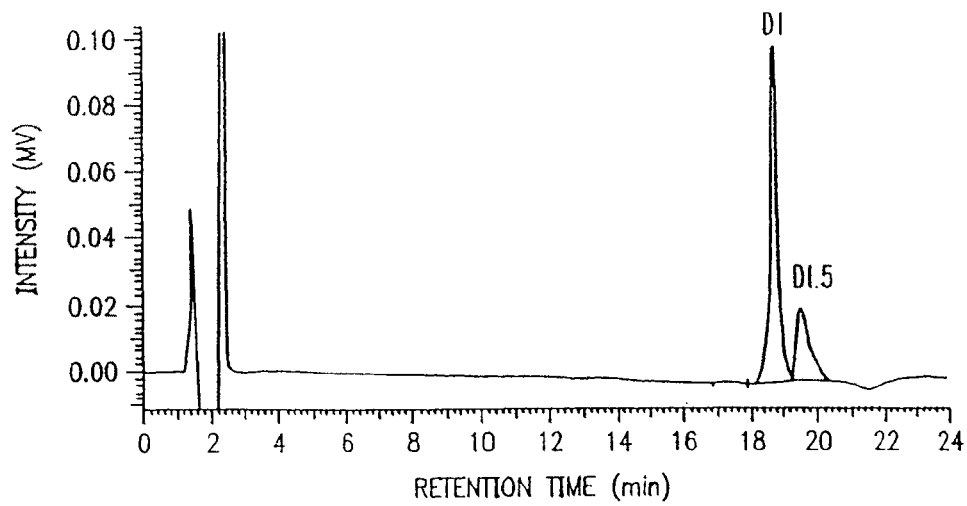
FIG. 34: Compound D1 after Waters C-18 column purification.
Figure 35:
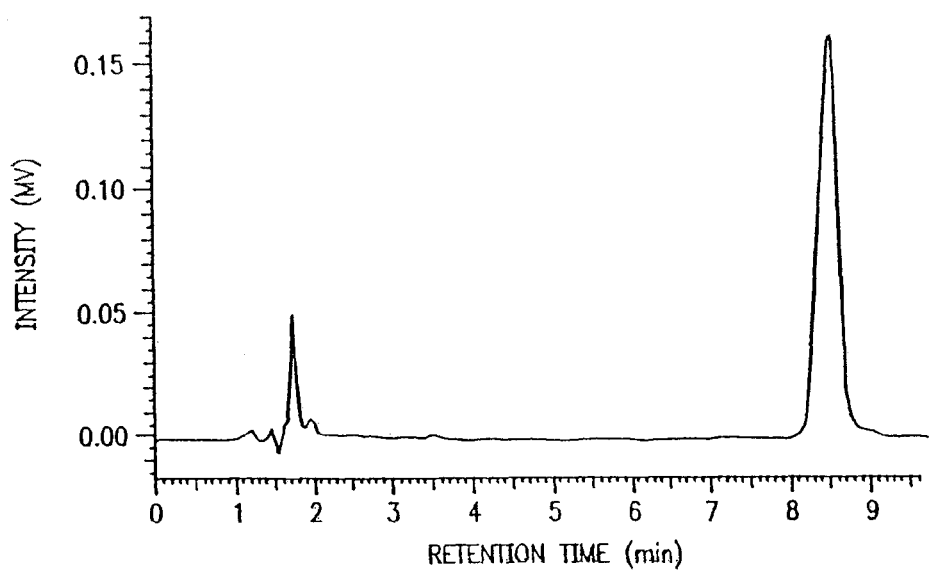
FIG. 35: Compound D1 after final C-18-Aq purification.

The fraction D (45% D1) from the PFP Prep column was first fractionated on a Waters C-18 column (25×100 mm). The mobile phase was 61% methanol in water with 0.1% TFA. The HPLC analysis showed that D1 was 78% pure (FIG. 34) and it contained another peak (named D1.5). A sample of D1 with 100% chromatographic purity (FIG. 35) was produced by further fractionation of the impure D1 on YMC C18-Aq column with 33% acetonitrile/water with 0.1% TFA as the mobile phase. It was observed that D1 is more stable in dilute acid solutions than in water at 40° C. Therefore, 0.1% TFA was included in solvents during the purification of D1.

4.4.1 Bioassays

The bioassays were performed on Jurkat cell lines and the effects of various sub-fractions and pure D1 and G1 are shown Tables 18, 19 and 20 respectively. D1 and G1 were tested at two different pH values. The results indicated a slightly higher activity at pH 6.5 vs pH 7.5. However, the cell growth was inhibited by about 40% at lower pH values.

4.4.2 Acid hydrolysis of D1

The saponin D1 in ethanol was hydrolyzed with 3N HCl for 3 h at 100° C. The aglycone produced was purified by HPLC. The mass spectral analysis showed molecular weight of the aglycone to be 652.

TABLE 18

Cytotoxicity fractions from Prep PFP column

| Fraction No. | Description | Weight (mg)* | Cytotoxicity IC$_{50}$ (µg/ml) |
|---|---|---|---|
| 2160-035-22 | Peak D | 1.7 | 0.52 |
| 2160-047-01 | Peaks G/H | 1.24 | 0.12 |
| 2160-047-03 | Peaks I/J/K | 1.66 | 0.19 |
| 2160-047-05 | Peak L region | 1.17 | 0.18 |
| 2160-047-07 | Peak M | 1.72 | 0.24 |
| 2160-007-34 | F094 | | 0.21 |

TABLE 19

Cytotoxicity fractions from G/H fractionation

| Fraction No. | Weight (mg)* | Cytotoxicity IC$_{50}$ (µg/ml) |
|---|---|---|
| 2160-53-8-G1 | 1.87 | 1.23 |
| 2160-53-11-G2 | 0.76 | 2.2 |
| 2160-53-14-G3 | 0.67 | 4.35 |
| 2160-53-17-H1 | 0.29 | 6.25 |
| 2160-53-20-H2 | 0.45 | 12.8 |
| 2160-007-34 (FO94) | | 0.38 |

TABLE 20

Cytotoxicity of D1 and G1 at pH 6.5 and 7.5

| Compound/Extract | Weight (mg)* | Cytotoxicity IC$_{50}$ (µg/ml) pH 6.5 | pH 7.5 |
|---|---|---|---|
| 2160-69-29 (D1) | 1.036 | 1.01 | 0.98 |
| 2160-083-30 (G1) | 1.951 | 0.3 | 0.49 |
| 2160-007-34 (F094) | | 0.15 | 0.22 |

Example 5

Structures of D1, G1, and B1

5.1 The Structure of D1

D1 is a major component of *Acacia victoriae* pods. Assays of this compound show that it has considerable biological activity.

5.1.1. Whole Molecule D1

Figure 36:
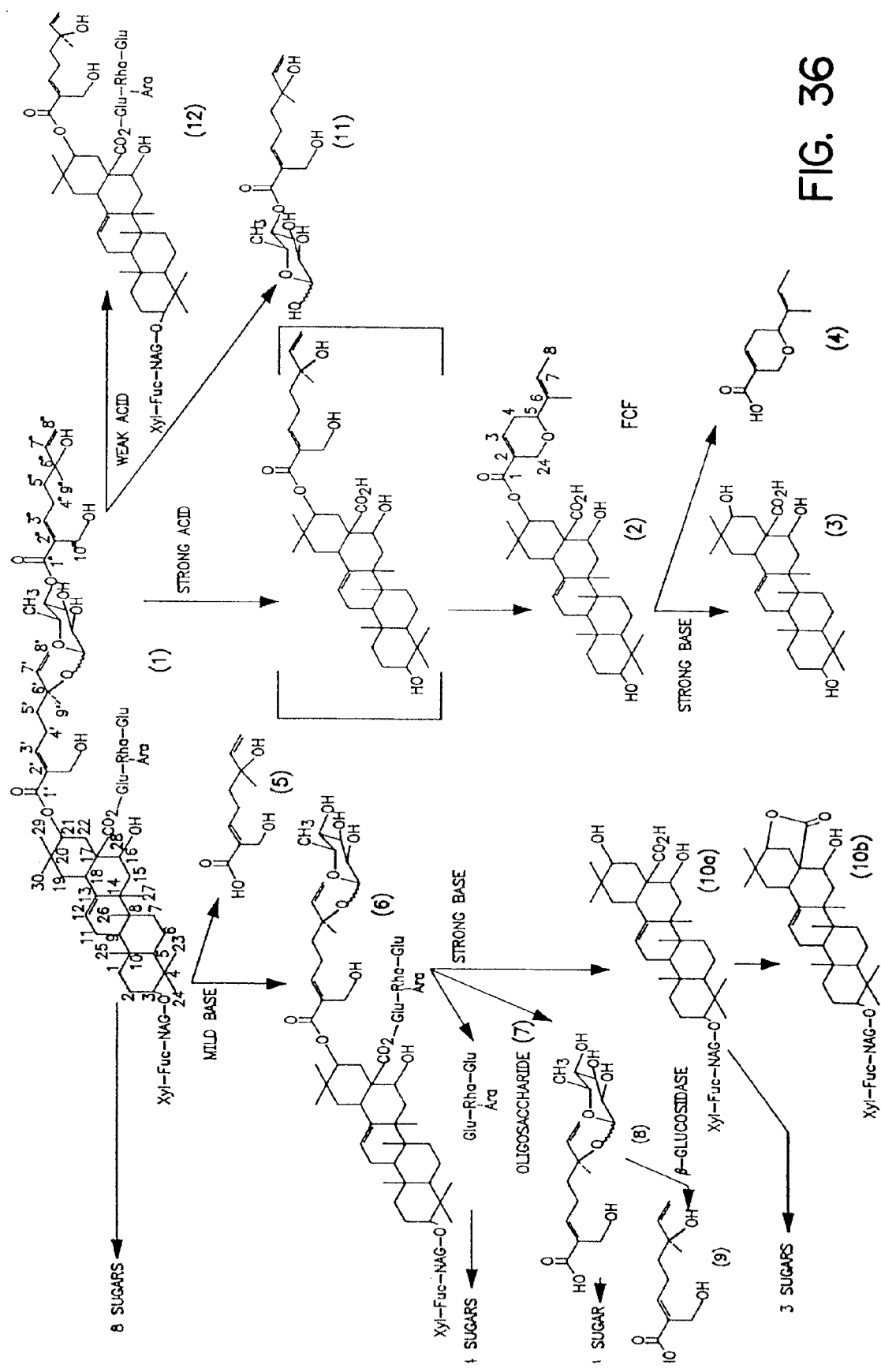
FIG. 36: Depicts compounds from the degradation of compound D1.

D1 was isolated as a colorless amorphous solid isolated from the partially purified extract F094 obtained using several preparative HPLC separations as described in the examples above. Its molecular weight from MALDI mass spectroscopy is 2104 amu which is the sodium adduct of 2081, the true molecular weight. A high resolution FAB mass spectroscopy confirmed this molecular weight and gave the molecular formula of $C_{98}H_{155}NO_{46}$. Such a molecule is too large for structure determination via spectroscopy alone and so a degradation program was undertaken as outlined in Scheme 1 shown in FIG. 36. In FIG. 36, D1 is represented by the structure labeled '(1)'.

The proton and carbon NMRs of D1 showed the presence of a triterpene, two monoterpenes and approximately eight sugars (See Table 21 for selected $^{13}$C-NMR assignments under (1)).

TABLE 21

$^{13}$C NMR (MeOH-d4) assignments of D1(1), G1(14), B1(21), Aglycone (2) and Acacic acid (3). (The numbers in brackets i.e., 1, 14, 21, 2 and 3, refer to structures of D1, G1, B1, Aglycone and Acacic acid, depicted in FIG. 36, FIG. 37 and FIG. 38 respectively.)

| Carbon No. | (1) | (14) | (21) | (2) in DMSO-d6 | (3) |
|---|---|---|---|---|---|
| Triterpene Part | | | | | |
| 1 | 36.13 | 36.13 | 36.13 | 36.07 | 38.90 |
| 2 | 27.15 | 27.15 | 27.15 | 29.28 | 28.03 |
| 3 | 89.86 | 89.84 | | 76.78 | 77.94 |
| 4 | | 40.09 | 39.85 | 39.71 | 39.28 |
| 5 | | 57.08 | | 54.84 | 55.78 |
| 6 | | 19.54 | | 18.03 | 18.71 |
| 7 | 34.59 | 34.59 | 34.58 | 34.27 | 33.51 |
| 8 | | 40.82 | 40.09 | 40.82 | 39.79 |
| 9 | | 48.08 | | 46.11 | 47.15 |
| 10 | | 37.94 | 37.94 | 36.59 | 37.31 |
| 11 | 24.29 | 24.54 | 24.49 | 26.97 | 23.77 |
| 12 | 124.04 | 124.04 | 124.09 | 122.04 | 122.61 |
| 13 | 143.70 | 143.7 | 143.68 | 142.61 | 144.29 |
| 14 | | 42.64 | 42.63 | | 42.01 |
| 15 | 36.20 | 36.39 | 36.51 | | 35.74 |
| 16 | | 74.26 | | 72.41 | 74.22 |
| 17 | | 52.29 | | 49.70 | 51.67 |
| 18 | | 41.64 | 41.60 | | 40.97 |
| 19 | 48.67 | 48.3 | | 46.85 | 48.42 |
| 20 | | 35.88 | 35.95 | | 36.64 |
| 21 | | 78.61 | | 76.78 | 73.32 |
| 22 | 39.86 | 41.7 | 41.94 | 38.07 | 41.97 |
| 23 | 28.62 | 28.61 | 28.65 | 26.60 | 28.65 |
| 24 | 17.12 | 17.11 | 17.11 | 16.06 | 15.55 |
| 25 | 16.22 | 16.22 | 16.25 | 15.19 | 16.47 |
| 26 | 17.73 | 17.72 | 18.07 | 16.78 | 17.43 |
| 27 | 27.40 | 27.32 | 27.40 | 28.24 | 27.11 |
| 28 | 173.39 | 175.34 | 175.39 | 176.64 | 179.14 |
| 29 | 29.41 | 29.43 | 29.41 | 28.77 | 29.97 |
| 30 | 19.42 | 19.42 | 19.53 | 18.65 | 18.26 |
| Outer Monoterpene | | | | | |
| 1 | 168.69 | 168.68 | 168.74 | | |
| 2 | 132.92 | 132.92 | 132.82 | | |
| 3 | 148.48 | 148.02 | | | |

TABLE 21-continued $^{13}$C NMR (MeOH-d4) assignments of D1(1), G1(14), B1(21), Aglycone (2) and Acacic acid (3). (The numbers in brackets i.e., 1, 14, 21, 2 and 3, refer to structures of D1, G1, B1, Aglycone and Acacic acid, depicted in FIG. 36, FIG. 37 and FIG. 38 respectively.)

| Carbon No. | (1) | (14) | (21) | (2) in DMSO-d6 | (3) |
|---|---|---|---|---|---|
| 4 | 24.49 | 24.58 | 24.56 | | |
| 5 | 41.95 | 41.33 | 40.83 | | |
| 6 | 81.01 | 81.0 | | | |
| 7 | 145.93 | 144.01 | | | |
| 8 | 112.53 | 112.44 | 112.53 | | |
| 9 | 16.75 | 16.7 | 16.74 | | |
| 10 | 56.51 | 12.49 | | | |
| Inner Monoterpene | | | | | |
| 1 | 168.17 | 169.01 | 168.19 | 164.0 | |
| 2 | 132.49 | 128.52 | 132.49 | 135.20 | |
| 3 | 148.03 | 145.95 | | 137.05 | |
| 4 | 24.29 | 24.29 | 24.30 | 22.86 | |
| 5 | 41.33 | 39.86 | 39.73 | 76.03 | |
| 6 | | 73.61 | | 129.41 | |
| 7 | 144.03 | 144.43 | | 119.80 | |
| 8 | 116.0 | 116.0 | 115.33 | 11.86 | |
| 9 | 23.76 | 23.7 | 24.21 | 12.81 | |
| 10 | 56.62 | 56.61 | | 64.28 | |

5.1.2. Vigorous Acid Hydrolysis of D1

Hydrolysis of D1 in 3N HCl at 100° C. for 2 hrs. produced "D1 aglycone", depicted as (2) in FIG. 36, which was shown by mass spectroscopy to have a molecular weight of 652. The NMR of D1 aglycone showed the presence of a triterpene and a modified monoterpene but no sugars. This material was further degraded by saponification (1.3N NaOH at 100° C. for 30 min. in MeOH) from which the following were isolated:

5.1.2.a. Triterpene The C-13 NMR of this material was identical with that reported previously for acacic acid (see FIG. 36 structure depicted by (3), and see Table 21 for $^{13}$C-NMR assignments under (3)) and its molecular weight by mass spectroscopy at 488 is consistent with this structure.

5.1.2.b. Cyclized Monoterpene The molecular weight and NMR of this compound indicated the presence of a carboxylic acid, two methyl groups attached to a double bond and two vinyl protons leading to the pyrane structure indicated. While this structural unit Structure depicted by (4) FIG. 36, was also present in "D1 aglycone", it was not present in the parent D 1. The D1 contains the acyclic monoterpene, depicted as structure (5) in FIG. 36, and this structure undergoes cyclization during the acid hydrolysis as shown below:

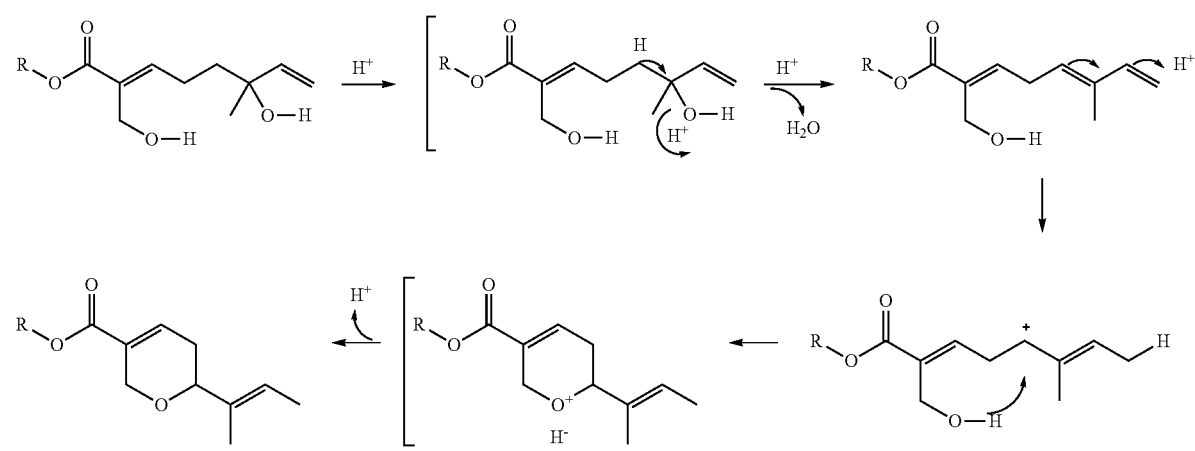

These structures along with the original molecular weight and spectral characteristics of D1 fit well with the structure of D1 aglycone depicted in FIG. 36 by the structure labeled (2). See Table 21 for selected $^{13}$C-NMR assignments under (2).

5.1.3. Mild Saponification of D1

When D1 was treated with 0.5N NH$_4$OH at room temperature for 1 hour there was complete conversion into two new compounds.

5.1.3.a. Monoterpene

This molecule had a molecular weight of 200 and NMR which indicated that it possessed an acyclic monoterpene structure, supporting the suspected degradation. This structure is depicted in FIG. 36 and is labeled (5).

5.1.3.b. Triterpene Monoterpene Oligosaccharide

This compound is more polar than D1 and its NMR is consistent with it containing acacic acid, one monoterpene and several monosaccharides. This structure is depicted in FIG. 36 and is labeled (6).

5.1.4. Sugar Analysis of D1

A vigorous acid hydrolysis of D1 (2N HCl at 100° C. for 2 hours) followed by derivatization (trimethylsilyl ethers) and GC/MS analysis confirmed the presence of eight sugar residues in the original molecule: arabinose, rhamnose, fucose, xylose, 6-deoxyglucose (i.e. quinovose), N-acetyl glucosamine and two molecules of glucose.

5.1.5. More Aggressive Saponification of the Triterpene Monoterpene Oligosaccharide When the triterpene monoterpene oligosaccharide was subjected to 0.3N NaOH for 1 hour at 60° C. three compounds were formed:

5.1.5.a. Oligosaccharide

Isolation and analysis of this very polar fragment suggested that it was an oligosaccharide. Sugar analysis performed by acid hydrolysis (2N HCl at 100° C. for 2 hours) and GC/MS analysis of the trimethylsilyl ethers of the monosaccharides confirmed that the oligosaccharide was a tetrasaccharide made up of two molecules of glucose and one each of arabinose and rhamnose.

5.1.5.b. Monoterpene Glycoside

This material has NMR's consistent with structure (8) depicted in FIG. 36. Acid hydrolysis (2N HCl at 100° C. for 2 hours) of this compound led to the identification of the sugar as 6-deoxy glucose. Treatment of this monoterpene glycoside with β-glucosidase gave the monoterpene with the structure depicted by (9) in FIG. 36, which has an NMR consistent with trans-2-hydroxymethyl-6-hydroxy-6-methyl-2,7-octadienoic acid. Hydrolysis of this linkage with a "beta"-glucosidase indicates that the linkage between these two groups is a beta linkage.

5.1.5.c. Triterpene Glycoside

This compound has a molecular weight of 951 and NMR's which is consistent with the acacic acid lactone containing a trisaccharide at the C-3 position depicted by structure (10b) in FIG. 36. Acid hydrolysis (2N HCl at 100° C. for 2 hours) of this compound allowed the identification of its constituent sugars as N-acetyl glucosamine, fucose, and xylose by GC/MS as trimethyl silyl derivatives. This molecule was observed in both the open acid/alcohol, which is depicted in FIG. 36 by the structure labeled (10a), and the closed lactone form, which is depicted in FIG. 36 by the structure labeled (10b).

Sugar analysis and molecular weight of the fragments as compared with those in the whole molecule D1 confirmed that all portions of D1 were accounted for in fragments depicted by structures labeled (5), (7), (8), and (10a) in FIG. 36.

5.1.6. Mild Acid hydrolysis of D1

Mild acid hydrolysis of D1(1N HCl for 16 hrs at 25° C.) allowed the formation of two new molecules:

5.1.6.a. Monoterpene Sugar

The molecular weight, NMR spectra, and sugar analysis were consistent with a monoterpene-6-deoxyglucose. The structure of this molecule is depicted in FIG. 36 by the structure labeled (11).

5.1.6.b. Triterpene-Monoterpene-Glycoside

The second molecule was identified to be a triterpene-monoterpene-glycoside and the structure of this molecule is depicted in FIG. 36 by the structure labeled (12).

5.1.7. The Attachment of Subgroups within D1

NMR studies indicate that the carboxylic acid of the outer monoterpene is esterified to C-4 of 6-deoxyglucose (quinovose). NMR and hydrolysis studies have shown that the anomeric carbon of the quinovose is attached to the C-6 hydroxy group of the inner monoterpene. The stereochemistry at the anomeric carbon of quinovose indicate a "beta" linkage.

Hydrolysis (2N HCl for 2 hrs at 100° C.) and sugar isomerization studies indicate that the sugars in the tetrasaccharide are two molecules of glucose, and one molecule each of rhamnose and arabinose. The unit is directly esterified to the C-28 carboxylic acid of the triterpene as shown in FIG. 39. Iron trap mass spectroscopy studies indicate that the tetrasaccharide structure has two glucose and one arabinose attached to a central rhamnose as shown in FIG. 39. The linkage of these sugars one to another is still unknown.

NMR studies indicate that N-acetyl glucosamine (NAG) is attached directly to the C-3 carbon of the triterpene. The remainder of the sequence of the sugars is fucose in the middle and xylose on the end by LC/MS studies of partial hydrolysis (1N HCl for 1 hr at 60° C. in 50% MeOH). The linkage of these sugars one to another is still unknown.

5.1.8. Elliptoside E

D1 contains a triterpene and two monoterpenes commonly found in sapohins reported from other species including other *Acacia*. Although the structure of D1 is similar to elliptoside E, (FIG. 24), reported from *Archidendron ellipticum*, (Beutler et al., 1997). In the present invention, the specific rotation of D1 has been determined to be $[\alpha]_D = -30.0°$ which is different than the reported value for elliptoside E at −24.3°.

Elliptoside E, described in Beutler et al. (1997, and D1 have different HPLC retention times (D1—15.2 min., elliptoside E—12.5 min.). Therefore, these two molecules must differ in some manner such as the specific attachment of their subunits or from the presence of optical or structural isomers.

The inventors observed that the specific rotation of the inner monoterpene, depicted by structure (9) in FIG. 36, is +11.2° in MeOH and +16° in chloroform. This same fragment in elliptoside E was reported to be −9.1° in chloroform. Furthermore, the only chiral center of the inner monoterpene of D1 was determined to have an "S" configuration which is opposite to that found in elliptoside E. The specific rotation of the outer monoterpene of D1 is being sought at this time. Furthermore, proton NMR shows that the monoterpene double bonds in D1 are "trans" whereas the monoterpene double bonds are "cis" in elliptoside E as shown in Beutler et al., 1997. These two features constitutes the first structural differences found between D1 and elliptoside E. Enzymatic catalytic hydrolysis of specific sugars has shown that the arrangements of sugars is the same as in elliptoside E.

5.2. The Structure of G1

Biological assays of this material shows that G1 is more biologically active than D1.

5.2.1. Whole Molecule G1(14)

The second structure determined in the present invention was G1. It was also isolated from F094 by prep HPLC but in low compound recovery. G1 is slightly less polar than D1. The molecular weight by MALDI mass spectroscopy indicates a molecular weight of 2065 which is 16 amu less than D1. Specific rotation of G1 was found to be −26.9° (MeOH). The proton NMR shows that G1 is also a saponin, very similar to D1 and indicates that it only differs from D1 by having one less oxygen in the outer monoterpene which is now trans-2,6-dimethyl-6-hydroxy-2,7-octadienoic acid. See FIG. 37, structure labeled (14), and Table 21 for selected $^{13}$C-NMR assignments under (14). G1 was degraded as shown in Scheme 2, FIG. 37.

5.2.2. Mild Saponification of G1

When G1 was treated with 0.5 N NH$_4$OH at room temperature for even a few minutes there is complete conversion into the more polar mild saponification product and a monoterpene.

Figure 37:
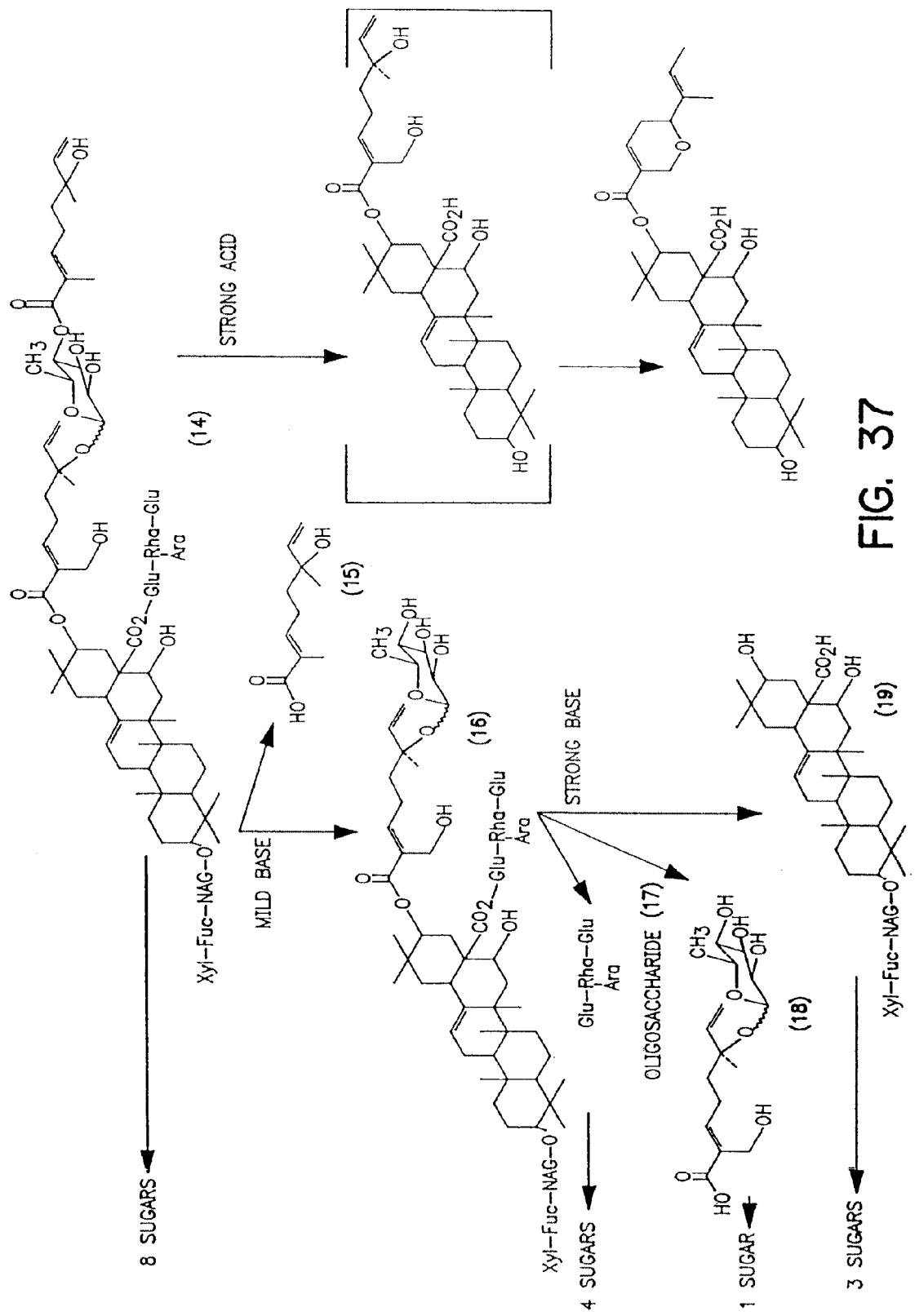
FIG. 37: Depicts compounds from the degradation of compound G1.

5.2.2.a. Monoterpene The molecular weight and NMR of this material indicates that it possesses a methyl group at the C-2 position where a hydroxymethyl had been in. This is depicted in FIG. 37 by the structure labeled (15).

5.2.2.b. Triterpene Monoterpene Oligosaccharide The NMR of this compound indicates that it was identical by HPLC retention time and by proton NMR with the structure labeled (16) depicted in FIG. 37, which is similar to the structure labeled (6) in FIG. 36 made from D1 and that it contains an acacic acid, one monoterpene and eight monosaccharides as was seen in D1. The similarity of (16) with (6) indicates a similar stereochemistry seen in D1 inner monoterpene.

5.2.3. Sugar Analysis of G1

A vigorous acid hydrolysis of G1 (2N HCl at 100° C. for 2 hours) produced the same monosaccharide units as were present in D1: arabinose, rhamnose, fucose, xylose, 6-deoxyglucose, N-acetyl glucosamine and two molecules of glucose.

5.2.4. Acid Hydrolysis of G1

An acid hydrolysis of the mild saponification product allowed the isolation of three molecules in a manner as in D1. NMR and sugar analyses (2N HCl at 100° C. for 2 hours) were performed on each. This is depicted in FIG. 37 by the structure labeled (16).

5.2.4.a. Oligosaccharide contained two molecules of glucose and one each of arabinose and rhamnose and is depicted in FIG. 37 by the structure labeled (17).

5.2.4.b. Monoterpene Glycoside contained an acyclic monoterpene (depicted in FIG. 37 by the structure labeled (5)), and 6-deoxyglucose and the whole structure is depicted in FIG. 37 by the structure labeled (18).

5.2.4.c. Triterpene Glycoside contained acacic acid and one molecule each of N-acetyl glucosamine, fucose, and xylose. The sugars in these fragments are arranged in the same order as in D1. This structure is depicted in FIG. 37 by the structure labeled (19).

5.2.5. Elliptoside A

Figure 24:
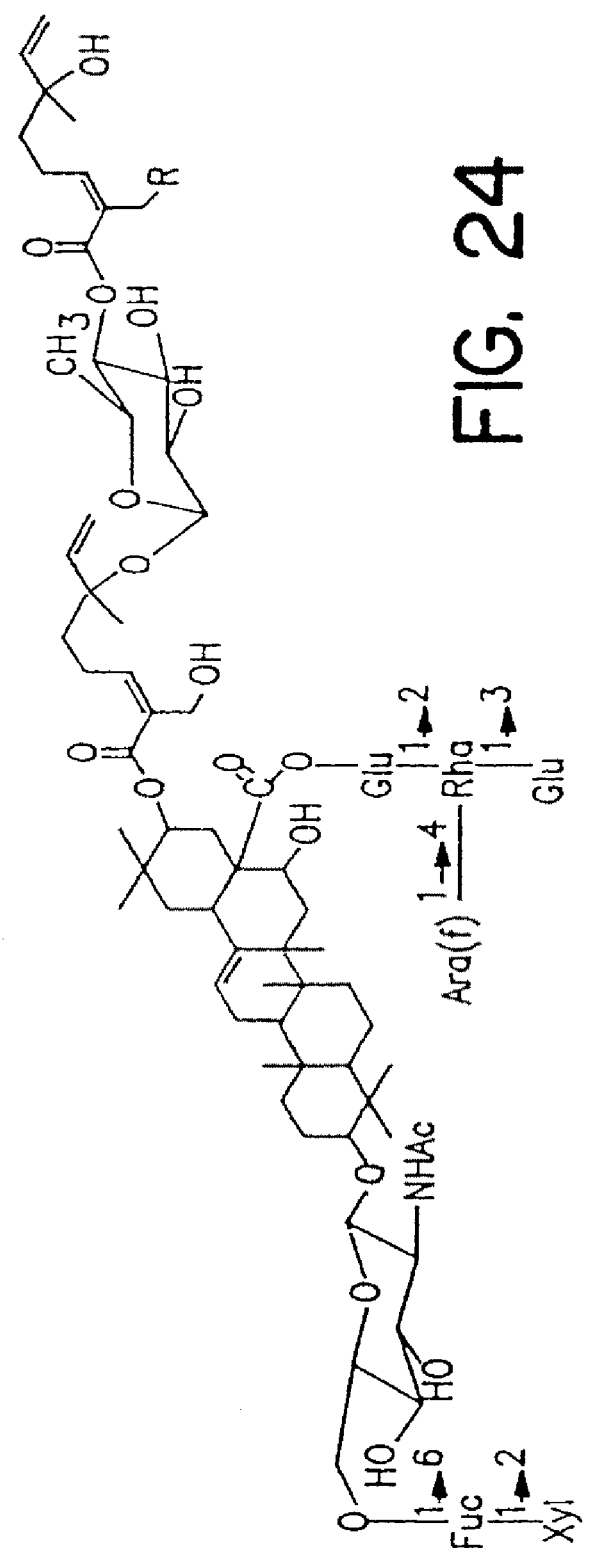
FIG. 24: Structure of Elliptoside A and Elliptoside E (Beutler, 1997).

G1 has the same terpene content and sugars as elliptoside A (see FIG. 24 and Beutler, 1997). However, elliptoside A was found to have a markedly different HPLC retention time (G1 −29.09 min. and elliptoside A −26.04 min.), which indicates that the two molecules must differ in some manner such as the specific attachment of their subunits or from the presence of optical isomers or both. A comparison of the proton and carbon NMR spectra of G1 and elliptoside A also show differences in chemical shifts. It is contemplated that the specific rotations of the inner and outer monoterpenes of these compounds may also differ. FIG. 37 structure (14) represents the structure of G1.

5.3. The Structure of B1

Bioactivity data indicates that Bi is much less active than D1 or G1.

5.3.1. Whole Molecule B1(21)

Figure 38:
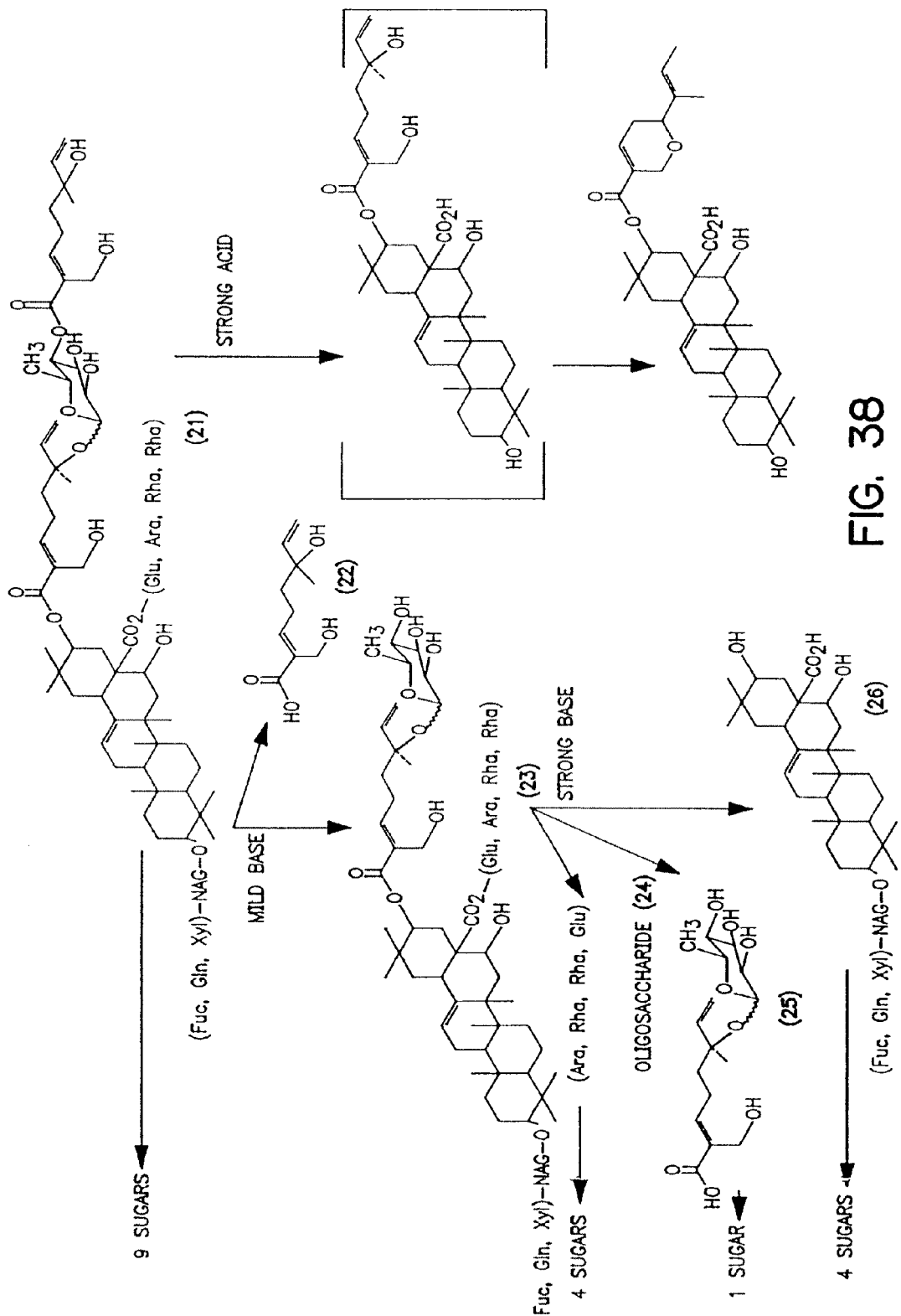
FIG. 38: Depicts compounds from the degradation of compound B1.

The isolation of B1 was accomplished by plant extraction and C-18 flash chromatography followed by C-18 prep and semi-prep chromatography. The NMR of B1 indicates the same triterpene/monoterpene/quinovose/monoterpene structure as has been seen throughout this saponin family. The NMR also indicates the presence of four deoxy sugars and one N-acetyl group, which indicates that this molecule must differ from D1 in its sugar portions. See Table 21 for specific $^{13}$C-NMR assignments under (21). This molecule was degraded as shown in FIG. 38.

5.3.2. Sugar Analysis of B1

NMR data indicate the presence of more than one copy of one of the 6-deoxy methyl sugars (i.e. fucose, rhamnose, 6-deoxyglucose). Sugar analysis of the total molecule after hydrolysis (2N HCl at 100° C. for 2 hours) indicates that nine sugars are present: one molecule each of fucose, arabinose, xylose, quinovose, and glucosamine and two molecules of glucose and rhamnose. Glucosamine, the remnant of an N-acetyl glucosamine, is present in the original molecule. The structure of B1 is depicted in FIG. 38, structure (21).

5.3.3. Mild Saponification of B1

When B 1 was treated with 0.5 N NH$_4$OH at room temperature for even a few minutes there is complete conversion into a more polar compound, the mild saponification product, and a monoterpene.

5.3.3.a. Monoterpene The molecular weight and NMR of this material indicates that it has the same structure as the monoterpene from D1, depicted in FIG. 37 by the structure labeled (5). This is depicted in FIG. 38 by the structure labeled (22).

5.33.b. Triterpene Monoterpene Oligosaccharide The NMR of this compound indicates that it contains acacic acid, one monoterpene and several monosaccharides. This is depicted in FIG. 38 by the structure labeled (23).

More Aggressive Saponification of the Triterpene Monoterpene Oligosaccharide

A more aggressive saponification (0.3N NaOH at 60° C. for 1 hour) of the mild saponification product allowed the isolation of three molecules in a similar manner as before in D1 and G1. Sugar analyses and NMR data were obtained for each.

5.3.4.a. Oligosaccharide contained glucose, arabinose and two molecules of rhamnose. This is depicted in FIG. 38 by the structure labeled (24).

5.3.4.b. Monoterpene Glycoside contained 6-deoxyglucose and a monoterpene. This is depicted in FIG. 38 by the structure labeled (25).

5.3.4.c. Triterpene Glycoside contained acacic acid with a tetrasaccharide attached at the C-3 position. The tetrasaccharide is composed of one molecule each of N-acetyl glucosamine, fucose, glucose, and xylose. This is depicted in FIG. 38 by the structure labeled (26).

Example 6

De-Esterification of the Triterpene Compounds of the Invention

F094 was de-esterified and the de-esterified products bioassayed to elucidate the active components. 1.00 g of F094 was dissolved in 100 ml of H$_2$O, followed by addition of 1 g of KOH and refluxing for 1.5 hrs. The solution was allowed to cool to room temperature and its pH adjusted to 7 with 1N HCl and then washed with hexanes (2×50 ml). The aqueous solution was then subjected to further stepwise extractions to yield fractions 159-162. For example, the solution was initially extracted with n-butanol (2×50 ml) to yield 0.127 g of organic soluble solid (F 159) after drying in vacuo. The aqueous layer was acidified to pH 5 with 1 N HCl and extracted with EtOAc (2×50 ml) to yield 0.397 g of an EtOAc soluble solid (F160), then n-butanol (2×50 L) to yield 0.338 g of solid (F 161) after removal of the organic solvents. The aqueous layer was finally neutralized to pH 7 with 1N NaOH. 1.808 g of solid (F162) was isolated from the final aqueous layer.

Bioassays revealed that the de-esterified products had little or no activity. F 159-162 were bioassayed for cytotoxicity against 769-P, Panc-1, HEY, MDA-MB-453 and Jurkat cell lines. The only activity found was for F161, which exhibited a cytotoxicity of 1.6% against MDA-MB-453 at 50 µg/ml and for F159 which exhibited cytotoxicities of 15.50%, 6.60%, and 3.80% against Jurkat cells at 50 µg/ml, 25 µg/ml, and 12.5 µg/ml, respectively. These results indicate that the ester side chain is necessary for bioactivity. It is believed that the ester side chain of the compounds of the invention exhibits anti-tumor activity and/or works in concert with the triterpene skeleton of the compounds of the invention to produce the potent anti-tumor activity exhibited.

Example 7

Sugar Hydrolysis of the Compounds of the Invention

Figure 17A:
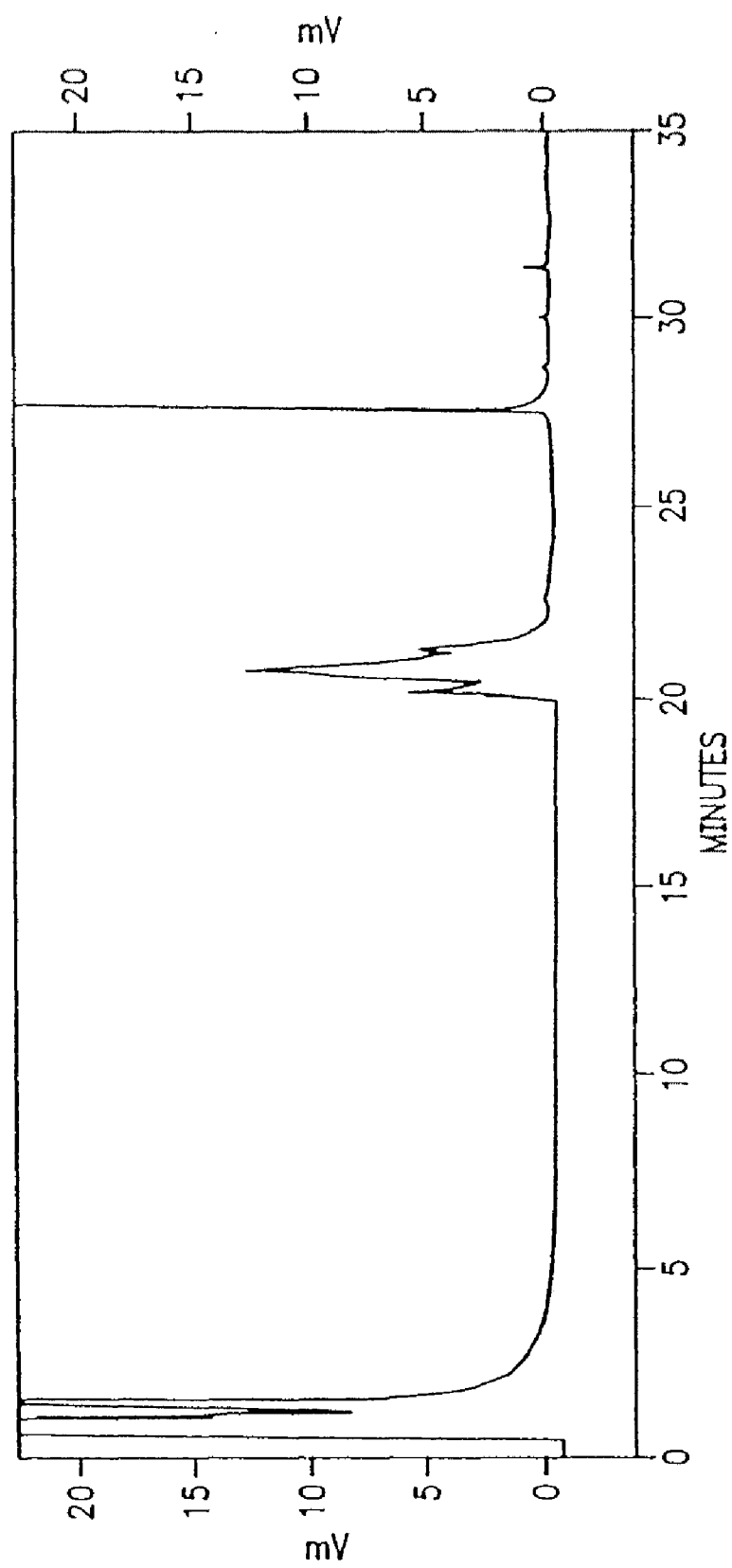
FIGS. 17A,B.
Figure 17B:
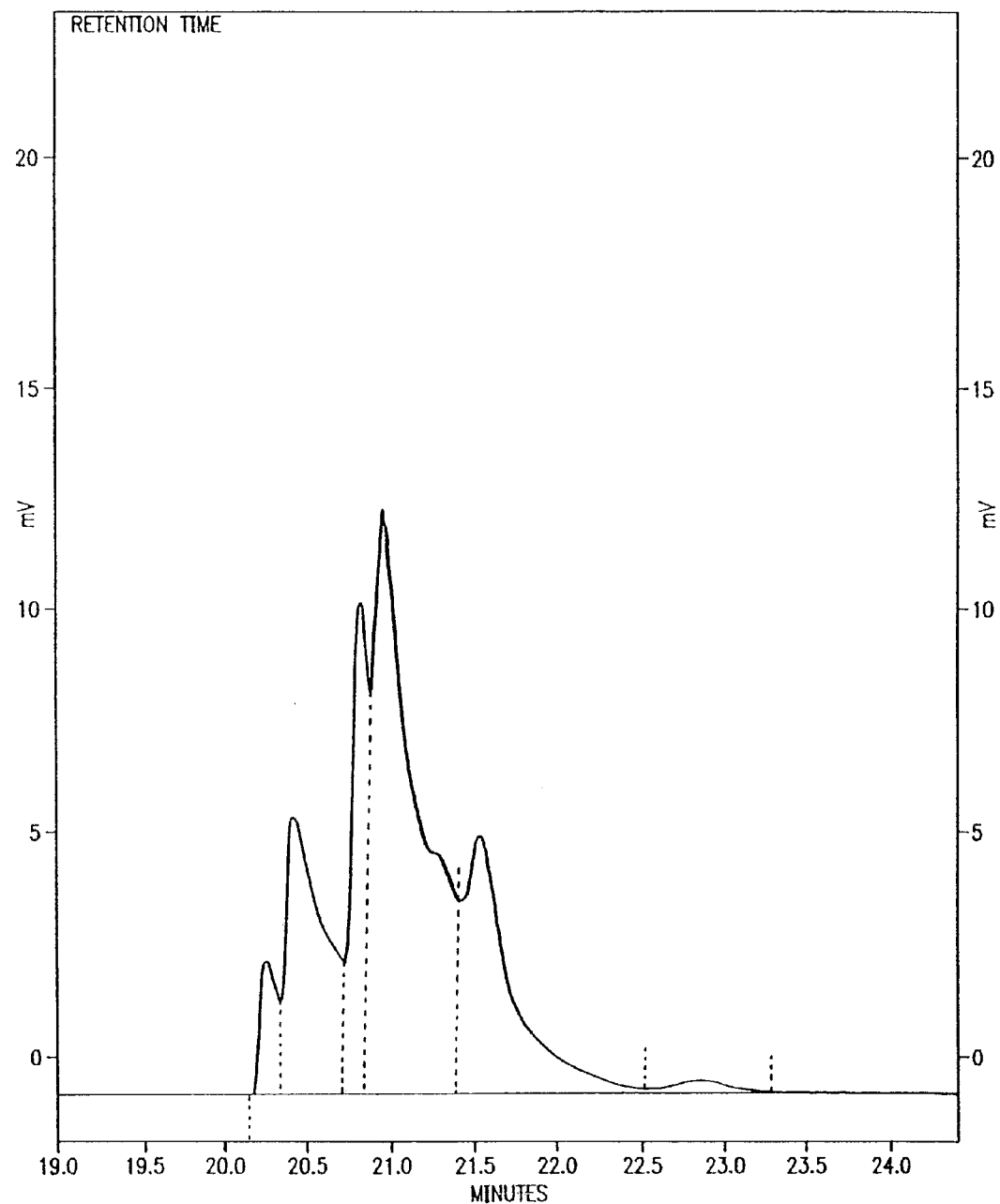
FIG. 17B: shows an HPLC spectrum of acetylated sugars isolated from the hydrolyzed active constituents found in F094.

The sugars contained in F094 were also hydrolyzed to aid in the characterization of the active components. 12 g of F094 was dissolved in 400 ml 2N $H_2SO_4$ and refluxed for 75 min during which time an insoluble material formed. The solution was cooled and filtered through sintered glass. The residue was washed with water, yielding 4.8 g of an aglycone(s) (F 191), as determined by TLC analysis. The dark amber filtrate was neutralized with KOH or NaOH. A white precipitate was formed and collected. The addition of isopropanol to the amber filtrate caused a second white precipitate. The solvent was removed in vacuo and the solvent re-suspended in MeOH which resulted in the formation of a white precipitate which probably corresponded to sulfate salts as determined by a flame test. The almost clear filtrate dried in vacuo and the residue acetylated and analyzed by HPLC to contain a mixture of sugars as shown in FIGS. 17A and 17B. This mixture probably contains at least 5 saccharides. These sugars may be further characterized by isolation of the TMS derivatives for GC-MS characterization; paper chromatography; isolation of the benzyl derivatives for HPLC separation or DEPT NMR; or $C^{13}$ NMR as fully described herein above. By standard 1-D and 2-D cellulose, paper and normal phase TLC, the main sugars have been identified as glucose, xylose, rhamnose and arabinose along with some minor additional sugar and a strong potential for an amino glycoside, especially an acetamido substituted sugar.

The number of different sugars probably explains the complicated HPLC spectra, which show the presence of dozens of closely-related compounds. In particular, some active constituents appear to be glycosylated at two different sites (an alcoholic and a carboxylic acid site). Combinations of six sugars attached to two sites would thus yield large numbers of closely-related compounds which would be hard to separate.

Alternatively, milder hydrolysis conditions run with 100% ethanol (azeotrope with 5% water) and 0.1 to 2.0 N $H_2SO_4$ (the remaining work-up is the same) under mild heating to the point of reflux, but not vigorous reflux, generates a similar mixture of aglycones. Some components are missing which indicates that some isomerization takes place under the stronger conditions.

The aglycone(s) F191 (1 g) was then methylated by refluxing 5-7 hours with methyl iodide (1 ml) and anhydrous $K_2CO_3$ (1 g) in anhydrous acetone (10 ml). This resulted in 0.315 g of an insoluble material and 0.54 g of methyl esters denoted F197. 500 mg of F197 was further separated by MPLC employing a 15×460 mm column (45 g $SiO_2$, 15-25 µm) where the sample was pre-adsorbed onto 1.5 g $SiO_2$, 15-25 µm. The compounds were eluted with 790 ml 7% isopropyl alcohol (IPA) in hexanes (subfractions 1-10), 470 ml 10% IPA in hexanes (subfractions 1-14), 275 ml 20% IPA/hexanes (subfractions 14-15), 200 ml dichloromethane, and 100 ml DCM/MeOH (1:1), in accordance with Table 22.

Bioassays of F191 and F197 yielded cytotoxicities for ovarian cancer cells (line HEY), renal cancer cells (line 769-P), pancreatic cancer cells (line Panc-1), Jurkat T-leukemic cells, and MDA-MB-453 breast cancer cells at corresponding dosages as indicated in Table 23.

TABLE 22

Fractionation of F197 to Fractions F198 to F208.

| Fraction Identifier | Subfractions Collected (volume (ml)) | Total Weight (mg) | Comments |
|---|---|---|---|
| F198 | 1 (100) | 14 | |
| F199 | 2-3 (120) | 126 | Further fractionated to F209-214. |
| F200 | 4 (40) | 8 | |
| F201 | 5-6 (110) | 86 | Further fractionated to F215-219. |
| F202 | 7-8 (170) | 37 | |
| F203 | 9-10 (250) | 17 | |
| F204 | 11 (100) | 5 | |
| F205 | 12 (150) | 38 | |
| F206 | 13 (150) | 10 | |
| F207 | 14-15 (345) | 86 | |
| F208 | 16-18 (300) | 105 | |

TABLE 23

Bioassay of Fractions F191 and F197.

|  | 50 µg/ml | 25 µg/ml | 12.5 µg/ml |
|---|---|---|---|
| F191 | | | |
| 769-P | 82.3 | 56.3 | 33.7 |
| Panc-1 | 90 | 64 | 40.3 |
| HEY | 94.5 | 71.6 | 0 |
| MDA-MB-453 | 53.5 | 22.3 | 7.3 |
| JURKAT | 69.6 | 68.6 | 45.3 |
| F197 | | | |
| 769-P | 84.3 | 61.1 | 40.5 |
| Panc-1 | 93.5 | 84.4 | 53.8 |
| HEY | 94.4 | 94.7 | 62.1 |
| MDA-MB-453 | 76.8 | 79.2 | 68.8 |
| JURKAT | 70.2 | 70.6 | 56.9 |

F199 (116 mg) was further fractionated by the same column used to fractionate F191 and eluted in 100 ml 2% IPA/hexanes, 525 ml 4% IPA/hexanes, and 250 ml 10% IPA/hexanes according to Table 24.

TABLE 24

Fractionation of F199 to Fractions F209 to F214.

| Fraction Identifier | Subfractions Collected (volume (ml)) | Total Weight (mg) | Comments |
|---|---|---|---|
| F209 | 1-7 (225) | 5 | |
| F210 | 8 (20) | 1 | |
| F211 | 9 (20) | 2 | |
| F212 | 10-14 (140) | 90 | Further fractionated to F220-F228. |
| F213 | 15-17 (220) | 17 | |
| F214 | 18 (250) | 10 | |

F212 (85 mg) was further fractionated by a Waters Prep LC 4000 HPLC on a 22×500 mm column (Alltech Econosil C18, 10 µm, equilibrated with 75% ACN/water) and eluted in 80% ACN/water and washed with ACN at a rate of 40 ml/min, for a detection limit of 220 nm and subfractions collected every 30 sec (20 ml) according to Table 25.

F223 was initially purified as its methyl ester derivative to give C-191. C-191 was subjected to a classical acetylation procedure. Specifically, C-191 (47 mg) was stirred overnight at room temperature in a 2:1 mixture of acetic anhydride and pyridine. The reaction was quenched with water and the solution partitioned with diethyl ether and 5N HCl. The organic layer was then washed until neutral, roto-evaporated and the residue subjected to PTLC—one 20 cm by 20 cm preparative plate eluted with 90:10 hexane:isopropyl alcohol, followed by subsequent PTLC's eluted with dichloromethane:methanol (98:2) to C-191 acetate (F229, which later was given the number C-194).

TABLE 25

Fractionation of F212 to Fractions F220 to F228.

| Fraction Identifier | Subfractions Collected (volume (ml)) | Total Weight (mg) | Comments |
|---|---|---|---|
| F220 | A (940) | 12 | |
| F221 | 1-24 | 1 | |
| F222 | 25-27 | 3 | |
| F223 | 28-38 | 55 | "C191" - targeted for characterization as its acetylated derivative by $^{13}$C- and $^{1}$H-DEPT NMR, HPLC, RP18 TLC and MS. |
| F224 | 39-41 | 3 | |
| F225 | 42-54 | 4 | |
| F226 | 55-74 | 1 | |
| F227 | 75-102 | 5 | |
| F228 | 103 | 2 | ACN wash |

F201 (85 mg) was also further fractionated by MPLC by a similar column as used to fractionate F199 and eluted and collected in 2% IPA/hexanes (120 ml), 4% IPA/hexanes (330 ml), 7% IPA/hexanes (460 ml), 20% IPA/hexanes (150 ml), DCM (50 ml), and DCM/MeOH (1:1) (70 ml) according to Table 26.

TABLE 26

Fractionation of F201 to Fractions F215 to F219.

| Fraction Identifier | Subfractions Collected (volume (ml)) | Total Weight (mg) | Comments |
|---|---|---|---|
| F215 | 1-5 (510) | 3 | |
| F216 | 6-10 (175) | 54 | "Aglyc II methyl ester" - also targeted for characterization. |
| F217 | 11-14 (225) | 4 | |
| F218 | 15 (150) | 14 | |
| F219 | 16 (120) | 10 | |

Example 8

Biological Characteristics of Active Triterpenes of the Invention

Angiogenesis or neovascularization is a process by which cells are recruited by factor(s) produced by a tumor to provide the tumor with a nourishing vascular system. Inhibiting angiogenesis inhibits tumor expansion by limiting blood supply to the tumor. This function was examined using a bovine capillary endothelial cell proliferation assay on cells treated with Fraction 35 (UA-BRF-004-DELEP-F035). The assay was carried out as follows: bovine capillary endothelial cells were obtained and grown using standard procedures (Folkman et al., 1979). The cells were washed with PBS and dispersed in a 0.05% trypsin solution. A cell suspension (25,000 cells/ml) was made with DMEM+10% BCS+1% GPS, plated onto gelatinized 24 well culture plates (0.5 ml/well) and the suspension incubated for 24 h at 37° C. The media was replaced with 0.25 ml of DMEM+5% BCS+1% GPS and different concentrations of UA-BRF-004-DELEP-F035 applied. After a 20 min incubation, media and bFGF were added to obtain a final volume of 0.5 ml DMEM+5% BCS+1% GPS+1 ng/ml bFGF. After 72 h the cells were dispersed in trypsin, resuspended in Hematall (Fischer Scientific, Pittsburg, Pa.) and counted by coulter counter (O'Reilly et al., 1997).

Figure 5:
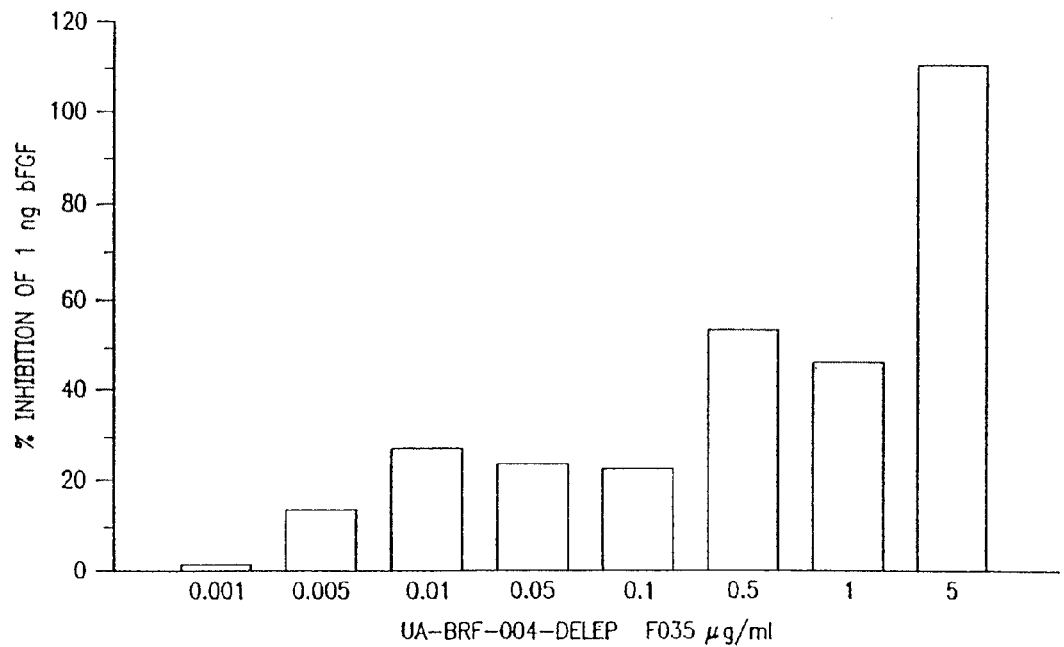
FIG. 5: Effect of Fraction 35 on endothelial cell proliferation.
Figure 6:
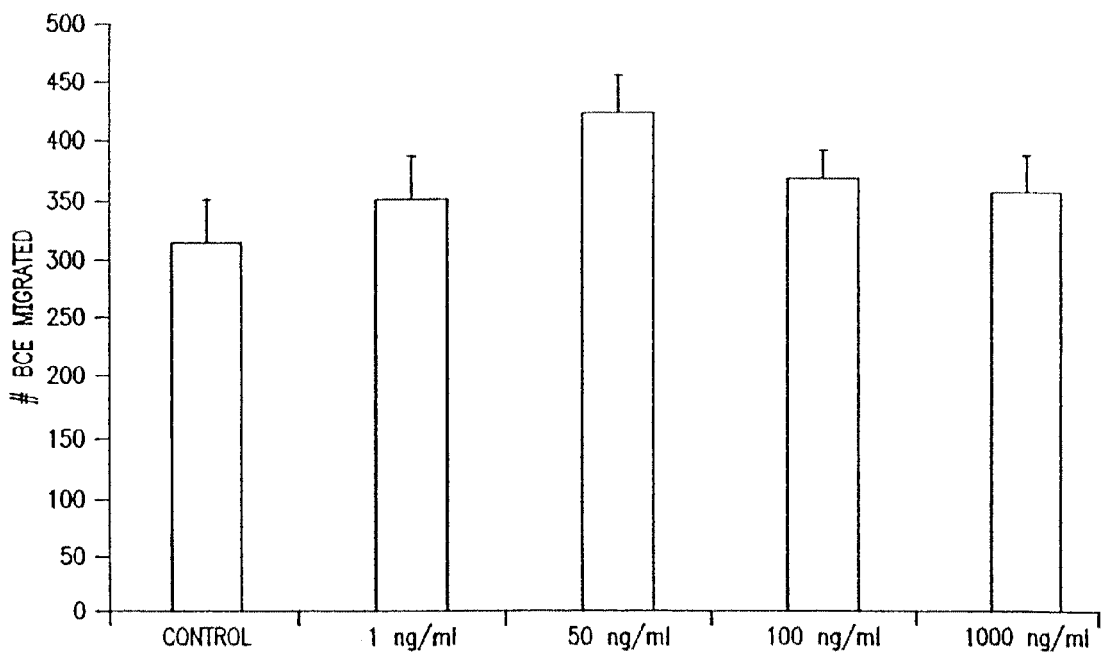
FIG. 6: Effect of Fraction 35 on migration of capillary endothelial cells.
Figure 7:
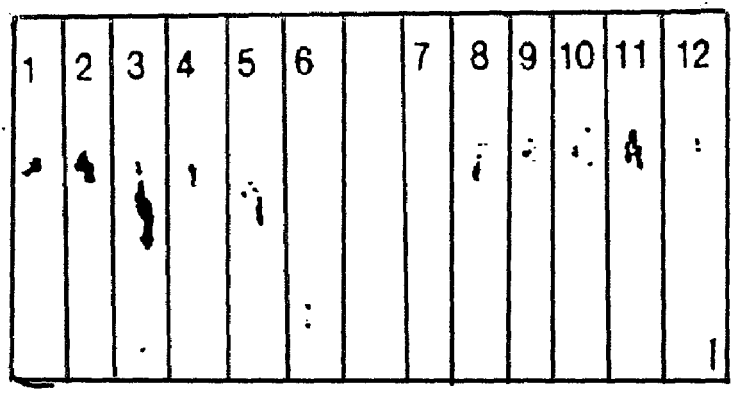
FIG. 7: Shows thin layer chromatography of, seedling and callus extracts. Lane 1, stem callus developed on BA-IAA medium; Lane 2, root callus developed on BA-IAA medium; Lane 3, hypocotyl callus; Lane 4, seedlings treated with methyl jasmonate (100 µM) on semi-solid medium; Lane 5, seedling control growing on semi-solid medium; Lane 6, standard F023; Lane 7, shoot developed on BA medium; Lane 8, seedling treated with 50 µM methyl jasmonate; Lane 9, seedling treated with 100 μM methyl jasmonate; Lane 10, seedling treated with 200 μM methyl jasmonate; Lane 11, seedling control; and Lane 12, standard F023.
Figure 8:
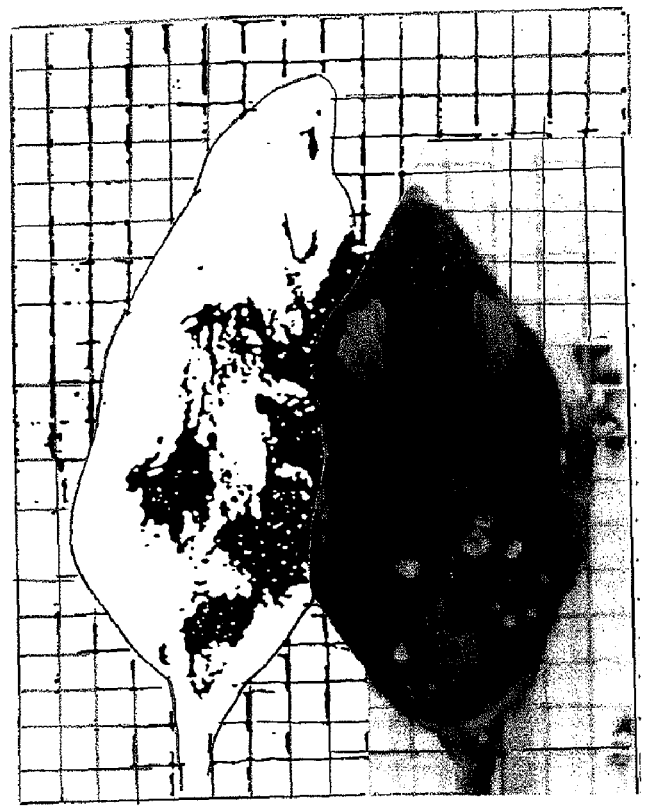
FIG. 8: Shows a photograph of the SENCAR mouse on the left and a cross of SENCAR and C57B1 on the right. Both were treated with repetitive 100 nmol DMBA doses for 8 weeks. At 15 weeks both had numerous papillomas but the cross of SENCAR and C57B1 mouse had fewer and smaller papillomas. The C57B1 strain is resistant to carcinogenesis and will not develop tumors.
Figure 9A:
FIGS. 9A-F: Show epidermal sections of mice treated with acetone, DMBA or DMBA+UA-BRF-004-DELEP-F035.
Figure 9B:
Figure 9C:
Figure 9D:
Figure 9E:
Figure 9F:
Figure 10A:
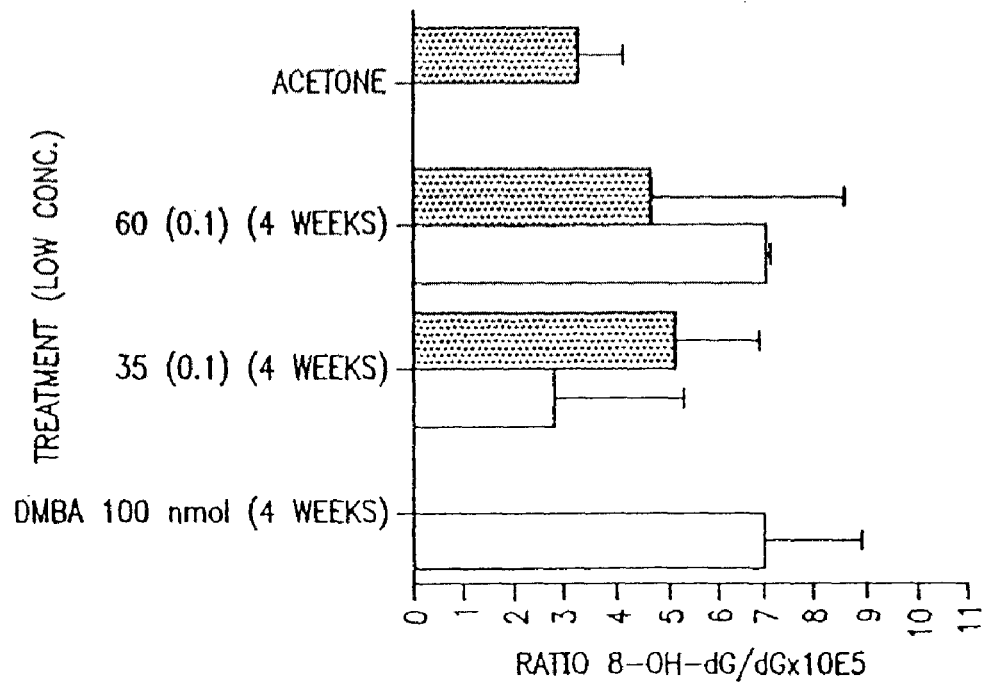
FIGS. 10A,B: Show the antioxidant effect on DNA of UA-BRF-004-DELEP-F035 after 4 weeks.
Figure 10B:
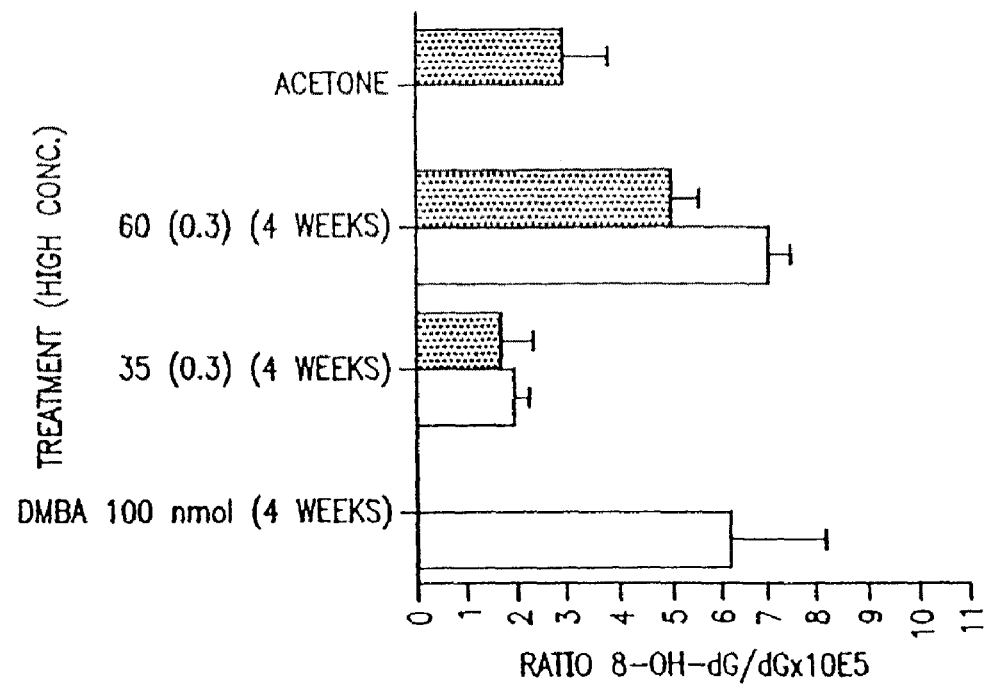
FIG. 10B: shows the antioxidant effects following treatment with a high concentration of UA-BRF-004-DELEP-F035 (0.3 mg/0.2 ml).
Figure 12:
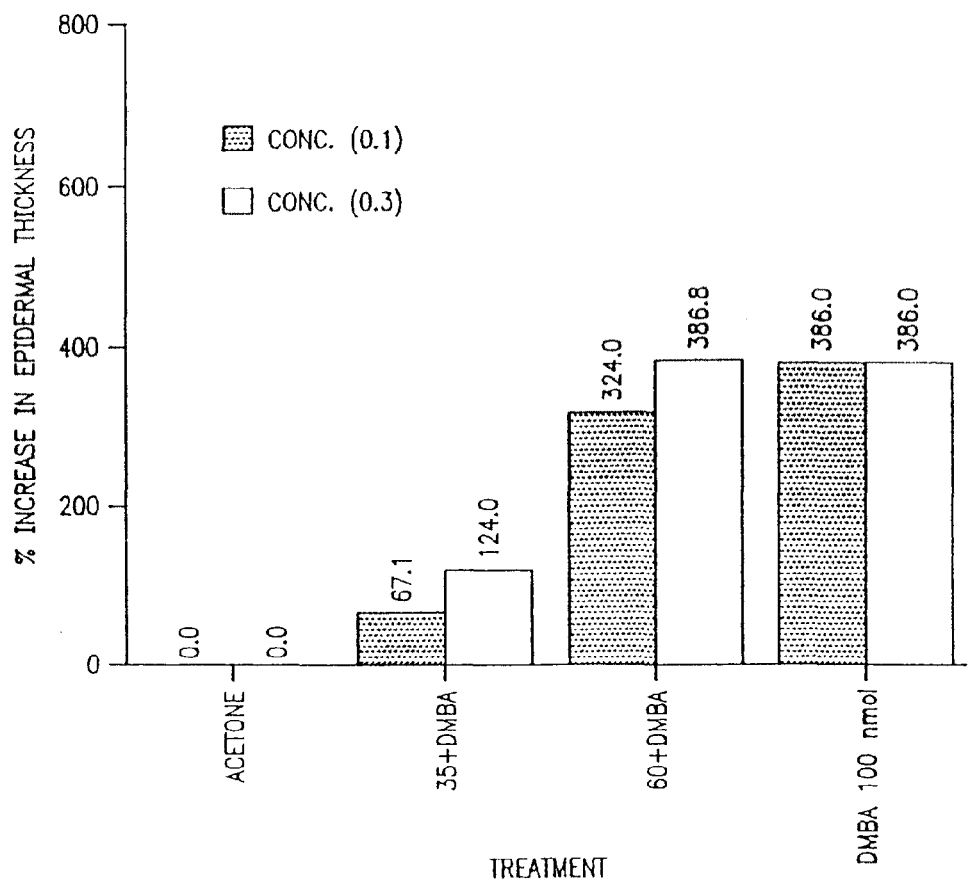
FIG. 12: Shows the percent increase in epidermal thickness after 4 weeks following treatment with DMBA at low (0.1 mg/0.2 ml) or high (0.3 mg/0.2 ml) concentration of UA-BRF-004-DELEP-F035.
Figure 13:
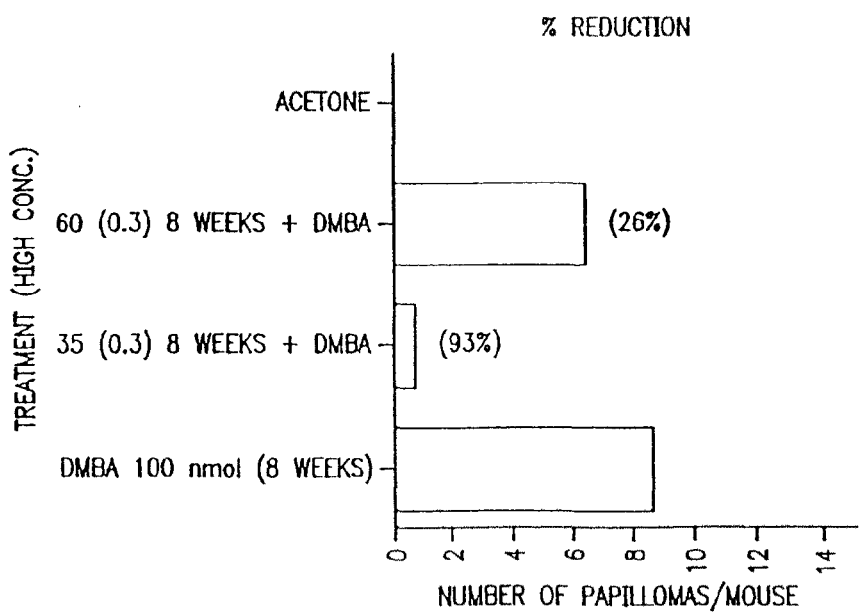
FIG. 13: Shows the percent reduction in papillomas after 8 weeks following treatment with DMBA at a low (0.1 mg/0.2 ml) or high (0.3 mg/0.2 ml) concentration of UA-BRF-004-DELEP-F035.

The results of the assay demonstrated significant inhibition of endothelial cell proliferation with or without basic fibroblast growth factor (FIG. 5). These results demonstrate that the active components of the plant extract are potent inhibitors of endothelial cell proliferation, which is often a predictor of in vivo suppression of angiogenesis. In addition, the fraction had no effect on migration of capillary endothelial cell, suggesting lack of toxicity to normal cells (FIG. 6).

A common problem encountered with steroidal saponins (i.e. digitonin, and the genin-diosgenin from yams) is the lysis of red blood cells. Using a simple culture tube blood assay there was very little detectable lysis following treatment with 1 mg/ml of UA-BRF-004-DELEP-F035. Alternatively, treatment with 10 to 25 dµg/ml digitonin resulted in 100% lysis in the culture tube blood assay.

Next, in order to further study the mechanism by which the active components inhibited tumor cells, the TNF-alpha induced activation of the transcription factor NF-κB was analyzed in Jurkat cells ($3\times10^6$) which had been treated with 1-2 µg/ml of UA-BRF-004-DELEP-F035 and UA-BRF-004Pod-DELEP-F094. The study was carried out as follows: Jurkat cells were pretreated with 1-2 µg/ml of F035 or F094 for 15 h at 37° C. Cells were harvested and resuspended in 1 ml RPMI and treated with 100 pM of TNF-alpha for 30 min at 37° C. After TNF-alpha treatment, nuclear extracts were prepared according to Schreiber et al. (1989). Briefly, the cells were washed with ice cold PBS and suspended in 0.4 ml of lysis buffer.(10 mM HEPES, pH 7.9, 10 mM KCl, 0.1 mM EDTA, 1 mM EDTA, 0.1 mM EGTA, 1 mM dithiothreitol, 0.5 mM PMSF, 2 µg/ml of leupeptin, 2 µg/ml of aprotinin and 0.5 mg/ml benzamidine). The cells were allowed to sit on ice for 15 min and 25 µl of 10% Nonidet-40 was added to the cells. The tubes were mixed on the vortex and microcentrifuged for 30 s. The nuclear pellet was resuspended in 25 µl of ice cold nuclear extraction buffer (20 mM HEPES, pH 7.9, 0.4 M NaCl, 1 mM EDTA, 1 mM EGTA, 1 mM dithiothreitol, 1 mM PMSF, 2 µg/ml leupeptin, 2.0 µg/ml aprotinin and 0.5 mg/ml benzamidine) and tubes were incubated on ice with intermittent agitation. The nuclear extract was microcentrifuged for 5 runs at 4° C. and supernatants were stored at −70° C.

An electrophoretic mobility shift assay was performed by incubating the nuclear extracts (7 µg of protein) with $^{32}$P-labeled NF-κB oligonucleotides (SEQ ID NO:1; NF-κB consensus oligonucleotide; Santa Cruz Biotechnology) in presence of 0.5 µg of poly di-dc in a binding buffer (25 mM HEPES, pH 7.9, 0.5 mM EDTA, 0.5 mM dithiothreitol, 1% Nonidet P-40, 5% glycerol and 50 mM NaCl for 20 min at 37° C.) (Nabel and Baltimore, 1987; Collart et al., 1990; Hassanain et al., 1993). The DNA-protein complex formed was separated from free oligonucleotide on 5% native polyacrylamide gel using buffer containing 50 mM Tris, 200 mM glycine and 1 mM EDTA. The gel was fixed in 10% acetic acid and dried and the bands were visualized using autoradiography with intensifying screen at −70° C.

Figure 20:
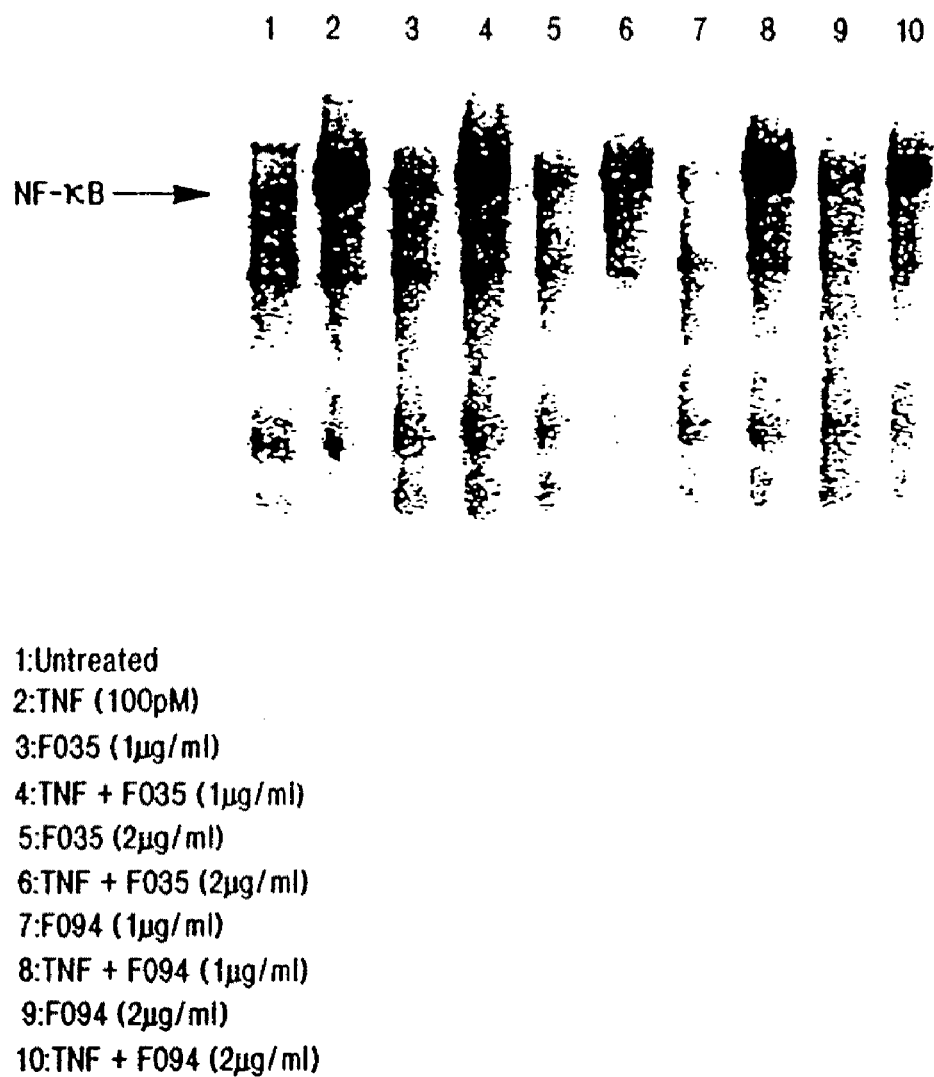
FIG. 20: EMSA demonstrating marked inhibition of TNF activated NF-κB by exposure of cells to UA-BRF-004-DELEP-F035 and UA-BRF-004Pod-DELEP-F094. Treatments were as follows: lane 1, untreated; lane 2, TNF (100 pM); lane 3, UA-BRF-004-DELEP-F035 (1 μg/ml); lane 4, TNF+F035 (1 μg/ml); lane 5, F035 (2 μg/ml); lane 6, TNF+F035 (2 μg/ml); lane 7, F094 (1 μg/ml); lane 8, TNF+F094 (1 μg/ml); lane 9, F094 (2 μg/ml); lane 10, TNF+F094 (2 μg/ml).

The results of the EMSA demonstrate that in untreated cells there is a low basal level of NF-κB which is activated by TNF (FIG. 20, Lanes 1 and 2). Pretreatment of cells with 1 μg/ml of F035 or F094 followed by TNF activation (FIG. 20, Lanes 4 and 8) resulted in no inhibition of NF-κB activation. When cells were treated with 2 μg/ml of UA-BRF-004-DELEP-F035 or UA-BRF-004Pod-DELEP-F094 (FIG. 20, Lanes 6 and 10), marked inhibition of TNF activated NF-κB was observed. The results of this study indicate that both F035 and F094 were capable of inducing a strong anti-inflammatory response. In addition to indicating the active triterpene compounds as potential anti-inflammatory compounds, the results are particularly significant given the increasing evidence demonstrating the central role that inflammation plays in carcinogenesis (Sieweke et al., 1990; Prehn, 1997; Schuh et al., 1990).

Example 9

Studies on Signal Transduction Pathway F035

In order to further elucidate the molecular targets of the active components of the *Acacia victoriae* plant extract, a study was conducted on the effect of F035 on phosphatidylinositol 3-kinase (PI3-kinase) activity, as well on AKT (protein kinase B, a serine-threonine kinase) activity, a downstream effector of PI3-kinase. PI3-kinase is an enzyme which is implicated in growth factor signal transduction by associating with receptor and non-receptor tyrosine kinases. There are two known PI3-kinase inhibitors: wortmannin, a fungal metabolite, and LY294002, a synthetic compound which is structurally similar to the plant bioflavonoid quercetin.

Figure 21:
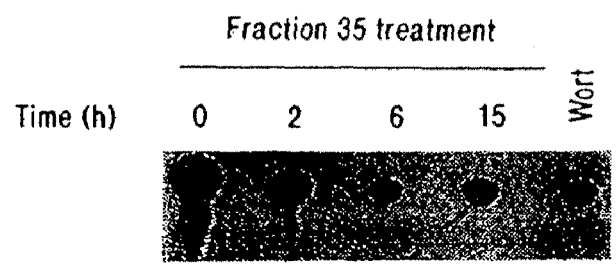
FIG. 21: Lipid kinase assay demonstrating inhibition of PI3-Kinase by UA-BRF-004-DELEP-F035 and wortmannin.

The assay was carried out as follows: Jurkat cells ($1 \times 10^7$) were starved overnight and exposed to different concentrations (1-8 μg/ml depending upon the cells line) of F035 for various times (2-16 h) at 37° C. After different time points, the cells were collected and washed with PBS at 2000 rpm for 10 min. The cells were lysed in 1% NP-40 lysis buffer for 30 min at 4° C. and the lysates isolated by centrifugation for 5 min at 15,000 rpm at 4° C. In order to conduct immunoprecipitation of PI3-kinase, 5 μl of rabbit anti-p85 antibody (tyrosine kinase receptor adapter protein; Upstate Biotechnology Inc.) was incubated with 1 ml of cell lysate for 90 min at 4° C. The immune complexes were isolated on 100 μl of 20% Protein A-Sepharose beads for an additional 90 min at 4 ° C. The immunoprecipitates were washed sequentially in a) PBS, 100 mM Na3VO4, 1% Triton -X100; b) 100 mM Tris, pH 7.6, 0.5 LiCl, 100 mM Na3VO4; c) 100 mM Tris, pH 7.6, 100 mM NaCl, 1 mM EDTA, 100 mM Na3VO4; and d) 20 mM Hepes pH 7.5, 50 mM NaCl, 5 mM EDTA, 30 mM NaPPi, 200 mM Na3VO4, 1 mM PMSF, 0.03% Triton X-100. Immunoprecipitates were then resuspended in 30 μl of kinase reaction buffer (33 mM Tris, pH 7.6, 125 mM NaCl, 15 mM $MgCl_2$, 200 mM of adenosine, 20 mM ATP, 30 μCi [g-32P] ATP). Phosphatidyle inositol (PI; 50 μl) was dried under nitrogen gas and resuspended in 20 mM HEPES, pH 7.5 at 2 mg/ml and sonicated on ice for 10 min. The PI3-kinase reaction was initiated by addition of 10 μl of the PI suspension and 10 μl of gamma-ATP. The reaction was allowed to proceed for 30 min at room temp, followed by termination of the reaction by addition of 100 p.1 of 1N HCl. Lipids were extracted with 600 μl chloroform: methanol (1:1) and resolved on silica gels (G60) by thin-layer chromatography (TLC) in chloroform : methanol: $NH_4OH:H_2O$ (60:47:2:11.3). Radio labeled phosphatidylinositol phosphate was visualized by autoradiography and inhibition was quantitated by storm system (Okada et al., 1994; Vlahos et al., 1994). The results (FIG. 21) indicate that 2 and 6 hours post-treatment with F035 (4 μg/ml) there was an inhibition of PI3-kinase activity. Similarly, when cells were exposed to 2 μg/ml of F035 for 15 h, a 95% inhibition was observed, similar to wortmannin (a fungal metabolite and known inhibitor of PI3-kinase) in Jurkat cells.

Next, the effect of F035 on AKT, a downstream effector of PI3-kinase, was studied. AKT, also known as protein kinase B, is a cellular homologue of viral oncogene v- AKT and is activated by number of growth factors and functions in a pathway involving PI3-K activation, which is sensitive to wortmannin. AKT codes for serine-threonine protein kinase, which has been shown to be amplified in 12.1% of ovarian carcinomas and 2.8% of breast cancers. AKT is involved in an anti-apoptotic pathway through phosphorylation of Bad, an anti-apoptotic molecule. Ovarian cancer patients with AKT alterations appear to have poor prognosis (Bellacosa et al., 1995). AKT has been shown to actively block apoptosis, partly by activation of p70S6 kinase (Kennedy et al., 1997). p70S6 kinase is a mitogen activated serine-threonine protein kinase required for cell growth and G1 cell cycle progression (Chou and Blenis, 1996). The activity of p70S6 kinase is controlled by multiple phosphorylation events located within catalytic and pseudosubstrate region (Cheatham et al., 1995; Weng et al., 1995).

Figure 22A:
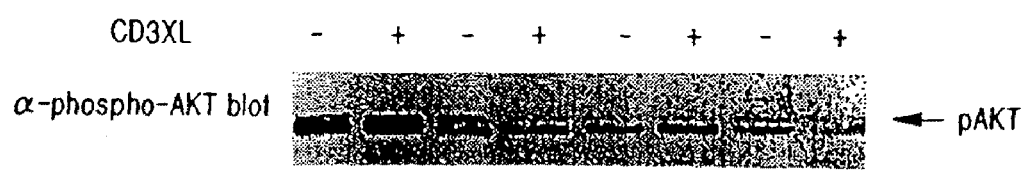
FIG. 22: SDS-PAGE gel analyzed by western-ECL using phospho-specific AKT and total AKT antibody. Post treatment of cells with 1 and 2 μg/ml of UA-BRF-004-DELEP-F035 caused a marked inhibition of AKT phosphorylation (active AKT), which was similar to a 2 hour treatment of cells with 1 μM of wortmannin.
Figure 22B:
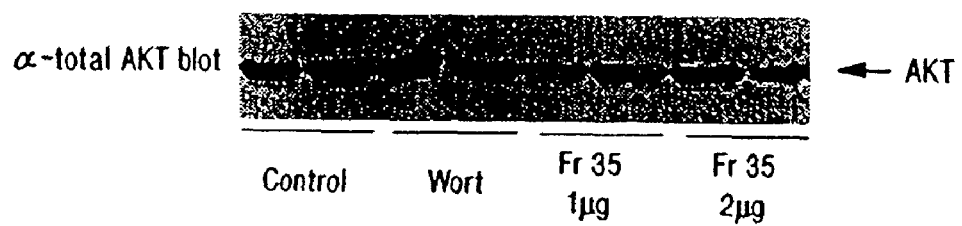
Figure 23:
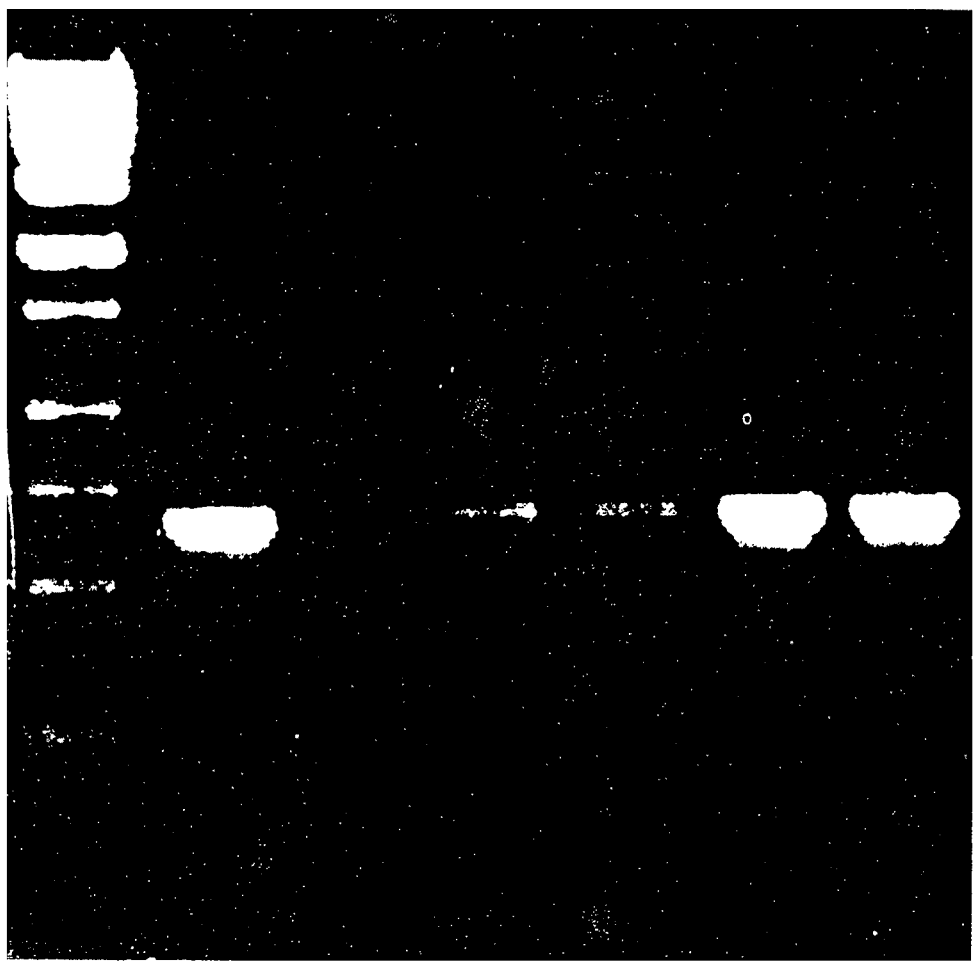
FIG. 23: Discloses PCR™ amplification of a portion of rol B gene from four independently transformed root clones. (Lanes, L-R, 1: Kb ladder, 2: positive control (Plasmid DNA from R1000 strain), 3: negative control (DNA from non-transformed root). 4-7: four independently transformed root clones. Note the amplification of a 645 by fragment in positive control and transformed roots.

The effect of F035 on phosphorylation of AKT was analyzed as follows. Jurkat cells ($5 \times 10^6$) were serum starved and exposed to F035 for 15 h and 2 h with wortmannin at 37° C. The cells were either induced with cd3XL (cd3 crosslink) or left uninduced for 10 min at 37° C. and lysed in AKT lysis buffer and the proteins were resolved on 8% SDS-PAGE gels and analyzed by western-ECL using phospho-specific AKT (Ser 473; New England Biolabs) and total AKT antibody. An assay of the effect of F035 on p70S6 kinase can be carried out similarly, but using a Phosphoplus p70S6 kinase antibody kit (New England Biolabs) for analysis of p70S6 kinase (Ser 411, thr421/ser424) phosphorylation. The results of the AKT analysis (FIG. 22), demonstrated that cd3 crosslink induces phospho AKT slightly. Post treatment of cells with 1 and 2 μg/ml of F035 caused a marked inhibition of AKT phosphorylation (active AKT), which is similar to a 2 h treatment of cells with 1 μM of wortmannin. There was, however, no change in the expression of total AKT. Similar inhibition of AKT phosphorylation was also demonstrated using ovarian cancer cells OVCAR-3 and C-2 (HEY variant), and with Jurkat cells treated with 2-4 μg/ml of F094. These findings demonstrate that F035 inhibits the phosphorylation of AKT in Jurkat cells and ovarian cancer cells. This is significant given that the PI3 kinase/AKT signaling pathway has been shown to deliver an anti-apoptotic signal (Kennedy et al., 1997). The results suggest F035 and F094 is mediating apoptosis of tumor cells through the suppression of the PI3-K signaling pathway.

Example 10

Cell-Cycle Analysis and Annexin-V Binding Assay To Detect Apoptosis

Figure 19A:
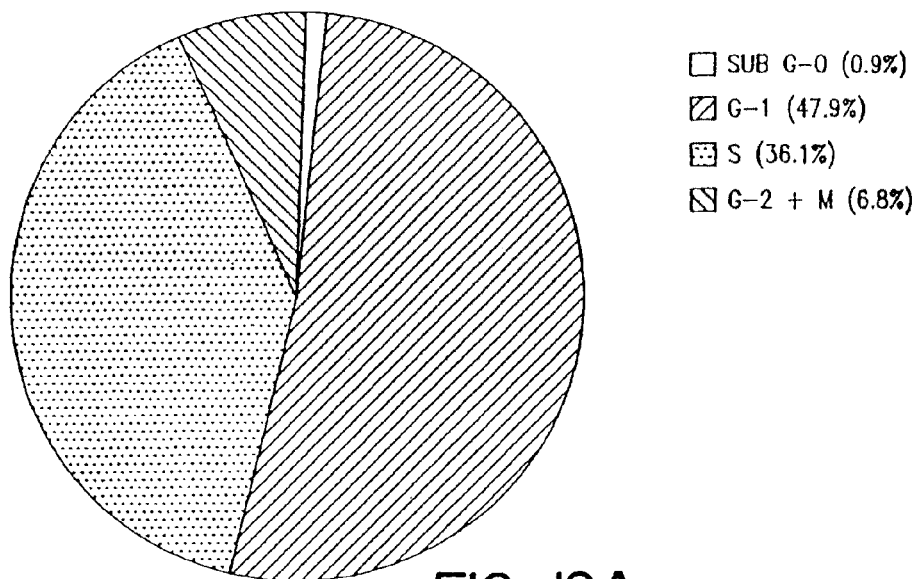
FIGS. 19A,B: Cell cycle analysis of OVCAR-3 cells pre and post treatment (48 h) with Fraction 35. The FIG. demonstrates that there is a ~8% increase in the number of cells in G1 phase and 10% decrease of cells in S phase of cell cycle post treatment with Fraction 35 showing a G1 arrest.
Figure 19B:
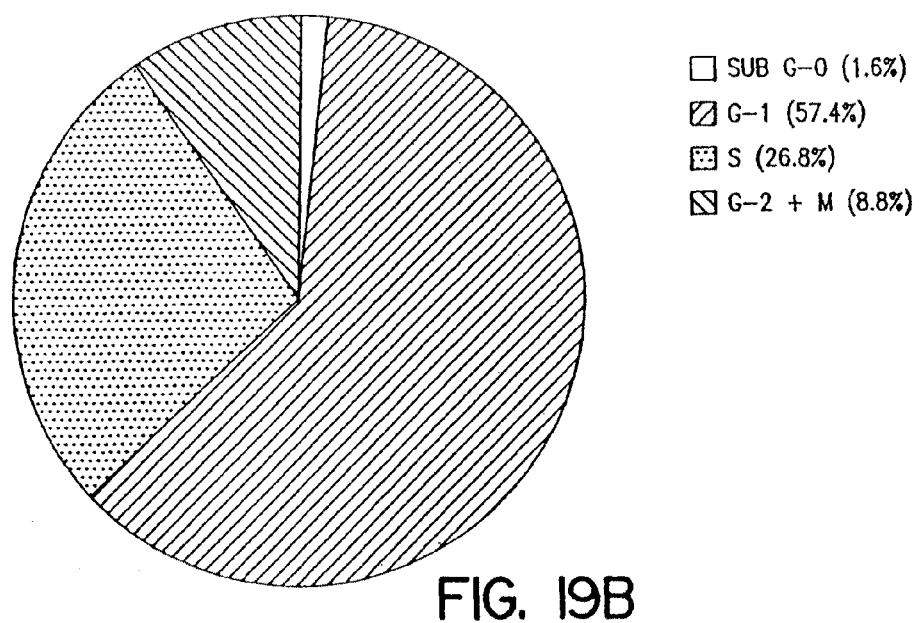
FIG. 19B: cell cycle analysis of OVCAR-3 tumor cells treated with Fraction 35.

In order to further characterize the mechanism of growth inhibition and cytotoxicity of the active compounds of the plant extract, approximately $1 \times 10^6$ OVCAR-3 tumor cells were plated in 60 mm³ dishes, treated with various concentrations of UA-BRF-004-DELEP-F035, and incubated for 18-24 hours at 37° C. The cells were harvested, washed with PBS twice and resuspended at 1×10⁶ cells/ml. Paraformaldehyde (1% final concentration) was added, drop-by-drop, to cells being gently vortexed. The cells were again washed with PBS after a 15 minute incubation on ice, and the pellet was resuspended in 70% ice cold ethanol and incubated at −20° C. overnight. Finally, the ethanol was washed off once with PBS and the cells were resuspended in 10 μg/ml of propidium iodide (Sigma Chemical Co.) with 0.1% RNase. The cells were once again incubated at room temperature for 30 minutes and then transferred to 4° C. and analyzed after 18 hours by flow cytometry (Pallavicini, 1987). The results demonstrate that prior to treatment of the cells with UA-BRF-004-DELEP-F035, 48% of the cells were in G0/G1 phase, 36% of the cells were in S phase and 7% of the cells were in G2/M phase. However, 48 h post treatment of OVCAR-3 cells with F035, 58% of the cells were in G1 and only 27% in S phase of the cell cycle, indicating an 8% increase of cells in G1 and ~10% decrease of cells in S phase of the cell cycle (FIG. 19A, B). The results demonstrate a definite G1 arrest of OVCAR-3 human ovarian carcinoma cells The effect of F035 on the cell cycle profile of human breast cancer cells was also examined. MDA-MB-435 and MDA-MB-453 breast cancer cells were exposed to different concentrations of F035 and analyzed 72 h later by cell cycle analysis as described above. The results demonstrate that F035 is inducing apoptosis of MDA-MB-435 cells by appearance of a Sub G0 peak (Table 27). In addition cell cycle regulation is also observed by reduction in the percent of cells in S and G2/M phase of cell cycle.

TABLE 27

Cell Cycle Analysis of MDA-MB-435 Breast Cancer Cells Post-Treatment with F035

|       | Control | F035 (6 μg/ml) | F035 (3 μg/ml) | F035 (1 μg/ml) |
|-------|---------|----------------|----------------|----------------|
| Sub G0 | 0.82%  | 16.0%          | 12.7%          | 0.90%          |
| G1    | 52.0%   | 50.0%          | 50.3%          | 51.0%          |
| S     | 35.0%   | 26.0%          | 26.0%          | 36.0%          |
| G2/M  | 16.0%   | 10.0%          | 2.0%           | 14.0%          |

Using the MDA-MB-453 cells, results demonstrate that F035 is inducing G1 cell cycle arrest by a ~10% increase of cells in G1 phase and 4-10% decrease of cell in S phase of cell cycle seventy-two hours post treatment with F035 (Table 28). These results demonstrate cell cycle arrest and apoptosis of tumor cells induced by the plant extract.

TABLE 28

Cell Cycle Analysis of MDA-MB-453 Breast Cancer Cells

|       | Control | F035 (6 μg/ml) | F035 (3 μg/ml) | F035 (1 μg/ml) |
|-------|---------|----------------|----------------|----------------|
| Sub G0 | 0.96%  | 2.2%           | 1.8%           | 1.5%           |
| G1    | 62.0%   | 72.0%          | 71.0%          | 69.0%          |
| S     | 26.0%   | 19.0%          | 16.3%          | 21.0%          |
| G2/M  | 12.5%   | 8.5%           | 10.4%          | 10.0%          |

Jurkat cells (1×10⁶) were treated with various concentrations of UA-BRF-004-DELEP-F035 (50-1000 ng/ml) for 18 hours at 37° C. The cells were washed once with PBS, resuspended in binding buffer (10 mM Hepes/NaOH, 140 mM NaCl, 2 mM $CaCl_2$) containing 5 μl of annexin-V-FITC conjugate (Biowhittaker, Walkersville, Md.) and incubated for 10 minutes in the dark. The cells were washed and resuspended in binding buffer containing 10 μl of 20 μg/ml propidium iodide (Sigma Chemical Co.) and analyzed by florescence activated cell sorter (FACS) analysis (Martin et al., 1995).

Results demonstrate that the purified active compounds were able to cause apoptosis in Jurkat cells. This finding was further confirmed by the ability of treated cells to bind annexin-V, an indication that cells were undergoing apoptosis (Table 29). Normally, phosphotidylserine (PS) is localized on the inner membrane of the plasma membrane. However, during the early stages of apoptosis, externalization of PS takes place. Annexin-V is a calcium binding protein which binds to PS and can be observed with annexin-V-FITC staining by flow cytometry (Martin et al., 1995).

TABLE 29

Apoptosis Measured by Annexin-V Binding in Jurkat Cells Treated with Various Concentrations of UA-BRF-004-DELEP-F035

| UA-BRF-004-DELEP-F035 (μg/ml) | % Annexin-V positive cells |
|-------------------------------|----------------------------|
| Untreated                     | 6                          |
| Anti-Fas (positive control)   | 20.0                       |
| 1 μg/ml                       | 16.0                       |
| 2 μg/ml                       | 18.0                       |

Example 11

UA-BRF-004-DELEP-F035 as a Chemoprotective Agent

The effect of UA-BRF-004-DELEP-F035 has been examined in a multi-stage skin carcinogenesis model in SENCAR mice. The animals were treated by painting the skin with acetone, the carcinogen DMBA (7,12-dimethylbenz[a]anthracene), DMBA+UA-BRF-004-DELEP-F035, and DMBA+Fraction 60 (negative control) at low (100 μg of UA-BRF-004-DELEP-F035 or Fraction 60 per mouse) and high (500 μg of UA-BRF-004-DELEP-F035 or Fraction 60 per mouse) doses of plant extract administered twice a week for 4 weeks. UA-BRF-004-DELEP-F035 or the control was applied to the skin of mice 5 minutes before applying DMBA. The animals were observed for the formation of papillomas, and were subsequently sacrificed and the tissues analyzed by histology (FIG. 9A-FIG. 9F). The results of the analysis are summarized in FIG. 10A, FIG. 10B, FIG. 11A, FIG. 11B, FIG. 12 and FIG. 13.

After 8 weeks of these experiments, the group of mice treated with DMBA had 8 papillomas per mouse, while those treated with DMBA and UA-BRF-004-DELEP-F035 had 0.66 papillomas per mouse, and those treated with DMBA and Fraction 60 (negative control) had 6.9 papillomas per mouse. These results indicated a significant protective effect of UA-BRF-004-DELEP-F035 against tumors, while there was essentially no protective effect of Fraction 60.

Further murine in vivo studies demonstrated that UA-BRF-004-DELEP-F035 is chemopreventative against carcinogen-induced tumors by preventing the mutation of the ras oncogene. The initiation stage of carcinogenesis in mouse skin is accomplished by direct-acting carcinogens (i.e. DMBA) and is essentially an irreversible stage. Inhibition of carcinogenesis was determined after 8 weeks by the reduction in formation of papillomas induced by DMBA. Molecular analysis of the treated skin demonstrated that UA-BRF-004-DELEP-F035 prevents DMBA's ability to mutate the ras oncogene (see Examples 14, 15 and 16, below).

Example 12

Procedure for Detection of Active Triterpenoids in *Acacia victoriae*

A procedure was utilized which allowed the efficient detection of active triterpenes in plant tissue sample. The procedure was carried out as follows. Approximately 5 g of leaves and twigs were cut into small pieces with scissors, or alternately, root samples were cut with a knife to produce small slices. The plant material was processed in a small blender, combined with approximately 25 ml of 80% methanol (v/v) and allowed to sit for at least 2 hours with shaking every 1 hour. Insoluble material was removed by centrifugation at 10,000 g. The extract was then used for thin layer chromatography with RP plates (aluminum TLC sheets, RP-C18 $F_{254S}$) and 40% acetonitrile (v/v). After exposure of the TLC plates to a 0.1% vanillin (4-hydroxy-3-methoxybenzaldehyde)/$H_2SO_4$ spray and baking at 70° C. for 15 to 30 minutes, active triterpenoid compounds were visible as brownish-red spots ($R_f$=0.2-0.3).

Example 13

Localization of Triterpene Compounds Within *Acacia victoriae* Plants

In initial studies, above-ground dry parts of the plants were collected in early summer for extractions. Subsequent re-collection in the fall was without activity. A systematic study was thereafter conducted to determine for the relative absence or presence of the active triterpene compounds in various parts of *Acacia victoriae* plants. After monitoring the chemistry of the plant, it was determined that essentially all of the active components in the above-ground part of the plant were concentrated in the pods, roots and seedlings while largely or completely absent in the branches, bark, leaves and seeds. Therefore, the active collecting period only lasts about three weeks from the start of pod formation until dehiscence. It was also determined that the roots of the plant produce the same active material with fluctuating ratios of sugars to active components. The latter characteristic indicates that aeroponics, which allows for vigorous root growth while maintaining normal plant development, may be well-suited for *Acacia victoriae*.

Example 14

Tumor Cell Lines and Growth Thereof

The following human cancer cell lines were obtained from American Type Tissue Culture Collection (ATCC, Rockville, Md.). SK-OV-3 and OVCAR-3 (ovarian), Jurkat (T-cell leukemia), U-937 (histiocytic lymphoma), MDA-MB-468, MDA-MB-453, MDA-MB-435, SK-BP-3, MCF-7, MDA-MB-231, BT-20 (breast), LNCaP, PC-3, DU145 (prostate), 769-P, 786-O, A498 (renal) and PANC-1 (pancreatic). HEY and Dov-13 (ovarian), cell lines were obtained from M. D. Anderson Cancer Center. The following non-transformed human cell lines MCF-10A and 10F (breast epithelium) were obtained from M. D. Anderson Cancer Center. Hs 27 (human foreskin fibroblasts) and L929 (mouse fibroblasts) were obtained from ATCC. SK-OV-3, MDA-MB-468, Hs 27, L929 were grown in minimal essential medium. OVCAR-3, Jurkat, U-937, LNCaP, DU-145, PC-3, HEY, Dov-13, PANG-1, MCF-10A, MCF-10F and remaining breast cancer cell lines were grown in RPMI 1640 and F-12 media was used to grow 769-P, 786-0 and A498. All the media used were supplemented with 10% fetal calf serum, 200 mM glutamine and 0.05% gentamicin.

Example 15

Amplification of Mouse Ha-ras Codon 61 CAA→CTA Mutations Using Mutation Specific Primers (MSP)

This protocol was derived from Nelson et al. (1992). A reverse primer, designated 3MSP61mut, was designed so that the 3' end nucleotide (A) base pairs with the middle nucleotide (underlined) of a CAA→CTA transversion in codon 61 of Ha-ras and selectively amplifies mutated DNA under the conditions described below. The assay is based on the fact that Taq polymerase lacks 3' exonuclease activity and thus cannot repair a mismatch at the 3' end of the annealed primer. The conditions of the assay depend on the reverse primer failing to anneal sufficiently to the wild type sequence so that extension does not occur. Using the same forward primer, one reaction is run with the reverse mismatch primer (3MSP61mut) and another reaction run with a reverse wild type primer (3MP61wt). This protocol detects only CAA→CTA transversions; however these mutations are the most prevalent in codon 61 point mutations. An Xba I RFLP site (T/CTAGA) is created in this transversion. The mutations can be verified by restriction of amplified DNA with Xba I or direct DNA sequencing using the $^{32}$P end labeled 5MSP61 primer. The reactions containing the mismatch products can be run on 2% low melt agarose for subsequent purification and sequencing. The sequence of the primers used, 5MSP61, 3MSP61mut, and 3MSP61wt, is given below and in SEQ ID N0:2, SEQ ID NO:3, and SEQ ID NO:4, respectively.

```
5MSP61 (23-mer)
5'-CTA AGC CTG TTG TTT TGC AGG AC-3'   (SEQ ID NO: 2)

3MSP61mut (20-mer)
5'-CAT GGC ACT ATA CTC TTC TA-3'       (SEQ ID NO: 3)

3MSP61wt (20-mer)
5'-CAT GGC ACT ATA CTC TTC TT-3'       (SEQ ID NO: 4)
```

The sequence of 3MSP61wt has 2 or 3 mismatches from N-ras and K-ras sequences, respectively, fragment size is 110 bp. The template DNA and amplification reagents were as follows:

| | |
|---|---|
| DNA (Positive Control) OR | 1.0 µg |
| DNA (Negative Control, i.e. wild type) OR | 1.0 µg |
| DNA (Sample i.e. paraffin block) OR | 5.0 µl |
| No DNA (i.e. $H_2O$) | 5.0 µl |
| Rxn Buffer (10X) (10X = 500 mM KCl, 100 mM Tris, pH 8.3, 15 mM $MgCl_2$) | 5.0 µl |
| dNTP mixture @ 500 µM each (final conc. = 20 µM) | 2.0 µl |
| [$^{32}$P] dCTP, 3000 Ci/mmol, 5 uCi, 1.7 pmol, 0.034 µM | 0.50 µl |
| 5' Primer (10 pmol/µl), 7.5 pmol (final conc. 0.15 µM) | 0.75 µl |
| 3' Primer (10 pmol/µl), 7.5 pmol (final conc. 0.15 µM) | 0.75 µl |
| Taq Polymerase (5 U/µl, 3.0 U) | 0.60 µl |
| $H_2O$ to 50.0 µl | 50.0 µl |
| Mineral Oil | 2 drops |

The amplification cycle conditions, using a Perkin Elmer thermocycler, were as follows:

| | | | |
|---|---|---|---|
| Preheat thermocycler to 95° C. | | | |
| File 512-21 | 95° C. | 1 min 30 sec | 1 Cycle |
| File 512-22 | 95° C. | 60 sec | |
| | 57° C. | 60 sec | |
| | 72° C. | 60 sec | 30 Cycles |
| File 512-10 | Soak 4° C. | | |

Figure 14:
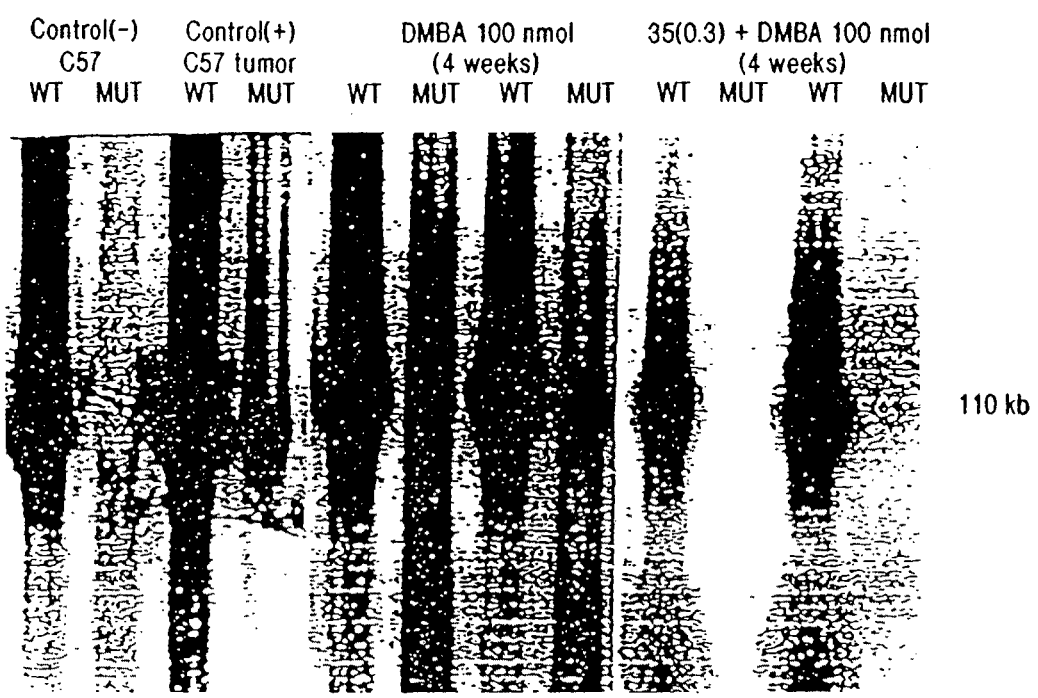
FIG. 14: Shows an autoradiograph of a PCR reaction showing amplification of mouse H-ras codon 61 mutation.

Validation of the assay was accomplished by running the following controls: Wild Type (WT), Wild Type Mutant (MUT), and negative control (H$_2$O). MUT DNA from the plasmid pHras61mut was used as a positive control sample. The plasmid pHras61 contains cloned exon 2 Ha-ras DNA from a Senear mouse tumor. The cloned mutation was verified by DNA sequencing. The mutation is the CA→CTA transversion in codon 61 (located in exon 2) of the mouse Ha-ras gene is a sample of DNA from tumor adenocarcinoma containing Ha-ras mutation in codon 61 (See FIG. 14).

Example 16

Hot PCR™/RFLP Mutation Assay for Mouse H-ras Codon 12/13

This assay is based on disruption of a naturally occurring Mnl I site spanning the three by of codon 12 and the first by of codon 13 (GGA GGC, nucleotides 34-37 in the rat and mouse Ha-ras coding sequence). The recognition site for Mnl I is N7GGAG. Mutations in any of these four positions will result in failure of Mnl I to cut the PCR™ fragment containing this region. The drawback of the assay is the occurrence of incomplete digestion by Mnl I. Such an event makes it difficult to distinguish between a small percentage of wild type DNA resistant to digestion and a low level of genuine mutations. This is sometimes observed when the source DNA contains a mixture of wild type and mutant DNA and when the assay employs $^{32}$P for fragment labeling to increase sensitivity. The PCR™ Primer Set used for the is assay is given below, and in SEQ ID NO:5 and SEQ ID NO:6. The H-ras 12 amplification product size is 214 bp.

```
Primer #3 (5'):
5'-CCTTGGCTAAGTGTGCTTCTCATTGG-3'      (SEQ ID NO: 5)

Primer #6 (3'):
5'-ACAGCCCACCTCTGGCAGGTAGG-3'         (SEQ ID NO: 6)
```

Primer #6 is used for sequencing at 55° C. using the following reaction conditions:

| | |
|---|---|
| Rxn Buffer (10X) | 1.0 µl |
| (10X = 500 mM KCl, 100 mM Tris, pH 8.3, 15 mM MgCl2 | |
| dNTP mixture @ 0.5 mM each | 1.0 µl |
| 5' Primer | 6 pmol |
| 3' Primer | 6 pmol |
| $^{32}$P-dCTP (3000 Ci/mMol) | 0.5 µl |
| Taq Polymerase (5 U/µl, 0.65 U) | 0.13 µl |
| H$_2$O | to 10.0 µl |
| DNA (Positive Control) | >200.0 ng |
| DNA (Negative Control i.e. wild type) | >200.0 ng |
| DNA (Sample i.e. paraffin block) | 5.0 µl |
| No DNA (i.e. H$_2$O) | 5.0 µl |
| Mineral Oil | 2 drops |

The amplification cycle conditions, using a Perkin Elmer PCR™ Kit, are as follows:

| | | | |
|---|---|---|---|
| Preheat thermocycler to 94° C. | | | |
| File 512-87 | 94° C. | 2 min | 1 Cycle |
| File 512-88 | 94° C. | 30 sec | |
| | 68° C. | 30 sec | |
| | 72° C. | 1 min | 8 Cycles |
| File 512-89 | 94° C. | 30 sec | |
| | 60° C. | 30 sec | |
| | 72° C. | 1 min | 32 Cycles |
| File 512-10 | Soak 4° C. | | |

Example 17

Assay Results: Detection of c-Ha-ras Mutations

Four days after the last administration of DMBA, the plant extract and the control, DNA isolated from freshly-frozen tissues of 5 mice per group was analyzed for mutations in codons 12 and 13, and codon 61 of c-Ha-ras by PCR™ analysis. The inventors have used 4-day specimens for this analysis-because some of the 2-day DNAs were degraded and therefore not suitable for Ha-ras analysis. In codons 12 and 13 there is a Mnl I restriction site which spans the three nucleotides of codon 12 and the first nucleotide of codon 13 in the wild type sequence. Mutations in any of these bases result in the loss of the Mnl I site. The inventors amplified exon 1 (which contains codons 12 and 13) of the c-Ha-ras gene from genomic DNA using a Perkin-Elmer thermal cycler. The reaction was extracted with phenol-CHCl$_3$ and the DNA was precipitated with ethanol. The DNA was then resuspended in enzyme buffer, and the PCR™ product was restricted with Mnl I and the digest electrophoresed on a 8% nondenaturing polyacrylamide gel. No loss of Mnl I restriction site was observed and the conclusion was that there are no mutations in codons 12 and 13 in the tested material. DNA for Ha-ras analysis was also obtained from paraffin-embedded sections cut a 8µ from samples collected two days after last dosing. The 25 sections from each paraffin block were placed in microfuge tubes, deparaffinized with xylene and ethanol, centrifuged and resuspended in 5% chelex with proteinase K.

The first procedure used for Ha-ras codon 61 was derived from Nelson et al. 1992 (Example 15, above). Using the same forward primer, one reaction was run with the reverse mismatch primer (3MSP61mut) and another reaction was run with a reverse wild type primer (3MSP61wt). This protocol detects only CAA→CTA transversion mutations that are the most prevalent in codon 61 point mutations. An Xba I RFLP site (T/CTAGA) is created in this transversion. The reactions containing the mismatch products were run on 2% low melt agarose for subsequent purification and sequencing. The ratio of the amount of cut (wild type DNA) to uncut (mutated DNA) was determined by quantifying ethidium bromide staining intensity or $^{32}$P labeling. The DNA from the plasmid pHras61mut was used as a positive control sample. The plasmid pHras61 contains cloned exon 2 Ha-ras DNA from a Sencar mouse tumor. The cloned mutation was verified by DNA sequencing. The mutation is the CAA→CTA transversion in codon 61 (located in exon 2) of the mouse Ha-ras gene. The reaction conditions were as described in Example 15.

Example 18

Effect of F035 on the Initiation of Aberrant Crypts in F344 Rats Treated with Azoxymethane Male rats (Fishcer, 3444) were obtained from Charles River (Raleigh, N.C.) at 6 weeks of age. The rats were fed ad libitum an AIN-76A diet that was purchased from Dyets Inc. (Bethlehem, Pa.). The diet consisted of 20% casein, 0.3% DL-methionine, 15% corn starch, 50% sucrose, 5% corn oil, 5% cellulose, 3.5% AIN-76 salt mix, 1% AIN-76 vitamin mixture and 0.2% choline bitartrate. The animals were also provided with tap water ad libitum. Azoxymethane (AOM), which induces aberrant crypts in rats, was purchased from Sigma Chemical Company (St. Louis, Mo.). Animals were fed rat chow for three days while in quarantine and then they were fed AIN-76A until 7 wk of age. The animals were randomized into three treatment groups (10 animals/group). The animals in group 1 were fed with AIN-76A diet alone, group 2 animals received AIN-76A diet+5 mg/kg of F035 and the animals in group 3 were fed the AIN-76A diet+10 mg/kg of F035 (Table 30).

TABLE 30

Treatment Groups for Study on the Effect of F035 on the Initiation of Aberrant Crypts in F344 Rats Using Azoxymethane

| Group | # Animals | F035 Dose (mg/kg diet) |
|---|---|---|
| 1 | 10 | 0 |
| 2 | 10 | 5 |
| 3 | 10 | 10 |

One week following feeding all the animals were given intraperitoneal injection of AOM (15 mg/kg body weight). The second AOM injection followed one week later. Animals were weighed weekly throughout the study. The animals were fed for 4 weeks. Thirty-one days later the animals were sacrificed by $CO_2$ asphyxiation. The colons were excised and flushed with cold PBS, cut along the longitudinal median axis, placed on a filter paper and fixed in 70% alcohol for at least 24 h. The colons were stained with methylene blue (0.25% in PBS) for ~1 min. Aberrant crypt foci were scored under a dissecting microscope at 20×. The aberrant crypts were distinguished from the surrounding normal crypts by their increased size, significantly increased distance from the luminal to basal surfaces of cells and enlarged pericryptal zone. All the specimens were coded and scored blindly by two scorers. Statistical significance was determined by checking for the differences between the groups using one way ANOVA. If the differences were found, a bonferroni t-test was used to test multiple comparisons of both doses of F035 to the control group. The scoring of the colons was done by two scorers, each blinded as to the experimental groups they were scoring. There was good agreement between the two scorer's results.

It was found that F035 significantly reduced the total number of aberrant crypt foci when added to the diet at 10 mg of F035 per kg of diet, which is roughly equivalent to a daily intake of one mg of F035 per kg of body weight (Table 31, Table 33). The same dose also significantly reduced the number of aberrant crypts in the singlets and doublets categories (Table 32, Table 34). The lower dose of F035, 5 mg per kg of diet (roughly equivalent to a daily intake of 500 micrograms of F035 per kg of body weight) did cause a reduction in the total, singlets and doublets categories of aberrant crypt foci, but the reduction was not significantly different from the control values (Table 32, Table 34). There was no difference in weight gain between the experimental and control groups over the course of the study (Table 35, Table 36, Table 37).

TABLE 31

Effect of F035 on Number of Aberrant Crypts/Colon in AOM-Treated Rats

| Dose of F035 g/kg diet | Aberrant Crypts/ Colon Averaged Scorer 1 & 2 | | | |
|---|---|---|---|---|
| | Means ± SEM | % Control | Result | Comments |
| 0 | 86 ± 5 | 100 | | |
| 0.005 | 73 ± 5 | 85 | − | C |
| 0.01 | 43 ± 4 | 50 | + | C |

− = Not significantly different from control
+ = Significantly different from control (p < 0.05)
C = Conclusive study

TABLE 32

Effect of F035 on Number of Aberrant Crypts per Focus in AOM-Treated Rats

| Agent & Dose | (g/kg Diet) | Number of Aberrant Crypts Per Focus (Averaged Scorer 1 and 2) | | | | | |
|---|---|---|---|---|---|---|---|
| | | 1 | | 2 | | ≦3 | |
| | | Mean ± SEM | % | Mean ± SEM | % | Mean ± SEM | % |
| Fraction 35 | 0 | 66 ± 5 | 100 | 17 ± 1 | 100 | 3 ± 1 | 100 |
| Fraction 35 | 0.005 | 56 ± 4 | 85 | 15 ± 1 | 88 | 3 ± 0 | 100 |
| Fraction 35 | 0.01 | 34 ± 3* | 52 | 8 ± 1* | 47 | 1 ± 0 | 33 |

*significantly different from control (p < 0.05)

TABLE 33

Summary of Raw Data from Analysis of the Effect of F035 on Mean Aberrant Crypts Per Colon in AOM Treated Rats

| n | AOM | Agent | Dose g/kg diet | Mean Aberrant Colon ± SEM | | Crypts/ Combined |
|---|---|---|---|---|---|---|
| | | | | Scorer 1 | Scorer 2 | |
| 10 | + | Carcinogen only (4 weeks)[a] | 0 | 76 ± 4 | 95 ± 9 | 86 ± 5[b] |
| 10 | + | F035 | 0.005 | 67 ± 4 | 80 ± 8 | 73 ± 5 |
| 10 | + | F035 | 0.01 | 34 ± 3[c] | 51 ± 7[c] | 43 ± 4[c] |

[a]AOM injected rats; no test agent
[b]Average of pooled AOM injected rats (n = 10) at 4 weeks
[c]significantly different from control (p < 0.05)

TABLE 34

Summary of Raw Data from Analysis of the Effect of F035 on Number of Aberrant Crypts Per Focus in AOM Treated Rats

| Agent | Dose | Scorer | Number of Aberrant Crypts Per Focus Mean ± SEM | | | |
|---|---|---|---|---|---|---|
| | | | 1 | 2 | 3 | Total |
| F035 | 5 mg | scorer 1 | 49 ± 4 | 15 ± 2 | 2 ± 0 | 67 ± 4 |
| | | scorer 2 | 63 ± 7 | 15 ± 1 | 3 ± 1 | 80 ± 8 |
| | | combined | 56 ± 4 | 15 ± 1 | 3 ± 0 | 73 ± 5 |
| | 10 mg | scorer 1 | 27 ± 3* | 7 ± 1* | 0 ± 0* | 34 ± 3* |
| | | scorer 2 | 41 ± 5* | 8 ± 1* | 3 ± 1 | 51 ± 7* |
| | | combined | 34 ± 3* | 8 ± 1* | 1 ± 0 | 43 ± 4* |
| Control | NA | scorer 1 | 57 ± 4 | 17 ± 1 | 3 ± 1 | 76 ± 4 |
| | | scorer 2 | 75 ± 8 | 18 ± 2 | 3 ± 1 | 95 ± 9 |
| | | combined | 66 ± 5 | 17 ± 1 | 3 ± 1 | 86 ± 5 |

*Significantly different from control values ($p < 0.05$)

TABLE 35

Animal Weights of AOM-Treated Rats Fed F035, 5 mg/kg diet

| Rat # | Week 1 | Week 2 | Week 3 | Week 4 | Week 5 |
|---|---|---|---|---|---|
| 1 | 154.4 | 198.2 | 215.0 | 219.7 | 235.8 |
| 2 | 149.8 | 195.1 | 210.6 | 210.6 | 232.9 |
| 3 | 154.1 | 200.7 | 228.1 | 228.1 | 248.0 |
| 4 | 154.1 | 199.8 | 216.2 | 220.8 | 242.9 |
| 5 | 158.0 | 208.4 | 228.4 | 231.5 | 256.8 |
| 6 | 154.8 | 196.0 | 208.3 | 213.4 | 230.2 |
| 7 | 164.2 | 210.1 | 224.4 | 225.5 | 246.8 |
| 8 | 161.7 | 202.3 | 218.8 | 220.4 | 237.8 |
| 9 | 153.0 | 199.7 | 217.0 | 218.1 | 238.1 |
| 10 | 158.8 | 198.5 | 212.8 | 212.3 | 231.6 |
| Mean | 156.3 | 200.9 | 218.0 | 220.0 | 240.1 |
| SEM | 1.4 | 1.6 | 2.2 | 2.2 | 2.7 |

TABLE 36

Animal Weights of AOM-Treated Rats Fed F035, 10 mg/kg diet

| Rat # | Week 1 | Week 2 | Week 3 | Week 4 | Week 5 |
|---|---|---|---|---|---|
| 1 | 148.6 | 187.1 | 201.9 | 205.6 | 224.8 |
| 2 | 148.3 | 189.9 | 196.0 | 199.0 | 220.8 |
| 3 | 149.0 | 197.7 | 211.2 | 216.2 | 237.2 |
| 4 | 146.2 | 189.1 | 206.1 | 209.2 | 230.0 |
| 5 | 151.9 | 197.2 | 214.9 | 218.6 | 241.2 |
| 6 | 152.2 | 190.0 | 205.2 | 208.1 | 226.6 |
| 7 | 136.1 | 187.8 | 211.8 | 216.2 | 241.2 |
| 8 | 157.4 | 207.1 | 224.1 | 224.8 | 246.0 |
| 9 | 141.9 | 187.8 | 207.7 | 211.1 | 235.6 |
| 10 | 155.7 | 185.9 | 196.4 | 194.9 | 213.9 |
| mean | 148.7 | 192.0 | 207.5 | 210.4 | 231.7 |
| SEM | 2.0 | 2.1 | 2.7 | 2.9 | 3.2 |

TABLE 37

Animal Weights of AOM-Treated Rats

| Rat # | Week 1 | Week 2 | Week 3 | Week 4 | Week 5 |
|---|---|---|---|---|---|
| 1 | 149.3 | 195.2 | 203.2 | 214.4 | 240.6 |
| 2 | 166.6 | 213.8 | 229.8 | 231.8 | 250.7 |
| 3 | 158.6 | 195.8 | 209.0 | 211.2 | 226.8 |
| 4 | 156.4 | 200.3 | 214.3 | 216.9 | 231.2 |
| 5 | 151.2 | 194.7 | 205.2 | 207.4 | 228.5 |
| 6 | 157.3 | 203.9 | 217.2 | 217.8 | 237.0 |
| 7 | 146.7 | 192.1 | 216.6 | 217.1 | 235.2 |
| 8 | 145.5 | 190.3 | 203.8 | 204.7 | 220.3 |
| 9 | 158.1 | 197.4 | 212.3 | 211.3 | 231.2 |
| 10 | 157.7 | 201.8 | 217.9 | 219.2 | 240.8 |

TABLE 37-continued

Animal Weights of AOM-Treated Rats

| Rat # | Week 1 | Week 2 | Week 3 | Week 4 | Week 5 |
|---|---|---|---|---|---|
| Mean | 154.7 | 198.5 | 212.9 | 215.2 | 234.2 |
| SEM | 2.0 | 2.2 | 2.6 | 2.4 | 2.7 |

Example 19

Antitumor Activity of Aglycones

Studies confirm the importance of the sugar to the biological activity as the removal of the sugars from the core triterpene molecule results in significant loss of biological activity. As shown in Table 38, UA-BRF-004Pod-DELEP-F164 (generated by hydrolysis of the sugars from UA-BRF-004Pod-DELEP-F094 with esters attached) and UA-BRF-004Pod-DELEP-F245 (a methyl ester mixture of the hydrolysis product of UA-BRF-004Pod-DELEP-F094) show marked loss of anti-tumor activity against a panel of tumor cell lines. Similarly, UA-BRF-004Pod-DELEP-C 194 (the purified acetate of aglycon 1) exhibits substantial of anti-tumor activity against a panel of tumor cell lines compared to the data of the triterpene glycoside Fraction 35. Thus, there is a marked loss of biological activity following hydrolysis of the sugar units from the triterpene glycoside disclosed herein.

TABLE 38

Bioassay of Fractions F164, F245 and C194.

| | 50 µg/ml | 25 µg/ml | 12.5 µg/ml | 6.25 µg/ml | 3.12 µg/ml |
|---|---|---|---|---|---|
| F164 | | | | | |
| 769-P | 45 | 20 | 0 | 0 | 0 |
| Panc-1 | 57 | 27 | 13 | 0 | 0 |
| Dov-13 | 80 | 56 | 16 | 12 | 10 |
| MDA-MB-453 | 66 | 30 | 13 | 0 | 0 |
| JURKAT | 93 | 86 | 55 | 39 | 16.5 |
| F245 | | | | | |
| 769-P | 26 | 14 | 14 | 7 | 0 |
| Panc-1 | 49 | 26 | 4 | 0 | 0 |
| Dov-13 | 91 | 90 | 25 | 28 | 13 |
| MDA-MB-453 | 90 | 75 | 8 | 8 | 0 |
| JURKAT | 93 | 89 | 64 | 23 | 0 |
| C194 | | | | | |
| 769-P | 13 | 6 | 0 | 0 | 0 |
| Panc-1 | 6 | 9 | 0 | 0 | 0 |
| Dov-13 | 3 | 0 | 0 | 0 | 0 |
| MDA-MB-453 | 16 | 0 | 0 | 0 | 0 |
| JURKAT | 34 | 18 | 9 | 2 | 0 |

Example 20

Analysis of the Effect of F035 on Cholesterol Metabolism

The purpose of this study is to analyze the effect of the biologically active triterpene glycosides of the invention on the prevention of cardiovascular disease. The long-term objective of this study is to demonstrate that the triterpene compounds added to the diets of mammals, including humans, will reduce serum cholesterol. The hyperlipidemic hamster model selected for the study is a rodent model, which in contrast to the rat model, closely mimics both the LDL receptor and human plasma lipoprotein changes in response to cholesterol content (Spady et al., 1993).

The triterpene glycoside is administered, at two different concentrations, into a purified hamster diet without any change in the level of calcium, potassium, phosphorus or other essential components of the diet. Two different levels of supplementation with triterpene glycoside are used in order to show a dose-response relationship. The animals are fed with free access to the Dyets purified hamster diet formulated according to NRC recommendations (Reeves et al., 1993) with or without 1% cholesterol (Davis et all, 1989). The Dyets purified hamster diet containing cholesterol is modified with triterpene glycoside using concentrations indicated below. Pelleted study and control diets are prepared by Dyets, Inc. (Bethlehem, Pa.) with no change in the content of calcium, phosphorus or any essential micronutrient. Animals are monitored for food intake and body weight gain weekly. The animals used are four-week old, male outbred, virus-free Golden Syrian hamsters (Charles River Laboratories, Wilmington, Mass.). Animals are randomized by weight using a random number generator in the Statview program, housed 3 per cage in a room illuminated 12 h per day and maintained at a temperature of 22° C.±1.0° C.

After 0, 4, and 8 wk on their respective diets with or without the triterpene glycoside, 12 animals per group are selected at random and killed at 9-11 a.m. The liver and kidneys are removed, weighed, processed, and stored at −70° C. for future studies. Blood is obtained at sacrifice by cardiac puncture prior to the removal of the liver and kidneys and analyzed for lipid profiles. The blood serum lipid profiles are analyzed between the treatment and control groups. There are two control groups (Groups 1 and 2) and two treatment groups (Groups 3 and 4). All the groups receive the NRC hamster diet during a two-week quarantine period. Group 1 continues on the NRC diet until the end of the study. Groups 2-4 are fed the NRC diet plus 1% cholesterol for another two-week period to induce hypercholesterolemia. Then, Group 2 will continue on this diet until the end of the study, while Groups 3 and 4 will be fed the same diet supplemented with the triterpene glycoside (e.g., F035 or F094). A summary of the treatment groups is given below, in Table 39.

TABLE 39

Scheme of Diet Modification

| Group No. | Initial Number of Hamsters | Symbol | Diet Modifier Concentration |
|---|---|---|---|
| 1 | 24 + 12[a] | None | — |
| 2 | 24 + 12[a] | Chol[b]+ | 1% Chol |
| 3 | 24 | Chol[b] + TG[c] | 1% Chol + 0.003% TG |
| 4 | 24 | Chol[b] + TG[c] | 1% Chol + 0.075% TG |

[a]To be sacrificed at the beginning of triterpene glycoside feeding.
[b]Chol = cholesterol
[c]TG = triterpene glycoside After 0 (control group only), 4, and 8 wk on their respective diets, with or without the triterpene glycoside, 12 animals per group are selected at random and killed at 9-11 a.m. The livers and kidneys of hamsters were removed, weighed and processed for possible abnormalities. A portion of each organ showing abnormalities was prepared for histology analysis, i.e., frozen for paraffin sections and sections stained with hematoxylin and eosin. Blood was obtained at sacrifice by cardiac puncture prior to surgical removal of the liver and kidneys. Serum was prepared and kept at −20° C. for lipid profile analysis. Hamsters were fasted overnight prior to sacrifice. Data is shown in Table 40 below.

Blood samples collected in the course of this study are used for determination of total cholesterol, triglycerides, HDL-cholesterol, and LDL-cholesterol plus VLDL-cholesterol (Mackness and Durrington, 1992) at the Roche Biomedical Laboratories, Burlington, N.C. Statistical analysis of the data is performed on a Power Macintosh 9600 computer with Macintosh software for one-way analysis of variance, p value, and linear regression (Armitage, 1971). In particular, data analysis of lipid profiles in each diet/drug group is performed by analysis of variance using Newman-Keuls mean separations (Steel and Torrie, 1980).

TABLE 40

Effect of Continual Feeding of Triterpene Glycoside (TG) to Hamsters for Six Weeks

| Diet Group | Total Cholesterol (mg/dL) Average | % Change | Triglycerides (mg/dL) Average | % Change | HDL Cholesterol (mg/dL) Average | % Change | LDL Cholesterol (mg/dL) Average | % Change |
|---|---|---|---|---|---|---|---|---|
| Control | 141 | — | 133 | — | 141 | — | 0 | — |
| Cholesterol | 341 | — | 247 | — | 281 | — | 31 | — |
| 0.015% TG | 329 | −3.5 | 260 | 5.3 | 250 | −11 | 36 | 16.1 |
| 0.03% TG | 303 | −11.1 | 236 | −4.4 | 246 | −12.4 | 15 | −51.6 |

12 hamsters/group fed purified hamster diet plus 1% cholesterol

Example 21

Study on the Prevention of UVB-Induced Carcinogenesis with Fraction 35

This study will focus on the prevention of UVB-induced carcinogenesis in the mouse skin model with the active triterpene glycosides of the invention. The long-term objective of the study is to demonstrate that in the mouse skin model the triterpene glycosides will prevent UVB-induced lesions. The mouse experimental model is used because the model closely resembles the human situation. In the study, the inventors will seek to demonstrate that topical application of the active triterpene compounds of the invention in acetone to the dorsal skin of SKH-1 hairless mice irradiated with UVB will prevent skin lesions caused by UVB.

In the study, SKH-1 hairless mice are irradiated with UVB radiation at the dose of 1.8 kJ/m$^2$ for up to 15 min. Mice are pretreated with two different doses of F035 of (2 mg and 4 mg per dose) as well as negative controls (F060 or acetone alone). It is believed a minimum of 10 mice per group are needed to obtain statistically meaningful results. Each test compound is applied topically 10 min before irradiation 3 times per wk for up to 6-10 wk. The studies are conducted for a short period of time to evaluate the preventive effect of the compounds. It is not expected to see visible tumors, even with UVB alone, only skin lesions within the specified time-frame. A slight erythema (minor redness of the skin) may be observed, which should disappear the next day after irradiation.

The UV apparatus used has eight Westinghouse FS40 sunlamps, an IL-1400A radiometer/photometer, and an attached IL-1403 UVB phototherapy radiometer with a SEL 240/UVB-1/TD detector. The middle part has several chambers, each holding an individual mouse. There are holes inside the chambers for proper ventilation while mice are being irradiated. The chambers rotate in circular motion during irradiation so each mouse is exposed to UVB light uniformly. There are doors in this device that could be closed while the UVB lamp is on, so the UVB light is contained inside the device. The amount of the UVB exposure will be measured with a UVB radiometer. Mice should stay in the chambers for not longer than 10 to 15 min.

The purpose of the study is to establish photoprotective effects against UVB injury in mouse skin. UVB is absorbed directly by cellular DNA and produces lesions that may cause mutations in the target gene(s), ultimately leading to cancer. Early detection of these lesions and prevention of such lesions may indicate chemoprotective effects (Berton et aL, 1997; Chatterjee et al., 1996; Youn et al., 1997; Shirazi et al., 1996; Baba et al., 1996; Takema et al., 1996).

TABLE 41

UVB-Irradiation Regimen

| | |
|---|---|
| UVB alone | 10 mice per group |
| Acetone/UVB | 10 mice per group |
| F035 (2 mg/dose) 5 to 10 min later UVB | 10 mice per group |
| F035 (4 mg/mouse) 5 to 10 min later UVB | 10 mice per group |
| F060 (2 mg/mouse) 5 to 10 min UVB | 10 mice per group |
| F060 (4 mg/mouse) 5 to 10 min UVB | 10 mice per group |

The treatment groups for the study are as indicated in Table 41. The size of the groups is deemed sufficient to control variation in skin hyperplasia and skin inflammation in a given group, inter-animal variation in epidermal thickness and skin inflammation in animals of the same age and the same developmental stage. Hyperplasia and skin inflammation are the main parameters measured in the study. Remaining skins are preserved for measurements of other biomarkers, like modified DNA bases (8-OH-dG) and oncogene expression (Ha-ras oncogene).

The animals will have free access to pelleted diets and drinking water throughout the study. Animals will be monitored for food intake and body weight gain weekly. The animals used are seven-week old, female outbred, virus-free SKH-1 hairless mice (Charles River Laboratories, Wilmington, Mass.). Animals are randomized by weight using a random generator in the Statview program, housed 5 per cage in a room illuminated 12 h per day and maintained at a temperature of 22° C.±1.0° C.

Statistical analysis of data is performed on a Power Macintosh G3 computer with Macintosh software for one-way analysis of variance, p value, and linear regression (Armitage, 1971). In particular, data analysis of epidermal thickness in each drug group is performed by analysis of variance (Armitage, 1971).

Example 22

Effect of Biologically Active Triterpenes on the Expression of Proteins Involved in Cell-Cycle Arrest and Apoptosis Apoptosis is defined as a normal physiologic process of programmed cell death which occurs during embryonic development and during maintenance of tissue homeostasis. The process of apoptosis can be subdivided into a series of metabolic changes in apoptotic cells. Individual enzymatic steps of several regulatory or signal transduction pathways can be assayed to demonstrate that apoptosis is occurring in a cell or cell population, or that the process of cell death is disrupted in cancer cells. The apoptotic program is also observed by morphological features which include changes in the plasma membrane (such as loss of asymmetry), a condensation of the cytoplasm and nucleus, and internucleosomal cleavage of DNA. This is culminated in cell death as the cell degenerates into "apoptotic bodies".

Techniques to assay several enzymatic and signaling processes involved in apoptosis have been developed as standard protocols for multiparameter apoptosis research. One example of an early step in apoptosis, is the release of cytochrome c from mitochondria followed by the activation of caspase-3 pathway (PharMingen, SanDiego, Calif.). Induction of the caspases (a series of cytosolic proteases) is one of the most consistently observed features of apoptosis. In particular, caspase-3 plays a central role in the process. When caspases are activated, they cleave target proteins; one of the most important of these is PARP (a protein located in the nucleus). Therefore, assays detecting release of cytochrome c, detecting caspase-3 activity and detecting PARP degradation are effective determinants of apoptosis.

Furthermore, agents that cause the release of cytochrome c from the mitochondria of malignant cells can be concluded to be likely therapies for restoring at least some aspects of cellular control of programmed cell death.

Another apoptotic assay is the Annexin-V detection (BioWhitaker, Walkerville, Md.). Normally, phosphotidylserine (PS) is localized on the inner membrane of the plasma membrane. However, during the early stages of apoptosis, externalization of PS takes place. Annexin-V is a calcium binding protein which binds to PS and can be observed with annexin-V-FITC staining by flow cytometry (Martin et al., 1995). The ability of cells treated with the *Acacia victoriae* compounds described in this invention, to bind annexin-V, is taken as an indication that cells were undergoing apoptosis.

In other examples, the inventors have used PI-3-Kinase assay and to detect the apoptotic activity in cells treated with the anti-cancer compounds isolated from *Acacia victoriae*. Phosphoinositide 3-kinase (PI3K), a cell membrane associated enzyme, is capable of phosphorylating the 3-position of the inositol ring of phosphatidylinositol, thus defining a new lipid signaling pathway in those cells where PI3K is active. When PI3K is active, a kinase called AKT is recruited to the cell membrane. AKT is the product of an oncogene which is catalytically activated after recruitment to the membrane. Fully activated AKT plays a crucial role in cell survival. The PI3K/AKT pathway provides a mechanism by which cells evade apoptosis. Thus, a means to inhibit PI3K in malignant cells, is a likely therapy for restoring at least some aspects of the cellular control of apoptosis.

Example 23

Cell Cycle Analysis

Cell cycle analysis was done by flow cytometry by standard methods with some modifications. Briefly, $1 \times 10^6$ cells were plated in 60-mm³ dishes and exposed to various concentrations of F035 for 72 h at 37° C. Cells were washed in PBS and resuspended at a concentration of 1×106 cells/ml. Cells were fixed first with 1% paraformaldehyde followed by ice cold 70% ethanol. The cells were then stained with propidium iodide (10 µg/ml; Sigma Chemical Co., St. Louis, Mo.) containing 0.1% RNAse (Sigma) for 30 min at room temperature and analyzed on a Beckton Dickinson FAC SCAN.

Example 24

AnnexinV- Fluorescein Isothiocyanate (FITC) Binding Assay

Induction of apoptosis in cancer cells was studied by AnnexinV- FITC binding assay. Jurkat cells (1×10⁶) were treated with various concentrations of mixture of triterpene glycosides (F035) and pure extracts D1 and G1 (0.5-2.0 µg/ml) for 18 h at 37° C. After washing the cells in PBS they were resuspended in binding buffer (10 mM HEPES/INaOH, 140 mM NaCl, 2 mM CaCl₂) containing 5 µl of annexin V-FITC conjugate (Bio Whittaker, Walkersville, Md.) and incubated for 10 min in the dark. Cells were next stained with propidium iodide (20 µg/ml) and analyzed by flow cytometry. (Martin et aL, 1995).

Example 25

Phosphatidylinositol 3-Kinase (PI3-Kinase) Assay

The serum starved Jurkat cells were treated with 2 of F035 for 2-15 h or 0.5 h with wortmannin at 37° C. PI 3-kinase activity was determined as described (Whitman et al., 1985; Royal and Park, 1995). PI3-kinase was immunoprecipitated from 1 mg of cellular protein using 5 µl rabbit anti p85 antiserum at 4° C. for 90 min. The immune complexes were collected on 20% protein A-sepharose beads for 90 min at 4° C. Next the immunoprecipitates were resuspended in 30 µl of kinase reaction buffer (33 mM Tris, pH 7.6, 125 mM NaCl, 15 mM MgCl₂, 200 mM of adenosine, 20 mM ATP, 30 uCi [g-32] adenosine triphosphate ATP). The PI3-kinase reaction was initiated by addition of 10 µl of the PI suspension and 10 µl of gamma-ATP and allowed to proceed for 30 min at room temp. Adding 100 µl of 1 N HCl terminated the reaction. Lipids were extracted from the reaction mixture with chloroform: methanol (1:1) and resolved by thin layer chromatography (TLC) in chloroform: methanol: NH₄OH: H₂O (60:47: 2:11.3) on silica gel G60 plates. Radio labeled phosphatidylinositol (PI) phosphate was visualized by autoradiography and inhibition was quantitated using a Storm 860 system (Molecular Dynamics).

Example 26

Analysis of the Total and Phosphorylated forms of AKT

The expression of total and phosphorylated forms of AKT was determined by western blot analysis. Jurkat cells cultured in medium containing 0.5% FBS were treated with F035 and pure extracts DI and G1 (2.0 µg/ml) for 15 h at 37° C. The cells were lysed in AKT lysis buffer (20 mM Tris-HCl, 150 mM NaCl, 1 mM EDTA, 1 mM EGTA, 1% Triton X-100, 2.5 mM sodium pyrophosphate, 1mM ß-glycerol phosphate, 1 mM Na₃VO₄, 1 ml leupeptin, 1 mM PMSF pH 7.5). Cellular protein (40 µg) was resolved on 8% SDS-polyacrylamide gel and electrotransferred onto nitrocellulose membrane. Membranes were probed first with phosphospecific AKT (Ser 473) or AKT antibody followed by goat anti rabbit antibody conjugated to horseradish peroxidase. Proteins were detected by chemiluminescence (ECL, Amersham, Arlington Heights, Ill.).

Example 27

Electrophoretic Mobility Shift Assay (EMSA)

An EMSA to study the effect of crude (F035) and pure extracts D1 and G1 on TNF (Genetech Inc.) induced NF-κB was done as described earlier. Jurkat cells (1×10⁶/ml) were treated with different concentrations of crude and pure extracts for 15 hr at 37° C. Next the cells were exposed to 100 pM of TNF for 15 min at 37° C. Nuclear extracts were prepared as described before. Nuclear extracts were incubated with 16 fmol ³²P-end-labeled 45-mer double-stranded NF-κB oligonucleotide from the human immunodeficiency virus long terminal repeat, (SEQ. ID NO. 9)
5'-TTGTTACAAGGGACTTTCCGCTGGGGACTTTCCAGGGAGGCTGG-3' for 15 min at 37° C. in the presence of 2 µg of poly (dI-dC). The DNA protein complex was separated from free oligonucleotide on 7.5% native polyacrylamide gels. The radioactive bands from the dried gels were visualized and quantitated by a PhosphoImager (Molecular Dynamics, Sunnyvale, Calif.) using ImageQuant software.

Example 28

Induction and Analysis of Inducible Nitric Oxide Synthase (iNOS)

U-937 and Jurkat cells were used for studying iNOS. U-937 cells were differentiated into macrophages by culturing them with PMA (100 nM) for 72 hr at 37° C. The differentiated cells were treated with F035 (2 µg/ml) for 15 hr followed by a 4 hr treatment with LPS (10 µg/ml) induce iNOS. In Jurkat cells the iNOS was induced by treating 0.5× 10⁶/ml cells with PHA (10 µg/ml) and PMA (10 ml) for 24 hr at 37° C. Cell lysates were prepared by repeated freezing and thawing in RIPA buffer (1% NP-40, 0.5% Na deoxycholate, 0.1% SDS in PBS). Cellular protein (200 µg) was resolved on a 7.5% SDS-polyacrylarnide gel, electrotransferred onto nitrocellulose membrane, probed with rabbit anti-iNOS antibody followed by goat anti-rabbit antibody conjugated to horseradish peroxidase. Protein bands were detected by chemiluminescence (ECL, Amersham, Arlington Heights, Ill.).

Example 29

Mixture and Pure Triterpene Glycosides Induce Tumor Cell Cytotoxicity

Figure 42:
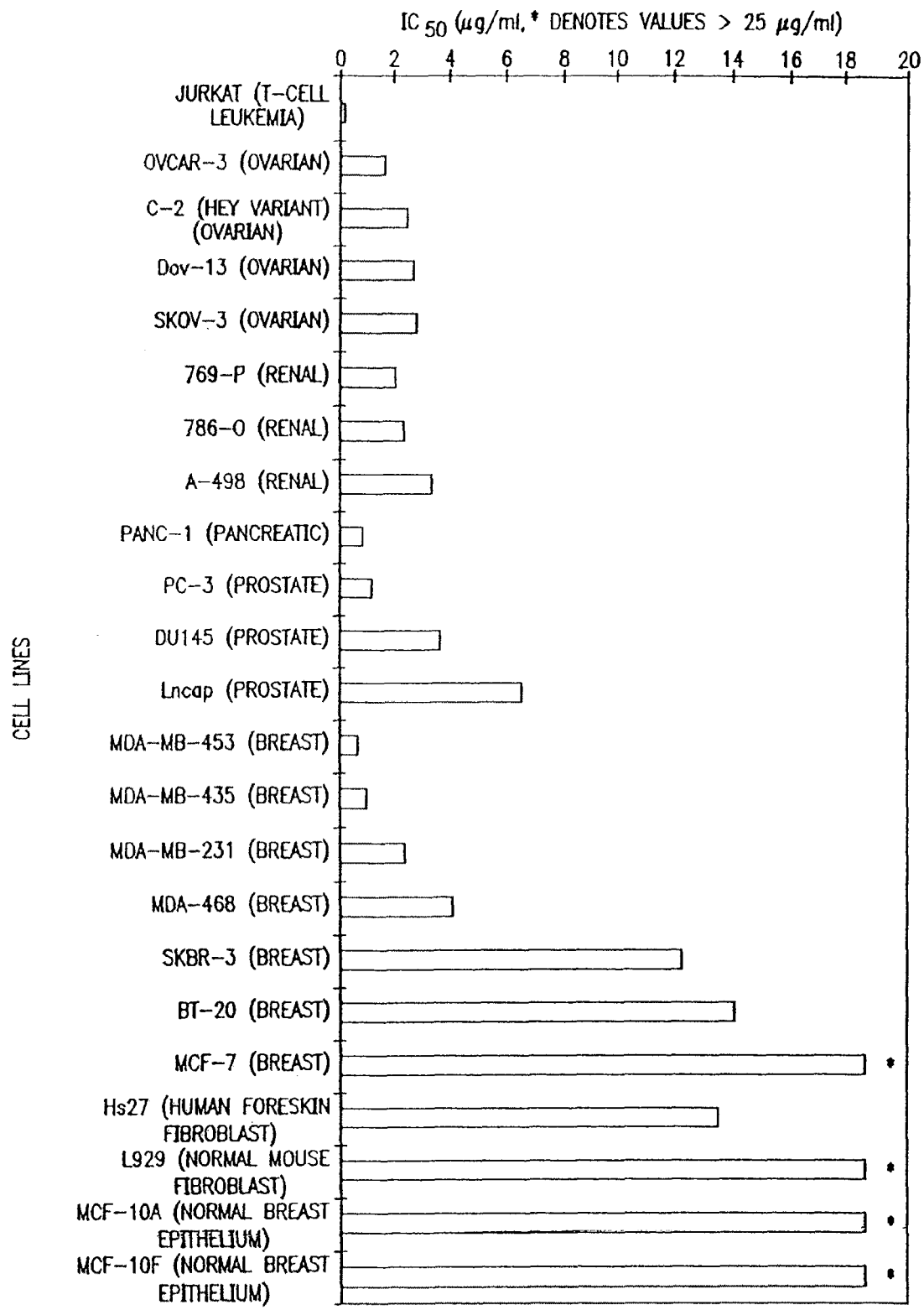
FIG. 42: Effect of mixture of triterpene glycosides (F035) on cancer and normal cell lines: F035 was evaluated for cytotoxicity by the procedures described in the examples. The activity of F035 was examined on panel of cancer and normal cell lines as shown in the FIG. The $IC_{50}$ ranged from 0.2-5.8 μg/ml for cancer cell lines. No significant cytotoxicity was observed ($IC_{50}$ 15 μg/ml to >25 μg/ml) on normal and immortalized cell lines.

The effect of the mixture of triterpene glycosides (F035) on the viability of a panel of cancer and non-transformed cells was studied as described in the methods. As shown in FIG. 42, Jurkat (T-cell leukemia) cells were highly sensitive to F035 with an IC₅₀ of 0.2 µg/ml. Similarly F035 inhibited the growth of number of cancer cell lines with inhibitory concentration IC₅₀ in range of 1.7-2.8 for (ovarian), 2.0-3.3 (renal), 0.93 (pancreatic), 1.2-6.5 (prostate) and 0.72-4.0 ml (some breast) cancer cells. However remaining breast cancer cell lines were resistant to cytotoxic effect of F035. The last four bars of FIG. 42 show that more than 25 g/ml of F035 was required to kill 50% of non-transformed (human and mouse fibroblasts and immortalized breast epithelium) cells suggesting that F035 is specifically cytotoxic the cancer cells.

In addition, two pure triterpene glycosides DI & G1 were tested for cytotoxicity on 5 cell lines. FIG. 43 shows that D1 has an $IC_{50}$ that is comparable to F035 in three cell lines (769-P, MDA-MB-453, & MDA-MB-231). In C-2 (HEY Variant) and Jurkat cells, D1 is twice as potent as F035. However, G1 was significantly more cytotoxic than F035 and D1 in most of the cells tested which could be because G1 is less polar than extract D1 (FIG. 43).

To understand the mechanism underlying the F035 induced cell kill, the inventors conducted annexin V-FITC binding assay using F035, D1 and G1 treated Jurkat cells. Table 43 shows the binding of annexin V to cells treated with 1 ml of F035, D1 and G1 (15-17%) thereby indicating an apoptotic pathway leading to cell death.

TABLE 43

Jurkat (T-cell leukemia), 72 Hour Cytotoxicity Assay
D1 Control, D1 Aglycone, D1 w/o Monoterpenes & Monoterpene-Sugar

| Dose μ * g/ml | D1 Control | D1 Aglycone | D1 minus monoterpene | D1 minus both monoterpenes | Monoterpene-sugar |
|---|---|---|---|---|---|
| 25.000 | | 100 | 56 | 7 | 6 |
| 12.500 | | 100 | 55 | 4 | 6 |
| 6.250 | 62 | 86 | 54 | 3 | 3 |
| 3.125 | 62 | 0 | 43 | 5 | 2 |
| 1.562 | 61 | 0 | 9 | 7 | 1 |
| 0.781 | 61 | 0 | 1 | 4 | 2 |
| 0.391 | 57 | 0 | 4 | 4 | 1 |
| 0.195 | 32 | 0 | 1 | 4 | 0 |
| 0.097 | 15 | 0 | 1 | 1 | 0 |
| 0.048 | | 0 | 0 | 0 | 0 |
| 0.000 | | 0 | 0 | 0 | 0 |
| $IC_{50}$ (μg/ml) | 0.329 | 3.634 | 5.787 | >25.000 | >25.000 |

Example 30

Cell Cycle Arrest and Induction of Apoptosis with Mixture of Triterpene Glycoside To study the effect of F035 on cell cycle, cancer cell lines MDA-MB-453 and MDA-MB-435 were treated with different concentrations F035. Table 42 showed an increase in the number of cells in G1 (7-10%) and a concomitant decrease in the %. of cells in S phase (6-10%) suggesting a GI arrest in MDA-MD-453 cells. In addition, after 72 hr post treatment with F035, 16% of MDA-MB435 (another breast cancer cell line) cells appeared to be in $SubG_o$ phase of cell cycle (Table 42) suggesting that the cells are undergoing apoptosis. This observation was further confirmed by studying apoptosis by TUNEL assay .

TABLE 42

Cell Cycle Analysis of F035 Treated Cells

| Cell Line | F035 (μg/m) | Phase of Cell Cycle (Percent of cells) | | | |
|---|---|---|---|---|---|
| | | SubGo | G1 | S | G2/M |
| MDA-MB-453 | 0 | 1.0 | 62 | 26 | 13 |
| | 1 | 1.5 | 69 | 21 | 10 |
| | 3 | 1.8 | 71 | 16 | 10 |
| | 6 | 2.2 | 72 | 19 | 9.0 |
| MDA-MB-435 | 0 | 1.0 | 52 | 35 | 16 |
| | 1 | 1.0 | 51 | 36 | 14 |
| | 3 | 13 | 50 | 26 | 12 |
| | 6 | 16 | 50 | 26 | 10 |

MDA-MB-453 & MDA-MB-435 cells were treated with different concentrations of F035 for 72 hr at 37° C.
Cell cycle analysis was done after propidium iodide staining as described in the methods.

Example 31

Mixture of Triterpene Glycosides Inhibit PI3-Kinase Activity

Figure 45A:
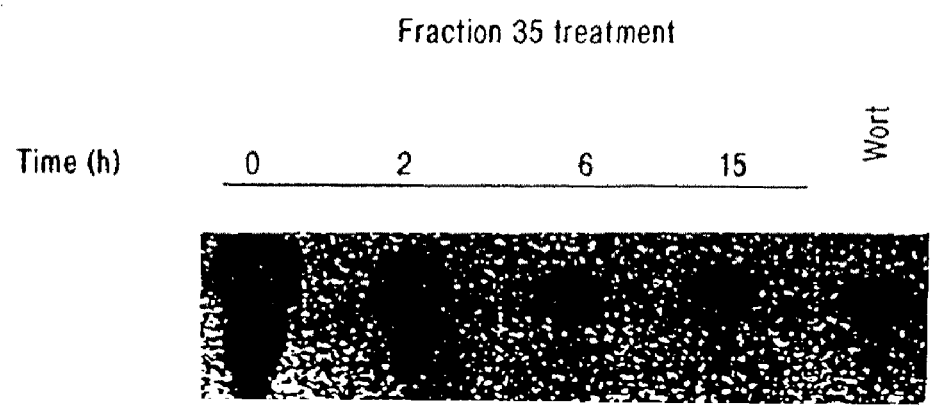
FIGS. 45A,B: Inhibition of PI3-kinase activity and AKT phosphorylation: The ability to phosphorylate phosphatidylinositol (PI) was measured for p85 protein immunoprecipitates from cellular lysates. Autoradiograms of the in vitro kinase assay separated on thin layer chromatography for p85 immunoprecipitates using Jurkat cells.

To study the molecular target(s) of F035, the inventors investigated the PI3-kinase signaling pathway. The results of immunoprecipitation with anti- p85 antibody (adapter protein) probe and subsequent lipid kinase assay showed that F035 inhibits the activity of PI3-kinase in Jurkat cells. FIG. 45A demonstrates about 50-70% inhibition of PI 3-kinase activity within in 2 hr post treatment with F035. By 6 hr 92-95% inhibition of PI3-kinase activity was observed which persisted up to 15 hr post treatment. Wortmannin [1 μM, 30 min post treatment], a known PI3-kinase inhibitor showed similar inhibition of enzyme activity in Jurkat cells (FIG. 45A).

Example 32

Mixture of Triterpene Glycosides, D1 & G1, Inhibit Phosphorylation of AKT

Figure 45B:
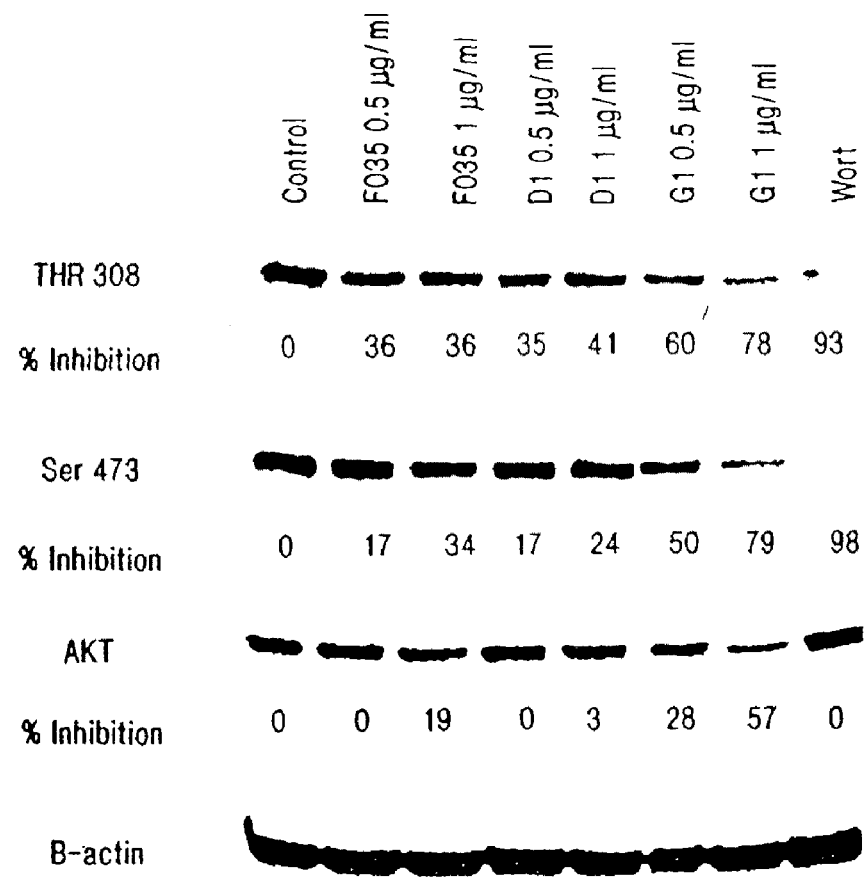
FIG. 45B: Inhibition of AKT phosphorylation on Ser-473 and Thr-308 with crude and pure triterpene glycosides. Jurkat cells were incubated with crude (F035) and purified extracts of D1 and G1 for 16 hours at 37° C. The cell lysates were resolved on 9% SDS-PAGE and analyzed by western blot-ECL analysis using anti Ser-473, Thr-308 and total AKT antibodies as probes.

The inventors determined the effect of F035 and pure extracts on AKT, a serine threonine kinase and a downstream effector of the PI3-kinase signaling pathway. In contrast to the rapid inhibition of PI3-kinase activity, inhibition of AKT phosphorylation did not occur till 15 hr post treatment . Treatment of Jurkat cells with F035 (2 ml) for 15 hr led to decreased phosphorylation of AKT. However, this treatment also led to lowered levels of total AKT protein as can be seen in FIG. 45B. The inventors confirmed the inhibition of AKT activity with pure triterpene glycosides. Pure triterpene glycosides D1 & G1 (2 μg/ml) also inhibited AKT phosphorylation and total AKT protein expression. (FIG. 45B). Treatment of Jurkat cells with LY 294002 and wortmannin (known PI3-kinase inhibitors) showed inhibition of AKT phosphorylation.

Example 33

Mixture of Triterpene Glycosides, D1 & G1, Inhibit TNF Induced NF-κB.

Figure 46A:
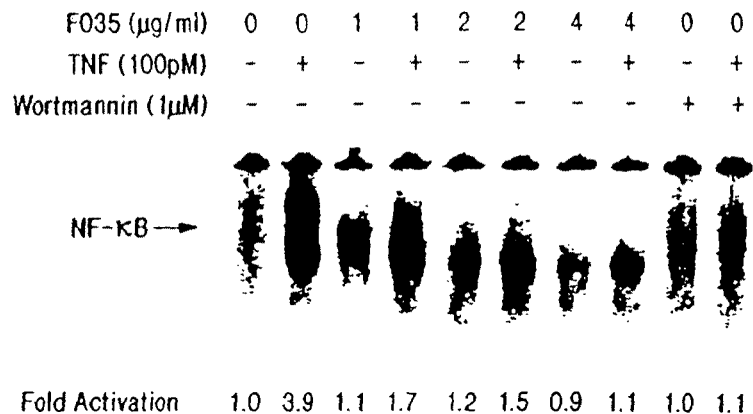
FIGS. 46A-D:Inhibition of TNF-induced NF-kB and induction of iNOS with triterpene glycosides: Jurkat cells were exposed to different concentrations of F035 (1-4 µg/ml.
Figure 46B:
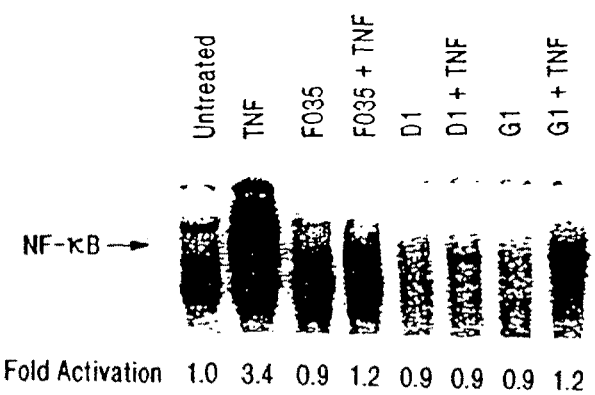

In order to further study the mediators of apoptotic pathway, the inventors evaluated the effects of F035, D1 and G1 on the transcription factor NF-κB which has been shown to be involved in apoptosis. The results in FIG. 46A show that in Jurkat cells, F035 inhibited the TNF-dependent activation of NF-κB in a dose dependent manner. Untreated cells and cells treated with F035 alone showed no activation of NF-κB. The inventors also confirmed these results with pure extracts D1 and G1. Pretreatment of cells with 2 ml of G1 and D1 resulted in 54% and 87% decrease in NF-κB levels respectively (FIG. 46B). Cells treated with D1 or G1 alone showed no activation of NF-κB (FIG. 46B). Since recently PI3-kinase has been shown to regulate NF-κB, pretreatment of cells with wortmannin (1 µM) resulted in almost total inhibition of TNF-induced NF-κB.

Example 34

Inhibition of iNOS with F035

Figure 46C:
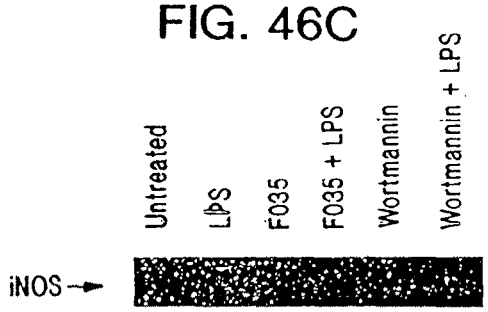

As the transcription of iNOS is regulated by NF-κB, the inventors investigated the effect of F035 on the induction of iNOS. In U-937 cells which were differentiated into macrophages the inventors induced iNOS in response to LPS (FIG. 46C). Pretreatment of these cells with F035 (1 µg/ml) totally blocked the induction of iNOS. Wortmannin also had a similar effect on LPS induced iNOS in these cells.

Figure 46D:
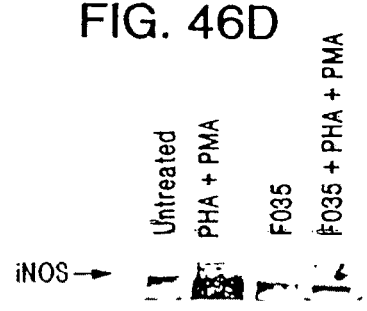

The inventors also examined the effect of F035 on induction of iNOS in Jurkat cells. iNOS was induced using PHA and PMA as described in the Methods. The results show that pretreatment of Jurkat cells with F035 blocked the induction of iNOS (FIG. 46D).

Example 35

Immunoblot Analysis of PARP Degradation

Apoptosis induced by. F035 & D1 was examined by proteolytic cleavage of poly (ADP-ribose) polymerase (PARP). Jurkat cells ($2\times10^6$/ml) were treated with F035 (2 µg/ml) and D1 (2 µg/ml) for different lengths of time. Cell lysates were prepared in buffer containing 20 mM HEPES, 250mM NaCl, 2 mM EDTA, 0.1% NP-40, 2 µg/ml leupeptin, 2 µg/ml aprotinin, 0.5 µg/ml benzamidine, 1 mM DTT and 1 mM PMSF. Cellular proteins (60 µg/ml) were separated on a 7.5% SDS polyacrylamide gel and electrotransferred onto a nitrocellulose membrane. The membrane was probed first with monclonal anti-PARP antibody (PharMingen) and then with anti-mouse antibody conjugated to horse radish peroxidase (HRPO). Protein bands were detected by chemiluminescense (ECL, Amersham). The extent of cleavage of the 116-kDa PARP into 85-kDa and 41-kDa peptide products was used as a measure of apoptosis (Tewari et al., 1995).

Example 36

Assay for Caspase-3 Protease

Caspase-3 activity was measured as described earlier (Enari et al., 1995) with some modifications. Briefly, Jurkat cells ($1\times10^6$/ml) were treated with F035, D1 & G1 for different lengths of time. Cytosolic extracts were prepared by repeated freeze thawing in 300 µl of extraction buffer (12.5 mM Tris, pH 7.0, 1 mM DTT, 0.125 mM EDTA, 5% glycerol, 1 µM PMSF, 1 µg/ml leupeptin, 1 µg/ml pepstatin and 1 µg/ml aprotinin). Cell lystates were diluted 1:2 with ICE buffer (50 mM Tris, pH 7.0, 0.5 mM EDTA, 4 mM DTT and 20% glycerol) and incubated with 20 µM of a caspase 3 substrate (acetyl-Asp-Glu-Val-Asp-aminomethylcoumarin) at 37° C. Caspase-3 activity was monitored by the production of fluorescent aminomethylcoumarin, which was measured at excitation 355 nM, emission 460 nM using Fluoroscan II (Labsystems, Helsinki, Finland).

Example 37

Detection of Cytochrome C Release from Mitochondria

Release of cytochrome c from mitochondria in response to treatment with F035 was detected by western blotting. Jurkat cells ($10\times10^6$) were treated with 2 µg/ml of F035 for 4 and 6 h at 37° C. Cell pellets were washed in sucrose buffer (0.25M sucrose, 30mM Tris, pH 7.7, 1 mM EDTA). To the cell pellets added 20 µl of sucrose buffer containing 1µM PMSF, 1 µg/ml leupeptin, 1 µg/ml pepstatin and 1 µg/ml aprotinin. Cells were disrupted by douncing 120 times in a 0.3 ml Kontes douncer with a B pestle (Kontes Glass company). Cellular protein (60 µg) was resolved on a 15% SDS-polyacrylamide gel and electrotransferred onto a nitrocellulose membrane. The membrane was probed first with monoclonal anti-cytochrome c antibody (PharMingen) and then with anti-mouse antibody conjugated to horse radish peroxidase (HRPO). Protein bands were detected by chemiluminescence (ECL, Amersham).

Example 38

F035 and D1 Induce Cleavage of PARP

Figure 47:
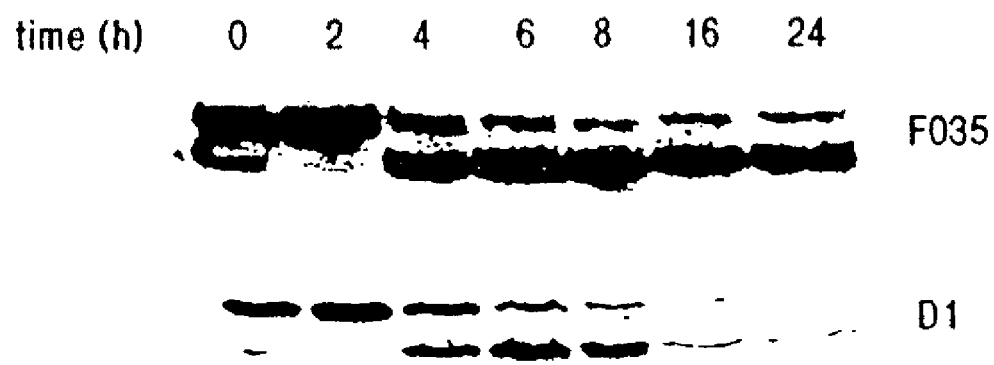
FIG. 47: Effect of F035 and D1 on cleavage of PARP in Jurkat cells.

F035 and D1 induced cleavage of PARP in Jurkat cells in a time dependent mariner. Results in FIG. 47 show that by 4 h both F035 and D1 begin to induce cleavage of PARP and close to complete cleavage occurs by 6-8 h. This indicates the play of caspases and thereby apoptosis being the mechanism involved in the cell kill induced by F035 and D1.

Example 39

Effect of z-vad fmk on F035 Induced Cell Kill

Figure 48:
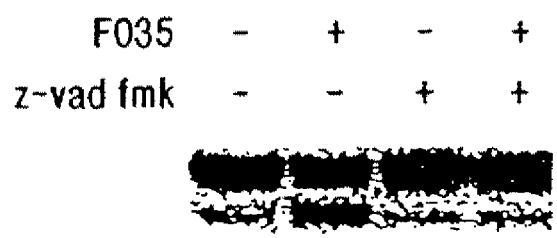
FIG. 48: Effect of z-vad fmk on F035 induced PARP cleavage in Jurkat cells.

To further confirm the role of caspases in F035 mediated cell kill the inventors studied the effect of z-vad fmk, and inhibitor of caspases on cells treated with F035. Pretreatment of Jurkat cells with 100 µM of z-vad fmk for 1 h at 37° C. completely reversed the F035 induced cleavage of PARP (FIG.48).

Example 40

F035 Induces Activation of Caspase 3

Figure 49:
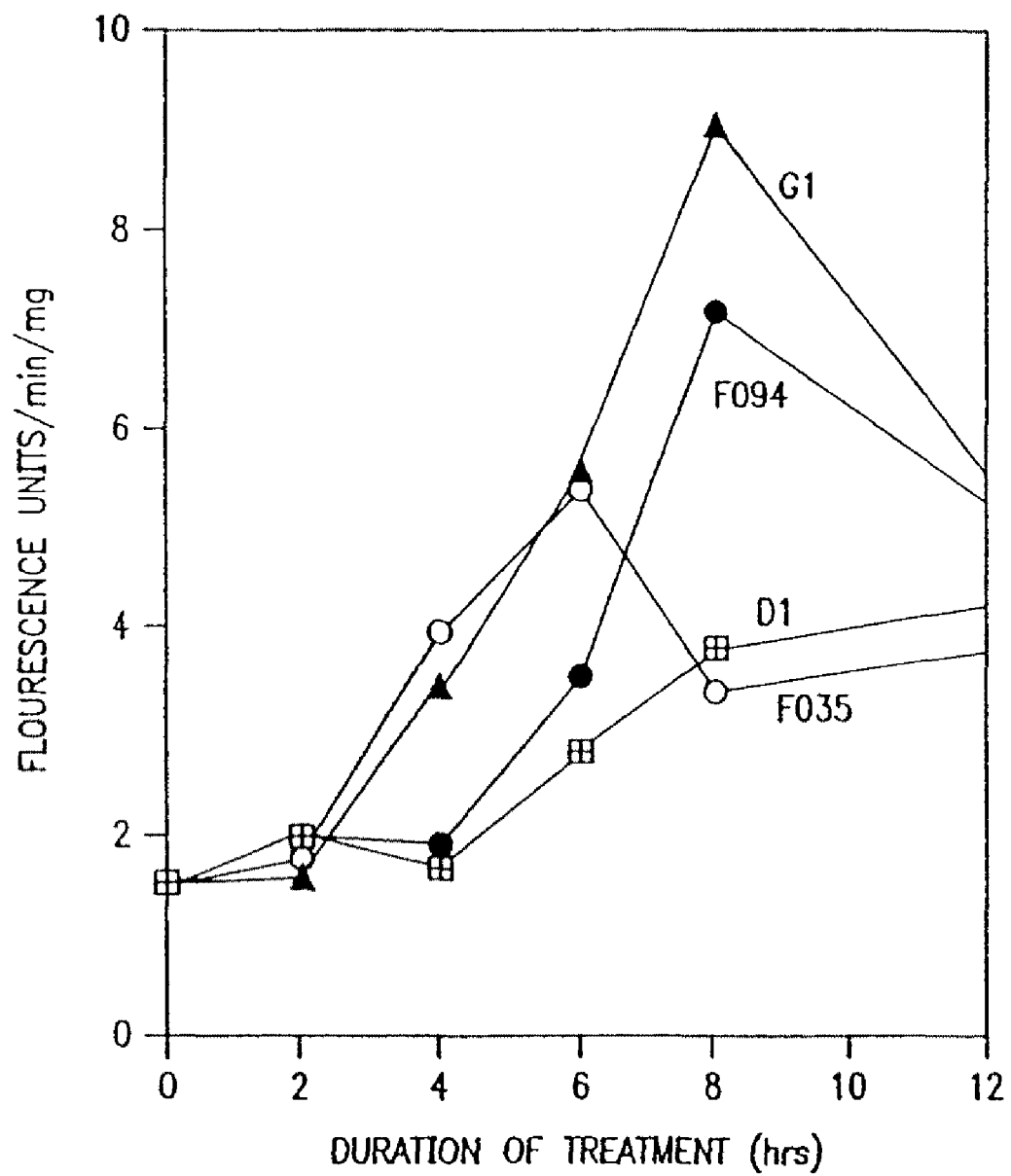
FIG. 49: Effect of F035, F094, D1 and G1 on caspase activity in Jurkat cells.

The inventors' results so far strongly suggest the role of caspases in F035 induced apoptosis. The inventors next studied the activation of caspase 3 in F035, F094, D1 & G1 treated cells since this protease lies immediately upstream of PARP in the caspase 3 in a time dependent fashion (FIG. 49). Activation starts at 4 h post treatment in all the cases, peaks at 6-8 h and falls thereafter.

Example 41

Cytochrome C Release from Mitochondria by F035

Figure 50:
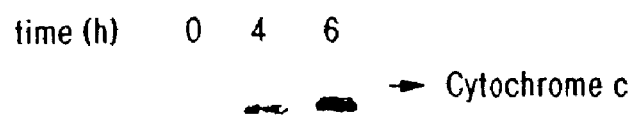
FIG. 50: Effect of F035 on cytochrome release from Jurkat mitochondria.

The release of cytochrome c is considered to be the cause of caspase 3 activation in some apoptotic pathways. To study if this was true in F035 induced apoptosis the inventors, looked at the levels of cytochrome c in the cytosolic extracts of F035 treated cells. The inventors found release of cytochrome c from the mitochondria of these cells in a time dependent manner (FIG. 50). The inventors see cytochrome c release 4 h following treatment with F035 which coincides with the time when activation of caspase 3 and cleavage of PARP begins. Earlier time points need to be studied for cytochrome c release to see if it precedes the activation of caspase 3.

Example 42

Aeroponic Growth System

In light of the finding that the triterpene compounds of the invention were concentrated in the roots and pods of *Acacia victoriae* plants, it was desired to create a method for propagating suitable tissue from which the compounds may be isolated. In order to achieve this goal, an aeroponic growth system was designed for the cultivation of *Acacia victoriae* roots. The aeroponic system is a closed system in which plant roots are suspended in air and misted with a complete nutrient solution. An 8×4×3.5 ft. box was made out of ¾ inch plywood sheets held together with screws and lined with fiberglass sheets to produce a watertight box. The top of the box was covered with two (2×8 ft) styrofoam sheets, with 12 circular holes drilled all the way through, although a new design incorporating PVC-coated poultry wire covered with opaque co-extruded white-on-black polyethylene is being considered as a chamber cover for future work. A program-repeating timer was used to mist the roots for a period of 12 seconds every 4.5 minutes.

The plumbing system design for the aeroponic chamber is a closed system constructed of ¾ inch PVC with six whirl-jet hollow cone polypropylene spray nozzles. A reservoir of 720 liters of nutrient solution is maintained in the bottom of the chamber, and sprayed on the roots of the plants from below using an external pump. The pump used was a Little Giant 4-MD 3250 RPM, 1/12 hp pump.

The pump is controlled by a Tork repeating timer set for intervals of 30 seconds of spray every 4.5 minutes. Temperatures were monitored with a Taylor electronic indoor/outdoor minimum/maximum thermometer and recorded by hand. Two Visi-therm 300W submersible aquarium heaters were used to heat the nutrient solution during the winter months, which was sufficient to keep the plants actively growing without heating the surrounding air in an unheated and uncooled outdoor shade-house in Tucson, Ariz.

The nutrient solution contained all of the essential elements the plants needs to complete its life cycle. Despite the fact that different plants require different levels and formulations for optimum growth, an over-all, single-balanced solution gives satisfactory results. The composition of the solution is given below, in Table 44.

TABLE 44

Aeroponic Nutrient Solution

| Compound | Element | Concentration (ppm) |
| --- | --- | --- |
| Calcium Nitrate | N | 150 |
| Potassium nitrate | Ca | 146 |
| Potassium Nitrate | K | 200 |
| Mono-potassium phosphate | P | 90 |
| Magnesium Sulphate | Mg | 50 |
|  | S | 134 |
| 10% Fe-chelate | Fe | 5 |
| Copper Sulfate | Cu | 0.07 |
| Manganese Chloride | Mn | 0.8 |
| Sodium Molybdate | Mo | 0.03 |
| Boric Acid | B | 0.3 |
| Zinc Sulfate | Zn | 0.1 |

Seeds of *Acacia victoriae* were then scarified and sown in a soil-less mix composed of 50% peat moss and 50% vermiculite. The seedlings were watered twice a day and fertilized with a single dose of osmacote. Once the seedlings were between 15-20 cm long, which was usually achieved after 3-4 months of growth, the root balls were washed thoroughly to remove all traces of peat moss and vermiculite. Next the roots were slipped through holes in the Styrofoam boards, and the top of the seedlings was supported from above by twine coming down from the greenhouse structure. A 7.0 cm tubular piece of foam was wrapped around the crown of the seedlings to prevent misting of the leaves and the surrounding area. The box was then filled with approximately 30 cm of nutrient solution, and the pump turned on.

Once the seedlings were in position and being misted, maintenance was limited to training the growing seedlings up the twine using plastic clips and replenishing the nutrient solution as the level dropped below 10 cm. While the seedlings were growing inside a greenhouse, temperature control of the nutrient solution was not necessary. However, if the aeroponic box is subjected to ambient environmental conditions, it is recommended to increase the nutrient solution temperature to 70° F. so that the plants will not become dormant during winter months.

For harvesting of roots, the root mass of a single plant is rinsed with water directly in the aeroponic box and the root mass is cut with scissors a few inches above the sprayer. The excess water is removed by patting dry with paper towels, followed by weighing of the sample. The root mass is then cut in 3-4 inch sections with scissors and subject to chemical extraction, as described above. Alternatively, for continual harvest of roots, the pump is turned off and roots are clipped from the growing root mass. These roots are then cut into 3-4 inch sections and extracted as described. Care is taken not to damage the non-harvested roots.

A number of advantages were realized by growing plants in the aeroponic system. First, the growth of the plants was approximately twice that achieved with conventional growing techniques. Second, the roots can be easily harvested as needed without harming the plants. This cutting of roots further leads to extensive lateral growth of fibrous roots. Therefore, the roots could be harvested several times a year. Further, the aeroponically grown plants flowered in their first year of growth, compared to 3-5 years for plants grown outdoors.

Example 43

Tissue Culturing and Germination of *Acacia victoriae*

Seeds/Substrate: Seeds were harvested from plants growing at the Campus Agricultural Center, University of Arizona, Tucson, Ariz. Seeds were washed thoroughly in tap water with an anti-microbial soap (Vionex, Viro Research International Inc., USA Durango, Colo.), then treated with commercial bleach 20% (v/v) for 15 min. After repeated washing in deionized water, they were treated with boiling water (ca 200 ml for 100 seeds) and left to cool overnight. Then they were treated with 20%(v/v) commercial bleach for 20 min, rinsed 2-3 times in sterile deionized water, and cultured on MS (Murashige and Skoog, 1962) and ½ strength MS medium. The medium was supplemented with MS vitamins, 2%(w/v) sucrose and gelled with either 0.7% agar or 0.2% Gelrite. In one study, the seeds were scarified with concentrated sulfuric acid, rinsed in sterile water, and cultured on medium. All media was autoclaved at 121° C. for 15 min. Cultures were maintained at 25+2° C. under 16-h light photoperiod at 1000 lux produced from cool white fluorescent tubes. Each study contained 18 replications.

Propagation: Shoot tips and nodal segments excised from three-week-old seedlings were cultured on MS medium alone and also MS supplemented with 0.1 mg/L of auxins (IAA, NAA or IBA) and BAP (0.1, 0.3, 0.5, 1.0 and 1.3 mg/L) either separately or in combinations. For rooting of shoots IAA (0.1 mg/L), IBA (0.1 and 0.6 mg/L) and NAA (0.1 and 0.2 mg/L) were tested. For transfer to soil, plantlets were removed from culture tubes, the roots were washed with tap water to remove the nutrients adhering to roots and the transferred to pots filled with desert-type soil. The plants were covered with Magenta boxes to maintain humidity and kept under mist and low light for 3 wk. After 3 wk, the Magenta boxes were removed and the plants were transferred from the mist to higher light in the greenhouse.

Induction of callus: Callus tissue was induced from hypocotyl and root segments excised from 3-week-old in vitro germinated seedlings. The explants were cultured on MS medium supplemented with 2,4-D (1 mg/L), NAA (0.5 & 1 mg/L), IAA (0.2 and 1 mg/L), Thidiazuron (0.2 mg/L), Dicamba (0.2 & 2 mg/L), BAP (0.3 mg/L) and KN (0.5 and 3 mg/L) either individually or in combinations.

Seed Germination: Seeds treated with hot water germinated with the emergence of the radicle in 3-4 days and the complete plantlets were obtained within 1 wk. Seeds cultured without hot water treatment did not germinate. A high percentage of seeds germinated on medium solidified with Gelrite (0.2%) as compared to agar (0.7%). The maximum germination percentage of 88.7% was noted on half strength MS medium solidified with Gelrite. The germination responses on different media are summarized in Table 45.

TABLE 45

Seed Germination of *Acacia victoriae*

| Media | No. of Seeds Cultured | No. of Seeds[a] Germinated |
|---|---|---|
| MS (agar solidified) | 42 | 36 (85.7) |
| MS (agar solidified) (decoated with sulfuric acid) | 41 | 24 (58) |
| ½ strength MS (agar solidified) | 60 | 48 (80) |
| ½ strength MS (Gelrite solidified) | 133 | 118 (88.7) |

[a]Numbers in parentheses are percent germination.

Transplantable seedlings were obtained in 3-4 wk time. The seeds of *A. victoriae* have low germination rates in vivo due to high levels of seed dormancy (Kaul and Ganguly, 1965; Grice and Westoby, 1987). To overcome dormancy, seed coats must be either nicked with a sharp instrument, subjected to acid scarification, or covered with boiling water and left to cool in the water overnight. The inventors found that the germination percentage can be increased up to 88.7% by using the boiling water treatment and subsequently culturing the seeds on ½ MS medium gelled with 0.2% Gelrite. According to Larsen (1964), *A. victoriae* seeds under in vivo conditions treated with boiling water can increase germination by 36%. Without pretreatment, the germination percentage was 19.4% (Kaul and Ganguly, 1965). In addition, it took 12 days for the radicle to emerge and complete seedlings were recovered after 79 days. In our protocol, the percent germination is increased (88.7%) and transplantable seedlings could be obtained in 3-4 wk time.

Shoot tip cultures: To investigate shoot multiplication, the shoot tips (about 1.0 cm in length) were cultured on either MS alone or MS supplemented with BA, and BA in combination with IAA. On MS alone the shoots had poor vigor, and a poor root growth (1-3 roots /culture). On medium containing BA(1.3 mg/L), the shoot tips produced multiple shoots (average of 3.94 shoots/culture). Among the multiple shoots, one or two shoots elongated and attained a height of 8.6 cm in 4 wk. The combinations of BA and IAA also favored multiple shoot induction. The responses are summarized in Table 46.

TABLE 46

Effect of Different Levels of BA And IAA (0.2 Mg/L) on Multiple Shoot Induction in *Acacia victoriae*.

| Media* BA (mg/L) | IAA (mg/L) | Average No. of shoots per shoot tip | Shoot Length (cm) |
|---|---|---|---|
| 1.3 | 0 | 3.94 + 1.846 | 8.6 + 3.0258 |
| 0.1 | 0.2 | 1.6 + 0.599 | 6.8 + 3.002 |
| 0.3 | 0.2 | 1.9 + 0.7071 | 5.8 + 2.794 |
| 0.5 | 0.2 | 2.8 + 1.1659 | 5.1 + 2.501 |
| 1.0 | 0.2 | 4.9 + 2.075 | 3.2 + 1.468 |

*MS. Data represents an average of 18 replicates + SE.

At higher BA concentrations (1.0 & 1.3 mg/L), the number of shoots increased. The combination of BA (1 mg/L)+IAA (0.2 mg/L) was found to be better for shoot multiplication. Callus was observed at the cut ends in all the BA-IAA combinations. Kaur, et al. (1998), reported the synergistic effect of BA-NAA on shoot bud induction in *Acacia catechu* and higher levels of NAA (1-2 mg/L) were not beneficial. They also stated that IAA was not effective in enhancing shoot bud formation; but instead callus was produced from the base of the explants.

To investigate rooting, in vitro-developed shoots were excised and transferred to medium containing IAA, NAA or IBA. The responses are summarized in Table 47. Among the treatments tested, ½ MS+NAA (0.2mg/L) was found better for rooting. Almost 100% of the shoots rooted. The shoots attained a height of 9-11 cm in four wk. In *Acacia catechu* (Kaur, et al., 1998) reported that intermittent callus formation at the junction of root and shoot and they employed reduced sucrose level from 3% to 1.5% to control the callus. Similar results were also reported in *Feronia limonia* (Purohit and Tak, 1992) and *Acacia auriculiformis* (Das, et al., 1993). In the present investigation, slight callusing was also noted at 3% sucrose and it was minimized at 2% sucrose. The rooted shoots were transferred to the greenhouse. The survival after transferring was 100%. The plantlets were acclimatized under mist for 3 wk and later the plantlets were grown in the regular greenhouse.

TABLE 47

Effect of IAA, NA and IBA on Rooting of Shoots of Acacia victoriae

| Media | No. of shoots cultured | No. of shoots[a] rooted | Mean No. of roots/culture |
|---|---|---|---|
| MS | 14 | 6 (42.8) | 2 + 0.816 |
| MS + IAA (0.1) | 12 | 8 (66.6) | 3.6 + 1.316 |
| MS + IBA (0.1) | 10 | 6 (60) | 3 + 0.816 |
| MS + IBA (0.6) | 14 | 8 (57) | 1.6 + 1.111 |
| MS + NAA (0.1) | 10 | 6 (60) | 2.16 + 1.067 |
| ½ MS + NAA (0.2) | 14 | 14 (100) | 3.07 + 1.032 |

[a]Numbers in parentheses are percent rooting.

Nodal segment cultures: Nodal segments (cotyledonary node) excised from in vitro germinated seedlings were cultured on MS medium supplemented with 0.1 mg/L IAA, NAA or IBA. Only one or two axillary shoots developed per explant. However, the growth of these shoots was slow. Hence, nodal explants were not used for further studies.

Induction of callus from hypocotyl and root segments: Callus was induced from hypocotyl segments excised from 3-wk-old in vitro germinated seedlings. The callus developed on 2,4-D (1 mg/L), Thidiazuron (0.2 mg/L), Dicamba (0.2 mg/L) was greenish, compact and hard. The quantity of callus developed was moderate in most of the concentrations tried (Table 51). Profuse callus development was noted on MS medium supplemented with 2,4-D (4 mg/L)+IAA (1 mg/L)+NAA (1 mg/L).

Root segments excised from three-week-old in vitro germinated seedlings were cultured on MS medium supplemented with 2, 4-D (1 mg/L) alone and 2,4-D in combination with KN (0.5 mg/L) showed the development of light yellowish soft callus with a few roots developing from the callus. The callusing was noted in 100% of the cultures. Whitish, soft, friable and profuse callusing was noted from root segments on medium added with BA (0.3 mg/L)+IAA (0.2 mg/L). Light yellowish profuse callusing was noted on the root segments cultured on medium added with 2,4-D (4 mg/L) in combination with 1 mg/L each of IAA and NAA. A similar type of callusing was noted in Thidiazuron (0.2 mg/L)+Dicamba (2 mg/L) and IAA (0.1 mg/L). Root segments cultured on medium with Dicamba (2 mg/L)+IAA (0.1 mg/L) formed light green compact hard callus. Attempts to regenerate the plantlets from the callus were not successful. Variation among explant types with respect to callus induction has been reported in several woody species such as Albizzia lebbeck (Lakshmana Rao and De, 1987) and Lonicera japonica (Georges, et al., 1993). In the inventors' studies, they also found that there is a difference between hypocotyl- and root-derived callus developed on the identical medium. Calli developed from hypocotyl on BA-IAA combinations were light greenish, hard and compact, whereas from the root segments it was whitish, soft, friable and also showed root differentiation from the callus in some of the combinations. In Dalbergia latifolia the callus on regenerating media became compact, hard and dark green and shoot buds were differentiated (Pradhan, et al., 1998). In the inventors' studies, a similar type of callus development was noted, but such callus failed to regenerate. In this investigation the inventors showed that A. victoriae can be propagated in vitro from shoot tips. The technique standardized is useful for the micropropagation of elite individuals detected among the heterogeneous seedling populations and maintenance of elite lines for future studies.

TABLE 48

Development of Callus from Hypocotyl and Root Segments of Acacia victoriae

| | Nature of callus | |
|---|---|---|
| Media* | Hypocotyl | Root |
| 1. MS + 2,4-D (1) | Moderate, green | Moderate, yellow |
| 2. MS + TD (0.2) | Scanty | Scanty |
| 3. MS + Dicamba (2) | Moderate, compact green | Moderate, soft yellow |
| 4. MS + 2,4-D (1) + KN (0.5) | Scanty, green | Scanty, light green |
| 5. MS + KN (3) + NAA (0.5) | Moderate, white | Scanty, light green |
| 6. MS + TD (0.2) + | Moderate, light green | Moderate, soft yellow |
| 7. MS + Dicamba (2) + IAA (0.2) | Scanty, compact yellow | Scanty, light green |
| 8. MS + 2,4-D (4) + IAA (1) + NAA (1) | Profuse, green, compact, hard | Moderate, yellow soft |
| 9. MS + BA (0.3) + IAA (0.2) | Moderate, compact | Profuse, white |

*Numbers in parentheses are mg/L.

Example 44

Induction of Hairy Roots from *Acacia victoriae* for the Production of Anti-Cancer Compounds Infection of *Acacia victoriae* plant material with *Agrobacterium rhizogenes* leads to the integration and expression of T-DNA in the plant genome, which causes development of a hairy root phenotype (Grant et al., 1991). Hairy root cultures grow rapidly, show plagiotropic root growth and are highly branched on hormone-free medium. Hairy roots also exhibit a high degree of genetic stability (Aird et al., 1988). Many dicotyledonous plants are susceptible to *A. rhizogenes*, and plants have been regenerated from hairy root cultures in many species (Christey, 1997).

Genetic transformation and the induction of hairy roots were performed by the inventors as a method for the production of the active triterpenes from *A. victoriae*. The natural ability of the soil bacterium *Agrobacterium rhizogenes* to transform genes into a host plant genome results in roots being formed at the site of infection is used to produce hairy root cultures. Hairy roots are characterized by numerous fast growing, highly branched adventitious roots, which continues to grow in vitro on hormone-free medium.

The inventors demonstrated induction of hairy roots in *Acacia victoriae* using *Agrobacterium rhizogenes* strain R 1000 (an engineered strain of *Agrobacterium tumefaciens* strain to which *Agrobacterium rhizogenes* plasmid pRiA$_4$ has been inserted, ATCC Number 43056). The production of the compound of interest in hairy roots was confirmed by HPLC. Induction of hairy roots was carried out as follows. First, *Acacia victoriae* seeds were collected from field-grown plants in Tucson, Ariz. Boiling water was poured over the seeds, which were soaked overnight as the water cooled and surface sterilized in 15% commercial bleach for 30 minutes. After repeated washing in sterile water, seeds were cultured on liquid MS medium (Murashige and Skoog, 1962) supplemented with MS vitamins and 2% sucrose in 250 ml conical flasks with 50 ml medium. The cultures were maintained in a gyratory shaker in a growth room at 25±2° C. in the dark. After four days of culture, embryo-axis were excised from the germinating seedlings and used for agroinfection.

Prior to agroinfection, *Agrobacterium rhizogenes* strain R1000 was grown overnight on YENB medium. YENB medium was prepared by adding 7.5 g/L Yeast Extract and 8 g/L Nutrient Broth (Difco Laboratories, Detroit, Mich.). The embryo-axis of the explants was infected with a fine stainless steel needle that had been dipped in bacterial solution. After infection, a drop of bacterial suspension (1:20 with MS medium) was put on the surface of the explants. Then the explants were transferred to MS medium and MS medium with acetosyringone (100 µM) (3,5 dimethoxy-4 hydroxy-acetophenone, Aldrich Chem. Co, Milwaukee, Wis.) for co-cultivation. Co-cultivation was carried out for three days in the dark. After three days of co-cultivation, the explants were transferred to MS+Cefotaxime (500 mg/l, Agri-Bio, North Miami, Fla.) to control the bacterial overgrowth. Root initiation was noted at the site of infection mostly from the young developing leaves from the embryo-axis in 3-4 weeks time. After 4 weeks, the explants along with the roots were transferred to MS medium alone and the dark incubation was continued for the development of hairy roots. Hairy root development was noted after a further 8 weeks. The hairy roots thus developed were multiplied routinely on MS medium by subculturing. The transgenic nature of the hairy roots was confirmed by PCR™ using a set of primers to amplify a portion of the rol B gene. The primers used were as follows:

```
1) 5' GAGGGGATCCGATTTGCTTTTG 3'    (SEQ ID NO. 7)

2) 5' CTGATCAGGCCCCGAGAGTC 3'     (SEQ ID NO. 8)
```

A 50 µl PCR™ reaction mix contained the primers (1 µM final concentration each), Taq polymerase (1.0U), 125 µM each dNTP, 1×PCR™ reaction buffer, 1.5 mM MgCl$_2$, 300 ng of isolated DNA. PCR™ conditions employed were 92° C. initial denaturation for five min followed by 35 cycles of 92° C. 50 seconds, 55° C. 1 min for annealing, 72° C. 1 and ½ min for extension and 72° C. 7 min final extension. A 645 by fragment was amplified.

Hairy root cultures in liquid medium: To optimize the conditions for the growth, hairy roots growing on MS semi-solid medium were excised and cultured in MS liquid medium in different capacity flasks (125, 250, 500 and 1,000 mL) with 20, 50, 100 and 400 mL medium respectively. The initial hairy root innoculum was 6 gm/L. The growth of hairy roots was also tested in the following basal media: MS, Nitsch and Nitsch (N and N) (1969), Schenk and Hilderbrandt (SH) (1972) and Woody Plant Medium (WPM) (Lloyd and McCown, 1981). To test the effect of different carbon sources on hairy root growth, 2% (w/v) of each of the following was added to MS medium: sucrose, glucose, fructose and mannose. The effect of gibberellic acid (0.1, 0.5 and 1 mg/L) on hairy root growth was tested by adding the filter-sterilized solution to MS medium after autoclaving.

Initiation of roots at the site of infection was noted in 3-4 weeks. Four independently transformed hairy root clones were established from embryo axes infected with R1000 strain in the presence of acetosyringone (100µM). The embryo axes co-cultivated with *A. rhizogenes* without acetosyringone did not develop hairy roots (Table 54). Three days co-cultivation in the presence of acetosyringone was found optimum for induction of hairy roots. A promoting effect of acetosyringone has been reported in *Salvia militiorrhiza* (Hu and Alfermann, 1993). The results showed that acetosyringone, an activator of the vir genes of *Agrobacterium*, increased the transformation frequency. Similarly, in this study, acetosyringone was required to induce hairy roots.

The transformed nature of the roots was confirmed by PCR™ amplification using a set of primers to amplify a portion of rol B gene. A diagnostic fragment of 645 by was amplified in the four hairy root clones tested.

The hairy roots grown on liquid medium developed vigorously. Among the different basal media tested, MS medium was found best for hairy root growth (Table 56). In a 125 mL flask, there was a 268-fold increase in growth in 4 weeks. With WPM and N and N medium, there was a 254- and 196-fold increase respectively. B$_5$ and SH medium did not favor the optimal growth of hairy roots. Hairy roots slowly started browning on these two media. In one study, hairy roots were grown in different capacity flasks (125, 250, 500 and 1000 mL) with 20, 50, 100 and 400 mL MS medium, respectively. The growth kinetics are summarized in Table 55. Initially, the growth of hairy roots is vigorous and attained a 25.77-fold increase in 4 weeks in 125 mL flasks with a starting inoculum of 150 mg. As the flask capacity was increased, the growth of roots slightly decreased.

The growth of hairy roots can be sensitive to medium composition, especially mineral ions and carbon source (Wysokinska and Chmiel, 1997). For *Acacia victoriae*, five different basal media (MS, N and N, SH, WPM and B$_5$) were tested for effect on hairy root growth. MS medium was found best for growth. Sasaki et al. (1998) compared the growths of *Coleus forskohlii* hairy roots on various nutrient media and found that WPM was best for hairy root growth.

In this study, sucrose favored the growth of hairy roots compared to other carbon sources (fructose, glucose and mannose). The maximum growth (24.52-fold increase) was found in sucrose-containing medium. Glucose-containing medium was slightly inhibitory for growth, and mannose completely inhibited the growth (Table 57). In *Catharanthus roseus*, catharanthine production could be doubled by the use of fructose as a carbon source in the medium. However, the authors reported that use of fructose resulted in an approximately 40% decrease in growth compared to sucrose (Jung et al., 1992).

Hairy roots do not require the addition of exogenous growth regulators for continued growth because genes that increase sensitivity to auxin are present in the Ri plasmid (Wysokinska and Chmiel, 1997). However, reports are available wherein exogenous hormones stimulate growth. The inventors tested the effect of gibberellic acid (0.1,0.5 and 1.0 mg/L) on hairy root growth. The growth of hairy roots was best in medium without GA$_3$, as compared to GA$_3$-containing medium (15.77-fold increase). Different levels of GA$_3$ did not affect the growth significantly (Table 58). In *Artemisia*, GA$_3$ did not enhance the overall biomass accumulation, but it facilitated reaching stationery phase sooner than cultures grown on medium without GA$_3$ (Smith et al., 1997). Rhodes et al., (1994) found that the response of hairy roots of *Brassica candida* to GA$_3$ depended largely on the clone examined. However, they observed that generally GA$_3$ exerted a positive effect on growth and a reduction in the accumulation of alkaloids accompanied with changes in patterns of production. Ohkawa et al., (1989) reported GA$_3$ at concentrations of 10 ng/L and 1 mg/L accelerated growth, enhanced elongation, and increased lateral branching in *Datura innoxia* hairy roots. Zobel (1989) suggested that GA$_3$ acts as a CO$_2$ analog for root growth. For *Acacia victoriae* hairy roots, GA$_3$ did not enhance the growth, which might indicate a differential response for various genotypes.

The use of hairy root cultures of *Acacia victoriae* will provide a suitable means for uniform culture of plant tissue from which the triterpene glycoside compositions of this invention, which include isolated mixtures or individual purified compounds, can be isolated.

TABLE 49

Agrobacterium rhizogenes Strain R1000 Infection of Embryo Axes of Acacia victoriae for Hairy Root Production

| Treatment | *Media for co-cultivation | No. of embryo axis infected | No. explants[a] with root development | No. of roots with hairy root morphology |
|---|---|---|---|---|
| Control (non infected) | MS | 20 | — | — |
|  | MS + Aceto. | 21 | — | — |
| Infected | MS | 33 | 5 (15) |  |
|  | MS + Aceto. | 38 | 9 (23) | 4 (17.3) |

*Acetosyringone (100 μM) was added after autoclaving into MS medium for co-cultivation
[a]Number in parenthesis indicates percentage.

TABLE 50

Effect of Different Flask Sizes on the Growth of Hairy Roots of Acacia victoriae

| Flask size (mL) | Initial Fresh weight (mg) | Fresh Weight after 4 weeks (mg)[a] | Fold increase |
|---|---|---|---|
| 125 | 150 | 3866 ± 0.569 | 25.77 |
| 250 | 300 | 6903 ± 0.344 | 23.01 |
| 500 | 1200 | 11817 ± 0.998 | 9.84 |
| 1000 | 2400 | 40080 ± 3.479 | 16.70 |

[a]Data represents an average of 6 replicates ± S.E., 125, 250, 500 and 1000 mL capacity flasks with 25, 50, 100 and 400 mL MS medium.

TABLE 51

Effect of Different Basal Media and Flask Size an the Growth of Hairy Roots of Acacia victoriae

| Media[a] | Flask Size[b] (mL) | Initial Fresh. Weight (mg) | Fresh. Weight after 4 weeks weeks(mg) | Fold Increase |
|---|---|---|---|---|
| MS | 125 | 10 | 2681 | 268 |
| $B_5$ | 125 | 10 | 1933 | 193 |
| N and N | 125 | 10 | 196 | 196 |
| SH | 125 | 10 | 170 | 170 |
| WPM | 125 | 10 | 2549 | 254 |
| MS | 250 | 300 | 751 | 25 |
| $B_5$ | 250 | 300 | 57 | 19 |
| N and N | 250 | 300 | 591 | 19.7 |
| SH | 250 | 300 | 54 | 18 |
| WPM | 250 | 300 | 659 | 21 |

[a]MS = Murashige and Skoog; $B_5$ = Gamborg's; N and N = Nitsch and Nitsch; SH = Schenk and Hilderbrandt; WPM = Woody plant medium.
[b]125 and 250 mL flasks with 25 and 50 mL medium.

TABLE 52

Effect of Various Carbon Sources in MS Medium on the Growth of Hairy Roots of Acacia victoriae

| Carbon source[a] (2% W/V) | Fresh weight after 4 weeks (gm)[b] | Fold increase |
|---|---|---|
| Sucrose | 7.356 ± 0.543[c] | 24.52 |
| Glucose | 2.87 ± 0.53 | 9.56 |
| Fructose | 5.85 ± 1.55 | 19.5 |
| Mannose | 0.305 ± 0.065 | 1.01 |

[a]2% (w/v) [b]The initial F.W. for each treatment was 300 mg.
[c]Data represents an average of 6 replicates ± S.E.

TABLE 53

Effect of $GA_3$ on the Growth of Hairy Roots of Acacia victoriae

| $GA_3$ (mg/L) | Fresh weight after[a] 4 weeks (gm) | Fold increase |
|---|---|---|
| 0 | 6.512 ± 1.569[b] | 21.70 |
| 0.1 | 4.732 ± 0.086 | 15.77 |
| 0.5 | 4.634 ± 0.088 | 15.44 |
| 1 | 4.310 ± 0.344 | 15.44 |

[a]The initial F.W. for each treatment was 300 mg.
[b]Data represents an average of 6 replicates ± S.E.

Different media were tested for growth of hairy roots. Best growth was obtained on MS medium containing 2% sucrose. The effect of different capacity flasks and gibberellic acid was tested on the growth of hairy roots. The hairy roots were also grown on MS liquid medium on gyratory shaker in a 125 ml conical flask with 20 ml medium. An increase in growth of 84 fold was noted in 4 weeks. The production of triterpene saponins corresponding to those identified in F035 was confirmed by HPLC analysis with a standard authentic sample.

All of the composition and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved.

All such similar substitutes and modifications apparent to those skilled in the art are deemed to be within the spirit, scope and concept of the invention as defined by the claims.

REFERENCES

The following references, to the extent that they provide exemplary procedural or other details supplementary to those set forth herein, are specifically incorporated herein by reference.

Aerts et al., *Plant J.*, 5:635-643, 1994.
Agrawal, "NMR spectroscopy in the structural elucidation of oligosaccharides and glycosides," Phytochemistry, 31:3307-3330, 1992.
Aird, Hamill, Rhodes, "Cytogenetic analysis of hairy root cultures from a number of species transformed by *Agrobacterium rhizogenes*," *Plant Cell Tissue Organ Cult.*, 15:47-57; 1988.
Akiyama et al., *J. Biol. Chem.*, 262:5592-5595, 1987.
Allen et al., "Leguminosae, A source book of characteristics uses and nodulation," The University of Wisconsin Press, Madison, Wis., 1981.
Armitage, *In: Statistical Methods in Medical Research*, Wiley and Sons, New York, N.Y., p 205, 1971.
Arnon, R., et al., *Proc. Natl. Acad Sci.* (USA) 77:6769-6772 1980.
Baba, Hanada, Hashimoto, "The study of ultraviolet B-induced apoptosis in cultured mouse keratinocytes and in mouse skin," *J Dermatol. Sci.*, 12:18-23, 1996.

Baxter, Price, Fenwick, "Sapogenin structure: analysis of the $^{13}$C- and $^1$H-NMR spectra of soyasapogenol b," *J. Nat. Prod.*, 53:298-302, 1990.

Bellacosa, Feo, Godwin, Bell, Cheng, et al., *Int. J Cancer*, 64:280-285, 1995.

Berton, Mitchell, Fischer, Locniskar, "Epidermal proliferation but not the quantity of DNA photodamage is correlated with UV-induced mouse skin carcinogenesis," *Invest. Dermatol.*, 109:340-347, 1997.

Beutler, Kashman, Pannell, Cardellina, Alexander, Balaschak, Prather, Shoemaker, Boyd, *Bioorganic and Medicinal Chemistry*, 5:1509-1517, (1997).

Boll and von Philipshorn, "NMR studies and the absolute configuration of *Solanum* alkaloids (spiroaminoketalalkaloids), *Acta Chem. Scand.*, 19:1365-1370, 1965.

Brinkmann et al., *Proc. Natl. Acad. Sci.*, USA, 88(19):8616-8620, 1991.

Burchell et al., *J. Immunol.*, 131(1):508-513, 1983.

Campbell, in Monoclonal Antibody Technology, Laboratory Techniques in Biochemistry and Molecular Biology Vol. 13, Burden and Von Knippenberg, Eds. pp. 75-83, Amsterdam, Elseview, 1984.

Capaldi et al., Biochem. *Biophys. Res. Comm.*, 76:425, 1977.

Capon and Thacker, "The nuclear magnetic resonance spectra of some aldofuranosides and acyclic aldose acetals," *Proc. Chem. Soc. Lond.*, 369, 1964.

Chatterjee, Agarwal, Muhtar, "Ultraviolet B radiation-induced DNA lesions in mouse epidermis," *Biochem. Biophys. Res. Commun.*, 229:590-595, 1996.

Cheatham et al., *Proc. Natl. Acad. Sci.*, 92:11696-11700, 1995.

Cheeke, *Can. J. Animal Sci.*, 51:621-632, 1971.

Chen and Snyder, "Diosgenin-bearing, molluscicidal saponins from *Allium vineale*: an NMR approach for the structural assignment of oligosaccharide units," *J. Org. Chem.*, 54:3679-3689, 1989.

Chen and Snyder, "Molluscicidal saponions form *Allium vineale*," *Tetrahedron Lett.*, 28:5603-5606, 1987.

Cho, Widhoim, Tanaka, Nakanishi, Murooka, "*Agrobacterium rhizogenes*-mediated transformation and regeneration of the legume *Astragalus sinicus* (Chinese milk vetch)," *Plant Science*, 138:53-65;1998.

Chou and Blenis, *Cell*, 85:573-583, 1996.

Christey, "Transgenic crop plants using *Agrobacterium rhizogenes*-mediated transformation," Doran, P. M., (ed.) *Hairy roots: Culture and applications*, Harwood, Amsterdam, 99-111, 1997.

Colcher et al., *Cancer Res.*, 47:1185 and 4218, 1987.

Coliart, Baeuerle, Vassalli, *Mol. Cell. Biol.*, 10:1498-1506, 1990.

Creelman et al., *Proc. Natl. Acad. Sci. USA*, 89:4938-4941, 1992.

Davis & Preston *Analytical Biochemistry*, 116(2):402-407, 1981.

Davis, Sinensky, Junker, *Pharmac. Ther.*, 43:221-36, 1989.

Defago, *Ber. Schweiz. Bot. Ges.*, 87:79-132, 1977.

Dillman et al., *Antibody Immunocon. Radiopharm.*, 1:65-77, 1988.

Doll, R. et al., *Lancet* 1:793, 1962.

Enari, Hug, Nagata, *Nature*, 375:78-81, 1995.

Folkman, Haudenschild, Zetter, *Proc. Natl. Acad. Sci.*, 76:5217-5221, 1979.

Franceschi et al., *Proc. Natl. Acad Sci. USA*, 88:6745-6749, 1991.

Frechet, Christ, du Sorbier, Fischer, Vuilhorgne, "Four triterpenoid saponins from dried roots of *Gypsophila* species," *Phytochemistry*, 30:927-931, 1991.

Gamborg, Miller, Ojima, "Nutrient requirements of suspension cultures of soybean root cells," *Exp. Cell Res.*, 50:151-158; 1968.

Gariboldi, Verotta, Gabetta, "Saponins from *Crossopteryx febrifuga*, *Phytochemistry*, 29:2629-2635, 1990.

Gefter et al., *Somatic Cell Genet.*, 3: 231-236, 1977.

Ghose et al., *CRC Critical Reviews in Therapeutic Drug Carrier Systems*, 3:262-359, 1987.

Ghose, et al., *Meth. Enzymology*, 93:280-333, 1983.

Goding, 1986, In: *Monoclonal Antibodies: Principles and Practice*, 2d ed., Academic Press, Orlando, Fla., pp. 60-61, and 71-74, 1986.

Grant, Dommisse, Christey, Conner, "Gene transfer to plants using *Agrobacterium*," In: Murray, D. R., (ed.) *Advanced methods in plant breeding and biotechnology*, CAB International, Wallingford, 1991:50-73.

Gundalch et al., *Proc. Natl. Acad. Sci. USA*, 89:2389-2393, 1992.

Hamburger, Slacanin, Hostettmann, Dyatmiko, Sutarjadi, "Acetylated saponins with molluscicidal activity from *Sapindus rarak*: unambiguous structure determination by proton nuclear magnetic resonance and quantitative analysis," *Phytochem. Anal.*, 3:231-237, 1992.

Hansen, Nielsen, Berg, *J. Immunological Methods*, 119:203-210, 1989.

Harlow and Lane, Antibodies: A Laboratory manual, Cold Spring Harbor Laboratory, 1988.

Harwood, Chandler, Pellarin, Bangerter, Wilkins, Long, Cosgrove, Malinow, Marzetta, Pettini, Savoy, Mayne, "Pharmacologic consequences of cholesterol absorption inhibition: alteration in cholesterol metabolism and reduction in plasma cholesterol concentration induced by the synthetic saponin β-tigogenin cellobioside (CP-88,818; tiqueside), *J. Lipid. Res.* 34:377-395, 1993.

Hassanain, Dai, Gupta, *Anal. Biochem.*, 213:162-167, 1993.

Hostettmann et al., "Chemistry and pharmacology of natural products," In Saponins, Cambridge University Press, pp. 1-548, 1995.

Hu, Alfermann, "Diterpenoid production in hairy root cultures of *Salvia miltiorrhiza*," *Phytochemistry*, 32(3):699-703; 1993.

Huang et al., *Zhongueo Yaoii Xuebao*, Chemical abstract No. 98100885, 3:286-288, 1982.

Ikeda, Fujiwara, Kinjo, Nohara, Ida, Shoji, Shingu, Isobe, Kajimoto, *Bull. Chem. Soc. Jpn.*, 68:3483-3490 (1995).

Inoue, H., et al., *Chem. Pharm. Bull.* 6) 2:897-901, 1986.

Jansakul, Baumann, Kenne, Samuelsson, "Ardisiacrispin A and B, two utero-contracting saponins from *Ardisia crispa*," *Planta Medica*, 53:405-409, 1987.

Jiang, Massiot, Lavaud, et al., "Triterpenoid glycosides from the bark of *Mimosa tenuiflora*, *Phytochemistry*, 30:2357-2360, 1991.

Jung, Kwak, Kim, Lee, Choi, Lin, "Improvement of the catharanthine productivity in hairy root cultures of *Catharanthus roseus* by using monosaccharides as a carbon source," *Biotech. Lett.*, 14:695-700; 1992.

Kamel, Ohtani, Kurokawa, et al., "Studies on *Balanites aegyptiaca* fruits, an antidiabetic Egyptian folk medicine," *Chem. Pharm. Bull.*, 39:1229-1233, 1991.

Kasiwada et al., *J. Org. Chem.*, 57:6946-6953, 1992.

Kelly and Tsai, "Effect of pectin, gum arabic and agar on cholesterol absorption, synthesis and turnover in rats," *J. Nutr.*, 108:630-639, 1978.

Kennedy, Wagner, Conzen, Jordan, Bellacosa, Tsichlis, Nissam, *Genes and Dev.*, 11:701-713, 1997.

Kimura et al., *Immunogenetics*, 11:373-381, 1983.

Kinjo, Araki, Fukui, Higuchi, Ikeda, Nohara, Ida, Takemoto, Miyakoshi, Shoji, *Chem. Pharm. Bull.* 40(12):3269-3273 (1992).

Kizu and Tomimori, "Studies on the constituents of *Clematis* species. V. On the saponins of the root of *Clematis chinensis* OSBECK," *Chem. Pharm. Bull.*, 30:3340-3346, 1982.

Kohler and Milstein, *Eur. J. Immunol.*, 6:511-519, 1976.

Kohler and Milstein, *Nature,* 256:495-497, 1975.

Kojima and Ogura, "Configurational studies on hydroxy groups at C-2, 3 and 23 or 24 of oleanene and ursene-type triterpenes by NMR spectroscopy," *Phytochemistry,* 28:1703-1710, 1989.

Kong et al., *Phytochemistry,* 33:427-430, 1993.

Konoshima and Sawada, *Chem. Pharm. Bull.,* 30:2747-2760, 1982.

Kutney, "Nuclear magnetic resonance (N.M.R.) study in the steroidal sapogenin series. Stereochemistry of the Spiro ketal system," *Steroids,* 2:225-235, 1963.

Lemieux, Kullnig, Bernstein, Schneider, "Configurational effects on the proton magnetic resonance spectra of six-membered ring compounds," *J. Am. Chem. Soc.,* 80:6098-6105, 1958.

Lister, P. R., P. Holford, T. Haigh, and D. A. Morrison. *Acacia in Australia: Ethnobotany and potential food crop.* p. 228-236. In: J. Janick (ed.), *Progress in new crops. ASHS Press, Alexandria, Va.,* 1996.

Lloyd, McCown, "Commercially feasible micropropagation of mountain laurel, *Kalmia latifolia* by use of shoot tip culture," *Comb. Proc. Intl. Plant Prop.Soc.,* 30:421-427; 1981.

Mackness, Durrington, Converse, Skinner (Eds.), In: *Lipoprotein Analysis: A Practical Approach,* Oxford University Press, Oxford, p 1, 1992.

Mahato, Pal, Nandy, *Tetrahedron,* 48:6717-6728 (1992).

Manabe et al., *J. Lab. Clin. Med.,* 104(3):445-454, 1984.

Martin et al., *J. Exp. Med.,* 182:1545-1556, 1995.

Martin, Reueelingsperger, McGahon, Rader, van Schie, Laface, Green, *J. Exp.Med.,* 182:1545-1556, 1995.

Massiot, Lavaud, Besson, Le Men-Olivier, van Binst, "Saponins from aerial parts of alfalfa (*Medicago sativa*)," *J. Agric. Food Chem.,* 39:78-82, 1991b.

Massiot, Lavaud, Delaude, van Binst, Miller, Fales, "Saponins from *Tridesmostemon claessenssi,*" *Phytochemistry,* 29:3291-3298, 1990.

Massiot, Lavaud, Guillaume, Le Men-Olivier, van Binst, "Identification and sequencing of sugars in saponins using 2D $^1$H NMR spectroscopy," *J. Chem. Soc., Chem. Commun.,* 1485-1487, 1986.

Massiot, Lavaud, Le Men-Olivier, van Binst, Miller, Fales, "Structural elucidation of alfalfa root saponins by mass spectrometry and nuclear magnetic resonance analysis," *J. Chem. Soc., Perkin Trans.,* 1:3071-3079, 1988.

Massiot, Lavaud, Nuzillard, "Révision des structures des chrysantéllines par résonance magnétique nucléaire," *Bull. Soc. Chim. Fr.,* 127:100-107, 1991a.

Miotti et al., *Cancer Res.,* 65:826, 1985.

Miyamoto, Togawa, Higuchi, Komori, Sasaki, "Six newly identified biologically active triterpenoid glycoside sulphates from the sea cucumber," *Cucumaria echinata. Annalen,* 453-460, 1990.

Monk, "Variegation in epigenetic inheritance", *TIG,* 6:110-114, 1990.

Mujoo, Maneval, Anderson, Gutterman, *Oncogene,* 12:1617-1623, 1996.

Murashige, Skoog, "A revised medium for rapid growth and bioassay of tobacco tissue culture," *Physiol. Plant.,* 15:473-482; 1962.

Murashige, T and Skoog, F. "A revised medium for rapid growth and bio-assays with tobacco tissue cultures," *Physiologia Plantarum* 15: 473-497, 1962.

Nabel and Baltimore, *Nature* 326:711-713, 1987.

Nagamoto et al., *Planta Medica.,* 54:305-307, 1988.

Nagao, Hachiyama, Oka, Yamauchi, "Studies on the constituents of *Aster tataricus* L. f. II. Structures of aster saponins isolated from the root," *Chem. Pharm. Bull.,* 37:1977-1983, 1989.

Nelson, Futscher, Kinsella, Wymer, Bowden, "Detection of mutant Ha-ras genes in chemically initiated mouse skin epidermis before the development of benign tumors," *Proc. Natl. Acad Sci. USA,* (14):6398-6402, 1992.

Nishino, Manabe, Enoki, Nagata, Tsushida, Hamaya, "The structure of the tetrasaccharide unit of camellidins, saponins, possessing antifungal activity," *J. Chem. Soc., Chem. Commun.,* 720-723, 1986.

Nitsch, Nitsch, "Haploid plants from pollen grains," *Science,* 163:85-87, 1969.

O'Reilly, Boehm, Shing, Fukai, Vasios, Lane, Flynn, Birkhead, Olsen, Folkman, *Cell,* 88:277-285, 1997.

Oakenfull et al., *Atherosclerosis,* 48:301 (1983).

Ohkawa, Kamada, Sudo, Harada, "Effects of gibberellic acid on hairy root growth in *Datura innoxia," J. Plant Physiol.,* 134:633-636; 1989.

Okabe, Nagao, Hachiyama, Yamauchi, "Studies on the constituents of *Luffa operculata* coGN. II. Isolation and structure elucidation of saponins in the herb," *Chem. Pharm. Bull.,* 37:895-900, 1989.

Okada, Koyama, Takahashi, Okuyama, Shibata, *Planta Med.* 40:185-192, (1980).

Okada, Sakuma, Fukui, Hazeki, Ui, *J. Bio. Chem.,* 269:3563-3567, 1994.

Pallavicini, In: *Techniques in Cell Cycle Analysis,* Gray and Parzynkiewicz (Eds.), Humana Press Inc.,Clifton, NJ, pp. 139, 1987.

Pant, Panwar, Negi, Rawat, Morris, Thompson, "Structure elucidation of a spirostanol glycoside from *Asparagus officinalis* fruits by concerted use of two-dimensional NMR techniques," *Mag. Reson. Chem.,* 26:911-918, 1988.

Penders, Delaude, Pepermans, van Binst, "Identification and sequencing of sugars in an acetylated saponin of *Blighia welwitschii* by N.M.R. spectroscopy," *Carbohyd. Res.,* 190:109-120, 1989.

Pietenpol et al., *Cancer Res.,* 55:1206-1210, 1995.

Pieterez et al., *Antibody Immunoconj. Radiopharm.,* 1:79-103, 35, 1988.

Pisha et al., *Nature Medicine,* 1:1046-1051, 1995.

Polyak et al., *Genes Dev.,* 8:9-22, 1994.

Potterat, Hostettmann, Stoeckli-Evans, Saadou, "Saponins with an unusual secoursene skeleton from *Sesamum alatum* THONN., *Hely. Chim. Acta,* 75:833-841, 1992.

Prehn, "Regeneration versus neoplastic growth," *Carcinogenesis,* 18(8):1439-1444, 1997.

Puri, Wong, Puri, "Solasodine and diosgenin: $^1$H and $^{13}$C assignments by two-dimensional NMR spectroscopy," *Mag. Res. Chem.,* 31:278-282, 1993.

Reeves, Nielson, Fahey, *Am. Inst. Nutr.,* 1939, 1993.

Reisfeld et al., Melanoma Antigens and Antibodies, p. 317, 1982.

Reznicek, Jurenitsch, Kubelka, Michl, Korhammer, Haslinger, "Isolierung and Struktur der vier Hauptsaponine aus *Solidago gigantea* var. *serotina,*" *Annalen,* 989-994, 1990.

Reznicek, Jurenitsch, Michl, Haslinger, "The first structurally confirmed saponin from *Solidago gigantea*: structure elucidation by modern NMR techniques," *Tetrahedron Lett.*, 30:4097-4100, 1989b.

Reznicek, Jurenitsch, Robien, Kubelka, "Saponins in *Cyclamen* species: configuration of cyclamiretin C and structure of isocyclamin," *Phytochemistry*, 28:825-828, 1989a.

Rhodes, et aL, "Influence of exogenous hormones on the growth and secondary metabolite formation in transformed root cultures," *Plant Cell Tissue Organ Culture*, 38:143-151; 1994.

Rodriguez, Castro, Riguera, "Holothurinosides: new antitumour non sulphated triterpenoid glycosides from the sea cucumber *Holothruia forskalii*," *Tetrahedron*, 47:4753-4762, 1991.

Royal I and Park M, *J. Biol. Chem.* 270:27780-27787, 1995.

Sasaki, Udagawa, Ishimaru, Hayashi, Alfermann, Nakanishi, Shimomura, "High forskolin production in hairy roots of *Coleus forskohlii*," *Plant Cell Reports* 17:457-459, 1998.

Sashida, Kawashima, Mimaki, "Novel polyhydroxylated steroidal saponins from *Allium giganteum*," *Chem. Pharm. Bull.*, 39:698-703, 1991.

Schenk, Hilderbrandt, "Medium and techniques for induction and growth of monocotyledonous and dicotyledonous plant cell cultures," *Can. J. Bot.*, 50:199-204; 1972.

Schöpke, Wray, Rzazewska, Hiller, "Bellissaponins $BA_1$ and $BA_2$, acylated saponins from *Bellis perennis*," *Phytochemistry*, 30:627-631, 1991.

Schreiber, Matthias, Muller, Schaffner, *Nucleic Acids Res.*, 17:6419, 1989.

Schuh et al., "Obligatory wounding requirement for tumorigenesis in v-jun transgenic mice," *Nature*, 346:756-760, 1990.

Shao, Kasai, Xu, Tanaka, "Saponins from roots of *Kalopanax septemlobus*. (THUNB.) KOIDZ., Ciqiu: structures of kalopanaxsaponins C, D, E and F," *Chem. Pharm. Bull.*, 37:311-314, 1989.

Shayesteh, Lu, Kuo, Baldocchi, Godfrey, Collins, Pinkel, Powell, Mills, Grey, *Nat. Gent.*, 21:99-102, 1999.

Shepard et al., *J. Clin. Immunol.*, 11:117-127, 1991.

Shirazi, Liu, Trott, "Exposure to ultraviolet B radiation increases the tolerance of mouse skin to daily X-radiation," *Rad. Res.*, 145:768-775, 1996.

Sieweke et al., "Mediation of wound-related rous sarcoma virus tumorigenesis by TGF-β," *Science*, 248:1656-1660, 1990.

Smith, Weathers, Cheetham, "Effects of gibberellic acid on hairy root cultures of *Artemisia annua*: growth and artemisinin production," *In Vitro Cell Dev. Biol.*, 33:75-79; 1997.

Spady, Wollett, Dietschy, *Annu. Rev. Nutr.*, 13:355, 1993.

Steel and Torrie, *In: Principals and Procedures of Statistics*, 2nd Ed., McGraw-Hill, New York, p 383, 1980.

Stevenson et al., *Chem. Immunol.*, 48:126-166, 1990.

Takema, Fujimura, Ohsu, Imokawa, "Unusual wrinkle formation after temporary skin fixation followed by UVB irradiation in hairless mouse skin," *Exp. Dermatol.*, 5:145-149, 1996.

Tewari, Quan, Rourke, Zeng, Beidler, Salvesan, Dixit, "Yama/CPP32 beta, a mammalian homolog of CED-3, is a CrmA-inhibitable protease that cleaves the death substrate poly (ADP-ribose) polymerase," *Cell*, 81:801, 1995.

Thompson et al., Cancer Epidemiol. *Biomarker Prevent.*, 1:597-602, 1992.

Thor et al, *Cancer Res.*, 46:3118, 1986.

Tomas-Barbaren et al., *Planta Medica.*, 54:266-267 (1988).

Tori and Aono, *Ann. Rept. Shionogi Res. Lab.*, 14:136, 1964.

Vaickus et al., *Cancer Invest.*, 9:195-209, 1991.

Vazquez, Quinoa, Riguera, San Martin, Darias, "Santiagoside, the first asterosaponin from an Antarctic starfish (*Neosmilaster georgianus*)," *Tetrahedron*, 48:6739-6746, 1992.

Vlahos and Matter, *FEBS Lett.*, 309:242-248, 1992.

Vlahos, Matter, Hui, Brown, *J. Bio. Chem.*, 269:5241-5248, 1994.

Waltho, Williams, Mahato, Pal, Barna, "Structure elucidation of two triterpenoid tetrasaccharides from *Androsace saxifragifolia*," *J. Chem. Soc., Perkin* 1:1527-1531, 1986.

Wang, He, Ling, Li, "Chemical study of Astragalus plant. II. Structures of asernestioside A and B, isolated from *Astragalus ernestii* COMB. *Huaxue Xuebao*, 47:583-587, *Chem. Abstr.*, 1989.

Weng eral., *Proc. Natl. Acad. Sci.*, 92:5744-5748, 1995.

White, *Genes Dev.*, 10:1-15, 1996.

Whitman M, Kaplan D. R., Schaffhausen B, Cantley L. C. and Roberts, T. M. *Nature*, 315: 239-242, 1985.

Willker and Leibfritz, "Complete assignment and conformational studies of tomatine and tomatidine," *Mag. Res. Chem.*, 30:645-650, 1992.

Wyllie, *Anticancer Res.*, 5:131-136, 1985.

Wysokinska, Chmiel, "Transformed root cultures for biotechnology," *Acta Biotechnol.*, 17:131-159; 1997.

Yang et al., *Anticancer Res.*, 15:2479-2488, 1995.

Yoshikawa, Shimono, Arihara, "Antisweet substances, jujubasaponins I-III from *Zizyphus jujuba*,. Revised structure of ziziphin," *Tetrahedron Lett.*, 32:7059-7062, 1991.

Yoshikawa, Suzaki, Tanaka, Arihara, Nigam, *J. Nat. Prod.*, 60:1269-1274 (1997).

Youn, Park, Chung, Lee, *Photodermatol Photoimmunol. Photomed.*, 13:109-114, 1997.

Yukimune et al., *Nature Biotech.*, 14:1129-1132, 1996.

Zobel, "Study-state control and investigation of root system morphology," In: Torrey J. G., Winship, L. J. (eds.) *Applications of continuous and steady-state methods to root biology*, Kluwer, Amsterdam, 165-182, 1989.

---

What is claimed is:

1. A mixture comprising one or more isolated triterpene glycosides isolated from *Acacia victoriae* tissue, wherein the mixture contains at least one triterpene glycoside having a molecular weight of about 1800 to 2600, and wherein the mixture induces cytotoxicity in a Jurkat cell and induces apoptosis in a Jurkat cell.

2. The mixture of claim 1, wherein the mixture induces cytotoxicity in the Jurkat cell with an $IC_{50}$ of about 0.12 μg/ml to about 0.40 μg/ml.

3. The mixture of claim 1, wherein the mixture further comprises a pharmacologically acceptable medium.

4. The mixture of claim 3, wherein the pharmaceutically acceptable medium is a buffer, a solvent, a diluent, an inert carrier, an oil, or an edible material.

5. The mixture of claim 1, wherein the mixture is an ointment, a cream, or a tablet.

6. The mixture of claim 1, wherein the mixture comprises dried or ground *Acacia victoriae* pod.

7. The mixture of claim 1, wherein the mixture is comprised in a capsule.

8. The mixture comprising a triterpene moiety attached to a monoterpene moiety having the claim 1, wherein the mixture comprises a compound of molecular formula:

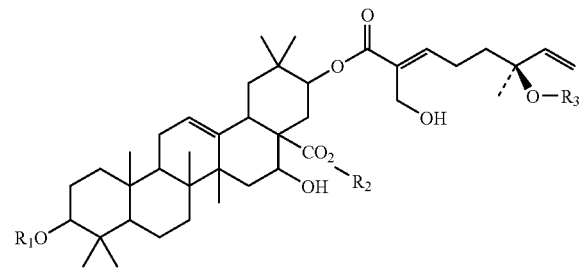

wherein (a) $R_1$ is selected from the group consisting of hydrogen, $C_1$-$C_5$ alkyl, and an oligosaccharide; (b) $R_2$ is selected from the group consisting of hydrogen, $C_1$-$C_5$ alkyl, and an oligosaccharide; (c) $R_3$ is selected from the group consisting of hydrogen, hydroxyl, $C_1$-$C_5$ alkyl, $C_1$-$C_5$ alkylene, $C_1$-$C_5$ alkyl carbonyl, a sugar, and a monoterpene group; and (d) the formula further comprises $R_4$, wherein $R_4$ is selected from the group consisting of hydrogen, hydroxyl, $C_1$-$C_5$ alkyl, $C_1$-$C_5$ alkylene, $C_1$-$C_5$ alkyl carbonyl, a sugar, $C_1$-$C_5$ alkyl ester, and a monoterpene group, wherein $R_4$ may be attached to the triterpene moiety or the monoterpene moiety.

9. The mixture of claim 8, wherein $R_1$ is an oligosaccharide.

10. The mixture of claim 9, wherein the oligosaccharide comprises a fucose, a xylose, and an N-acetyl glucosamine.

11. The mixture of claim 8, wherein R2 is an oligosaccharide.

12. The mixture of claim 11, wherein the oligosaccharide comprises a glucose, an arabinose and a rhamnose.

* * * * *

UNITED STATES PATENT AND TRADEMARK OFFICE
CERTIFICATE OF CORRECTION

PATENT NO.      : 7,985,435 B2
APPLICATION NO. : 12/688651
DATED           : July 26, 2011
INVENTOR(S)     : Charles J. Arntzen et al.

Page 1 of 1

It is certified that error appears in the above-identified patent and that said Letters Patent is hereby corrected as shown below:

In claim 8, column 141, lines 47-49, delete
"The mixture comprising a triterpene moiety atta ched to a monoterpene moiety having the claim 1, wherein the mixture comprises a compound of molecular formula" and
insert
--The mixture of claim 1, wherein the mixture comprises a compound comprising a triterpene moiety attached to a monoterpene moiety having the molecular formula-- therefor.

Signed and Sealed this
Twenty-seventh Day of December, 2011

David J. Kappos
*Director of the United States Patent and Trademark Office*